(12) United States Patent
Besong et al.

(10) Patent No.: US 10,023,590 B2
(45) Date of Patent: Jul. 17, 2018

(54) SUBSTITUTED PYRIDINE COMPOUNDS HAVING HERBICIDAL ACTIVITY

(71) Applicant: BASF SE, Ludwigshafen (DE)

(72) Inventors: Gilbert Besong, Bad Duerkheim (DE); Matthias Witschel, Bad Duerkeim (DE); Ruediger Reingruber, Ludwigshafen (DE); Helmut Kraus, Wissenbourg (FR); Thomas Seitz, Viernheim (DE); Liliana Parra Rapado, Offenburg (DE); Trevor William Newton, Neustadt (DE); Gerd Kraemer, Kerzenheim (DE); Richard Roger Evans, Limburgerhof (DE); Michael Rack, Eppelheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/304,126

(22) PCT Filed: Apr. 7, 2015

(86) PCT No.: PCT/EP2015/057458
§ 371 (c)(1),
(2) Date: Oct. 14, 2016

(87) PCT Pub. No.: WO2015/158565
PCT Pub. Date: Oct. 22, 2015

(65) Prior Publication Data
US 2017/0121343 A1    May 4, 2017

(30) Foreign Application Priority Data
Apr. 17, 2014 (EP) ...................... 14165225

(51) Int. Cl.
A01N 43/40 (2006.01)
C07D 495/04 (2006.01)
A01N 43/90 (2006.01)

(52) U.S. Cl.
CPC ........... C07D 495/04 (2013.01); A01N 43/90 (2013.01)

(58) Field of Classification Search
CPC .............................. A01N 43/90; C07D 495/04
USPC ....................................................... 504/246
See application file for complete search history.

(56) References Cited

U.S. PATENT DOCUMENTS 8,877,683 B2 * 11/2014 Witschel ................ A01N 43/90
504/246

FOREIGN PATENT DOCUMENTS

| CN | 102822179 | 12/2012 |
|---|---|---|
| WO | WO 2009063180 | 5/2009 |
| WO | WO 2010029311 | 3/2010 |
| WO | WO 2010130970 | 11/2010 |
| WO | 2011117151 | 9/2011 |
| WO | WO 2011117152 | 9/2011 |
| WO | WO 2012084755 | 6/2012 |
| WO | WO 2012085265 | 6/2012 |
| WO | WO 2013072528 | 5/2013 |
| WO | WO 2013076315 | 5/2013 |
| WO | WO 2013076316 | 5/2013 |
| WO | WO 2013083859 | 6/2013 |
| WO | WO 2013174693 | 11/2013 |
| WO | WO 2013174694 | 11/2013 |
| WO | WO 2013178585 | 12/2013 |
| WO | WO 2013182472 | 12/2013 |
| WO | WO 2013189984 | 12/2013 |
| WO | WO 2014012811 | 1/2014 |
| WO | WO 2014026845 | 2/2014 |
| WO | WO 2014026893 | 2/2014 |
| WO | WO 2014026928 | 2/2014 |
| WO | WO 2014064094 | 5/2014 |
| WO | WO 2014080316 | 5/2014 |
| WO | WO 2014097085 | 6/2014 |
| WO | WO 2014102065 | 7/2014 |
| WO | WO 2014102069 | 7/2014 |
| WO | WO 2014108266 | 7/2014 |
| WO | WO 2014124850 | 8/2014 |
| WO | WO 2014177990 | 11/2014 |
| WO | WO 2014177991 | 11/2014 |
| WO | WO 2014177992 | 11/2014 |
| WO | WO 2014177993 | 11/2014 |
| WO | WO 2014177999 | 11/2014 |

(Continued)

OTHER PUBLICATIONS

International Search Report, issued in PCT/EP2015/057458, dated Jun. 25, 2015.

(Continued)

*Primary Examiner* — Johann R Richter
(74) *Attorney, Agent, or Firm* — Brinks Gilson & Lione

(57) ABSTRACT

The present invention provides a substituted pyridine compound of the formula I

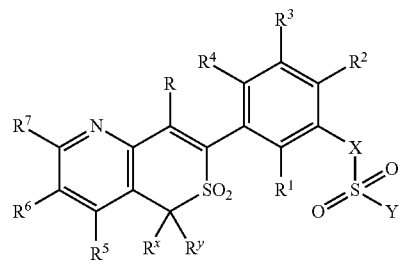

or an agriculturally suitable salt or N-oxide thereof, wherein the variables in the formula I are defined as in the description. Substituted pyridine compounds of formula I are useful as herbicides.

15 Claims, No Drawings

(56) References Cited

FOREIGN PATENT DOCUMENTS

| | | |
|---|---|---|
| WO | WO 2014184014 | 11/2014 |
| WO | WO 2014184015 | 11/2014 |
| WO | WO 2014184016 | 11/2014 |
| WO | WO 2014184017 | 11/2014 |
| WO | WO 2014184019 | 11/2014 |
| WO | WO 2014184058 | 11/2014 |
| WO | WO 2014184073 | 11/2014 |
| WO | WO 2014184074 | 11/2014 |
| WO | WO 2014187705 | 11/2014 |
| WO | WO 2014202589 | 12/2014 |
| WO | WO 2015003858 | 1/2015 |
| WO | WO 2015007564 | 1/2015 |
| WO | WO 2015007711 | 1/2015 |
| WO | WO 2015022634 | 2/2015 |
| WO | WO 2015022636 | 2/2015 |
| WO | WO 2015022639 | 2/2015 |
| WO | WO 2015049160 | 4/2015 |
| WO | WO 2015049360 | 4/2015 |
| WO | WO 2015052152 | 4/2015 |
| WO | WO 2015052153 | 4/2015 |
| WO | WO 2015052173 | 4/2015 |
| WO | WO 2015052178 | 4/2015 |
| WO | WO 2015067494 | 5/2015 |
| WO | WO 2015075067 | 5/2015 |
| WO | WO 2015082415 | 6/2015 |
| WO | WO 2015082422 | 6/2015 |
| WO | WO 2015086698 | 6/2015 |
| WO | WO 2015091045 | 6/2015 |
| WO | WO 2015092706 | 6/2015 |
| WO | WO 2015124651 | 8/2015 |
| WO | WO 2015144451 | 10/2015 |
| WO | WO 2015144881 | 10/2015 |
| WO | WO 2015150541 | 10/2015 |
| WO | WO 2015155129 | 10/2015 |
| WO | WO 2015155236 | 10/2015 |
| WO | WO 2015155271 | 10/2015 |
| WO | WO 2015155272 | 10/2015 |
| WO | WO 2015155273 | 10/2015 |
| WO | WO 2015158518 | 10/2015 |
| WO | WO 2015158565 | 10/2015 |

OTHER PUBLICATIONS

International Preliminary Report on Patentability, issued in PCT/EP2015/057458, dated Oct. 27, 2016.
Search Report, issued in EP Application No. 141656225.5, dated Oct. 21, 2014.

* cited by examiner

SUBSTITUTED PYRIDINE COMPOUNDS HAVING HERBICIDAL ACTIVITY

This application is a National Stage application of International Application No. PCT/EP2015/057458, filed Apr. 7, 2015. This application also claims priority under 35 U.S.C. § 119 to European Patent Application No. 14165225.5, filed Apr. 17, 2014.

The present invention relates to substituted pyridine compounds of the general formula I defined below and to their use as herbicides. Moreover, the invention relates to compositions for crop protection and to a method for controlling unwanted vegetation.

WO 2009/063180 and WO 2010/029311 describe certain herbicidal pyridopyrazines.

WO 2010/130970 describes certain 6,6-dioxo-6-thia-1,4-diaza-naphthalene derivatives having herbicidal activity.

WO 2011/117152, WO 2012/084755 and WO 2013/178585 all describe certain substituted pyridine compounds having herbicidal activity.

However, the herbicidal properties of these known compounds with regard to the harmful plants are not always entirely satisfactory.

Moreover, the protection of crops from undesirable weeds can also interfere with the crop growth. In particular, many of the highly effective herbicides are not fully compatible with (i.e. not sufficiently selective in) the crop plants, in particular with important crops such as corn (maize), rice or cereals.

One approach to overcome this problem is the development of selective herbicides which can control weeds without exhibiting unacceptable phytotoxicity to the crop plants. Thus, there is still need for new herbicides, especially selective herbicides and in particular those which can be employed selectively against harmful plants in crops, in particular in major crops such as corn (maize), rice and cereals.

It is therefore an object of the present invention to provide compounds having improved herbicidal action. To be provided are in particular compounds which have high herbicidal activity, in particular even at low application rates, and which are sufficiently compatible with crop plants for commercial utilization.

Another object of the present invention is to provide compounds which are sufficiently compatible with (i.e. sufficiently selective in) crop plants (in particular important crop plants such as corn (maize), rice and cereals) without essentially reducing their herbicidal action against harmful plants.

These and further objects are achieved by substituted pyridine compounds of formula (I), defined below, and by their agriculturally suitable salts or N-oxides.

Accordingly, the present invention provides substituted pyridine compound of the formula I

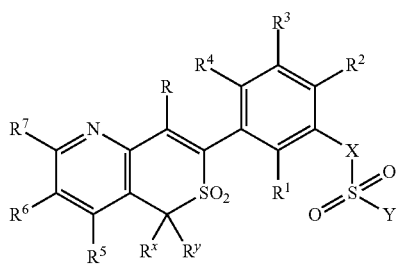

I wherein
R is hydroxyl or O—$R^4$ where $R^4$ is $C_1$-$C_8$-alkyl, $C_2$-$C_8$-alkenyl, $C_2$-$C_8$-alkynyl, $C_1$-$C_8$-alkylcarbonyl-, $C_3$-$C_6$-cycloalkylcarbonyl-, $C_1$-$C_8$-alkoxycarbonyl-, $C_1$-$C_8$-alkylthiocarbonyl-, $C_1$-$C_8$-alkoxycarbonyloxy-$C_1$-$C_3$-alkyl-, $C_1$-$C_8$-alkylcarbonyloxy-$C_1$-$C_3$-alkyl-, tri($C_1$-$C_4$-alkyl)silyl-, $C_1$-$C_8$-alkyl-S(O)$_n$—, aryl-S(O)$_n$—, aryl-$C_1$-$C_4$-alkyl-, arylcarbonyl-, where the aryl moiety is unsubstituted or substituted by one to five $R^a$ and each $R^a$ is independently halogen, nitro, cyano, $C_1$-$C_8$-alkyl, $C_1$-$C_6$-haloalkyl, $C_1$-$C_8$-alkoxy, $C_1$-$C_8$-haloalkoxy, or $C_1$-$C_4$-alkyl-S(O)$_n$—;

$R^1$ and $R^2$ independently of one another are hydrogen, halogen, cyano, nitro, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy, $C_1$-$C_6$-alkoxy-$C_1$-$C_4$-alkyl-, $C_1$-$C_6$-haloalkoxy-$C_1$-$C_4$-alkyl-, $C_3$-$C_6$-cycloalkyl-$C_1$-$C_3$-alkyl-, $C_3$-$C_6$-cycloakyl-$C_1$-$C_3$-alkoxy-, $C_1$-$C_6$-alkoxy-$C_2$-$C_6$-alkoxy-, $C_1$-$C_6$-alkoxy-$C_2$-$C_6$-alkoxy-$C_1$-$C_3$-alkyl-, $C_1$-$C_6$-alkylthio-, $C_1$-$C_6$-haloalkylthio-, $C_1$-$C_6$-alkylsulfonyl-, $C_1$-$C_6$-haloalkylsulfonyl-, $C_1$-$C_3$-alkylaminosulfonyl-, $C_1$-$C_3$-dialkylaminosulfonyl-, $C_1$-$C_3$-alkylamino-sulfonyl-$C_1$-$C_3$-alkyl-, $C_1$-$C_3$-dialkylamino-sulfonyl-$C_1$-$C_3$-alkyl-, $C_1$-$C_3$-alkylcarbonylamino-, N—$C_1$-$C_3$-alkyl-N—$C_1$-$C_3$-alkylcarbonylamino-, $C_1$-$C_3$-alkylsulfonylamino-, N—$C_1$-$C_3$-alkyl-N—$C_1$-$C_3$-alkylsulfonylamino-, $C_1$-$C_3$-alkylsulfonylamino-$C_1$-$C_3$-alkyl-, $C_1$-$C_3$-alkylaminocarbonyl-$C_1$-$C_3$-alkyl-, $C_1$-$C_3$-dialkylaminocarbonyl-$C_1$-$C_3$-alkyl-, N—$C_1$-$C_3$-alkylcarbonyl-N—$C_1$-$C_3$-alkylamino-$C_1$-$C_3$-alkyl-, N—$C_1$-$C_3$-alkylsulfonyl-N—$C_1$-$C_3$-alkylamino-$C_1$-$C_3$-alkyl-, $C_1$-$C_3$-alkylcarbonylamino-$C_1$-$C_3$-alkyl-, Z-heterocyclyl or Z-heterocyclyloxy wherein said heterocyclyls are 5 or 6 membered heterocyclyls containing 1, 2 or 3 heteroatoms selected from the group consisting of O, N and S, and are unsubstituted or partially or fully substituted by substituents selected from the group consisting of halogen, $C_1$-$C_3$-alkyl, $C_3$-$C_6$-cycloalkyl, $C_1$-$C_3$-haloalkyl, $C_1$-$C_3$-alkoxy, $C_1$-$C_3$-haloalkoxy, $C_1$-$C_6$-alkyl-S(O)$_n$—, cyano, nitro and phenyl;

$R^3$ is hydrogen;
$R^4$ is hydrogen or halogen;
$R^5$, $R^6$, and $R^7$ independently of one another are hydrogen, halogen or $C_1$-$C_4$-alkyl;
$R^x$, $R^y$ independently of one another are hydrogen, $C_1$-$C_5$-alkyl, $C_2$-$C_5$-alkenyl, $C_2$-$C_5$-alkynyl, $C_1$-$C_5$-haloalkyl, $C_1$-$C_2$-alkoxy-$C_1$-$C_2$-alkyl- or halogen; or $R^x$ and $R^y$ are together a $C_2$-$C_5$-alkylene or $C_2$-$C_5$-alkenylene chain and form a 3-, 4-, 5- or 6-membered saturated, partially unsaturated or fully unsaturated monocyclic ring together with the carbon atom they are bonded to, wherein 1 or 2 of any of the CH$_2$ or CH groups in the $C_2$-$C_5$-alkylene or $C_2$-$C_5$-alkenylene chain may be replaced by 1 or 2 heteroatoms independently selected from O or S;

X is O, NH, N—$C_1$-$C_4$-alkyl, N—$C_1$-$C_4$-alkoxy-$C_1$-$C_4$-alkyl, N—$C_3$-$C_6$-cycloalkyl, or N-allyl;
Y is $C_1$-$C_4$-alkyl, $C_1$-$C_4$-haloalkyl, $C_3$-$C_6$-cycloalkyl, $C_3$-$C_6$-cycloalkyl-$C_1$-$C_3$-alkyl-, or $C_1$-$C_3$-dialkylamino-;
Z is independently a covalent bond or $C_1$-$C_4$-alkylene;
n is independently 0, 1 or 2;
or an agriculturally suitable salt or N-oxide thereof.

The present invention also provides agrochemical compositions comprising at least one substituted pyridine compound of formula I and auxiliaries customary for formulating crop protection agents.

The present invention also provides herbicidal compositions comprising at least one substituted pyridine compound of formula I (component A) and at least one further compound selected from the herbicidal compounds B (component B) and safeners C (component C).

The present invention also provides the use of the substituted pyridine compound of formula I as herbicides, i.e. for controlling harmful plants.

The present invention also provides the use of the substituted pyridine compound of formula I as a selective herbicide in monocotyledonous (herein also referred to as "monocot") crops.

The present invention also provides a method for controlling unwanted vegetation where a herbicidally effective amount of at least one substituted pyridine compound of the formula I is allowed to act on plants, their seeds and/or their habitat.

The present invention also provides a method for selectively controlling unwanted vegetation in a monocotyledonous crop wherein a herbicidally effective amount of at least one substituted pyridine compound of the formula I is allowed to act on plants, their seeds and/or their habitat.

In the above-mentioned methods of the present invention, application can be done before, during and/or after, preferably during and/or after, the emergence of the undesirable plants.

Moreover, the invention relates to processes and intermediates for preparing the substituted pyridine compound of formula I.

As used herein, the terms "controlling" and "combating" are synonyms.

As used herein, the terms "unwanted vegetation", "undesirable vegetation", "undesirable plants" and "harmful plants" are synonyms.

If the compounds of formula I, the herbicidal compounds B and/or the safeners C as described herein are capable of forming geometrical isomers, for example E/Z isomers, it is possible to use both, the pure isomers and mixtures thereof, in the compositions according to the invention.

If the compounds of formula I, the herbicidal compounds B and/or the safeners C as described herein have one or more centres of chirality and, as a consequence, are present as enantiomers or diastereomers, it is possible to use both, the pure enantiomers and diastereomers and their mixtures, in the compositions according to the invention.

If the compounds of formula I, the herbicidal compounds B and/or the safeners C as described herein have ionizable functional groups, they can also be employed in the form of their agriculturally acceptable salts. Suitable are, in general, the salts of those cations and the acid addition salts of those acids whose cations and anions, respectively, have no adverse effect on the activity of the active compounds.

Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, heptylammonium, dodecylammonium, tetradecylammonium, tetramethylammonium, tetraethylammonium, tetrabutylammonium, 2-hydroxyethylammonium (olamine salt), 2-(2-hydroxyeth-1-oxy)eth-1-ylammonium (diglycolamine salt), di(2-hydroxyeth-1-yl)ammonium (diolamine salt), tris(2-hydroxyethyl)ammonium (trolamine salt), tris(2-hydroxypropyl)ammonium, benzyltrimethylammonium, benzyltriethylammonium, N,N,N-trimethylethanolammonium (choline salt), furthermore phosphonium ions, sulfonium ions, preferably tri($C_1$-$C_4$-alkyl)sulfonium, such as trimethylsulfonium, and sulfoxonium ions, preferably tri($C_1$-$C_4$-alkyl)sulfoxonium, and finally the salts of polybasic amines such as N,N-bis-(3-aminopropyl)methylamine and diethylenetriamine.

Anions of useful acid addition salts are primarily chloride, bromide, fluoride, iodide, hydrogensulfate, methylsulfate, sulfate, dihydrogenphosphate, hydrogenphosphate, nitrate, bicarbonate, carbonate, hexafluorosilicate, hexafluorophosphate, benzoate and also the anions of $C_1$-$C_4$-alkanoic acids, preferably formate, acetate, propionate and butyrate.

Compounds of formula I, herbicidal compounds B and/or safeners C as described herein having a carboxyl group can be employed in the form of the acid, in the form of an agriculturally suitable salt as mentioned above or else in the form of an agriculturally acceptable derivative, for example as amides, such as mono- and di-$C_1$-$C_6$-alkylamides or arylamides, as esters, for example as allyl esters, propargyl esters, $C_1$-$C_{10}$-alkyl esters, alkoxyalkyl esters, tefuryl ((tetrahydrofuran-2-yl)methyl) esters and also as thioesters, for example as $C_1$-$C_{10}$-alkylthio esters. Preferred mono- and di-$C_1$-$C_6$-alkylamides are the methyl and the dimethylamides. Preferred arylamides are, for example, the anilides and the 2-chloroanilides. Preferred alkyl esters are, for example, the methyl, ethyl, propyl, isopropyl, butyl, isobutyl, pentyl, mexyl (1-methylhexyl), meptyl (1-methylheptyl), heptyl, octyl or isooctyl (2-ethylhexyl) esters. Preferred $C_1$-$C_4$-alkoxy-$C_1$-$C_4$-alkyl esters are the straight-chain or branched $C_1$-$C_4$-alkoxy ethyl esters, for example the 2-methoxyethyl, 2-ethoxyethyl, 2-butoxyethyl (butotyl), 2-butoxypropyl or 3-butoxypropyl ester. An example of a straight-chain or branched $C_1$-$C_{10}$-alkylthio ester is the ethylthio ester.

Further embodiments of the present invention are evident from the claims, the description and the examples. It is to be understood that the features mentioned above and still to be illustrated below of the subject matter of the invention can be applied not only in the combination given in each particular case but also in other combinations, without leaving the scope of the invention.

The organic moieties mentioned in the definition of the variables R, $R^1$, $R^2$, $R^4$, $R^5$, $R^6$, $R^7$, $R^x$, $R^y$, $R^A$, $R^a$, X, Y and Z are—like the term halogen—collective terms for individual enumerations of the individual group members. The term halogen denotes in each case fluorine, chlorine, bromine or iodine. All hydrocarbon chains, e.g. alkyl, alkenyl or alkynyl chains, can be straight-chain or branched, the prefix $C_n$-$C_m$ denoting in each case the possible number of carbon atoms in the group.

Examples of such meanings are:
$C_1$-$C_2$-alkyl and also the $C_1$-$C_2$-alkyl moieties of $C_1$-$C_2$-alkoxy-$C_1$-$C_2$-alkyl include $CH_3$ and $C_2H_5$;
$C_1$-$C_3$-alkyl and also the $C_1$-$C_3$-alkyl moieties of $C_1$-$C_8$-alkoxycarbonyloxy-$C_1$-$C_3$-alkyl-, $C_1$-$C_8$-alkylcarbonyloxy-$C_1$-$C_3$-alkyl-, $C_3$-$C_6$-cycloalkyl-$C_1$-$C_3$-alkyl-, $C_1$-$C_6$-alkoxy-$C_2$-$C_6$-alkoxy-$C_1$-$C_3$-alkyl-, $C_1$-$C_3$-alkylaminosulfonyl-, $C_1$-$C_3$-dialkylaminosulfonyl-, $C_1$-$C_3$-alkylamino-sulfonyl-$C_1$-$C_3$-alkyl-, $C_1$-$C_3$-dialkylamino-sulfonyl-$C_1$-$C_3$-alkyl-, $C_1$-$C_3$-alkylcarbonylamino-, N—$C_1$-$C_3$-alkyl-N—$C_1$-$C_3$-alkylcarbonylamino-, $C_1$-$C_3$-alkylsulfonylamino-, N—$C_1$-$C_3$-alkyl-N—$C_1$-$C_3$-alkylsulfonylamino-, $C_1$-$C_3$-alkylsulfonylamino-$C_1$-$C_3$-alkyl-, $C_1$-$C_3$-alkylaminocarbonyl-$C_1$-$C_3$-alkyl-, $C_1$-$C_3$-dialkylaminocarbonyl-$C_1$-$C_3$-alkyl-, N—$C_1$-$C_3$-alkylcarbonyl-N—$C_1$-$C_3$-alkylamino-$C_1$-$C_3$-alkyl-, N—$C_1$-$C_3$-alkylsulfonyl-N—$C_1$-$C_3$-alkylamino-$C_1$-$C_3$-alkyl-, $C_1$-$C_3$-alkylcarbonylamino-$C_1$-$C_3$-alkyl- and $C_1$-$C_3$-dialkylamino-: for example $CH_3$, $C_2H_5$, n-propyl, and $CH(CH_3)_2$;

$C_1$-$C_4$-alkyl and also the $C_1$-$C_4$-alkyl moieties of tri($C_1$-$C_4$-alkyl)silyl, aryl-$C_1$-$C_4$-alkyl-, $C_1$-$C_4$-alkyl-S(O)$_n$—, $C_1$-$C_6$-alkoxy-$C_1$-$C_4$-alkyl-, $C_1$-$C_6$-haloalkoxy-$C_1$-$C_4$-alkyl-, N—$C_1$-$C_4$-alkyl, N—$C_1$-$C_4$-alkoxy-$C_1$-$C_4$-alkyl, $C_1$-$C_4$-alkylthio and $C_1$-$C_4$-alkylsulfonyl: $C_1$-$C_3$-alkyl as mentioned above, and also, for example, n-butyl, $CH(CH_3)$—$C_2H_5$, $CH_2$—$CH(CH_3)_2$ and $C(CH_3)_3$;

$C_1$-$C_5$-alkyl: $C_1$-$C_4$-alkyl as mentioned above, and also, for example, n-pentyl, 1-methylbutyl, 2-methylbutyl, 3-methylbutyl, 2,2-dimethylpropyl, 1,1-dimethylpropyl, 1,2-dimethylpropyl, and 1-ethylpropyl;

$C_1$-$C_6$-alkyl and also the $C_1$-$C_6$-alkyl moieties of $C_1$-$C_6$-alkylthio-, $C_1$-$C_6$-alkylsulfonyl- and $C_1$-$C_6$-alkyl-S(O)$_n$—: $C_1$-$C_5$-alkyl as mentioned above, and also, for example, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$-$C_8$-alkyl and also the $C_1$-$C_8$-alkyl moieties of $C_1$-$C_8$-alkylcarbonyl-, $C_1$-$C_8$-alkylthiocarbonyl-, $C_1$-$C_8$-alkylcarbonyloxy-$C_1$-$C_3$-alkyl- and $C_1$-$C_8$-alkyl-S(O)$_n$—: $C_1$-$C_6$-alkyl as mentioned above, and also, for example, n-heptyl, n-octyl or 2-ethylhexyl;

$C_1$-$C_3$-haloalkyl: a $C_1$-$C_3$-alkyl radical as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl or 1-(bromomethyl)-2-bromoethyl;

$C_1$-$C_4$-haloalkyl: $C_1$-$C_3$-haloalkyl as mentioned above, and also, for example, 4-fluorobutyl, 4-chlorobutyl, 4-bromobutyl, nonafluorobutyl, 1,1,2,2,-tetrafluoroethyl and 1-trifluoromethyl-1,2,2,2-tetrafluoroethyl;

$C_1$-$C_5$-haloalkyl: $C_1$-$C_4$-haloalkyl as mentioned above, and also, for example, 5-fluoropentyl, 5-chloropentyl, 5-bromopentyl, 5-iodopentyl and undecafluoropentyl;

$C_1$-$C_6$-haloalkyl and also the $C_1$-$C_6$-haloalkyl moieties of $C_1$-$C_6$-haloalkylthio- and $C_1$-$C_6$-haloalkylsulfonyl-: $C_1$-$C_5$-haloalkyl as mentioned above, and also, for example, 6-fluorohexyl, 6-chlorohexyl, 6-bromohexyl, 6-iodohexyl and dodecafluorohexyl;

$C_3$-$C_6$-cycloalkyl and also the $C_3$-$C_6$-cycloalkyl moieties of $C_3$-$C_6$-cycloalkylcarbonyl-, $C_3$-$C_6$-cycloalkyl-$C_1$-$C_3$-alkyl- and N—$C_3$-$C_6$-cycloalkyl: monocyclic saturated hydrocarbons having 3 to 6 ring members, such as cyclopropyl, cyclobutyl, cyclopentyl and cyclohexyl;

$C_2$-$C_5$-alkenyl: for example ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl and 1-ethyl-2-propenyl;

$C_2$-$C_8$-alkenyl: $C_2$-$C_5$-alkenyl as mentioned above, and also, for example, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1-heptenyl, 2-heptenyl, 3-heptenyl, 1-octenyl, 2-octenyl, 3-octenyl and 4-octenyl;

$C_2$-$C_5$-alkynyl: for example ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, and 1-ethyl-2-propynyl;

$C_2$-$C_8$-alkynyl: $C_2$-$C_5$-alkynyl as mentioned above, and also, for example, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl, 1-heptynyl, 2-heptynyl, 1-octynyl and 2-octynyl;

$C_1$-$C_2$-alkoxy and also the $C_1$-$C_2$-alkoxy moieties of $C_1$-$C_2$-alkoxy-$C_1$-$C_2$-alkyl: for example methoxy and ethoxy;

$C_1$-$C_3$-alkoxy and also the $C_1$-$C_3$-alkoxy moieties of $C_3$-$C_6$-cycloalkyl-$C_1$-$C_3$-alkoxy-: $C_1$-$C_2$-alkoxy as mentioned above, and also, for example, propoxy and 1-methylethoxy;

$C_1$-$C_4$-alkoxy and also the $C_1$-$C_4$-alkoxy moieties of N—$C_1$-$C_4$-alkoxy-$C_1$-$C_4$-alkyl: $C_1$-$C_3$-alkoxy as mentioned above, and also, for example, butoxy, 1-methylpropoxy, 2-methylpropoxy and 1,1-dimethylethoxy;

$C_1$-$C_6$-alkoxy and also the $C_1$-$C_6$-alkoxy moieties of $C_1$-$C_6$-alkoxy-$C_1$-$C_4$-alkyl-, $C_1$-$C_6$-alkoxy-$C_2$-$C_6$-alkoxy- and $C_1$-$C_6$-alkoxy-$C_2$-$C_6$-alkoxy-$C_1$-$C_3$-alkyl-: $C_1$-$C_4$-alkoxy as mentioned above, and also, for example, pentoxy, 1-methylbutoxy, 2-methylbutoxy, 3-methoxybutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$-$C_8$-alkoxy and also the $C_1$-$C_8$-alkoxy moieties of $C_1$-$C_8$-alkoxycarbonyl- and $C_1$-$C_8$-alkoxycarbonyloxy-$C_1$-$C_3$-alkyl-: $C_1$-$C_6$-alkoxy as mentioned above, and also, for example, heptoxy, octoxy, 1,1,3,3-tetramethyl butoxy and 2-ethylhexoxy;

$C_1$-$C_3$-haloalkoxy: for example $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy $C_1$-$C_4$-haloalkoxy: $C_1$-$C_3$-haloalkoxy as mentioned above, and also, for example, 4-fluorobutoxy, 4-chlorobutoxy, 4-bromobutoxy or nonafluorobutoxy;

$C_1$-$C_6$-haloalkoxy and also the $C_1$-$C_6$-haloalkoxy moieties of $C_1$-$C_6$-haloalkoxy-$C_1$-$C_4$-alkyl-: $C_1$-$C_4$-haloalkoxy as mentioned above, and also, for example, 5-fluoropentoxy, 5-chloropentoxy, 5-brompentoxy, 5-iodopentoxy, undecafluoropentoxy, 6-fluorohexoxy, 6-chlorohexoxy, 6-bromohexoxy, 6-iodohexoxy or dodecafluorohexoxy;

$C_1$-$C_8$-haloalkoxy: $C_1$-$C_6$-haloalkoxy as mentioned above, and also, for example, 7-fluoroheptoxy, 7-chloroheptoxy, 7-bromoheptoxy, 7-iodoheptoxy, perfluoroheptoxy, 8-fluorooctoxy, 8-chlorooctoxy, 8-bromooctoxy, 8-iodooctoxy and octadecafluorooctoxy;

$C_1$-$C_4$-alkylthio also the $C_1$-$C_4$-alkylthio moieties of Z—$C_1$-$C_4$-alkylthio, Z—$C_1$-$C_4$-alkylthio-$C_1$-$C_4$-alkylthio and $C_1$-$C_4$-alkylthio-$C_1$-$C_4$-alkyl: for example methylthio, ethylthio, propylthio, 1-methylethylthio, butylthio, 1-methylpropylthio, 2-methylpropylthio and 1,1-dimethylethylthio;

$C_1$-$C_6$-alkylthio: $C_1$-$C_4$-alkylthio as mentioned above, and also, for example, pentylthio and hexylthio;

$C_1$-$C_6$-haloalkylthio: for example $SCH_2F$, $SCHF_2$, $SCF_3$, $SCH_2Cl$, $SCHCl_2$, $SCCl_3$, chlorofluoromethylthio, dichlorofluoromethylthio, chlorodifluoromethylthio, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or $SC_2F_5$. $C_1$-$C_4$-haloalkylthio is additionally, for example, 2-fluoropropylthio, 3-fluoropropylthio, 2,2-difluoropropylthio, 2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, $SCH_2$—$C_2F_5$, $SCF_2$—$C_2F_5$, 1-($CH_2F$)-2-fluoroethylthio, 1-($CH_2Cl$)-2-chloroethylthio, 1-($CH_2Br$)-2-bromoethylthio, 4-fluorobutylthio, 4-chlorobutylthio, 4-bromobutylthio, nonafluorobutylthio, 5-fluoropentylthio, 5-chloropentylthio, 5-brompentylthio, 5-iodopentylthio, undecafluoropentylthio, 6-fluorohexylthio, 6-chlorohexylthio, 6-bromohexylthio, 6-iodohexylthio or dodecafluorohexylthio;

$C_1$-$C_4$-alkylene and also the $C_1$-$C_4$-alkylene moieties in $C_1$-$C_4$-alkyleneoxy, $C_1$-$C_4$-oxyalkylene and $C_1$-$C_4$-alkyleneoxy-$C_1$-$C_4$-alkylene: a straight carbon chain having from 1 to 4 carbon atoms and having only carbon-carbon single bonds, for example methylene ($CH_2$), ethylene ($CH_2CH_2$), n-propylene ($CH_2CH_2CH_2$) and n-butylene ($CH_2CH_2CH_2CH_2$);

$C_2$-$C_5$-alkylene: $C_1$-$C_4$-alkylene as mentioned above, and also n-pentylene ($CH_2CH_2CH_2CH_2CH_2$);

$C_2$-$C_5$-alkenylene chain: a straight carbon chain having from 2 to 5 carbon atoms and at least one carbon-carbon double bond and no carbon-carbon triple bond, for example, CH=CH, CH=CH—$CH_2$, CH=CH—$CH_2CH_2$, CH=CH—CH=$CH_2$ and CH=CH—$CH_2CH_2CH_2$;

a 3- to 7-membered monocyclic or 9- or 10-membered bicyclic saturated, unsaturated or aromatic heterocycle which contains 1, 2, 3 or 4 heteroatoms selected from the group consisting of O, N and S means, for example, pyridazin-3-yl, pyridazin-4-yl, pyrimidin-2-yl, pyrimidin-4-yl, pyrimidin-5-yl, pyrazin-2-yl, piperidin-1-yl, morpholin-4-yl, thiomorpholin-4-yl, pyrollidin-1-yl, 2-furyl, 3-furyl, 2-thienyl, 3-thienyl, pyrazol-1-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-1-yl, imidazol-2-yl, imidazol-4-yl, oxazol-2-yl, oxazol-4-yl, oxazol-5-yl, thiazol-2-yl, thiazol-4-yl, thiazol-5-yl, pyrazol-3-yl, imidazol-5-yl, oxazol-2-yl, thiazol-2-yl, thiazol-4-yl, thiazol-5-yl, pyridin-2-yl, pyridin-3-yl, pyridin-4-yl, pyrimidin-2-yl, pyrimidin-4-yl, pyrimidin-5-yl, pyridazin-4-yl, pyrazin-2-yl, [1H]-tetrazol-5-yl; [2H]-tetrazol-5-yl, 2-tetrahydrofuryl, 3-tetrahydrofuryl, 2-oxetanyl, 3-oxetanyl and azetidin-1-yl;

the term "5- or 6-membered heterocyclyls containing 1, 2 or 3 heteroatoms selected from the group consisting of O, N and S" means, for example: pyridazin-3-yl, pyridazin-4-yl, pyrimidin-2-yl, pyrimidin-4-yl, pyrimidin-5-yl, pyrazin-2-yl, piperidin-1-yl, morpholin-4-yl, thiomorpholin-4-yl, pyrollidin-1-yl, 2-furyl, 3-furyl, 2-thienyl, 3-thienyl, pyrazol-1-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-1-yl, imidazol-2-yl, imidazol-4-yl, oxazol-2-yl, oxazol-4-yl, oxazol-5-yl, thiazol-2-yl, thiazol-4-yl and thiazol-5-yl, pyrazol-3-yl, imidazol-5-yl, oxazol-2-yl, thiazol-2-yl, thiazol-4-yl, thiazol-5-yl, pyridin-2-yl, pyridin-3-yl, pyridin-4-yl, pyrimidin-2-yl, pyrimidin-4-yl, pyrimidin-5-yl, pyridazin-4-yl, pyrazin-2-yl, [1H]-tetrazol-5-yl and [2H]-tetrazol-5-yl, 2-tetrahydrofuryl and 3-tetrahydrofuryl;

the term "aryl" refers to an unsaturated aromatic carbocyclic group of from 6 to 20 carbon atoms having a single ring (e.g., phenyl) or multiple condensed (fused) rings, wherein at least one ring is aromatic (e.g. naphthalenyl or dihydrophenanthrenyl). Examples of aryls include phenyl, naphthalenyl, anthracenyl, indenyl or phenanthrenyl. A preferred aryl group is phenyl.

The preferred embodiments of the invention mentioned herein below have to be understood as being preferred either independently from each other or in combination with one another.

According to a preferred embodiment of the invention preference is also given to those compounds of formula I, wherein the variables, either independently of one another or in combination with one another, have the following meanings:

Preferably, R is is selected from the group consisting of hydroxyl, benzyloxy-, allyloxy-, propargyloxy-, methoxy-, cyclopropylcarbonyloxy-, propyl-2-ylcarbonyloxy-, 2-methyl-prop-2-ylcarbonyloxy-, methylsulfonyloxy-, ethoxycarbonyloxy-, isopropoxycarbonyloxy-, ethylthiocarbonyloxy-, 2-methyl-prop-2-ylcarbonyloxymethoxy-, ethoxycarbonyloxyethoxy-, isopropoxycarbonlyoxymethoxy-, methoxycarbonyloxyethoxy-, and ethoxycarbonyloxymethoxy-.

More preferably, R is selected from the group consisting of hydroxyl, 2-methyl-prop-2-ylcarbonyloxy-, prop-2-ylcarbonyloxy, cyclopropylcarbonyloxy- and methoxycarbonyloxyethoxy-.

In another embodiment, R is hydroxy or O—$R^A$, where $R^A$ is $C_1$-$C_8$-alkylcarbonyl.

In one embodiment, R is hydroxy.

In one embodiment, R is O—$R^A$, where $R^A$ is $C_1$-$C_8$-alkylcarbonyl, in particular 2-methyl-prop-2-ylcarbonyloxy.

In particular, R is hydroxy or 2-methyl-prop-2-ylcarbonyloxy.

Preferably, $R^1$ is selected from the group consisting of halogen, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy, $C_1$-$C_6$-haloalkoxy-$C_1$-$C_4$-alkyl-, $C_1$-$C_6$-alkoxy-$C_2$-$C_6$-alkoxy-$C_1$-$C_3$-alkyl-, $C_1$-$C_6$-alkylsulfonyl-, $C_1$-$C_3$-dialkylaminosulfonyl-, and unsubstituted 5- or 6-membered heterocyclyl containing 1, 2 or 3 heteroatoms selected from the group consisting of O, N and S.

More preferably, $R^1$ is selected from the group consisting of halogen, $C_1$-$C_6$-alkyl, $C_1$-$C_6$-haloalkyl, and $C_1$-$C_6$-alkylsulfonyl-.

Examples of preferred $R^1$ groups include fluoro, chloro, bromo, methyl, ethyl, cyclopropyl, trifluoromethyl, trifluoromethoxy, methoxy, ethoxy, methoxyethoxymethyl, methylsulfonyl, ethylsulfonyl, isoxazolin-3-yl, isoxazolin-5-yl, dimethylaminosulfonyl, and trifluoromethoxymethyl.

Even more preferably, $R^1$ is selected from the group consisting of chloro, methyl, trifluoromethyl and methylsulfonyl.

In a preferred embodiment of the compounds of the formula I, $R^2$ is selected from the group consisting of hydrogen, halogen, cyano, $C_1$-$C_4$-alkyl, $C_3$-$C_6$-cycloalkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-alkylsulfonyl.

More preferably, $R^2$ is selected from the group consisting of hydrogen, fluoro, chloro, bromo, methyl, cyclopropyl, trifluoromethyl, difluoromethyl, methoxy, trifluoromethoxy, difluoromethoxy, thiomethyl, thioethyl, methylsulfonyl and ethylsulfonyl.

Even more preferably, $R^2$ is selected from the group hydrogen, fluoro, chloro and methyl.

Particularly preferably, $R^2$ is hydrogen or chlorine.

In yet another preferred embodiment of the compounds of the formula I, $R^4$ is hydrogen, fluorine or chlorine and in particular hydrogen.

Particularly preferred are compounds of formula I wherein $R^1$ and $R^2$ are both halogen (in particular chlorine) and $R^4$ is hydrogen.

In further preferred aspects of the compound of formula I, the groups $R^1$, $R^2$ and $R^4$ together form a substitution pattern selected from the group consisting of:

$R^1$=Cl, $R^2$=H, $R^4$=H;
$R^1$=Cl, $R^2$=Cl, $R^4$=H;
$R^1$=Cl, $R^2$=H, $R^4$=Cl;
$R^1$=$CH_3$, $R^2$=H, $R^4$=H;
$R^1$=$CH_3$, $R^2$=Cl, $R^4$=H;
$R^1$=$CF_3$, $R^2$=H, $R^4$=H;
$R^1$=$CF_3$, $R^2$=Cl, $R^4$=H; and
$R^1$=$CH_3SO_2$, $R^2$=H, $R^4$=H.

In a preferred embodiment, $R^x$ and $R^y$, independently of one another, are H, $C_1$-$C_5$-alkyl (in particular $CH_3$, $C_2H_5$, n-$C_3H_7$, $CH(CH_3)_2$, n-$C_3H_9$, or $C(CH_3)_3$), $C_3$-$C_5$-alkenyl (in particular $CH_2CH=CH_2$, $CH_2C(CH_3)=CH_2$, $CH_2CH_2H=CH_2$, $CH_2CH_2C(CH_3)=CH_2$, or $CH_2CH_2CH_2CH=CH_2$), $C_3$-$C_5$-alkynyl (in particular $CH_2C\equiv CH$), $C_1$-$C_5$-haloalkyl (in particular $CH_2CF_3$ or $CH_2CHF_2$), or $R^x$ and $R^y$ together form a bridge —$CH_2$—$CH_2$—.

More preferably, $R^x$ and $R^y$ are, independently of one another, H, $C_1$-$C_5$-alkyl, or $C_1$-$C_4$-haloalkyl, or $R^x$ and $R^y$ together form a bridge —$CH_2$—$CH_2$—.

Even more preferably, $R^x$ and $R^y$, independently of one another, are H or $C_1$-$C_5$-alkyl, or $R^x$ and $R^y$ together form a bridge —$CH_2$—$CH_2$—.

Particularly preferably, $R^x$ and $R^y$, independently of one another, are H or $C_1$-$C_5$-alkyl, preferably H, $CH_3$, or $C_2H_5$ and more preferably H or $CH_3$.

In another embodiment of the compounds of the formula I, $R^x$ and $R^y$ together form a bridge —$CH_2$—$CH_2$—.

Especially preferably, $R^x$ and $R^y$ are both hydrogen.

In an even more preferred embodiment, $R^x$ and $R^y$ are $C_1$-$C_5$-alkyl, in particular $CH_3$.

In a preferred embodiment of the compounds of the formula I, X is selected from the group consisting of O, N-methyl, N-ethyl, N-isopropyl, N-methoxymethyl and N-cyclopropyl.

More preferably, X is selected from the group consisting of N-methyl, N-ethyl, N-isopropyl, and N-cyclopropyl.

In another preferred embodiment, X is N—$C_1$-$C_4$-alkyl, more preferably N-methyl, N-ethyl or N-isopropyl and in particular N-methyl.

In another preferred embodiment of the compounds of the formula I, Y is selected from the group consisting of methyl, ethyl, isopropyl, cyclopropyl, difluoromethyl, trifluoromethyl, cyclopropylmethyl and dimethylamino.

More preferably, Y is selected from the group consisting of methyl, ethyl, cyclopropyl and difluoromethyl.

In yet another preferred embodiment, Y is $C_1$-$C_4$-alkyl or $C_3$-$C_6$-cycloalkyl, more preferably methyl, ethyl or cyclopropyl and in particular methyl or cyclopropyl.

Particularly preferably, Y is $C_1$-$C_4$-alkyl, in particular methyl or ethyl and most preferably methyl.

In another preferred embodiment of the compounds of the formula I, $R^5$ is hydrogen.

In yet another preferred embodiment of the compounds of the formula I, $R^6$ is hydrogen or halogen, in particular hydrogen or fluorine.

In still another preferred embodiment of the compounds of the formula I, $R^7$ is hydrogen.

More preferably, $R^5$ is hydrogen, $R^6$ is hydrogen or fluorine and $R^7$ is hydrogen.

In yet another preferred embodiment of the compounds of the formula I, $R^5$ and $R^7$ are hydrogen. These compounds correspond to formula I.a I.a in which the variables have the meanings defined at the outset and preferably those mentioned above.

In still another preferred embodiment of the compounds of the formula I, $R^5$, $R^6$ and $R^7$ are hydrogen. These compounds correspond to formula I.b I.b in which the variables have the meanings defined at the outset and preferably those mentioned above.

In yet another preferred embodiment of the compounds of the formula I, $R^5$ is hydrogen, $R^6$ is fluorine and $R^7$ is hydrogen. These compounds correspond to formula I.c I.c in which the variables have the meanings defined at the outset and preferably those mentioned above.

Among the compounds of the formula I, very particular preference is given to those in which the variables R, $R^1$, $R^2$, $R^4$, $R^5$, $R^6$, $R^7$, $R^x$, $R^y$, X and Y, either independently of one another or in combination with one another, have the following meanings:

R is hydroxy or O—$R^A$ wherein $R^A$ is $C_1$-$C_6$-alkylcarbonyl, in particular hydroxy or 2-methyl-prop-2-ylcarbonyloxy;

$R^1$ is halogen, $C_1$-$C_4$-alkyl, $C_1$-$C_4$-haloalkyl or $C_1$-$C_4$-alkylsulfonyl, in particular chloro, methyl, trifluoromethyl or methylsulfonyl;

$R^2$ is hydrogen, halogen or $C_1$-$C_4$-alkyl (more preferably hydrogen or halogen), in particular hydrogen, fluoro, chloro or methyl (more preferably hydrogen or chloro);

$R^4$ is hydrogen or halogen, preferably hydrogen, chloro or fluoro and in particular hydrogen or chloro;

$R^5$ is hydrogen;

$R^6$ is hydrogen or halogen, in particular hydrogen or fluoro;

$R^7$ is hydrogen;

$R^x$, $R^y$ are, independently of one another, H or $C_1$-$C_5$-alkyl, in particular H or $CH_3$;

X is O, N—H, N—$C_1$-$C_4$-alkyl or N—$C_3$-$C_6$-cycloalkyl, in particular O, N—H, N-methyl, N-ethyl, N-isopropyl or N-cyclopropyl; and Y is $C_1$-$C_4$-alkyl, $C_3$-$C_6$-cycloalkyl, $C_3$-$C_6$-cycloalkyl-$C_1$-$C_3$-alkyl- or $C_1$-$C_3$-dialkylamino-, in particular methyl, ethyl, isopropyl, cyclopropyl, cyclopropylmethyl or dimethylamino.

A further embodiment relates to the N-oxides of the compounds of the formula I.

A further embodiment relates to salts of the compounds of the formula I, in particular those which are obtainable by quaternization of a pyridine nitrogen atom, which may preferably take place by alkylation or arylation of the compounds of the formula I. Preferred salts of the compounds are thus the N-alkyl salts, in particular the N-methyl salts, and the N-phenyl salts.

In particular with a view to their use, preference is given to the compounds of the formula I compiled in the Tables below, which compounds correspond to the formula I.a as shown above. The groups mentioned for a substituent in the tables are furthermore per se, independently of the combination in which they are mentioned, a particularly preferred aspect of the substituent in question.

Table 1

Compounds of the formula I, in which $R^x$ is H, $R^y$ is H, R is OH, $R^4$ is H, $R^6$ is H and the combination of $R^1$, $R^2$, X and Y for a compound corresponds in each case to one row of table A Table 2

Compounds of the formula I, in which $R^x$ is $CH_3$, $R^Y$ is H, R is OH, $R^4$ is H, $R^6$ is H and the combination of $R^1$, $R^2$, X and Y for a compound corresponds in each case to one row of table A Table 3

Compounds of the formula I, in which $R^x$ is H, $R^y$ is $CH_3$, R is OH, $R^4$ is H, $R^6$ is H and the combination of $R^1$, $R^2$, X and Y for a compound corresponds in each case to one row of table A Table 4

Compounds of the formula I, in which $R^x$ is $CH_3$, $R^Y$ is $CH_3$, R is OH, $R^4$ is H, $R^6$ is H and the combination of $R^1$, $R^2$, X and Y for a compound corresponds in each case to one row of table A Table 5

Compounds of the formula I, in which $R^x$ is H, $R^y$ is H, R is $OC(O)C(CH_3)_3$, $R^4$ is H, $R^6$ is H and the combination of $R^1$, $R^2$, X and Y for a compound corresponds in each case to one row of table A Table 6

Compounds of the formula I, in which $R^x$ is $CH_3$, $R^Y$ is H, R is $OC(O)C(CH_3)_3$, $R^4$ is H, $R^6$ is H and the combination of $R^1$, $R^2$, X and Y for a compound corresponds in each case to one row of table A Table 7
Compounds of the formula I, in which $R^x$ is H, $R^y$ is $CH_3$, R is $OC(O)C(CH_3)_3$, $R^4$ is H, $R^6$ is H and the combination of $R^1$, $R^2$, X and Y for a compound corresponds in each case to one row of table A Table 8
Compounds of the formula I, in which $R^x$ is $CH_3$, $R^Y$ is $CH_3$, R is $OC(O)C(CH_3)_3$, $R^4$ is H, $R^6$ is H and the combination of $R^1$, $R^2$, X and Y for a compound corresponds in each case to one row of table A Table 9
Compounds of the formula I, in which $R^x$ is H, $R^y$ is H, R is OH, $R^4$ is Cl, $R^6$ is H and the combination of $R^1$, $R^2$, X and Y for a compound corresponds in each case to one row of table A Table 10
Compounds of the formula I, in which $R^x$ is $CH_3$, $R^Y$ is H, R is OH, $R^4$ is Cl, $R^6$ is H and the combination of $R^1$, $R^2$, X and Y for a compound corresponds in each case to one row of table A Table 11
Compounds of the formula I, in which $R^x$ is H, $R^y$ is $CH_3$, R is OH, $R^4$ is Cl, $R^6$ is H and the combination of $R^1$, $R^2$, X and Y for a compound corresponds in each case to one row of table A Table 12
Compounds of the formula I, in which $R^x$ is $CH_3$, $R^Y$ is $CH_3$, R is OH, $R^4$ is Cl, $R^6$ is H and the combination of $R^1$, $R^2$, X and Y for a compound corresponds in each case to one row of table A Table 13
Compounds of the formula I, in which $R^x$ is H, $R^y$ is H, R is $OC(O)C(CH_3)_3$, $R^4$ is Cl, $R^6$ is H and the combination of $R^1$, $R^2$, X and Y for a compound corresponds in each case to one row of table A Table 14
Compounds of the formula I, in which $R^x$ is $CH_3$, $R^y$ is H, R is $OC(O)C(CH_3)_3$, $R^4$ is Cl, $R^6$ is H and the combination of $R^1$, $R^2$, X and Y for a compound corresponds in each case to one row of table A Table 15
Compounds of the formula I, in which $R^x$ is H, $R^y$ is $CH_3$, R is $OC(O)C(CH_3)_3$, $R^4$ is Cl, $R^6$ is H and the combination of $R^1$, $R^2$, X and Y for a compound corresponds in each case to one row of table A Table 16
Compounds of the formula I, in which $R^x$ is $CH_3$, $R^y$ is $CH_3$, R is $OC(O)C(CH_3)_3$, $R^4$ is Cl, $R^6$ is H and the combination of $R^1$, $R^2$, X and Y for a compound corresponds in each case to one row of table A Table 17
Compounds of the formula I, in which $R^x$ is H, $R^y$ is H, R is OH, $R^4$ is H, $R^6$ is F and the combination of $R^1$, $R^2$, X and Y for a compound corresponds in each case to one row of table A Table 18
Compounds of the formula I, in which $R^x$ is $CH_3$, $R^Y$ is H, R is OH, $R^4$ is H, $R^6$ is F and the combination of $R^1$, $R^2$, X and Y for a compound corresponds in each case to one row of table A Table 19
Compounds of the formula I, in which $R^x$ is H, $R^y$ is $CH_3$, R is OH, $R^4$ is H, $R^6$ is F and the combination of $R^1$, $R^2$, X and Y for a compound corresponds in each case to one row of table A Table 20
Compounds of the formula I, in which $R^x$ is $CH_3$, $R^y$ is $CH_3$, R is OH, $R^4$ is H, $R^6$ is F and the combination of $R^1$, $R^2$, X and Y for a compound corresponds in each case to one row of table A Table 21
Compounds of the formula I, in which $R^x$ is H, $R^y$ is H, R is $OC(O)C(CH_3)_3$, $R^4$ is H, $R^6$ is F and the combination of $R^1$, $R^2$, X and Y for a compound corresponds in each case to one row of table A Table 22
Compounds of the formula I, in which $R^x$ is $CH_3$, $R^Y$ is H, R is $OC(O)C(CH_3)_3$, $R^4$ is H, $R^6$ is F and the combination of $R^1$, $R^2$, X and Y for a compound corresponds in each case to one row of table A Table 23
Compounds of the formula I, in which $R^x$ is H, $R^y$ is $CH_3$, R is $OC(O)C(CH_3)_3$, $R^4$ is H, $R^6$ is F and the combination of $R^1$, $R^2$, X and Y for a compound corresponds in each case to one row of table A Table 24
Compounds of the formula I, in which $R^x$ is $CH_3$, $R^y$ is $CH_3$, R is $OC(O)C(CH_3)_3$, $R^4$ is H, $R^6$ is F and the combination of $R^1$, $R^2$, X and Y for a compound corresponds in each case to one row of table A Table 25
Compounds of the formula I, in which $R^x$ is H, $R^y$ is H, R is OH, $R^4$ is Cl, $R^6$ is F and the combination of $R^1$, $R^2$, X and Y for a compound corresponds in each case to one row of table A Table 26
Compounds of the formula I, in which $R^x$ is $CH_3$, $R^y$ is H, R is OH, $R^4$ is Cl, $R^6$ is F and the combination of $R^1$, $R^2$, X and Y for a compound corresponds in each case to one row of table A Table 27
Compounds of the formula I, in which $R^x$ is H, $R^y$ is $CH_3$, R is OH, $R^4$ is Cl, $R^6$ is F and the combination of $R^1$, $R^2$, X and Y for a compound corresponds in each case to one row of table A Table 28
Compounds of the formula I, in which $R^x$ is $CH_3$, $R^Y$ is $CH_3$, R is OH, $R^4$ is Cl, $R^6$ is F and the combination of $R^1$, $R^2$, X and Y for a compound corresponds in each case to one row of table A Table 29
Compounds of the formula I, in which $R^x$ is H, $R^y$ is H, R is $OC(O)C(CH_3)_3$, $R^4$ is Cl, $R^6$ is F and the combination of $R^1$, $R^2$, X and Y for a compound corresponds in each case to one row of table A Table 30
Compounds of the formula I, in which $R^x$ is $CH_3$, $R^Y$ is H, R is $OC(O)C(CH_3)_3$, $R^4$ is Cl, $R^6$ is F and the combination of $R^1$, $R^2$, X and Y for a compound corresponds in each case to one row of table A Table 31
Compounds of the formula I, in which $R^x$ is H, $R^y$ is $CH_3$, R is $OC(O)C(CH_3)_3$, $R^4$ is Cl, $R^6$ is F and the combination of $R^1$, $R^2$, X and Y for a compound corresponds in each case to one row of table A Table 32
Compounds of the formula I, in which $R^x$ is $CH_3$, $R^Y$ is $CH_3$, R is $OC(O)C(CH_3)_3$, $R^4$ is Cl, $R^6$ is F and the combination of $R^1$, $R^2$, X and Y for a compound corresponds in each case to one row of table A

TABLE A

Compounds of the formula I which correspond to the formula I.a as shown above

| No. | R¹ | R² | X | Y |
|---|---|---|---|---|
| I.a.1 | F | F | O | N(CH₃)₂ |
| I.a.2 | Cl | F | O | N(CH₃)₂ |
| I.a.3 | CH₃ | F | O | N(CH₃)₂ |
| I.a.4 | CF₃ | F | O | N(CH₃)₂ |
| I.a.5 | SO₂CH₃ | F | O | N(CH₃)₂ |
| I.a.6 | F | Cl | O | N(CH₃)₂ |
| I.a.7 | Cl | Cl | O | N(CH₃)₂ |
| I.a.8 | CH₃ | Cl | O | N(CH₃)₂ |
| I.a.9 | CF₃ | Cl | O | N(CH₃)₂ |
| I.a.10 | SO₂CH₃ | Cl | O | N(CH₃)₂ |
| I.a.11 | F | CF₃ | O | N(CH₃)₂ |
| I.a.12 | Cl | CF₃ | O | N(CH₃)₂ |
| I.a.13 | CH₃ | CF₃ | O | N(CH₃)₂ |
| I.a.14 | CF₃ | CF₃ | O | N(CH₃)₂ |
| I.a.15 | SO₂CH₃ | CF₃ | O | N(CH₃)₂ |
| I.a.16 | F | c-Pr | O | N(CH₃)₂ |
| I.a.17 | Cl | c-Pr | O | N(CH₃)₂ |
| I.a.18 | CH₃ | c-Pr | O | N(CH₃)₂ |
| I.a.19 | CF₃ | c-Pr | O | N(CH₃)₂ |
| I.a.20 | SO₂CH₃ | c-Pr | O | N(CH₃)₂ |
| I.a.21 | F | SO₂CH₃ | O | N(CH₃)₂ |
| I.a.22 | Cl | SO₂CH₃ | O | N(CH₃)₂ |
| I.a.23 | CH₃ | SO₂CH₃ | O | N(CH₃)₂ |
| I.a.24 | CF₃ | SO₂CH₃ | O | N(CH₃)₂ |
| I.a.25 | SO₂CH₃ | SO₂CH₃ | O | N(CH₃)₂ |
| I.a.26 | F | OCHF₂ | O | N(CH₃)₂ |
| I.a.27 | Cl | OCHF₂ | O | N(CH₃)₂ |
| I.a.28 | CH₃ | OCHF₂ | O | N(CH₃)₂ |
| I.a.29 | CF₃ | OCHF₂ | O | N(CH₃)₂ |
| I.a.30 | SO₂CH₃ | OCHF₂ | O | N(CH₃)₂ |
| I.a.31 | F | CHF₂ | O | N(CH₃)₂ |
| I.a.32 | Cl | CHF₂ | O | N(CH₃)₂ |
| I.a.33 | CH₃ | CHF₂ | O | N(CH₃)₂ |
| I.a.34 | CF₃ | CHF₂ | O | N(CH₃)₂ |
| I.a.35 | SO₂CH₃ | CHF₂ | O | N(CH₃)₂ |
| I.a.36 | F | F | NH | CH₃ |
| I.a.37 | Cl | F | NH | CH₃ |
| I.a.38 | CH₃ | F | NH | CH₃ |
| I.a.39 | CF₃ | F | NH | CH₃ |
| I.a.40 | SO₂CH₃ | F | NH | CH₃ |
| I.a.41 | F | Cl | NH | CH₃ |
| I.a.42 | Cl | Cl | NH | CH₃ |
| I.a.43 | CH₃ | Cl | NH | CH₃ |
| I.a.44 | CF₃ | Cl | NH | CH₃ |
| I.a.45 | SO₂CH₃ | Cl | NH | CH₃ |
| I.a.46 | F | CF₃ | NH | CH₃ |
| I.a.47 | Cl | CF₃ | NH | CH₃ |
| I.a.48 | CH₃ | CF₃ | NH | CH₃ |
| I.a.49 | CF₃ | CF₃ | NH | CH₃ |
| I.a.50 | SO₂CH₃ | CF₃ | NH | CH₃ |
| I.a.51 | F | c-Pr | NH | CH₃ |
| I.a.52 | Cl | c-Pr | NH | CH₃ |
| I.a.53 | CH₃ | c-Pr | NH | CH₃ |
| I.a.54 | CF₃ | c-Pr | NH | CH₃ |
| I.a.55 | SO₂CH₃ | c-Pr | NH | CH₃ |
| I.a.56 | F | SO₂CH₃ | NH | CH₃ |
| I.a.57 | Cl | SO₂CH₃ | NH | CH₃ |
| I.a.58 | CH₃ | SO₂CH₃ | NH | CH₃ |
| I.a.59 | CF₃ | SO₂CH₃ | NH | CH₃ |
| I.a.60 | SO₂CH₃ | SO₂CH₃ | NH | CH₃ |
| I.a.61 | F | OCHF₂ | NH | CH₃ |
| I.a.62 | Cl | OCHF₂ | NH | CH₃ |
| I.a.63 | CH₃ | OCHF₂ | NH | CH₃ |
| I.a.64 | CF₃ | OCHF₂ | NH | CH₃ |
| I.a.65 | SO₂CH₃ | OCHF₂ | NH | CH₃ |
| I.a.66 | F | CHF₂ | NH | CH₃ |
| I.a.67 | Cl | CHF₂ | NH | CH₃ |
| I.a.68 | CH₃ | CHF₂ | NH | CH₃ |
| I.a.69 | CF₃ | CHF₂ | NH | CH₃ |
| I.a.70 | SO₂CH₃ | CHF₂ | NH | CH₃ |
| I.a.71 | F | F | NCH₃ | CH₃ |
| I.a.72 | Cl | F | NCH₃ | CH₃ |
| I.a.73 | CH₃ | F | NCH₃ | CH₃ |
| I.a.74 | CF₃ | F | NCH₃ | CH₃ |
| I.a.75 | SO₂CH₃ | F | NCH₃ | CH₃ |
| I.a.76 | F | Cl | NCH₃ | CH₃ |
| I.a.77 | Cl | Cl | NCH₃ | CH₃ |
| I.a.78 | CH₃ | Cl | NCH₃ | CH₃ |
| I.a.79 | CF₃ | Cl | NCH₃ | CH₃ |
| I.a.80 | SO₂CH₃ | Cl | NCH₃ | CH₃ |
| I.a.81 | F | CF₃ | NCH₃ | CH₃ |
| I.a.82 | Cl | CF₃ | NCH₃ | CH₃ |
| I.a.83 | CH₃ | CF₃ | NCH₃ | CH₃ |
| I.a.84 | CF₃ | CF₃ | NCH₃ | CH₃ |
| I.a.85 | SO₂CH₃ | CF₃ | NCH₃ | CH₃ |
| I.a.86 | F | c-Pr | NCH₃ | CH₃ |
| I.a.87 | Cl | c-Pr | NCH₃ | CH₃ |
| I.a.88 | CH₃ | c-Pr | NCH₃ | CH₃ |
| I.a.89 | CF₃ | c-Pr | NCH₃ | CH₃ |
| I.a.90 | SO₂CH₃ | c-Pr | NCH₃ | CH₃ |
| I.a.91 | F | SO₂CH₃ | NCH₃ | CH₃ |
| I.a.92 | Cl | SO₂CH₃ | NCH₃ | CH₃ |
| I.a.93 | CH₃ | SO₂CH₃ | NCH₃ | CH₃ |
| I.a.94 | CF₃ | SO₂CH₃ | NCH₃ | CH₃ |
| I.a.95 | SO₂CH₃ | SO₂CH₃ | NCH₃ | CH₃ |
| I.a.96 | F | OCHF₂ | NCH₃ | CH₃ |
| I.a.97 | Cl | OCHF₂ | NCH₃ | CH₃ |
| I.a.98 | CH₃ | OCHF₂ | NCH₃ | CH₃ |
| I.a.99 | CF₃ | OCHF₂ | NCH₃ | CH₃ |
| I.a.100 | SO₂CH₃ | OCHF₂ | NCH₃ | CH₃ |
| I.a.101 | F | CHF₂ | NCH₃ | CH₃ |
| I.a.102 | Cl | CHF₂ | NCH₃ | CH₃ |
| I.a.103 | CH₃ | CHF₂ | NCH₃ | CH₃ |
| I.a.104 | CF₃ | CHF₂ | NCH₃ | CH₃ |
| I.a.105 | SO₂CH₃ | CHF₂ | NCH₃ | CH₃ |
| I.a.106 | F | F | NCH₂CH₃ | CH₃ |
| I.a.107 | Cl | F | NCH₂CH₃ | CH₃ |
| I.a.108 | CH₃ | F | NCH₂CH₃ | CH₃ |
| I.a.109 | CF₃ | F | NCH₂CH₃ | CH₃ |
| I.a.110 | SO₂CH₃ | F | NCH₂CH₃ | CH₃ |
| I.a.111 | F | Cl | NCH₂CH₃ | CH₃ |
| I.a.112 | Cl | Cl | NCH₂CH₃ | CH₃ |
| I.a.113 | CH₃ | Cl | NCH₂CH₃ | CH₃ |
| I.a.114 | CF₃ | Cl | NCH₂CH₃ | CH₃ |
| I.a.115 | SO₂CH₃ | Cl | NCH₂CH₃ | CH₃ |
| I.a.116 | F | CF₃ | NCH₂CH₃ | CH₃ |
| I.a.117 | Cl | CF₃ | NCH₂CH₃ | CH₃ |
| I.a.118 | CH₃ | CF₃ | NCH₂CH₃ | CH₃ |
| I.a.119 | CF₃ | CF₃ | NCH₂CH₃ | CH₃ |
| I.a.120 | SO₂CH₃ | CF₃ | NCH₂CH₃ | CH₃ |
| I.a.121 | F | c-Pr | NCH₂CH₃ | CH₃ |
| I.a.122 | Cl | c-Pr | NCH₂CH₃ | CH₃ |
| I.a.123 | CH₃ | c-Pr | NCH₂CH₃ | CH₃ |
| I.a.124 | CF₃ | c-Pr | NCH₂CH₃ | CH₃ |
| I.a.125 | SO₂CH₃ | c-Pr | NCH₂CH₃ | CH₃ |
| I.a.126 | F | SO₂CH₃ | NCH₂CH₃ | CH₃ |
| I.a.127 | Cl | SO₂CH₃ | NCH₂CH₃ | CH₃ |
| I.a.128 | CH₃ | SO₂CH₃ | NCH₂CH₃ | CH₃ |
| I.a.129 | CF₃ | SO₂CH₃ | NCH₂CH₃ | CH₃ |
| I.a.130 | SO₂CH₃ | SO₂CH₃ | NCH₂CH₃ | CH₃ |
| I.a.131 | F | OCHF₂ | NCH₂CH₃ | CH₃ |
| I.a.132 | Cl | OCHF₂ | NCH₂CH₃ | CH₃ |
| I.a.133 | CH₃ | OCHF₂ | NCH₂CH₃ | CH₃ |
| I.a.134 | CF₃ | OCHF₂ | NCH₂CH₃ | CH₃ |
| I.a.135 | SO₂CH₃ | OCHF₂ | NCH₂CH₃ | CH₃ |
| I.a.136 | F | CHF₂ | NCH₂CH₃ | CH₃ |
| I.a.137 | Cl | CHF₂ | NCH₂CH₃ | CH₃ |
| I.a.138 | CH₃ | CHF₂ | NCH₂CH₃ | CH₃ |
| I.a.139 | CF₃ | CHF₂ | NCH₂CH₃ | CH₃ |
| I.a.140 | SO₂CH₃ | CHF₂ | NCH₂CH₃ | CH₃ |
| I.a.141 | F | F | N—iPr | CH₃ |
| I.a.142 | Cl | F | N—iPr | CH₃ |
| I.a.143 | CH₃ | F | N—iPr | CH₃ |
| I.a.144 | CF₃ | F | N—iPr | CH₃ |
| I.a.145 | SO₂CH₃ | F | N—iPr | CH₃ |
| I.a.146 | F | Cl | N—iPr | CH₃ |
| I.a.147 | Cl | Cl | N—iPr | CH₃ |
| I.a.148 | CH₃ | Cl | N—iPr | CH₃ |
| I.a.149 | CF₃ | Cl | N—iPr | CH₃ |
| I.a.150 | SO₂CH₃ | Cl | N—iPr | CH₃ |

TABLE A-continued

Compounds of the formula I which correspond to the formula I.a as shown above

| No. | $R^1$ | $R^2$ | X | Y |
|---|---|---|---|---|
| I.a.151 | F | $CF_3$ | N—iPr | $CH_3$ |
| I.a.152 | Cl | $CF_3$ | N—iPr | $CH_3$ |
| I.a.153 | $CH_3$ | $CF_3$ | N—iPr | $CH_3$ |
| I.a.154 | $CF_3$ | $CF_3$ | N—iPr | $CH_3$ |
| I.a.155 | $SO_2CH_3$ | $CF_3$ | N—iPr | $CH_3$ |
| I.a.156 | F | c-Pr | N—iPr | $CH_3$ |
| I.a.157 | Cl | c-Pr | N—iPr | $CH_3$ |
| I.a.158 | $CH_3$ | c-Pr | N—iPr | $CH_3$ |
| I.a.159 | $CF_3$ | c-Pr | N—iPr | $CH_3$ |
| I.a.160 | $SO_2CH_3$ | c-Pr | N—iPr | $CH_3$ |
| I.a.161 | F | $SO_2CH_3$ | N—iPr | $CH_3$ |
| I.a.162 | Cl | $SO_2CH_3$ | N—iPr | $CH_3$ |
| I.a.163 | $CH_3$ | $SO_2CH_3$ | N—iPr | $CH_3$ |
| I.a.164 | $CF_3$ | $SO_2CH_3$ | N—iPr | $CH_3$ |
| I.a.165 | $SO_2CH_3$ | $SO_2CH_3$ | N—iPr | $CH_3$ |
| I.a.166 | F | $OCHF_2$ | N—iPr | $CH_3$ |
| I.a.167 | Cl | $OCHF_2$ | N—iPr | $CH_3$ |
| I.a.168 | $CH_3$ | $OCHF_2$ | N—iPr | $CH_3$ |
| I.a.169 | $CF_3$ | $OCHF_2$ | N—iPr | $CH_3$ |
| I.a.170 | $SO_2CH_3$ | $OCHF_2$ | N—iPr | $CH_3$ |
| I.a.171 | F | $CHF_2$ | N—iPr | $CH_3$ |
| I.a.172 | Cl | $CHF_2$ | N—iPr | $CH_3$ |
| I.a.173 | $CH_3$ | $CHF_2$ | N—iPr | $CH_3$ |
| I.a.174 | $CF_3$ | $CHF_2$ | N—iPr | $CH_3$ |
| I.a.175 | $SO_2CH_3$ | $CHF_2$ | N—iPr | $CH_3$ |
| I.a.176 | F | F | N—cPr | $CH_3$ |
| I.a.177 | Cl | F | N—cPr | $CH_3$ |
| I.a.178 | $CH_3$ | F | N—cPr | $CH_3$ |
| I.a.179 | $CF_3$ | F | N—cPr | $CH_3$ |
| I.a.180 | $SO_2CH_3$ | F | N—cPr | $CH_3$ |
| I.a.181 | F | Cl | N—cPr | $CH_3$ |
| I.a.182 | Cl | Cl | N—cPr | $CH_3$ |
| I.a.183 | $CH_3$ | Cl | N—cPr | $CH_3$ |
| I.a.184 | $CF_3$ | Cl | N—cPr | $CH_3$ |
| I.a.185 | $SO_2CH_3$ | Cl | N—cPr | $CH_3$ |
| I.a.186 | F | $CF_3$ | N—cPr | $CH_3$ |
| I.a.187 | Cl | $CF_3$ | N—cPr | $CH_3$ |
| I.a.188 | $CH_3$ | $CF_3$ | N—cPr | $CH_3$ |
| I.a.189 | $CF_3$ | $CF_3$ | N—cPr | $CH_3$ |
| I.a.190 | $SO_2CH_3$ | $CF_3$ | N—cPr | $CH_3$ |
| I.a.191 | F | c-Pr | N—cPr | $CH_3$ |
| I.a.192 | Cl | c-Pr | N—cPr | $CH_3$ |
| I.a.193 | $CH_3$ | c-Pr | N—cPr | $CH_3$ |
| I.a.194 | $CF_3$ | c-Pr | N—cPr | $CH_3$ |
| I.a.195 | $SO_2CH_3$ | c-Pr | N—cPr | $CH_3$ |
| I.a.196 | F | $SO_2CH_3$ | N—cPr | $CH_3$ |
| I.a.197 | Cl | $SO_2CH_3$ | N—cPr | $CH_3$ |
| I.a.198 | $CH_3$ | $SO_2CH_3$ | N—cPr | $CH_3$ |
| I.a.199 | $CF_3$ | $SO_2CH_3$ | N—cPr | $CH_3$ |
| I.a.200 | $SO_2CH_3$ | $SO_2CH_3$ | N—cPr | $CH_3$ |
| I.a.201 | F | $OCHF_2$ | N—cPr | $CH_3$ |
| I.a.202 | Cl | $OCHF_2$ | N—cPr | $CH_3$ |
| I.a.203 | $CH_3$ | $OCHF_2$ | N—cPr | $CH_3$ |
| I.a.204 | $CF_3$ | $OCHF_2$ | N—cPr | $CH_3$ |
| I.a.205 | $SO_2CH_3$ | $OCHF_2$ | N—cPr | $CH_3$ |
| I.a.206 | F | $CHF_2$ | N—cPr | $CH_3$ |
| I.a.207 | Cl | $CHF_2$ | N—cPr | $CH_3$ |
| I.a.208 | $CH_3$ | $CHF_2$ | N—cPr | $CH_3$ |
| I.a.209 | $CF_3$ | $CHF_2$ | N—cPr | $CH_3$ |
| I.a.210 | $SO_2CH_3$ | $CHF_2$ | N—cPr | $CH_3$ |
| I.a.211 | F | F | NH | $CH_2CH_3$ |
| I.a.212 | Cl | F | NH | $CH_2CH_3$ |
| I.a.213 | $CH_3$ | F | NH | $CH_2CH_3$ |
| I.a.214 | $CF_3$ | F | NH | $CH_2CH_3$ |
| I.a.215 | $SO_2CH_3$ | F | NH | $CH_2CH_3$ |
| I.a.216 | F | Cl | NH | $CH_2CH_3$ |
| I.a.217 | Cl | Cl | NH | $CH_2CH_3$ |
| I.a.218 | $CH_3$ | Cl | NH | $CH_2CH_3$ |
| I.a.219 | $CF_3$ | Cl | NH | $CH_2CH_3$ |
| I.a.220 | $SO_2CH_3$ | Cl | NH | $CH_2CH_3$ |
| I.a.221 | F | $CF_3$ | NH | $CH_2CH_3$ |
| I.a.222 | Cl | $CF_3$ | NH | $CH_2CH_3$ |
| I.a.223 | $CH_3$ | $CF_3$ | NH | $CH_2CH_3$ |
| I.a.224 | $CF_3$ | $CF_3$ | NH | $CH_2CH_3$ |
| I.a.225 | $SO_2CH_3$ | $CF_3$ | NH | $CH_2CH_3$ |
| I.a.226 | F | c-Pr | NH | $CH_2CH_3$ |
| I.a.227 | Cl | c-Pr | NH | $CH_2CH_3$ |
| I.a.228 | $CH_3$ | c-Pr | NH | $CH_2CH_3$ |
| I.a.229 | $CF_3$ | c-Pr | NH | $CH_2CH_3$ |
| I.a.230 | $SO_2CH_3$ | c-Pr | NH | $CH_2CH_3$ |
| I.a.231 | F | $SO_2CH_3$ | NH | $CH_2CH_3$ |
| I.a.232 | Cl | $SO_2CH_3$ | NH | $CH_2CH_3$ |
| I.a.233 | $CH_3$ | $SO_2CH_3$ | NH | $CH_2CH_3$ |
| I.a.234 | $CF_3$ | $SO_2CH_3$ | NH | $CH_2CH_3$ |
| I.a.235 | $SO_2CH_3$ | $SO_2CH_3$ | NH | $CH_2CH_3$ |
| I.a.236 | F | $OCHF_2$ | NH | $CH_2CH_3$ |
| I.a.237 | Cl | $OCHF_2$ | NH | $CH_2CH_3$ |
| I.a.238 | $CH_3$ | $OCHF_2$ | NH | $CH_2CH_3$ |
| I.a.239 | $CF_3$ | $OCHF_2$ | NH | $CH_2CH_3$ |
| I.a.240 | $SO_2CH_3$ | $OCHF_2$ | NH | $CH_2CH_3$ |
| I.a.241 | F | $CHF_2$ | NH | $CH_2CH_3$ |
| I.a.242 | Cl | $CHF_2$ | NH | $CH_2CH_3$ |
| I.a.243 | $CH_3$ | $CHF_2$ | NH | $CH_2CH_3$ |
| I.a.244 | $CF_3$ | $CHF_2$ | NH | $CH_2CH_3$ |
| I.a.245 | $SO_2CH_3$ | $CHF_2$ | NH | $CH_2CH_3$ |
| I.a.246 | F | F | $NCH_3$ | $CH_2CH_3$ |
| I.a.247 | Cl | F | $NCH_3$ | $CH_2CH_3$ |
| I.a.248 | $CH_3$ | F | $NCH_3$ | $CH_2CH_3$ |
| I.a.249 | $CF_3$ | F | $NCH_3$ | $CH_2CH_3$ |
| I.a.250 | $SO_2CH_3$ | F | $NCH_3$ | $CH_2CH_3$ |
| I.a.251 | F | Cl | $NCH_3$ | $CH_2CH_3$ |
| I.a.252 | Cl | Cl | $NCH_3$ | $CH_2CH_3$ |
| I.a.253 | $CH_3$ | Cl | $NCH_3$ | $CH_2CH_3$ |
| I.a.254 | $CF_3$ | Cl | $NCH_3$ | $CH_2CH_3$ |
| I.a.255 | $SO_2CH_3$ | Cl | $NCH_3$ | $CH_2CH_3$ |
| I.a.256 | F | $CF_3$ | $NCH_3$ | $CH_2CH_3$ |
| I.a.257 | Cl | $CF_3$ | $NCH_3$ | $CH_2CH_3$ |
| I.a.258 | $CH_3$ | $CF_3$ | $NCH_3$ | $CH_2CH_3$ |
| I.a.259 | $CF_3$ | $CF_3$ | $NCH_3$ | $CH_2CH_3$ |
| I.a.260 | $SO_2CH_3$ | $CF_3$ | $NCH_3$ | $CH_2CH_3$ |
| I.a.261 | F | c-Pr | $NCH_3$ | $CH_2CH_3$ |
| I.a.262 | Cl | c-Pr | $NCH_3$ | $CH_2CH_3$ |
| I.a.263 | $CH_3$ | c-Pr | $NCH_3$ | $CH_2CH_3$ |
| I.a.264 | $CF_3$ | c-Pr | $NCH_3$ | $CH_2CH_3$ |
| I.a.265 | $SO_2CH_3$ | c-Pr | $NCH_3$ | $CH_2CH_3$ |
| I.a.266 | F | $SO_2CH_3$ | $NCH_3$ | $CH_2CH_3$ |
| I.a.267 | Cl | $SO_2CH_3$ | $NCH_3$ | $CH_2CH_3$ |
| I.a.268 | $CH_3$ | $SO_2CH_3$ | $NCH_3$ | $CH_2CH_3$ |
| I.a.269 | $CF_3$ | $SO_2CH_3$ | $NCH_3$ | $CH_2CH_3$ |
| I.a.270 | $SO_2CH_3$ | $SO_2CH_3$ | $NCH_3$ | $CH_2CH_3$ |
| I.a.271 | F | $OCHF_2$ | $NCH_3$ | $CH_2CH_3$ |
| I.a.272 | Cl | $OCHF_2$ | $NCH_3$ | $CH_2CH_3$ |
| I.a.273 | $CH_3$ | $OCHF_2$ | $NCH_3$ | $CH_2CH_3$ |
| I.a.274 | $CF_3$ | $OCHF_2$ | $NCH_3$ | $CH_2CH_3$ |
| I.a.275 | $SO_2CH_3$ | $OCHF_2$ | $NCH_3$ | $CH_2CH_3$ |
| I.a.276 | F | $CHF_2$ | $NCH_3$ | $CH_2CH_3$ |
| I.a.277 | Cl | $CHF_2$ | $NCH_3$ | $CH_2CH_3$ |
| I.a.278 | $CH_3$ | $CHF_2$ | $NCH_3$ | $CH_2CH_3$ |
| I.a.279 | $CF_3$ | $CHF_2$ | $NCH_3$ | $CH_2CH_3$ |
| I.a.280 | $SO_2CH_3$ | $CHF_2$ | $NCH_3$ | $CH_2CH_3$ |
| I.a.281 | F | F | $NCH_2CH_3$ | $CH_2CH_3$ |
| I.a.282 | Cl | F | $NCH_2CH_3$ | $CH_2CH_3$ |
| I.a.283 | $CH_3$ | F | $NCH_2CH_3$ | $CH_2CH_3$ |
| I.a.284 | $CF_3$ | F | $NCH_2CH_3$ | $CH_2CH_3$ |
| I.a.285 | $SO_2CH_3$ | F | $NCH_2CH_3$ | $CH_2CH_3$ |
| I.a.286 | F | Cl | $NCH_2CH_3$ | $CH_2CH_3$ |
| I.a.287 | Cl | Cl | $NCH_2CH_3$ | $CH_2CH_3$ |
| I.a.288 | $CH_3$ | Cl | $NCH_2CH_3$ | $CH_2CH_3$ |
| I.a.289 | $CF_3$ | Cl | $NCH_2CH_3$ | $CH_2CH_3$ |
| I.a.290 | $SO_2CH_3$ | Cl | $NCH_2CH_3$ | $CH_2CH_3$ |
| I.a.291 | F | $CF_3$ | $NCH_2CH_3$ | $CH_2CH_3$ |
| I.a.292 | Cl | $CF_3$ | $NCH_2CH_3$ | $CH_2CH_3$ |
| I.a.293 | $CH_3$ | $CF_3$ | $NCH_2CH_3$ | $CH_2CH_3$ |
| I.a.294 | $CF_3$ | $CF_3$ | $NCH_2CH_3$ | $CH_2CH_3$ |
| I.a.295 | $SO_2CH_3$ | $CF_3$ | $NCH_2CH_3$ | $CH_2CH_3$ |
| I.a.296 | F | c-Pr | $NCH_2CH_3$ | $CH_2CH_3$ |
| I.a.297 | Cl | c-Pr | $NCH_2CH_3$ | $CH_2CH_3$ |
| I.a.298 | $CH_3$ | c-Pr | $NCH_2CH_3$ | $CH_2CH_3$ |
| I.a.299 | $CF_3$ | c-Pr | $NCH_2CH_3$ | $CH_2CH_3$ |
| I.a.300 | $SO_2CH_3$ | c-Pr | $NCH_2CH_3$ | $CH_2CH_3$ |

TABLE A-continued

Compounds of the formula I which correspond to the formula I.a as shown above

| No. | R¹ | R² | X | Y |
|---|---|---|---|---|
| I.a.301 | F | SO₂CH₃ | NCH₂CH₃ | CH₂CH₃ |
| I.a.302 | Cl | SO₂CH₃ | NCH₂CH₃ | CH₂CH₃ |
| I.a.303 | CH₃ | SO₂CH₃ | NCH₂CH₃ | CH₂CH₃ |
| I.a.304 | CF₃ | SO₂CH₃ | NCH₂CH₃ | CH₂CH₃ |
| I.a.305 | SO₂CH₃ | SO₂CH₃ | NCH₂CH₃ | CH₂CH₃ |
| I.a.306 | F | OCHF₂ | NCH₂CH₃ | CH₂CH₃ |
| I.a.307 | Cl | OCHF₂ | NCH₂CH₃ | CH₂CH₃ |
| I.a.308 | CH₃ | OCHF₂ | NCH₂CH₃ | CH₂CH₃ |
| I.a.309 | CF₃ | OCHF₂ | NCH₂CH₃ | CH₂CH₃ |
| I.a.310 | SO₂CH₃ | OCHF₂ | NCH₂CH₃ | CH₂CH₃ |
| I.a.311 | F | CHF₂ | NCH₂CH₃ | CH₂CH₃ |
| I.a.312 | Cl | CHF₂ | NCH₂CH₃ | CH₂CH₃ |
| I.a.313 | CH₃ | CHF₂ | NCH₂CH₃ | CH₂CH₃ |
| I.a.314 | CF₃ | CHF₂ | NCH₂CH₃ | CH₂CH₃ |
| I.a.315 | SO₂CH₃ | CHF₂ | NCH₂CH₃ | CH₂CH₃ |
| I.a.316 | F | F | N—iPr | CH₂CH₃ |
| I.a.317 | Cl | F | N—iPr | CH₂CH₃ |
| I.a.318 | CH₃ | F | N—iPr | CH₂CH₃ |
| I.a.319 | CF₃ | F | N—iPr | CH₂CH₃ |
| I.a.320 | SO₂CH₃ | F | N—iPr | CH₂CH₃ |
| I.a.321 | F | Cl | N—iPr | CH₂CH₃ |
| I.a.322 | Cl | Cl | N—iPr | CH₂CH₃ |
| I.a.323 | CH₃ | Cl | N—iPr | CH₂CH₃ |
| I.a.324 | CF₃ | Cl | N—iPr | CH₂CH₃ |
| I.a.325 | SO₂CH₃ | Cl | N—iPr | CH₂CH₃ |
| I.a.326 | F | CF₃ | N—iPr | CH₂CH₃ |
| I.a.327 | Cl | CF₃ | N—iPr | CH₂CH₃ |
| I.a.328 | CH₃ | CF₃ | N—iPr | CH₂CH₃ |
| I.a.329 | CF₃ | CF₃ | N—iPr | CH₂CH₃ |
| I.a.330 | SO₂CH₃ | CF₃ | N—iPr | CH₂CH₃ |
| I.a.331 | F | c-Pr | N—iPr | CH₂CH₃ |
| I.a.332 | Cl | c-Pr | N—iPr | CH₂CH₃ |
| I.a.333 | CH₃ | c-Pr | N—iPr | CH₂CH₃ |
| I.a.334 | CF₃ | c-Pr | N—iPr | CH₂CH₃ |
| I.a.335 | SO₂CH₃ | c-Pr | N—iPr | CH₂CH₃ |
| I.a.336 | F | SO₂CH₃ | N—iPr | CH₂CH₃ |
| I.a.337 | Cl | SO₂CH₃ | N—iPr | CH₂CH₃ |
| I.a.338 | CH₃ | SO₂CH₃ | N—iPr | CH₂CH₃ |
| I.a.339 | CF₃ | SO₂CH₃ | N—iPr | CH₂CH₃ |
| I.a.340 | SO₂CH₃ | SO₂CH₃ | N—iPr | CH₂CH₃ |
| I.a.341 | F | OCHF₂ | N—iPr | CH₂CH₃ |
| I.a.342 | Cl | OCHF₂ | N—iPr | CH₂CH₃ |
| I.a.343 | CH₃ | OCHF₂ | N—iPr | CH₂CH₃ |
| I.a.344 | CF₃ | OCHF₂ | N—iPr | CH₂CH₃ |
| I.a.345 | SO₂CH₃ | OCHF₂ | N—iPr | CH₂CH₃ |
| I.a.346 | F | CHF₂ | N—iPr | CH₂CH₃ |
| I.a.347 | Cl | CHF₂ | N—iPr | CH₂CH₃ |
| I.a.348 | CH₃ | CHF₂ | N—iPr | CH₂CH₃ |
| I.a.349 | CF₃ | CHF₂ | N—iPr | CH₂CH₃ |
| I.a.350 | SO₂CH₃ | CHF₂ | N—iPr | CH₂CH₃ |
| I.a.351 | F | F | N—cPr | CH₂CH₃ |
| I.a.352 | Cl | F | N—cPr | CH₂CH₃ |
| I.a.353 | CH₃ | F | N—cPr | CH₂CH₃ |
| I.a.354 | CF₃ | F | N—cPr | CH₂CH₃ |
| I.a.355 | SO₂CH₃ | F | N—cPr | CH₂CH₃ |
| I.a.356 | F | Cl | N—cPr | CH₂CH₃ |
| I.a.357 | Cl | Cl | N—cPr | CH₂CH₃ |
| I.a.358 | CH₃ | Cl | N—cPr | CH₂CH₃ |
| I.a.359 | CF₃ | Cl | N—cPr | CH₂CH₃ |
| I.a.360 | SO₂CH₃ | Cl | N—cPr | CH₂CH₃ |
| I.a.361 | F | CF₃ | N—cPr | CH₂CH₃ |
| I.a.362 | Cl | CF₃ | N—cPr | CH₂CH₃ |
| I.a.363 | CH₃ | CF₃ | N—cPr | CH₂CH₃ |
| I.a.364 | CF₃ | CF₃ | N—cPr | CH₂CH₃ |
| I.a.365 | SO₂CH₃ | CF₃ | N—cPr | CH₂CH₃ |
| I.a.366 | F | c-Pr | N—cPr | CH₂CH₃ |
| I.a.367 | Cl | c-Pr | N—cPr | CH₂CH₃ |
| I.a.368 | CH₃ | c-Pr | N—cPr | CH₂CH₃ |
| I.a.369 | CF₃ | c-Pr | N—cPr | CH₂CH₃ |
| I.a.370 | SO₂CH₃ | c-Pr | N—cPr | CH₂CH₃ |
| I.a.371 | F | SO₂CH₃ | N—cPr | CH₂CH₃ |
| I.a.372 | Cl | SO₂CH₃ | N—cPr | CH₂CH₃ |
| I.a.373 | CH₃ | SO₂CH₃ | N—cPr | CH₂CH₃ |
| I.a.374 | CF₃ | SO₂CH₃ | N—cPr | CH₂CH₃ |
| I.a.375 | SO₂CH₃ | SO₂CH₃ | N—cPr | CH₂CH₃ |
| I.a.376 | F | OCHF₂ | N—cPr | CH₂CH₃ |
| I.a.377 | Cl | OCHF₂ | N—cPr | CH₂CH₃ |
| I.a.378 | CH₃ | OCHF₂ | N—cPr | CH₂CH₃ |
| I.a.379 | CF₃ | OCHF₂ | N—cPr | CH₂CH₃ |
| I.a.380 | SO₂CH₃ | OCHF₂ | N—cPr | CH₂CH₃ |
| I.a.381 | F | CHF₂ | N—cPr | CH₂CH₃ |
| I.a.382 | Cl | CHF₂ | N—cPr | CH₂CH₃ |
| I.a.383 | CH₃ | CHF₂ | N—cPr | CH₂CH₃ |
| I.a.384 | CF₃ | CHF₂ | N—cPr | CH₂CH₃ |
| I.a.385 | SO₂CH₃ | CHF₂ | N—cPr | CH₂CH₃ |
| I.a.386 | F | F | NH | iPr |
| I.a.387 | Cl | F | NH | iPr |
| I.a.388 | CH₃ | F | NH | iPr |
| I.a.389 | CF₃ | F | NH | iPr |
| I.a.390 | SO₂CH₃ | F | NH | iPr |
| I.a.391 | F | Cl | NH | iPr |
| I.a.392 | Cl | Cl | NH | iPr |
| I.a.393 | CH₃ | Cl | NH | iPr |
| I.a.394 | CF₃ | Cl | NH | iPr |
| I.a.395 | SO₂CH₃ | Cl | NH | iPr |
| I.a.396 | F | CF₃ | NH | iPr |
| I.a.397 | Cl | CF₃ | NH | iPr |
| I.a.398 | CH₃ | CF₃ | NH | iPr |
| I.a.399 | CF₃ | CF₃ | NH | iPr |
| I.a.400 | SO₂CH₃ | CF₃ | NH | iPr |
| I.a.401 | F | c-Pr | NH | iPr |
| I.a.402 | Cl | c-Pr | NH | iPr |
| I.a.403 | CH₃ | c-Pr | NH | iPr |
| I.a.404 | CF₃ | c-Pr | NH | iPr |
| I.a.405 | SO₂CH₃ | c-Pr | NH | iPr |
| I.a.406 | F | SO₂CH₃ | NH | iPr |
| I.a.407 | Cl | SO₂CH₃ | NH | iPr |
| I.a.408 | CH₃ | SO₂CH₃ | NH | iPr |
| I.a.409 | CF₃ | SO₂CH₃ | NH | iPr |
| I.a.410 | SO₂CH₃ | SO₂CH₃ | NH | iPr |
| I.a.411 | F | OCHF₂ | NH | iPr |
| I.a.412 | Cl | OCHF₂ | NH | iPr |
| I.a.413 | CH₃ | OCHF₂ | NH | iPr |
| I.a.414 | CF₃ | OCHF₂ | NH | iPr |
| I.a.415 | SO₂CH₃ | OCHF₂ | NH | iPr |
| I.a.416 | F | CHF₂ | NH | iPr |
| I.a.417 | Cl | CHF₂ | NH | iPr |
| I.a.418 | CH₃ | CHF₂ | NH | iPr |
| I.a.419 | CF₃ | CHF₂ | NH | iPr |
| I.a.420 | SO₂CH₃ | CHF₂ | NH | iPr |
| I.a.421 | F | F | NCH₃ | iPr |
| I.a.422 | Cl | F | NCH₃ | iPr |
| I.a.423 | CH₃ | F | NCH₃ | iPr |
| I.a.424 | CF₃ | F | NCH₃ | iPr |
| I.a.425 | SO₂CH₃ | F | NCH₃ | iPr |
| I.a.426 | F | Cl | NCH₃ | iPr |
| I.a.427 | Cl | Cl | NCH₃ | iPr |
| I.a.428 | CH₃ | Cl | NCH₃ | iPr |
| I.a.429 | CF₃ | Cl | NCH₃ | iPr |
| I.a.430 | SO₂CH₃ | Cl | NCH₃ | iPr |
| I.a.431 | F | CF₃ | NCH₃ | iPr |
| I.a.432 | Cl | CF₃ | NCH₃ | iPr |
| I.a.433 | CH₃ | CF₃ | NCH₃ | iPr |
| I.a.434 | CF₃ | CF₃ | NCH₃ | iPr |
| I.a.435 | SO₂CH₃ | CF₃ | NCH₃ | iPr |
| I.a.436 | F | c-Pr | NCH₃ | iPr |
| I.a.437 | Cl | c-Pr | NCH₃ | iPr |
| I.a.438 | CH₃ | c-Pr | NCH₃ | iPr |
| I.a.439 | CF₃ | c-Pr | NCH₃ | iPr |
| I.a.440 | SO₂CH₃ | c-Pr | NCH₃ | iPr |
| I.a.441 | F | SO₂CH₃ | NCH₃ | iPr |
| I.a.442 | Cl | SO₂CH₃ | NCH₃ | iPr |
| I.a.443 | CH₃ | SO₂CH₃ | NCH₃ | iPr |
| I.a.444 | CF₃ | SO₂CH₃ | NCH₃ | iPr |
| I.a.445 | SO₂CH₃ | SO₂CH₃ | NCH₃ | iPr |
| I.a.446 | F | OCHF₂ | NCH₃ | iPr |
| I.a.447 | Cl | OCHF₂ | NCH₃ | iPr |
| I.a.448 | CH₃ | OCHF₂ | NCH₃ | iPr |
| I.a.449 | CF₃ | OCHF₂ | NCH₃ | iPr |
| I.a.450 | SO₂CH₃ | OCHF₂ | NCH₃ | iPr |

TABLE A-continued

Compounds of the formula I which correspond to the formula I.a as shown above

| No. | R¹ | R² | X | Y |
|---|---|---|---|---|
| I.a.451 | F | CHF$_2$ | NCH$_3$ | iPr |
| I.a.452 | Cl | CHF$_2$ | NCH$_3$ | iPr |
| I.a.453 | CH$_3$ | CHF$_2$ | NCH$_3$ | iPr |
| I.a.454 | CF$_3$ | CHF$_2$ | NCH$_3$ | iPr |
| I.a.455 | SO$_2$CH$_3$ | CHF$_2$ | NCH$_3$ | iPr |
| I.a.456 | F | F | NCH$_2$CH$_3$ | iPr |
| I.a.457 | Cl | F | NCH$_2$CH$_3$ | iPr |
| I.a.458 | CH$_3$ | F | NCH$_2$CH$_3$ | iPr |
| I.a.459 | CF$_3$ | F | NCH$_2$CH$_3$ | iPr |
| I.a.460 | SO$_2$CH$_3$ | F | NCH$_2$CH$_3$ | iPr |
| I.a.461 | F | Cl | NCH$_2$CH$_3$ | iPr |
| I.a.462 | Cl | Cl | NCH$_2$CH$_3$ | iPr |
| I.a.463 | CH$_3$ | Cl | NCH$_2$CH$_3$ | iPr |
| I.a.464 | CF$_3$ | Cl | NCH$_2$CH$_3$ | iPr |
| I.a.465 | SO$_2$CH$_3$ | Cl | NCH$_2$CH$_3$ | iPr |
| I.a.466 | F | CF$_3$ | NCH$_2$CH$_3$ | iPr |
| I.a.467 | Cl | CF$_3$ | NCH$_2$CH$_3$ | iPr |
| I.a.468 | CH$_3$ | CF$_3$ | NCH$_2$CH$_3$ | iPr |
| I.a.469 | CF$_3$ | CF$_3$ | NCH$_2$CH$_3$ | iPr |
| I.a.470 | SO$_2$CH$_3$ | CF$_3$ | NCH$_2$CH$_3$ | iPr |
| I.a.471 | F | c-Pr | NCH$_2$CH$_3$ | iPr |
| I.a.472 | Cl | c-Pr | NCH$_2$CH$_3$ | iPr |
| I.a.473 | CH$_3$ | c-Pr | NCH$_2$CH$_3$ | iPr |
| I.a.474 | CF$_3$ | c-Pr | NCH$_2$CH$_3$ | iPr |
| I.a.475 | SO$_2$CH$_3$ | c-Pr | NCH$_2$CH$_3$ | iPr |
| I.a.476 | F | SO$_2$CH$_3$ | NCH$_2$CH$_3$ | iPr |
| I.a.477 | Cl | SO$_2$CH$_3$ | NCH$_2$CH$_3$ | iPr |
| I.a.478 | CH$_3$ | SO$_2$CH$_3$ | NCH$_2$CH$_3$ | iPr |
| I.a.479 | CF$_3$ | SO$_2$CH$_3$ | NCH$_2$CH$_3$ | iPr |
| I.a.480 | SO$_2$CH$_3$ | SO$_2$CH$_3$ | NCH$_2$CH$_3$ | iPr |
| I.a.481 | F | OCHF$_2$ | NCH$_2$CH$_3$ | iPr |
| I.a.482 | Cl | OCHF$_2$ | NCH$_2$CH$_3$ | iPr |
| I.a.483 | CH$_3$ | OCHF$_2$ | NCH$_2$CH$_3$ | iPr |
| I.a.484 | CF$_3$ | OCHF$_2$ | NCH$_2$CH$_3$ | iPr |
| I.a.485 | SO$_2$CH$_3$ | OCHF$_2$ | NCH$_2$CH$_3$ | iPr |
| I.a.486 | F | CHF$_2$ | NCH$_2$CH$_3$ | iPr |
| I.a.487 | Cl | CHF$_2$ | NCH$_2$CH$_3$ | iPr |
| I.a.488 | CH$_3$ | CHF$_2$ | NCH$_2$CH$_3$ | iPr |
| I.a.489 | CF$_3$ | CHF$_2$ | NCH$_2$CH$_3$ | iPr |
| I.a.490 | SO$_2$CH$_3$ | CHF$_2$ | NCH$_2$CH$_3$ | iPr |
| I.a.491 | F | F | N—iPr | iPr |
| I.a.492 | Cl | F | N—iPr | iPr |
| I.a.493 | CH$_3$ | F | N—iPr | iPr |
| I.a.494 | CF$_3$ | F | N—iPr | iPr |
| I.a.495 | SO$_2$CH$_3$ | F | N—iPr | iPr |
| I.a.496 | F | Cl | N—iPr | iPr |
| I.a.497 | Cl | Cl | N—iPr | iPr |
| I.a.498 | CH$_3$ | Cl | N—iPr | iPr |
| I.a.499 | CF$_3$ | Cl | N—iPr | iPr |
| I.a.500 | SO$_2$CH$_3$ | Cl | N—iPr | iPr |
| I.a.501 | F | CF$_3$ | N—iPr | iPr |
| I.a.502 | Cl | CF$_3$ | N—iPr | iPr |
| I.a.503 | CH$_3$ | CF$_3$ | N—iPr | iPr |
| I.a.504 | CF$_3$ | CF$_3$ | N—iPr | iPr |
| I.a.505 | SO$_2$CH$_3$ | CF$_3$ | N—iPr | iPr |
| I.a.506 | F | c-Pr | N—iPr | iPr |
| I.a.507 | Cl | c-Pr | N—iPr | iPr |
| I.a.508 | CH$_3$ | c-Pr | N—iPr | iPr |
| I.a.509 | CF$_3$ | c-Pr | N—iPr | iPr |
| I.a.510 | SO$_2$CH$_3$ | c-Pr | N—iPr | iPr |
| I.a.511 | F | SO$_2$CH$_3$ | N—iPr | iPr |
| I.a.512 | Cl | SO$_2$CH$_3$ | N—iPr | iPr |
| I.a.513 | CH$_3$ | SO$_2$CH$_3$ | N—iPr | iPr |
| I.a.514 | CF$_3$ | SO$_2$CH$_3$ | N—iPr | iPr |
| I.a.515 | SO$_2$CH$_3$ | SO$_2$CH$_3$ | N—iPr | iPr |
| I.a.516 | F | OCHF$_2$ | N—iPr | iPr |
| I.a.517 | Cl | OCHF$_2$ | N—iPr | iPr |
| I.a.518 | CH$_3$ | OCHF$_2$ | N—iPr | iPr |
| I.a.519 | CF$_3$ | OCHF$_2$ | N—iPr | iPr |
| I.a.520 | SO$_2$CH$_3$ | OCHF$_2$ | N—iPr | iPr |
| I.a.521 | F | CHF$_2$ | N—iPr | iPr |
| I.a.522 | Cl | CHF$_2$ | N—iPr | iPr |
| I.a.523 | CH$_3$ | CHF$_2$ | N—iPr | iPr |
| I.a.524 | CF$_3$ | CHF$_2$ | N—iPr | iPr |
| I.a.525 | SO$_2$CH$_3$ | CHF$_2$ | N—iPr | iPr |
| I.a.526 | F | F | N—cPr | iPr |
| I.a.527 | Cl | F | N—cPr | iPr |
| I.a.528 | CH$_3$ | F | N—cPr | iPr |
| I.a.529 | CF$_3$ | F | N—cPr | iPr |
| I.a.530 | SO$_2$CH$_3$ | F | N—cPr | iPr |
| I.a.531 | F | Cl | N—cPr | iPr |
| I.a.532 | Cl | Cl | N—cPr | iPr |
| I.a.533 | CH$_3$ | Cl | N—cPr | iPr |
| I.a.534 | CF$_3$ | Cl | N—cPr | iPr |
| I.a.535 | SO$_2$CH$_3$ | Cl | N—cPr | iPr |
| I.a.536 | F | CF$_3$ | N—cPr | iPr |
| I.a.537 | Cl | CF$_3$ | N—cPr | iPr |
| I.a.538 | CH$_3$ | CF$_3$ | N—cPr | iPr |
| I.a.539 | CF$_3$ | CF$_3$ | N—cPr | iPr |
| I.a.540 | SO$_2$CH$_3$ | CF$_3$ | N—cPr | iPr |
| I.a.541 | F | c-Pr | N—cPr | iPr |
| I.a.542 | Cl | c-Pr | N—cPr | iPr |
| I.a.543 | CH$_3$ | c-Pr | N—cPr | iPr |
| I.a.544 | CF$_3$ | c-Pr | N—cPr | iPr |
| I.a.545 | SO$_2$CH$_3$ | c-Pr | N—cPr | iPr |
| I.a.546 | F | SO$_2$CH$_3$ | N—cPr | iPr |
| I.a.547 | Cl | SO$_2$CH$_3$ | N—cPr | iPr |
| I.a.548 | CH$_3$ | SO$_2$CH$_3$ | N—cPr | iPr |
| I.a.549 | CF$_3$ | SO$_2$CH$_3$ | N—cPr | iPr |
| I.a.550 | SO$_2$CH$_3$ | SO$_2$CH$_3$ | N—cPr | iPr |
| I.a.551 | F | OCHF$_2$ | N—cPr | iPr |
| I.a.552 | Cl | OCHF$_2$ | N—cPr | iPr |
| I.a.553 | CH$_3$ | OCHF$_2$ | N—cPr | iPr |
| I.a.554 | CF$_3$ | OCHF$_2$ | N—cPr | iPr |
| I.a.555 | SO$_2$CH$_3$ | OCHF$_2$ | N—cPr | iPr |
| I.a.556 | F | CHF$_2$ | N—cPr | iPr |
| I.a.557 | Cl | CHF$_2$ | N—cPr | iPr |
| I.a.558 | CH$_3$ | CHF$_2$ | N—cPr | iPr |
| I.a.559 | CF$_3$ | CHF$_2$ | N—cPr | iPr |
| I.a.560 | SO$_2$CH$_3$ | CHF$_2$ | N—cPr | iPr |
| I.a.561 | F | F | NH | cPr |
| I.a.562 | Cl | F | NH | cPr |
| I.a.563 | CH$_3$ | F | NH | cPr |
| I.a.564 | CF$_3$ | F | NH | cPr |
| I.a.565 | SO$_2$CH$_3$ | F | NH | cPr |
| I.a.566 | F | Cl | NH | cPr |
| I.a.567 | Cl | Cl | NH | cPr |
| I.a.568 | CH$_3$ | Cl | NH | cPr |
| I.a.569 | CF$_3$ | Cl | NH | cPr |
| I.a.570 | SO$_2$CH$_3$ | Cl | NH | cPr |
| I.a.571 | F | CF$_3$ | NH | cPr |
| I.a.572 | Cl | CF$_3$ | NH | cPr |
| I.a.573 | CH$_3$ | CF$_3$ | NH | cPr |
| I.a.574 | CF$_3$ | CF$_3$ | NH | cPr |
| I.a.575 | SO$_2$CH$_3$ | CF$_3$ | NH | cPr |
| I.a.576 | F | c-Pr | NH | cPr |
| I.a.577 | Cl | c-Pr | NH | cPr |
| I.a.578 | CH$_3$ | c-Pr | NH | cPr |
| I.a.579 | CF$_3$ | c-Pr | NH | cPr |
| I.a.580 | SO$_2$CH$_3$ | c-Pr | NH | cPr |
| I.a.581 | F | SO$_2$CH$_3$ | NH | cPr |
| I.a.582 | Cl | SO$_2$CH$_3$ | NH | cPr |
| I.a.583 | CH$_3$ | SO$_2$CH$_3$ | NH | cPr |
| I.a.584 | CF$_3$ | SO$_2$CH$_3$ | NH | cPr |
| I.a.585 | SO$_2$CH$_3$ | SO$_2$CH$_3$ | NH | cPr |
| I.a.586 | F | OCHF$_2$ | NH | cPr |
| I.a.587 | Cl | OCHF$_2$ | NH | cPr |
| I.a.588 | CH$_3$ | OCHF$_2$ | NH | cPr |
| I.a.589 | CF$_3$ | OCHF$_2$ | NH | cPr |
| I.a.590 | SO$_2$CH$_3$ | OCHF$_2$ | NH | cPr |
| I.a.591 | F | CHF$_2$ | NH | cPr |
| I.a.592 | Cl | CHF$_2$ | NH | cPr |
| I.a.593 | CH$_3$ | CHF$_2$ | NH | cPr |
| I.a.594 | CF$_3$ | CHF$_2$ | NH | cPr |
| I.a.595 | SO$_2$CH$_3$ | CHF$_2$ | NH | cPr |
| I.a.596 | F | F | NCH$_3$ | cPr |
| I.a.597 | Cl | F | NCH$_3$ | cPr |
| I.a.598 | CH$_3$ | F | NCH$_3$ | cPr |
| I.a.599 | CF$_3$ | F | NCH$_3$ | cPr |
| I.a.600 | SO$_2$CH$_3$ | F | NCH$_3$ | cPr |

TABLE A-continued

Compounds of the formula I which correspond to the formula I.a as shown above

| No. | R$^1$ | R$^2$ | X | Y |
|---|---|---|---|---|
| I.a.601 | F | Cl | NCH$_3$ | cPr |
| I.a.602 | Cl | Cl | NCH$_3$ | cPr |
| I.a.603 | CH$_3$ | Cl | NCH$_3$ | cPr |
| I.a.604 | CF$_3$ | Cl | NCH$_3$ | cPr |
| I.a.605 | SO$_2$CH$_3$ | Cl | NCH$_3$ | cPr |
| I.a.606 | F | CF$_3$ | NCH$_3$ | cPr |
| I.a.607 | Cl | CF$_3$ | NCH$_3$ | cPr |
| I.a.608 | CH$_3$ | CF$_3$ | NCH$_3$ | cPr |
| I.a.609 | CF$_3$ | CF$_3$ | NCH$_3$ | cPr |
| I.a.610 | SO$_2$CH$_3$ | CF$_3$ | NCH$_3$ | cPr |
| I.a.611 | F | c-Pr | NCH$_3$ | cPr |
| I.a.612 | Cl | c-Pr | NCH$_3$ | cPr |
| I.a.613 | CH$_3$ | c-Pr | NCH$_3$ | cPr |
| I.a.614 | CF$_3$ | c-Pr | NCH$_3$ | cPr |
| I.a.615 | SO$_2$CH$_3$ | c-Pr | NCH$_3$ | cPr |
| I.a.616 | F | SO$_2$CH$_3$ | NCH$_3$ | cPr |
| I.a.617 | Cl | SO$_2$CH$_3$ | NCH$_3$ | cPr |
| I.a.618 | CH$_3$ | SO$_2$CH$_3$ | NCH$_3$ | cPr |
| I.a.619 | CF$_3$ | SO$_2$CH$_3$ | NCH$_3$ | cPr |
| I.a.620 | SO$_2$CH$_3$ | SO$_2$CH$_3$ | NCH$_3$ | cPr |
| I.a.621 | F | OCHF$_2$ | NCH$_3$ | cPr |
| I.a.622 | Cl | OCHF$_2$ | NCH$_3$ | cPr |
| I.a.623 | CH$_3$ | OCHF$_2$ | NCH$_3$ | cPr |
| I.a.624 | CF$_3$ | OCHF$_2$ | NCH$_3$ | cPr |
| I.a.625 | SO$_2$CH$_3$ | OCHF$_2$ | NCH$_3$ | cPr |
| I.a.626 | F | CHF$_2$ | NCH$_3$ | cPr |
| I.a.627 | Cl | CHF$_2$ | NCH$_3$ | cPr |
| I.a.628 | CH$_3$ | CHF$_2$ | NCH$_3$ | cPr |
| I.a.629 | CF$_3$ | CHF$_2$ | NCH$_3$ | cPr |
| I.a.630 | SO$_2$CH$_3$ | CHF$_2$ | NCH$_3$ | cPr |
| I.a.631 | F | F | NCH$_2$CH$_3$ | cPr |
| I.a.632 | Cl | F | NCH$_2$CH$_3$ | cPr |
| I.a.633 | CH$_3$ | F | NCH$_2$CH$_3$ | cPr |
| I.a.634 | CF$_3$ | F | NCH$_2$CH$_3$ | cPr |
| I.a.635 | SO$_2$CH$_3$ | F | NCH$_2$CH$_3$ | cPr |
| I.a.636 | F | Cl | NCH$_2$CH$_3$ | cPr |
| I.a.637 | Cl | Cl | NCH$_2$CH$_3$ | cPr |
| I.a.638 | CH$_3$ | Cl | NCH$_2$CH$_3$ | cPr |
| I.a.639 | CF$_3$ | Cl | NCH$_2$CH$_3$ | cPr |
| I.a.640 | SO$_2$CH$_3$ | Cl | NCH$_2$CH$_3$ | cPr |
| I.a.641 | F | CF$_3$ | NCH$_2$CH$_3$ | cPr |
| I.a.642 | Cl | CF$_3$ | NCH$_2$CH$_3$ | cPr |
| I.a.643 | CH$_3$ | CF$_3$ | NCH$_2$CH$_3$ | cPr |
| I.a.644 | CF$_3$ | CF$_3$ | NCH$_2$CH$_3$ | cPr |
| I.a.645 | SO$_2$CH$_3$ | CF$_3$ | NCH$_2$CH$_3$ | cPr |
| I.a.646 | F | c-Pr | NCH$_2$CH$_3$ | cPr |
| I.a.647 | Cl | c-Pr | NCH$_2$CH$_3$ | cPr |
| I.a.648 | CH$_3$ | c-Pr | NCH$_2$CH$_3$ | cPr |
| I.a.649 | CF$_3$ | c-Pr | NCH$_2$CH$_3$ | cPr |
| I.a.650 | SO$_2$CH$_3$ | c-Pr | NCH$_2$CH$_3$ | cPr |
| I.a.651 | F | SO$_2$CH$_3$ | NCH$_2$CH$_3$ | cPr |
| I.a.652 | Cl | SO$_2$CH$_3$ | NCH$_2$CH$_3$ | cPr |
| I.a.653 | CH$_3$ | SO$_2$CH$_3$ | NCH$_2$CH$_3$ | cPr |
| I.a.654 | CF$_3$ | SO$_2$CH$_3$ | NCH$_2$CH$_3$ | cPr |
| I.a.655 | SO$_2$CH$_3$ | SO$_2$CH$_3$ | NCH$_2$CH$_3$ | cPr |
| I.a.656 | F | OCHF$_2$ | NCH$_2$CH$_3$ | cPr |
| I.a.657 | Cl | OCHF$_2$ | NCH$_2$CH$_3$ | cPr |
| I.a.658 | CH$_3$ | OCHF$_2$ | NCH$_2$CH$_3$ | cPr |
| I.a.659 | CF$_3$ | OCHF$_2$ | NCH$_2$CH$_3$ | cPr |
| I.a.660 | SO$_2$CH$_3$ | OCHF$_2$ | NCH$_2$CH$_3$ | cPr |
| I.a.661 | F | CHF$_2$ | NCH$_2$CH$_3$ | cPr |
| I.a.662 | Cl | CHF$_2$ | NCH$_2$CH$_3$ | cPr |
| I.a.663 | CH$_3$ | CHF$_2$ | NCH$_2$CH$_3$ | cPr |
| I.a.664 | CF$_3$ | CHF$_2$ | NCH$_2$CH$_3$ | cPr |
| I.a.665 | SO$_2$CH$_3$ | CHF$_2$ | NCH$_2$CH$_3$ | cPr |
| I.a.666 | F | F | N—iPr | cPr |
| I.a.667 | Cl | F | N—iPr | cPr |
| I.a.668 | CH$_3$ | F | N—iPr | cPr |
| I.a.669 | CF$_3$ | F | N—iPr | cPr |
| I.a.670 | SO$_2$CH$_3$ | F | N—iPr | cPr |
| I.a.671 | F | Cl | N—iPr | cPr |
| I.a.672 | Cl | Cl | N—iPr | cPr |
| I.a.673 | CH$_3$ | Cl | N—iPr | cPr |
| I.a.674 | CF$_3$ | Cl | N—iPr | cPr |
| I.a.675 | SO$_2$CH$_3$ | Cl | N—iPr | cPr |
| I.a.676 | F | CF$_3$ | N—iPr | cPr |
| I.a.677 | Cl | CF$_3$ | N—iPr | cPr |
| I.a.678 | CH$_3$ | CF$_3$ | N—iPr | cPr |
| I.a.679 | CF$_3$ | CF$_3$ | N—iPr | cPr |
| I.a.680 | SO$_2$CH$_3$ | CF$_3$ | N—iPr | cPr |
| I.a.681 | F | c-Pr | N—iPr | cPr |
| I.a.682 | Cl | c-Pr | N—iPr | cPr |
| I.a.683 | CH$_3$ | c-Pr | N—iPr | cPr |
| I.a.684 | CF$_3$ | c-Pr | N—iPr | cPr |
| I.a.685 | SO$_2$CH$_3$ | c-Pr | N—iPr | cPr |
| I.a.686 | F | SO$_2$CH$_3$ | N—iPr | cPr |
| I.a.687 | Cl | SO$_2$CH$_3$ | N—iPr | cPr |
| I.a.688 | CH$_3$ | SO$_2$CH$_3$ | N—iPr | cPr |
| I.a.689 | CF$_3$ | SO$_2$CH$_3$ | N—iPr | cPr |
| I.a.690 | SO$_2$CH$_3$ | SO$_2$CH$_3$ | N—iPr | cPr |
| I.a.691 | F | OCHF$_2$ | N—iPr | cPr |
| I.a.692 | Cl | OCHF$_2$ | N—iPr | cPr |
| I.a.693 | CH$_3$ | OCHF$_2$ | N—iPr | cPr |
| I.a.694 | CF$_3$ | OCHF$_2$ | N—iPr | cPr |
| I.a.695 | SO$_2$CH$_3$ | OCHF$_2$ | N—iPr | cPr |
| I.a.696 | F | CHF$_2$ | N—iPr | cPr |
| I.a.697 | Cl | CHF$_2$ | N—iPr | cPr |
| I.a.698 | CH$_3$ | CHF$_2$ | N—iPr | cPr |
| I.a.699 | CF$_3$ | CHF$_2$ | N—iPr | cPr |
| I.a.700 | SO$_2$CH$_3$ | CHF$_2$ | N—iPr | cPr |
| I.a.701 | F | F | N—cPr | cPr |
| I.a.702 | Cl | F | N—cPr | cPr |
| I.a.703 | CH$_3$ | F | N—cPr | cPr |
| I.a.704 | CF$_3$ | F | N—cPr | cPr |
| I.a.705 | SO$_2$CH$_3$ | F | N—cPr | cPr |
| I.a.706 | F | Cl | N—cPr | cPr |
| I.a.707 | Cl | Cl | N—cPr | cPr |
| I.a.708 | CH$_3$ | Cl | N—cPr | cPr |
| I.a.709 | CF$_3$ | Cl | N—cPr | cPr |
| I.a.710 | SO$_2$CH$_3$ | Cl | N—cPr | cPr |
| I.a.711 | F | CF$_3$ | N—cPr | cPr |
| I.a.712 | Cl | CF$_3$ | N—cPr | cPr |
| I.a.713 | CH$_3$ | CF$_3$ | N—cPr | cPr |
| I.a.714 | CF$_3$ | CF$_3$ | N—cPr | cPr |
| I.a.715 | SO$_2$CH$_3$ | CF$_3$ | N—cPr | cPr |
| I.a.716 | F | c-Pr | N—cPr | cPr |
| I.a.717 | Cl | c-Pr | N—cPr | cPr |
| I.a.718 | CH$_3$ | c-Pr | N—cPr | cPr |
| I.a.719 | CF$_3$ | c-Pr | N—cPr | cPr |
| I.a.720 | SO$_2$CH$_3$ | c-Pr | N—cPr | cPr |
| I.a.721 | F | SO$_2$CH$_3$ | N—cPr | cPr |
| I.a.722 | Cl | SO$_2$CH$_3$ | N—cPr | cPr |
| I.a.723 | CH$_3$ | SO$_2$CH$_3$ | N—cPr | cPr |
| I.a.724 | CF$_3$ | SO$_2$CH$_3$ | N—cPr | cPr |
| I.a.725 | SO$_2$CH$_3$ | SO$_2$CH$_3$ | N—cPr | cPr |
| I.a.726 | F | OCHF$_2$ | N—cPr | cPr |
| I.a.727 | Cl | OCHF$_2$ | N—cPr | cPr |
| I.a.728 | CH$_3$ | OCHF$_2$ | N—cPr | cPr |
| I.a.729 | CF$_3$ | OCHF$_2$ | N—cPr | cPr |
| I.a.730 | SO$_2$CH$_3$ | OCHF$_2$ | N—cPr | cPr |
| I.a.731 | F | CHF$_2$ | N—cPr | cPr |
| I.a.732 | Cl | CHF$_2$ | N—cPr | cPr |
| I.a.733 | CH$_3$ | CHF$_2$ | N—cPr | cPr |
| I.a.734 | CF$_3$ | CHF$_2$ | N—cPr | cPr |
| I.a.735 | SO$_2$CH$_3$ | CHF$_2$ | N—cPr | cPr |
| I.a.736 | F | F | NH | CHF$_2$ |
| I.a.737 | Cl | F | NH | CHF$_2$ |
| I.a.738 | CH$_3$ | F | NH | CHF$_2$ |
| I.a.739 | CF$_3$ | F | NH | CHF$_2$ |
| I.a.740 | SO$_2$CH$_3$ | F | NH | CHF$_2$ |
| I.a.741 | F | Cl | NH | CHF$_2$ |
| I.a.742 | Cl | Cl | NH | CHF$_2$ |
| I.a.743 | CH$_3$ | Cl | NH | CHF$_2$ |
| I.a.744 | CF$_3$ | Cl | NH | CHF$_2$ |
| I.a.745 | SO$_2$CH$_3$ | Cl | NH | CHF$_2$ |
| I.a.746 | F | CF$_3$ | NH | CHF$_2$ |
| I.a.747 | Cl | CF$_3$ | NH | CHF$_2$ |
| I.a.748 | CH$_3$ | CF$_3$ | NH | CHF$_2$ |
| I.a.749 | CF$_3$ | CF$_3$ | NH | CHF$_2$ |
| I.a.750 | SO$_2$CH$_3$ | CF$_3$ | NH | CHF$_2$ |

TABLE A-continued

Compounds of the formula I which correspond to the formula I.a as shown above

| No. | R¹ | R² | X | Y |
|---|---|---|---|---|
| I.a.751 | F | c-Pr | NH | $CHF_2$ |
| I.a.752 | Cl | c-Pr | NH | $CHF_2$ |
| I.a.753 | $CH_3$ | c-Pr | NH | $CHF_2$ |
| I.a.754 | $CF_3$ | c-Pr | NH | $CHF_2$ |
| I.a.755 | $SO_2CH_3$ | c-Pr | NH | $CHF_2$ |
| I.a.756 | F | $SO_2CH_3$ | NH | $CHF_2$ |
| I.a.757 | Cl | $SO_2CH_3$ | NH | $CHF_2$ |
| I.a.758 | $CH_3$ | $SO_2CH_3$ | NH | $CHF_2$ |
| I.a.759 | $CF_3$ | $SO_2CH_3$ | NH | $CHF_2$ |
| I.a.760 | $SO_2CH_3$ | $SO_2CH_3$ | NH | $CHF_2$ |
| I.a.761 | F | $OCHF_2$ | NH | $CHF_2$ |
| I.a.762 | Cl | $OCHF_2$ | NH | $CHF_2$ |
| I.a.763 | $CH_3$ | $OCHF_2$ | NH | $CHF_2$ |
| I.a.764 | $CF_3$ | $OCHF_2$ | NH | $CHF_2$ |
| I.a.765 | $SO_2CH_3$ | $OCHF_2$ | NH | $CHF_2$ |
| I.a.766 | F | $CHF_2$ | NH | $CHF_2$ |
| I.a.767 | Cl | $CHF_2$ | NH | $CHF_2$ |
| I.a.768 | $CH_3$ | $CHF_2$ | NH | $CHF_2$ |
| I.a.769 | $CF_3$ | $CHF_2$ | NH | $CHF_2$ |
| I.a.770 | $SO_2CH_3$ | $CHF_2$ | NH | $CHF_2$ |
| I.a.771 | F | F | $NCH_3$ | $CHF_2$ |
| I.a.772 | Cl | F | $NCH_3$ | $CHF_2$ |
| I.a.773 | $CH_3$ | F | $NCH_3$ | $CHF_2$ |
| I.a.774 | $CF_3$ | F | $NCH_3$ | $CHF_2$ |
| I.a.775 | $SO_2CH_3$ | F | $NCH_3$ | $CHF_2$ |
| I.a.776 | F | Cl | $NCH_3$ | $CHF_2$ |
| I.a.777 | Cl | Cl | $NCH_3$ | $CHF_2$ |
| I.a.778 | $CH_3$ | Cl | $NCH_3$ | $CHF_2$ |
| I.a.779 | $CF_3$ | Cl | $NCH_3$ | $CHF_2$ |
| I.a.780 | $SO_2CH_3$ | Cl | $NCH_3$ | $CHF_2$ |
| I.a.781 | F | $CF_3$ | $NCH_3$ | $CHF_2$ |
| I.a.782 | Cl | $CF_3$ | $NCH_3$ | $CHF_2$ |
| I.a.783 | $CH_3$ | $CF_3$ | $NCH_3$ | $CHF_2$ |
| I.a.784 | $CF_3$ | $CF_3$ | $NCH_3$ | $CHF_2$ |
| I.a.785 | $SO_2CH_3$ | $CF_3$ | $NCH_3$ | $CHF_2$ |
| I.a.786 | F | c-Pr | $NCH_3$ | $CHF_2$ |
| I.a.787 | Cl | c-Pr | $NCH_3$ | $CHF_2$ |
| I.a.788 | $CH_3$ | c-Pr | $NCH_3$ | $CHF_2$ |
| I.a.789 | $CF_3$ | c-Pr | $NCH_3$ | $CHF_2$ |
| I.a.790 | $SO_2CH_3$ | c-Pr | $NCH_3$ | $CHF_2$ |
| I.a.791 | F | $SO_2CH_3$ | $NCH_3$ | $CHF_2$ |
| I.a.792 | Cl | $SO_2CH_3$ | $NCH_3$ | $CHF_2$ |
| I.a.793 | $CH_3$ | $SO_2CH_3$ | $NCH_3$ | $CHF_2$ |
| I.a.794 | $CF_3$ | $SO_2CH_3$ | $NCH_3$ | $CHF_2$ |
| I.a.795 | $SO_2CH_3$ | $SO_2CH_3$ | $NCH_3$ | $CHF_2$ |
| I.a.796 | F | $OCHF_2$ | $NCH_3$ | $CHF_2$ |
| I.a.797 | Cl | $OCHF_2$ | $NCH_3$ | $CHF_2$ |
| I.a.798 | $CH_3$ | $OCHF_2$ | $NCH_3$ | $CHF_2$ |
| I.a.799 | $CF_3$ | $OCHF_2$ | $NCH_3$ | $CHF_2$ |
| I.a.800 | $SO_2CH_3$ | $OCHF_2$ | $NCH_3$ | $CHF_2$ |
| I.a.801 | F | $CHF_2$ | $NCH_3$ | $CHF_2$ |
| I.a.802 | Cl | $CHF_2$ | $NCH_3$ | $CHF_2$ |
| I.a.803 | $CH_3$ | $CHF_2$ | $NCH_3$ | $CHF_2$ |
| I.a.804 | $CF_3$ | $CHF_2$ | $NCH_3$ | $CHF_2$ |
| I.a.805 | $SO_2CH_3$ | $CHF_2$ | $NCH_3$ | $CHF_2$ |
| I.a.806 | F | F | $NCH_2CH_3$ | $CHF_2$ |
| I.a.807 | Cl | F | $NCH_2CH_3$ | $CHF_2$ |
| I.a.808 | $CH_3$ | F | $NCH_2CH_3$ | $CHF_2$ |
| I.a.809 | $CF_3$ | F | $NCH_2CH_3$ | $CHF_2$ |
| I.a.810 | $SO_2CH_3$ | F | $NCH_2CH_3$ | $CHF_2$ |
| I.a.811 | F | Cl | $NCH_2CH_3$ | $CHF_2$ |
| I.a.812 | Cl | Cl | $NCH_2CH_3$ | $CHF_2$ |
| I.a.813 | $CH_3$ | Cl | $NCH_2CH_3$ | $CHF_2$ |
| I.a.814 | $CF_3$ | Cl | $NCH_2CH_3$ | $CHF_2$ |
| I.a.815 | $SO_2CH_3$ | Cl | $NCH_2CH_3$ | $CHF_2$ |
| I.a.816 | F | $CF_3$ | $NCH_2CH_3$ | $CHF_2$ |
| I.a.817 | Cl | $CF_3$ | $NCH_2CH_3$ | $CHF_2$ |
| I.a.818 | $CH_3$ | $CF_3$ | $NCH_2CH_3$ | $CHF_2$ |
| I.a.819 | $CF_3$ | $CF_3$ | $NCH_2CH_3$ | $CHF_2$ |
| I.a.820 | $SO_2CH_3$ | $CF_3$ | $NCH_2CH_3$ | $CHF_2$ |
| I.a.821 | F | c-Pr | $NCH_2CH_3$ | $CHF_2$ |
| I.a.822 | Cl | c-Pr | $NCH_2CH_3$ | $CHF_2$ |
| I.a.823 | $CH_3$ | c-Pr | $NCH_2CH_3$ | $CHF_2$ |
| I.a.824 | $CF_3$ | c-Pr | $NCH_2CH_3$ | $CHF_2$ |
| I.a.825 | $SO_2CH_3$ | c-Pr | $NCH_2CH_3$ | $CHF_2$ |
| I.a.826 | F | $SO_2CH_3$ | $NCH_2CH_3$ | $CHF_2$ |
| I.a.827 | Cl | $SO_2CH_3$ | $NCH_2CH_3$ | $CHF_2$ |
| I.a.828 | $CH_3$ | $SO_2CH_3$ | $NCH_2CH_3$ | $CHF_2$ |
| I.a.829 | $CF_3$ | $SO_2CH_3$ | $NCH_2CH_3$ | $CHF_2$ |
| I.a.830 | $SO_2CH_3$ | $SO_2CH_3$ | $NCH_2CH_3$ | $CHF_2$ |
| I.a.831 | F | $OCHF_2$ | $NCH_2CH_3$ | $CHF_2$ |
| I.a.832 | Cl | $OCHF_2$ | $NCH_2CH_3$ | $CHF_2$ |
| I.a.833 | $CH_3$ | $OCHF_2$ | $NCH_2CH_3$ | $CHF_2$ |
| I.a.834 | $CF_3$ | $OCHF_2$ | $NCH_2CH_3$ | $CHF_2$ |
| I.a.835 | $SO_2CH_3$ | $OCHF_2$ | $NCH_2CH_3$ | $CHF_2$ |
| I.a.836 | F | $CHF_2$ | $NCH_2CH_3$ | $CHF_2$ |
| I.a.837 | Cl | $CHF_2$ | $NCH_2CH_3$ | $CHF_2$ |
| I.a.838 | $CH_3$ | $CHF_2$ | $NCH_2CH_3$ | $CHF_2$ |
| I.a.839 | $CF_3$ | $CHF_2$ | $NCH_2CH_3$ | $CHF_2$ |
| I.a.840 | $SO_2CH_3$ | $CHF_2$ | $NCH_2CH_3$ | $CHF_2$ |
| I.a.841 | F | F | N—iPr | $CHF_2$ |
| I.a.842 | Cl | F | N—iPr | $CHF_2$ |
| I.a.843 | $CH_3$ | F | N—iPr | $CHF_2$ |
| I.a.844 | $CF_3$ | F | N—iPr | $CHF_2$ |
| I.a.845 | $SO_2CH_3$ | F | N—iPr | $CHF_2$ |
| I.a.846 | F | Cl | N—iPr | $CHF_2$ |
| I.a.847 | Cl | Cl | N—iPr | $CHF_2$ |
| I.a.848 | $CH_3$ | Cl | N—iPr | $CHF_2$ |
| I.a.849 | $CF_3$ | Cl | N—iPr | $CHF_2$ |
| I.a.850 | $SO_2CH_3$ | Cl | N—iPr | $CHF_2$ |
| I.a.851 | F | $CF_3$ | N—iPr | $CHF_2$ |
| I.a.852 | Cl | $CF_3$ | N—iPr | $CHF_2$ |
| I.a.853 | $CH_3$ | $CF_3$ | N—iPr | $CHF_2$ |
| I.a.854 | $CF_3$ | $CF_3$ | N—iPr | $CHF_2$ |
| I.a.855 | $SO_2CH_3$ | $CF_3$ | N—iPr | $CHF_2$ |
| I.a.856 | F | c-Pr | N—iPr | $CHF_2$ |
| I.a.857 | Cl | c-Pr | N—iPr | $CHF_2$ |
| I.a.858 | $CH_3$ | c-Pr | N—iPr | $CHF_2$ |
| I.a.859 | $CF_3$ | c-Pr | N—iPr | $CHF_2$ |
| I.a.860 | $SO_2CH_3$ | c-Pr | N—iPr | $CHF_2$ |
| I.a.861 | F | $SO_2CH_3$ | N—iPr | $CHF_2$ |
| I.a.862 | Cl | $SO_2CH_3$ | N—iPr | $CHF_2$ |
| I.a.863 | $CH_3$ | $SO_2CH_3$ | N—iPr | $CHF_2$ |
| I.a.864 | $CF_3$ | $SO_2CH_3$ | N—iPr | $CHF_2$ |
| I.a.865 | $SO_2CH_3$ | $SO_2CH_3$ | N—iPr | $CHF_2$ |
| I.a.866 | F | $OCHF_2$ | N—iPr | $CHF_2$ |
| I.a.867 | Cl | $OCHF_2$ | N—iPr | $CHF_2$ |
| I.a.868 | $CH_3$ | $OCHF_2$ | N—iPr | $CHF_2$ |
| I.a.869 | $CF_3$ | $OCHF_2$ | N—iPr | $CHF_2$ |
| I.a.870 | $SO_2CH_3$ | $OCHF_2$ | N—iPr | $CHF_2$ |
| I.a.871 | F | $CHF_2$ | N—iPr | $CHF_2$ |
| I.a.872 | Cl | $CHF_2$ | N—iPr | $CHF_2$ |
| I.a.873 | $CH_3$ | $CHF_2$ | N—iPr | $CHF_2$ |
| I.a.874 | $CF_3$ | $CHF_2$ | N—iPr | $CHF_2$ |
| I.a.875 | $SO_2CH_3$ | $CHF_2$ | N—iPr | $CHF_2$ |
| I.a.876 | F | F | N—cPr | $CHF_2$ |
| I.a.877 | Cl | F | N—cPr | $CHF_2$ |
| I.a.878 | $CH_3$ | F | N—cPr | $CHF_2$ |
| I.a.879 | $CF_3$ | F | N—cPr | $CHF_2$ |
| I.a.880 | $SO_2CH_3$ | F | N—cPr | $CHF_2$ |
| I.a.881 | F | Cl | N—cPr | $CHF_2$ |
| I.a.882 | Cl | Cl | N—cPr | $CHF_2$ |
| I.a.883 | $CH_3$ | Cl | N—cPr | $CHF_2$ |
| I.a.884 | $CF_3$ | Cl | N—cPr | $CHF_2$ |
| I.a.885 | $SO_2CH_3$ | Cl | N—cPr | $CHF_2$ |
| I.a.886 | F | $CF_3$ | N—cPr | $CHF_2$ |
| I.a.887 | Cl | $CF_3$ | N—cPr | $CHF_2$ |
| I.a.888 | $CH_3$ | $CF_3$ | N—cPr | $CHF_2$ |
| I.a.889 | $CF_3$ | $CF_3$ | N—cPr | $CHF_2$ |
| I.a.890 | $SO_2CH_3$ | $CF_3$ | N—cPr | $CHF_2$ |
| I.a.891 | F | c-Pr | N—cPr | $CHF_2$ |
| I.a.892 | Cl | c-Pr | N—cPr | $CHF_2$ |
| I.a.893 | $CH_3$ | c-Pr | N—cPr | $CHF_2$ |
| I.a.894 | $CF_3$ | c-Pr | N—cPr | $CHF_2$ |
| I.a.895 | $SO_2CH_3$ | c-Pr | N—cPr | $CHF_2$ |
| I.a.896 | F | $SO_2CH_3$ | N—cPr | $CHF_2$ |
| I.a.897 | Cl | $SO_2CH_3$ | N—cPr | $CHF_2$ |
| I.a.898 | $CH_3$ | $SO_2CH_3$ | N—cPr | $CHF_2$ |
| I.a.899 | $CF_3$ | $SO_2CH_3$ | N—cPr | $CHF_2$ |
| I.a.900 | $SO_2CH_3$ | $SO_2CH_3$ | N—cPr | $CHF_2$ |

TABLE A-continued

Compounds of the formula I which correspond to the formula I.a as shown above

| No. | R¹ | R² | X | Y |
|---|---|---|---|---|
| I.a.901 | F | OCHF₂ | N—cPr | CHF₂ |
| I.a.902 | Cl | OCHF₂ | N—cPr | CHF₂ |
| I.a.903 | CH₃ | OCHF₂ | N—cPr | CHF₂ |
| I.a.904 | CF₃ | OCHF₂ | N—cPr | CHF₂ |
| I.a.905 | SO₂CH₃ | OCHF₂ | N—cPr | CHF₂ |
| I.a.906 | F | CHF₂ | N—cPr | CHF₂ |
| I.a.907 | Cl | CHF₂ | N—cPr | CHF₂ |
| I.a.908 | CH₃ | CHF₂ | N—cPr | CHF₂ |
| I.a.909 | CF₃ | CHF₂ | N—cPr | CHF₂ |
| I.a.910 | SO₂CH₃ | CHF₂ | N—cPr | CHF₂ |
| I.a.911 | F | F | NH | CF₃ |
| I.a.912 | Cl | F | NH | CF₃ |
| I.a.913 | CH₃ | F | NH | CF₃ |
| I.a.914 | CF₃ | F | NH | CF₃ |
| I.a.915 | SO₂CH₃ | F | NH | CF₃ |
| I.a.916 | F | Cl | NH | CF₃ |
| I.a.917 | Cl | Cl | NH | CF₃ |
| I.a.918 | CH₃ | Cl | NH | CF₃ |
| I.a.919 | CF₃ | Cl | NH | CF₃ |
| I.a.920 | SO₂CH₃ | Cl | NH | CF₃ |
| I.a.921 | F | CF₃ | NH | CF₃ |
| I.a.922 | Cl | CF₃ | NH | CF₃ |
| I.a.923 | CH₃ | CF₃ | NH | CF₃ |
| I.a.924 | CF₃ | CF₃ | NH | CF₃ |
| I.a.925 | SO₂CH₃ | CF₃ | NH | CF₃ |
| I.a.926 | F | c-Pr | NH | CF₃ |
| I.a.927 | Cl | c-Pr | NH | CF₃ |
| I.a.928 | CH₃ | c-Pr | NH | CF₃ |
| I.a.929 | CF₃ | c-Pr | NH | CF₃ |
| I.a.930 | SO₂CH₃ | c-Pr | NH | CF₃ |
| I.a.931 | F | SO₂CH₃ | NH | CF₃ |
| I.a.932 | Cl | SO₂CH₃ | NH | CF₃ |
| I.a.933 | CH₃ | SO₂CH₃ | NH | CF₃ |
| I.a.934 | CF₃ | SO₂CH₃ | NH | CF₃ |
| I.a.935 | SO₂CH₃ | SO₂CH₃ | NH | CF₃ |
| I.a.936 | F | OCHF₂ | NH | CF₃ |
| I.a.937 | Cl | OCHF₂ | NH | CF₃ |
| I.a.938 | CH₃ | OCHF₂ | NH | CF₃ |
| I.a.939 | CF₃ | OCHF₂ | NH | CF₃ |
| I.a.940 | SO₂CH₃ | OCHF₂ | NH | CF₃ |
| I.a.941 | F | CHF₂ | NH | CF₃ |
| I.a.942 | Cl | CHF₂ | NH | CF₃ |
| I.a.943 | CH₃ | CHF₂ | NH | CF₃ |
| I.a.944 | CF₃ | CHF₂ | NH | CF₃ |
| I.a.945 | SO₂CH₃ | CHF₂ | NH | CF₃ |
| I.a.946 | F | F | NCH₃ | CF₃ |
| I.a.947 | Cl | F | NCH₃ | CF₃ |
| I.a.948 | CH₃ | F | NCH₃ | CF₃ |
| I.a.949 | CF₃ | F | NCH₃ | CF₃ |
| I.a.950 | SO₂CH₃ | F | NCH₃ | CF₃ |
| I.a.951 | F | Cl | NCH₃ | CF₃ |
| I.a.952 | Cl | Cl | NCH₃ | CF₃ |
| I.a.953 | CH₃ | Cl | NCH₃ | CF₃ |
| I.a.954 | CF₃ | Cl | NCH₃ | CF₃ |
| I.a.955 | SO₂CH₃ | Cl | NCH₃ | CF₃ |
| I.a.956 | F | CF₃ | NCH₃ | CF₃ |
| I.a.957 | Cl | CF₃ | NCH₃ | CF₃ |
| I.a.958 | CH₃ | CF₃ | NCH₃ | CF₃ |
| I.a.959 | CF₃ | CF₃ | NCH₃ | CF₃ |
| I.a.960 | SO₂CH₃ | CF₃ | NCH₃ | CF₃ |
| I.a.961 | F | c-Pr | NCH₃ | CF₃ |
| I.a.962 | Cl | c-Pr | NCH₃ | CF₃ |
| I.a.963 | CH₃ | c-Pr | NCH₃ | CF₃ |
| I.a.964 | CF₃ | c-Pr | NCH₃ | CF₃ |
| I.a.965 | SO₂CH₃ | c-Pr | NCH₃ | CF₃ |
| I.a.966 | F | SO₂CH₃ | NCH₃ | CF₃ |
| I.a.967 | Cl | SO₂CH₃ | NCH₃ | CF₃ |
| I.a.968 | CH₃ | SO₂CH₃ | NCH₃ | CF₃ |
| I.a.969 | CF₃ | SO₂CH₃ | NCH₃ | CF₃ |
| I.a.970 | SO₂CH₃ | SO₂CH₃ | NCH₃ | CF₃ |
| I.a.971 | F | OCHF₂ | NCH₃ | CF₃ |
| I.a.972 | Cl | OCHF₂ | NCH₃ | CF₃ |
| I.a.973 | CH₃ | OCHF₂ | NCH₃ | CF₃ |
| I.a.974 | CF₃ | OCHF₂ | NCH₃ | CF₃ |
| I.a.975 | SO₂CH₃ | OCHF₂ | NCH₃ | CF₃ |
| I.a.976 | F | CHF₂ | NCH₃ | CF₃ |
| I.a.977 | Cl | CHF₂ | NCH₃ | CF₃ |
| I.a.978 | CH₃ | CHF₂ | NCH₃ | CF₃ |
| I.a.979 | CF₃ | CHF₂ | NCH₃ | CF₃ |
| I.a.980 | SO₂CH₃ | CHF₂ | NCH₃ | CF₃ |
| I.a.981 | F | F | NCH₂CH₃ | CF₃ |
| I.a.982 | Cl | F | NCH₂CH₃ | CF₃ |
| I.a.983 | CH₃ | F | NCH₂CH₃ | CF₃ |
| I.a.984 | CF₃ | F | NCH₂CH₃ | CF₃ |
| I.a.985 | SO₂CH₃ | F | NCH₂CH₃ | CF₃ |
| I.a.986 | F | Cl | NCH₂CH₃ | CF₃ |
| I.a.987 | Cl | Cl | NCH₂CH₃ | CF₃ |
| I.a.988 | CH₃ | Cl | NCH₂CH₃ | CF₃ |
| I.a.989 | CF₃ | Cl | NCH₂CH₃ | CF₃ |
| I.a.990 | SO₂CH₃ | Cl | NCH₂CH₃ | CF₃ |
| I.a.991 | F | CF₃ | NCH₂CH₃ | CF₃ |
| I.a.992 | Cl | CF₃ | NCH₂CH₃ | CF₃ |
| I.a.993 | CH₃ | CF₃ | NCH₂CH₃ | CF₃ |
| I.a.994 | CF₃ | CF₃ | NCH₂CH₃ | CF₃ |
| I.a.995 | SO₂CH₃ | CF₃ | NCH₂CH₃ | CF₃ |
| I.a.996 | F | c-Pr | NCH₂CH₃ | CF₃ |
| I.a.997 | Cl | c-Pr | NCH₂CH₃ | CF₃ |
| I.a.998 | CH₃ | c-Pr | NCH₂CH₃ | CF₃ |
| I.a.999 | CF₃ | c-Pr | NCH₂CH₃ | CF₃ |
| I.a.1000 | SO₂CH₃ | c-Pr | NCH₂CH₃ | CF₃ |
| I.a.1001 | F | SO₂CH₃ | NCH₂CH₃ | CF₃ |
| I.a.1002 | Cl | SO₂CH₃ | NCH₂CH₃ | CF₃ |
| I.a.1003 | CH₃ | SO₂CH₃ | NCH₂CH₃ | CF₃ |
| I.a.1004 | CF₃ | SO₂CH₃ | NCH₂CH₃ | CF₃ |
| I.a.1005 | SO₂CH₃ | SO₂CH₃ | NCH₂CH₃ | CF₃ |
| I.a.1006 | F | OCHF₂ | NCH₂CH₃ | CF₃ |
| I.a.1007 | Cl | OCHF₂ | NCH₂CH₃ | CF₃ |
| I.a.1008 | CH₃ | OCHF₂ | NCH₂CH₃ | CF₃ |
| I.a.1009 | CF₃ | OCHF₂ | NCH₂CH₃ | CF₃ |
| I.a.1010 | SO₂CH₃ | OCHF₂ | NCH₂CH₃ | CF₃ |
| I.a.1011 | F | CHF₂ | NCH₂CH₃ | CF₃ |
| I.a.1012 | Cl | CHF₂ | NCH₂CH₃ | CF₃ |
| I.a.1013 | CH₃ | CHF₂ | NCH₂CH₃ | CF₃ |
| I.a.1014 | CF₃ | CHF₂ | NCH₂CH₃ | CF₃ |
| I.a.1015 | SO₂CH₃ | CHF₂ | NCH₂CH₃ | CF₃ |
| I.a.1016 | F | F | N—iPr | CF₃ |
| I.a.1017 | Cl | F | N—iPr | CF₃ |
| I.a.1018 | CH₃ | F | N—iPr | CF₃ |
| I.a.1019 | CF₃ | F | N—iPr | CF₃ |
| I.a.1020 | SO₂CH₃ | F | N—iPr | CF₃ |
| I.a.1021 | F | Cl | N—iPr | CF₃ |
| I.a.1022 | Cl | Cl | N—iPr | CF₃ |
| I.a.1023 | CH₃ | Cl | N—iPr | CF₃ |
| I.a.1024 | CF₃ | Cl | N—iPr | CF₃ |
| I.a.1025 | SO₂CH₃ | Cl | N—iPr | CF₃ |
| I.a.1026 | F | CF₃ | N—iPr | CF₃ |
| I.a.1027 | Cl | CF₃ | N—iPr | CF₃ |
| I.a.1028 | CH₃ | CF₃ | N—iPr | CF₃ |
| I.a.1029 | CF₃ | CF₃ | N—iPr | CF₃ |
| I.a.1030 | SO₂CH₃ | CF₃ | N—iPr | CF₃ |
| I.a.1031 | F | c-Pr | N—iPr | CF₃ |
| I.a.1032 | Cl | c-Pr | N—iPr | CF₃ |
| I.a.1033 | CH₃ | c-Pr | N—iPr | CF₃ |
| I.a.1034 | CF₃ | c-Pr | N—iPr | CF₃ |
| I.a.1035 | SO₂CH₃ | c-Pr | N—iPr | CF₃ |
| I.a.1036 | F | SO₂CH₃ | N—iPr | CF₃ |
| I.a.1037 | Cl | SO₂CH₃ | N—iPr | CF₃ |
| I.a.1038 | CH₃ | SO₂CH₃ | N—iPr | CF₃ |
| I.a.1039 | CF₃ | SO₂CH₃ | N—iPr | CF₃ |
| I.a.1040 | SO₂CH₃ | SO₂CH₃ | N—iPr | CF₃ |
| I.a.1041 | F | OCHF₂ | N—iPr | CF₃ |
| I.a.1042 | Cl | OCHF₂ | N—iPr | CF₃ |
| I.a.1043 | CH₃ | OCHF₂ | N—iPr | CF₃ |
| I.a.1044 | CF₃ | OCHF₂ | N—iPr | CF₃ |
| I.a.1045 | SO₂CH₃ | OCHF₂ | N—iPr | CF₃ |
| I.a.1046 | F | CHF₂ | N—iPr | CF₃ |
| I.a.1047 | Cl | CHF₂ | N—iPr | CF₃ |
| I.a.1048 | CH₃ | CHF₂ | N—iPr | CF₃ |
| I.a.1049 | CF₃ | CHF₂ | N—iPr | CF₃ |
| I.a.1050 | SO₂CH₃ | CHF₂ | N—iPr | CF₃ |

TABLE A-continued

Compounds of the formula I which correspond to the formula I.a as shown above

| No. | R¹ | R² | X | Y |
|---|---|---|---|---|
| I.a.1051 | F | F | N—cPr | CF₃ |
| I.a.1052 | Cl | F | N—cPr | CF₃ |
| I.a.1053 | CH₃ | F | N—cPr | CF₃ |
| I.a.1054 | CF₃ | F | N—cPr | CF₃ |
| I.a.1055 | SO₂CH₃ | F | N—cPr | CF₃ |
| I.a.1056 | F | Cl | N—cPr | CF₃ |
| I.a.1057 | Cl | Cl | N—cPr | CF₃ |
| I.a.1058 | CH₃ | Cl | N—cPr | CF₃ |
| I.a.1059 | CF₃ | Cl | N—cPr | CF₃ |
| I.a.1060 | SO₂CH₃ | Cl | N—cPr | CF₃ |
| I.a.1061 | F | CF₃ | N—cPr | CF₃ |
| I.a.1062 | Cl | CF₃ | N—cPr | CF₃ |
| I.a.1063 | CH₃ | CF₃ | N—cPr | CF₃ |
| I.a.1064 | CF₃ | CF₃ | N—cPr | CF₃ |
| I.a.1065 | SO₂CH₃ | CF₃ | N—cPr | CF₃ |
| I.a.1066 | F | c-Pr | N—cPr | CF₃ |
| I.a.1067 | Cl | c-Pr | N—cPr | CF₃ |
| I.a.1068 | CH₃ | c-Pr | N—cPr | CF₃ |
| I.a.1069 | CF₃ | c-Pr | N—cPr | CF₃ |
| I.a.1070 | SO₂CH₃ | c-Pr | N—cPr | CF₃ |
| I.a.1071 | F | SO₂CH₃ | N—cPr | CF₃ |
| I.a.1072 | Cl | SO₂CH₃ | N—cPr | CF₃ |
| I.a.1073 | CH₃ | SO₂CH₃ | N—cPr | CF₃ |
| I.a.1074 | CF₃ | SO₂CH₃ | N—cPr | CF₃ |
| I.a.1075 | SO₂CH₃ | SO₂CH₃ | N—cPr | CF₃ |
| I.a.1076 | F | OCHF₂ | N—cPr | CF₃ |
| I.a.1077 | Cl | OCHF₂ | N—cPr | CF₃ |
| I.a.1078 | CH₃ | OCHF₂ | N—cPr | CF₃ |
| I.a.1079 | CF₃ | OCHF₂ | N—cPr | CF₃ |
| I.a.1080 | SO₂CH₃ | OCHF₂ | N—cPr | CF₃ |
| I.a.1081 | F | CHF₂ | N—cPr | CF₃ |
| I.a.1082 | Cl | CHF₂ | N—cPr | CF₃ |
| I.a.1083 | CH₃ | CHF₂ | N—cPr | CF₃ |
| I.a.1084 | CF₃ | CHF₂ | N—cPr | CF₃ |
| I.a.1085 | SO₂CH₃ | CHF₂ | N—cPr | CF₃ |
| I.a.1086 | F | F | NH | CH₂—cPr |
| I.a.1087 | Cl | F | NH | CH₂—cPr |
| I.a.1088 | CH₃ | F | NH | CH₂—cPr |
| I.a.1089 | CF₃ | F | NH | CH₂—cPr |
| I.a.1090 | SO₂CH₃ | F | NH | CH₂—cPr |
| I.a.1091 | F | Cl | NH | CH₂—cPr |
| I.a.1092 | Cl | Cl | NH | CH₂—cPr |
| I.a.1093 | CH₃ | Cl | NH | CH₂—cPr |
| I.a.1094 | CF₃ | Cl | NH | CH₂—cPr |
| I.a.1095 | SO₂CH₃ | Cl | NH | CH₂—cPr |
| I.a.1096 | F | CF₃ | NH | CH₂—cPr |
| I.a.1097 | Cl | CF₃ | NH | CH₂—cPr |
| I.a.1098 | CH₃ | CF₃ | NH | CH₂—cPr |
| I.a.1099 | CF₃ | CF₃ | NH | CH₂—cPr |
| I.a.1100 | SO₂CH₃ | CF₃ | NH | CH₂—cPr |
| I.a.1101 | F | c-Pr | NH | CH₂—cPr |
| I.a.1102 | Cl | c-Pr | NH | CH₂—cPr |
| I.a.1103 | CH₃ | c-Pr | NH | CH₂—cPr |
| I.a.1104 | CF₃ | c-Pr | NH | CH₂—cPr |
| I.a.1105 | SO₂CH₃ | c-Pr | NH | CH₂—cPr |
| I.a.1106 | F | SO₂CH₃ | NH | CH₂—cPr |
| I.a.1107 | Cl | SO₂CH₃ | NH | CH₂—cPr |
| I.a.1108 | CH₃ | SO₂CH₃ | NH | CH₂—cPr |
| I.a.1109 | CF₃ | SO₂CH₃ | NH | CH₂—cPr |
| I.a.1110 | SO₂CH₃ | SO₂CH₃ | NH | CH₂—cPr |
| I.a.1111 | F | OCHF₂ | NH | CH₂—cPr |
| I.a.1112 | Cl | OCHF₂ | NH | CH₂—cPr |
| I.a.1113 | CH₃ | OCHF₂ | NH | CH₂—cPr |
| I.a.1114 | CF₃ | OCHF₂ | NH | CH₂—cPr |
| I.a.1115 | SO₂CH₃ | OCHF₂ | NH | CH₂—cPr |
| I.a.1116 | F | CHF₂ | NH | CH₂—cPr |
| I.a.1117 | Cl | CHF₂ | NH | CH₂—cPr |
| I.a.1118 | CH₃ | CHF₂ | NH | CH₂—cPr |
| I.a.1119 | CF₃ | CHF₂ | NH | CH₂—cPr |
| I.a.1120 | SO₂CH₃ | CHF₂ | NH | CH₂—cPr |
| I.a.1121 | F | F | NCH₃ | CH₂—cPr |
| I.a.1122 | Cl | F | NCH₃ | CH₂—cPr |
| I.a.1123 | CH₃ | F | NCH₃ | CH₂—cPr |
| I.a.1124 | CF₃ | F | NCH₃ | CH₂—cPr |
| I.a.1125 | SO₂CH₃ | F | NCH₃ | CH₂—cPr |
| I.a.1126 | F | Cl | NCH₃ | CH₂—cPr |
| I.a.1127 | Cl | Cl | NCH₃ | CH₂—cPr |
| I.a.1128 | CH₃ | Cl | NCH₃ | CH₂—cPr |
| I.a.1129 | CF₃ | Cl | NCH₃ | CH₂—cPr |
| I.a.1130 | SO₂CH₃ | Cl | NCH₃ | CH₂—cPr |
| I.a.1131 | F | CF₃ | NCH₃ | CH₂—cPr |
| I.a.1132 | Cl | CF₃ | NCH₃ | CH₂—cPr |
| I.a.1133 | CH₃ | CF₃ | NCH₃ | CH₂—cPr |
| I.a.1134 | CF₃ | CF₃ | NCH₃ | CH₂—cPr |
| I.a.1135 | SO₂CH₃ | CF₃ | NCH₃ | CH₂—cPr |
| I.a.1136 | F | c-Pr | NCH₃ | CH₂—cPr |
| I.a.1137 | Cl | c-Pr | NCH₃ | CH₂—cPr |
| I.a.1138 | CH₃ | c-Pr | NCH₃ | CH₂—cPr |
| I.a.1139 | CF₃ | c-Pr | NCH₃ | CH₂—cPr |
| I.a.1140 | SO₂CH₃ | c-Pr | NCH₃ | CH₂—cPr |
| I.a.1141 | F | SO₂CH₃ | NCH₃ | CH₂—cPr |
| I.a.1142 | Cl | SO₂CH₃ | NCH₃ | CH₂—cPr |
| I.a.1143 | CH₃ | SO₂CH₃ | NCH₃ | CH₂—cPr |
| I.a.1144 | CF₃ | SO₂CH₃ | NCH₃ | CH₂—cPr |
| I.a.1145 | SO₂CH₃ | SO₂CH₃ | NCH₃ | CH₂—cPr |
| I.a.1146 | F | OCHF₂ | NCH₃ | CH₂—cPr |
| I.a.1147 | Cl | OCHF₂ | NCH₃ | CH₂—cPr |
| I.a.1148 | CH₃ | OCHF₂ | NCH₃ | CH₂—cPr |
| I.a.1149 | CF₃ | OCHF₂ | NCH₃ | CH₂—cPr |
| I.a.1150 | SO₂CH₃ | OCHF₂ | NCH₃ | CH₂—cPr |
| I.a.1151 | F | CHF₂ | NCH₃ | CH₂—cPr |
| I.a.1152 | Cl | CHF₂ | NCH₃ | CH₂—cPr |
| I.a.1153 | CH₃ | CHF₂ | NCH₃ | CH₂—cPr |
| I.a.1154 | CF₃ | CHF₂ | NCH₃ | CH₂—cPr |
| I.a.1155 | SO₂CH₃ | CHF₂ | NCH₃ | CH₂—cPr |
| I.a.1156 | F | F | NCH₂CH₃ | CH₂—cPr |
| I.a.1157 | Cl | F | NCH₂CH₃ | CH₂—cPr |
| I.a.1158 | CH₃ | F | NCH₂CH₃ | CH₂—cPr |
| I.a.1159 | CF₃ | F | NCH₂CH₃ | CH₂—cPr |
| I.a.1160 | SO₂CH₃ | F | NCH₂CH₃ | CH₂—cPr |
| I.a.1161 | F | Cl | NCH₂CH₃ | CH₂—cPr |
| I.a.1162 | Cl | Cl | NCH₂CH₃ | CH₂—cPr |
| I.a.1163 | CH₃ | Cl | NCH₂CH₃ | CH₂—cPr |
| I.a.1164 | CF₃ | Cl | NCH₂CH₃ | CH₂—cPr |
| I.a.1165 | SO₂CH₃ | Cl | NCH₂CH₃ | CH₂—cPr |
| I.a.1166 | F | CF₃ | NCH₂CH₃ | CH₂—cPr |
| I.a.1167 | Cl | CF₃ | NCH₂CH₃ | CH₂—cPr |
| I.a.1168 | CH₃ | CF₃ | NCH₂CH₃ | CH₂—cPr |
| I.a.1169 | CF₃ | CF₃ | NCH₂CH₃ | CH₂—cPr |
| I.a.1170 | SO₂CH₃ | CF₃ | NCH₂CH₃ | CH₂—cPr |
| I.a.1171 | F | c-Pr | NCH₂CH₃ | CH₂—cPr |
| I.a.1172 | Cl | c-Pr | NCH₂CH₃ | CH₂—cPr |
| I.a.1173 | CH₃ | c-Pr | NCH₂CH₃ | CH₂—cPr |
| I.a.1174 | CF₃ | c-Pr | NCH₂CH₃ | CH₂—cPr |
| I.a.1175 | SO₂CH₃ | c-Pr | NCH₂CH₃ | CH₂—cPr |
| I.a.1176 | F | SO₂CH₃ | NCH₂CH₃ | CH₂—cPr |
| I.a.1177 | Cl | SO₂CH₃ | NCH₂CH₃ | CH₂—cPr |
| I.a.1178 | CH₃ | SO₂CH₃ | NCH₂CH₃ | CH₂—cPr |
| I.a.1179 | CF₃ | SO₂CH₃ | NCH₂CH₃ | CH₂—cPr |
| I.a.1180 | SO₂CH₃ | SO₂CH₃ | NCH₂CH₃ | CH₂—cPr |
| I.a.1181 | F | OCHF₂ | NCH₂CH₃ | CH₂—cPr |
| I.a.1182 | Cl | OCHF₂ | NCH₂CH₃ | CH₂—cPr |
| I.a.1183 | CH₃ | OCHF₂ | NCH₂CH₃ | CH₂—cPr |
| I.a.1184 | CF₃ | OCHF₂ | NCH₂CH₃ | CH₂—cPr |
| I.a.1185 | SO₂CH₃ | OCHF₂ | NCH₂CH₃ | CH₂—cPr |
| I.a.1186 | F | CHF₂ | NCH₂CH₃ | CH₂—cPr |
| I.a.1187 | Cl | CHF₂ | NCH₂CH₃ | CH₂—cPr |
| I.a.1188 | CH₃ | CHF₂ | NCH₂CH₃ | CH₂—cPr |
| I.a.1189 | CF₃ | CHF₂ | NCH₂CH₃ | CH₂—cPr |
| I.a.1190 | SO₂CH₃ | CHF₂ | NCH₂CH₃ | CH₂—cPr |
| I.a.1191 | F | F | N—iPr | CH₂—cPr |
| I.a.1192 | Cl | F | N—iPr | CH₂—cPr |
| I.a.1193 | CH₃ | F | N—iPr | CH₂—cPr |
| I.a.1194 | CF₃ | F | N—iPr | CH₂—cPr |
| I.a.1195 | SO₂CH₃ | F | N—iPr | CH₂—cPr |
| I.a.1196 | F | Cl | N—iPr | CH₂—cPr |
| I.a.1197 | Cl | Cl | N—iPr | CH₂—cPr |
| I.a.1198 | CH₃ | Cl | N—iPr | CH₂—cPr |
| I.a.1199 | CF₃ | Cl | N—iPr | CH₂—cPr |
| I.a.1200 | SO₂CH₃ | Cl | N—iPr | CH₂—cPr |

TABLE A-continued

Compounds of the formula I which correspond to the formula I.a as shown above

| No. | R¹ | R² | X | Y |
|---|---|---|---|---|
| I.a.1201 | F | CF₃ | N—iPr | CH₂—cPr |
| I.a.1202 | Cl | CF₃ | N—iPr | CH₂—cPr |
| I.a.1203 | CH₃ | CF₃ | N—iPr | CH₂—cPr |
| I.a.1204 | CF₃ | CF₃ | N—iPr | CH₂—cPr |
| I.a.1205 | SO₂CH₃ | CF₃ | N—iPr | CH₂—cPr |
| I.a.1206 | F | c-Pr | N—iPr | CH₂—cPr |
| I.a.1207 | Cl | c-Pr | N—iPr | CH₂—cPr |
| I.a.1208 | CH₃ | c-Pr | N—iPr | CH₂—cPr |
| I.a.1209 | CF₃ | c-Pr | N—iPr | CH₂—cPr |
| I.a.1210 | SO₂CH₃ | c-Pr | N—iPr | CH₂—cPr |
| I.a.1211 | F | SO₂CH₃ | N—iPr | CH₂—cPr |
| I.a.1212 | Cl | SO₂CH₃ | N—iPr | CH₂—cPr |
| I.a.1213 | CH₃ | SO₂CH₃ | N—iPr | CH₂—cPr |
| I.a.1214 | CF₃ | SO₂CH₃ | N—iPr | CH₂—cPr |
| I.a.1215 | SO₂CH₃ | SO₂CH₃ | N—iPr | CH₂—cPr |
| I.a.1216 | F | OCHF₂ | N—iPr | CH₂—cPr |
| I.a.1217 | Cl | OCHF₂ | N—iPr | CH₂—cPr |
| I.a.1218 | CH₃ | OCHF₂ | N—iPr | CH₂—cPr |
| I.a.1219 | CF₃ | OCHF₂ | N—iPr | CH₂—cPr |
| I.a.1220 | SO₂CH₃ | OCHF₂ | N—iPr | CH₂—cPr |
| I.a.1221 | F | CHF₂ | N—iPr | CH₂—cPr |
| I.a.1222 | Cl | CHF₂ | N—iPr | CH₂—cPr |
| I.a.1223 | CH₃ | CHF₂ | N—iPr | CH₂—cPr |
| I.a.1224 | CF₃ | CHF₂ | N—iPr | CH₂—cPr |
| I.a.1225 | SO₂CH₃ | CHF₂ | N—iPr | CH₂—cPr |
| I.a.1226 | F | F | N—cPr | CH₂—cPr |
| I.a.1227 | Cl | F | N—cPr | CH₂—cPr |
| I.a.1228 | CH₃ | F | N—cPr | CH₂—cPr |
| I.a.1229 | CF₃ | F | N—cPr | CH₂—cPr |
| I.a.1230 | SO₂CH₃ | F | N—cPr | CH₂—cPr |
| I.a.1231 | F | Cl | N—cPr | CH₂—cPr |
| I.a.1232 | Cl | Cl | N—cPr | CH₂—cPr |
| I.a.1233 | CH₃ | Cl | N—cPr | CH₂—cPr |
| I.a.1234 | CF₃ | Cl | N—cPr | CH₂—cPr |
| I.a.1235 | SO₂CH₃ | Cl | N—cPr | CH₂—cPr |
| I.a.1236 | F | CF₃ | N—cPr | CH₂—cPr |
| I.a.1237 | Cl | CF₃ | N—cPr | CH₂—cPr |
| I.a.1238 | CH₃ | CF₃ | N—cPr | CH₂—cPr |
| I.a.1239 | CF₃ | CF₃ | N—cPr | CH₂—cPr |
| I.a.1240 | SO₂CH₃ | CF₃ | N—cPr | CH₂—cPr |
| I.a.1241 | F | c-Pr | N—cPr | CH₂—cPr |
| I.a.1242 | Cl | c-Pr | N—cPr | CH₂—cPr |
| I.a.1243 | CH₃ | c-Pr | N—cPr | CH₂—cPr |
| I.a.1244 | CF₃ | c-Pr | N—cPr | CH₂—cPr |
| I.a.1245 | SO₂CH₃ | c-Pr | N—cPr | CH₂—cPr |
| I.a.1246 | F | SO₂CH₃ | N—cPr | CH₂—cPr |
| I.a.1247 | Cl | SO₂CH₃ | N—cPr | CH₂—cPr |
| I.a.1248 | CH₃ | SO₂CH₃ | N—cPr | CH₂—cPr |
| I.a.1249 | CF₃ | SO₂CH₃ | N—cPr | CH₂—cPr |
| I.a.1250 | SO₂CH₃ | SO₂CH₃ | N—cPr | CH₂—cPr |
| I.a.1251 | F | OCHF₂ | N—cPr | CH₂—cPr |
| I.a.1252 | Cl | OCHF₂ | N—cPr | CH₂—cPr |
| I.a.1253 | CH₃ | OCHF₂ | N—cPr | CH₂—cPr |
| I.a.1254 | CF₃ | OCHF₂ | N—cPr | CH₂—cPr |
| I.a.1255 | SO₂CH₃ | OCHF₂ | N—cPr | CH₂—cPr |
| I.a.1256 | F | CHF₂ | N—cPr | CH₂—cPr |
| I.a.1257 | Cl | CHF₂ | N—cPr | CH₂—cPr |
| I.a.1258 | CH₃ | CHF₂ | N—cPr | CH₂—cPr |
| I.a.1259 | CF₃ | CHF₂ | N—cPr | CH₂—cPr |
| I.a.1260 | SO₂CH₃ | CHF₂ | N—cPr | CH₂—cPr | wherein iPr denotes iso-propyl and cPr denotes cyclopropyl

Preferred compounds of the formula I according to the invention are selected from the group consisting of the compounds I-1 to I-38 as listed below (see also Table I in the Section "Synthesis examples"):

N-[2,6-dichloro-3-(8-hydroxy-6,6-dioxo-5H-thiopyrano[4,3-b]pyridin-7-yl)phenyl]methanesulfonamide of the formula I-1

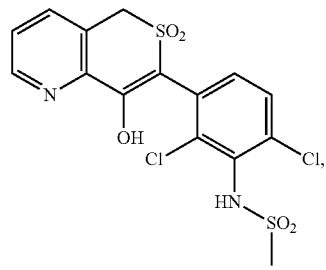

I-1

N-[2,6-dichloro-3-(8-hydroxy-5,5-dimethyl-6,6-dioxo-thiopyrano[4,3-b]pyridin-7-yl)phenyl]-N-methyl-methanesulfonamide of the formula I-2

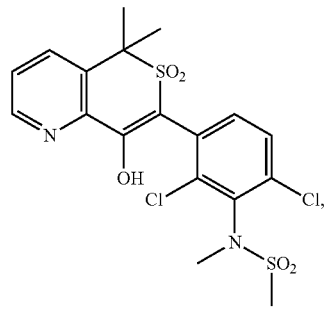

I-2

N-[2,6-dichloro-3-(8-hydroxy-6,6-dioxo-5H-thiopyrano[4,3-b]pyridin-7-yl)phenyl]-N-methyl-methanesulfonamide of the formula I-3

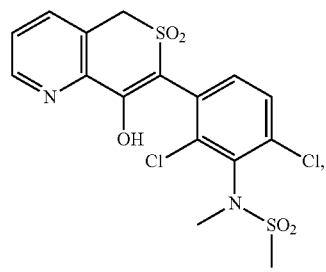

I-3

N-[2,4-dichloro-3-(8-hydroxy-6,6-dioxo-5H-thiopyrano[4,3-b]pyridin-7-yl)phenyl]-N-methyl-methanesulfonamide of the formula I-4

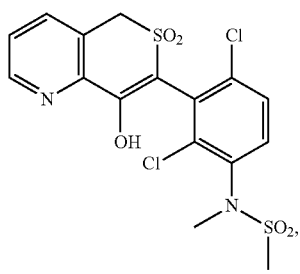

I-4

N-[2,4-dichloro-3-(8-hydroxy-6,6-dioxo-5H-thiopyrano[4,3-b]pyridin-7-yl)phenyl]methanesulfonamide of the formula I-5

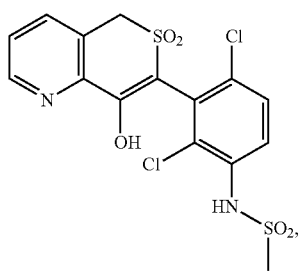

I-5

N-[2,4-dichloro-3-(8-hydroxy-5,5-dimethyl-6,6-dioxo-thiopyrano[4,3-b]pyridin-7-yl)phenyl]methanesulfonamide of the formula I-6

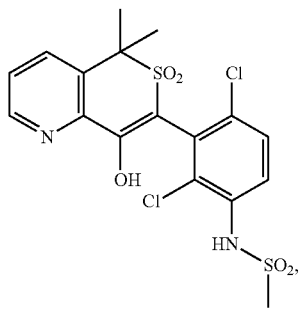

I-6

N-[2,4-dichloro-3-(8-hydroxy-5,5-dimethyl-6,6-dioxo-thiopyrano[4,3-b]pyridin-7-yl)phenyl]-methyl-methanesulfonamide of the formula I-7

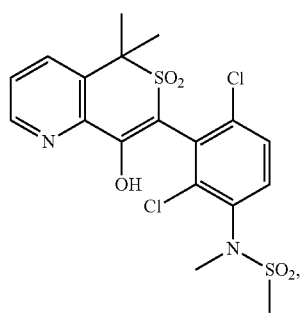

I-7

N-[2,6-dichloro-3-(8-hydroxy-6,6-dioxo-5H-thiopyrano[4,3-b]pyridin-7-yl)phenyl]-N-ethyl-methanesulfonamide of the formula I-8

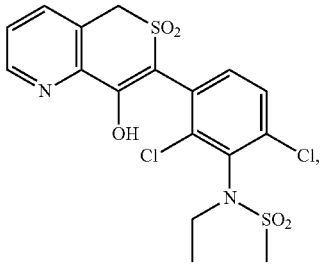

I-8

N-[2,6-dichloro-3-(8-hydroxy-5,5-dimethyl-6,6-dioxo-thiopyrano[4,3-b]pyridin-7-yl)phenyl]-ethyl-methanesulfonamide of the formula I-9

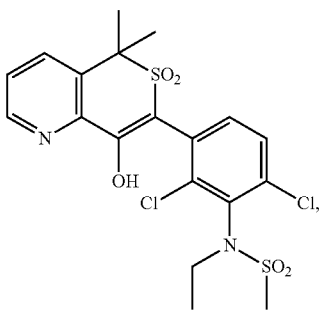

I-9

N-[2,6-dichloro-3-(8-hydroxy-6,6-dioxo-5H-thiopyrano[4,3-b]pyridin-7-yl)phenyl]-N-isopropyl-methanesulfonamide of the formula I-10

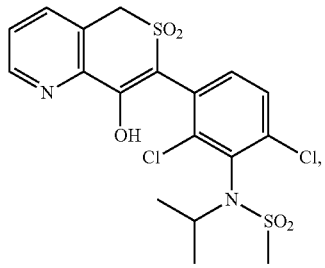

I-10

N-[2,6-dichloro-3-(8-hydroxy-5,5-dimethyl-6,6-dioxo-thiopyrano[4,3-b]pyridin-7-yl)phenyl]-N-isopropyl-methanesulfonamide of the formula I-11

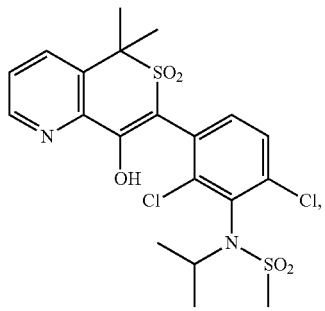

I-11

N-[3-(8-hydroxy-6,6-dioxo-5H-thiopyrano[4,3-b]pyridin-7-yl)-2-methyl-phenyl]-N-methyl-methanesulfonamide of the formula I-12

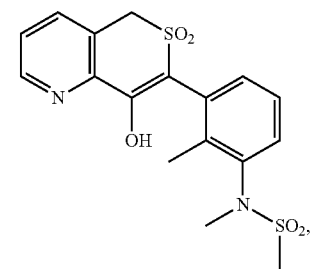

I-12

[5,5-dimethyl-7-[2-methyl-3-[methyl(methylsulfonyl)amino]phenyl]-6,6-dioxo-thiopyrano[4,3-b]pyridin-8-yl] 2,2-dimethylpropanoate of the formula I-13

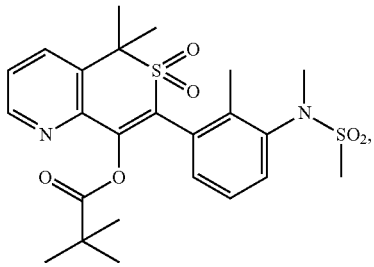

I-13

N-[3-(8-hydroxy-5,5-dimethyl-6,6-dioxo-thiopyrano[4,3-b]pyridin-7-yl)-2-methyl-phenyl]-N-methyl-methanesulfonamide of the formula I-14

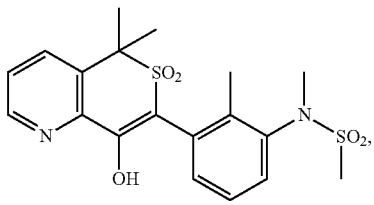

I-14

N-[2-chloro-3-(8-hydroxy-6,6-dioxo-5H-thiopyrano[4,3-b]pyridin-7-yl)phenyl]-N-methyl-methanesulfonamide of the formula I-15

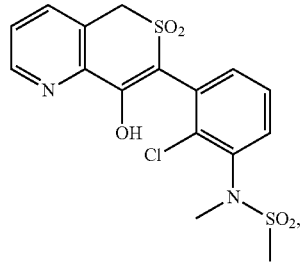

I-15

[7-[2-chloro-3-[methyl(methylsulfonyl)amino]phenyl]-5,5-dimethyl-6,6-dioxo-thiopyrano[4,3-b]pyridin-8-yl] 2,2-dimethylpropanoate of the formula I-16

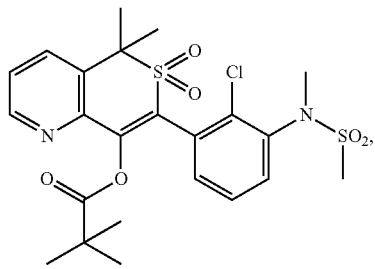

N-[2-chloro-3-(8-hydroxy-5,5-dimethyl-6,6-dioxo-thiopyrano[4,3-b]pyridin-7-yl)phenyl]-N-methyl-methanesulfonamide of the formula I-17

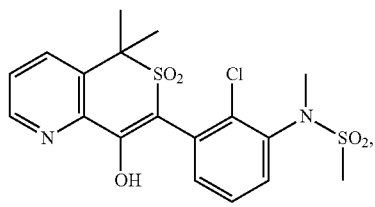

N-[2,6-dichloro-3-(8-hydroxy-6,6-dioxo-5H-thiopyrano[4,3-b]pyridin-7-yl)phenyl]-N-methyl-ethanesulfonamide of the formula I-18

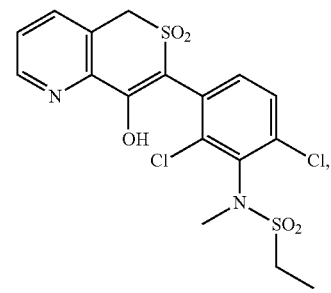

N-[2,6-dichloro-3-(8-hydroxy-5,5-dimethyl-6,6-dioxo-thiopyrano[4,3-b]pyridin-7-yl)phenyl]-N-methyl-ethanesulfonamide of the formula I-19

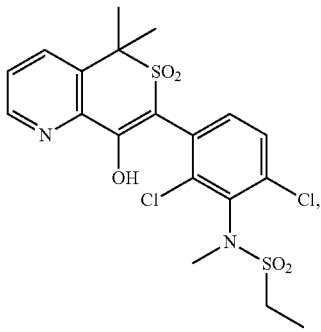

1-cyclopropyl-N-[2,6-dichloro-3-(8-hydroxy-6,6-dioxo-5H-thiopyrano[4,3-b]pyridin-7-yl)phenyl]-methyl-methanesulfonamide of the formula I-20

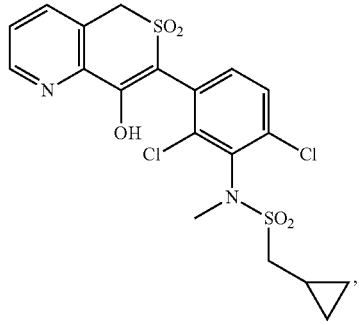

1-cyclopropyl-N-[2,6-dichloro-3-(8-hydroxy-5,5-dimethyl-6,6-dioxo-thiopyrano[4,3-b]pyridin-7-yl)phenyl]-N-methyl-methanesulfonamide of the formula I-21

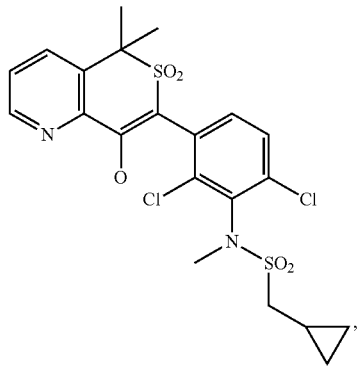

2,6-dichloro-3-(8-hydroxy-6,6-dioxo-5H-thiopyrano[4,3-b]pyridin-7-yl)phenyl] N,N-dimethylsulfamate of the formula I-22

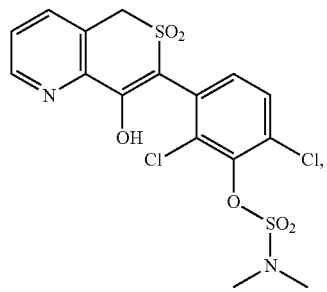

I-22

N-cyclopropyl-N-[2,6-dichloro-3-(8-hydroxy-5,5-dimethyl-6,6-dioxo-thiopyrano[4,3-b]pyridin-7-yl)phenyl]methanesulfonamide of the formula I-25

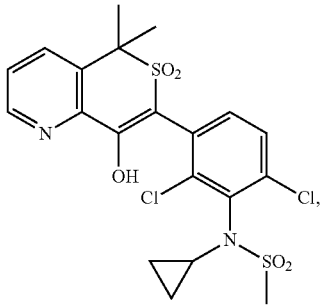

I-25

2,6-dichloro-3-(8-hydroxy-5,5-dimethyl-6,6-dioxo-thiopyrano[4,3-b]pyridin-7-yl)phenyl] N,N-dimethylsulfamate of the formula I-23

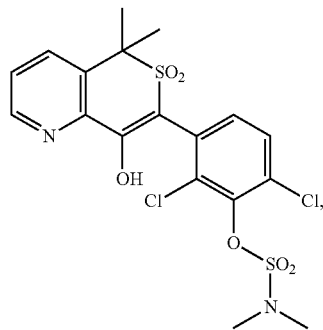

I-23

N-[6-chloro-3-(8-hydroxy-6,6-dioxo-5H-thiopyrano[4,3-b]pyridin-7-yl)-2-methyl-phenyl]-N-methyl-methanesulfonamide of the formula I-26

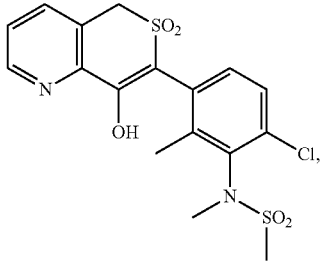

I-26

N-cyclopropyl-N-[2,6-dichloro-3-(8-hydroxy-6,6-dioxo-5H-thiopyrano[4,3-b]pyridin-7-yl)phenyl] methanesulfonamide of the formula I-24

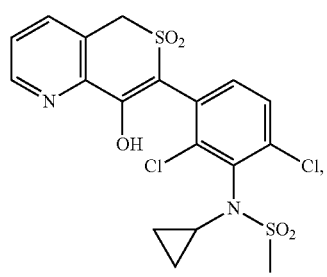

I-24

N-[2,6-dichloro-3-(8-hydroxy-6,6-dioxo-5H-thiopyrano[4,3-b]pyridin-7-yl)phenyl]-N-methyl-cyclopropanesulfonamide of the formula I-27

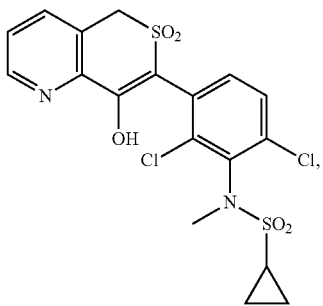

I-27

N-[2,6-dichloro-3-(8-hydroxy-5,5-dimethyl-6,6-dioxo-thiopyrano[4,3-b]pyridin-7-yl)phenyl]-N-methyl-cyclopropanesulfonamide of the formula I-28

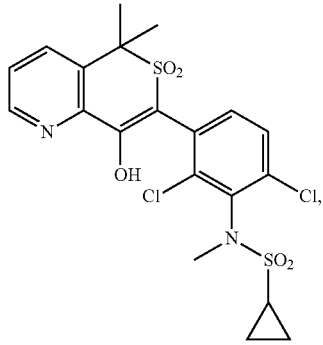

N-[6-chloro-3-(8-hydroxy-5,5-dimethyl-6,6-dioxo-thiopyrano[4,3-b]pyridin-7-yl)-2-methyl-phenyl]-N-methyl-methanesulfonamide of the formula I-29

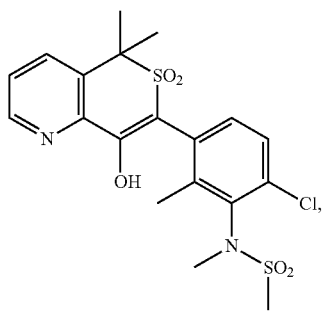

7-[2,4-dichloro-3-[methyl(methylsulfonyl)amino]phenyl]-5,5-dimethyl-6,6-dioxo-thiopyrano[4,3-b]pyridin-8-yl] 2,2-dimethylpropanoate of the formula I-30

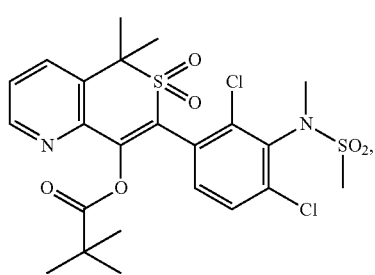

N-[6-chloro-3-(8-hydroxy-6,6-dioxo-5H-thiopyrano[4,3-b]pyridin-7-yl)-2-(trifluoromethyl)phenyl]-N-methyl-methanesulfonamide of the formula I-31

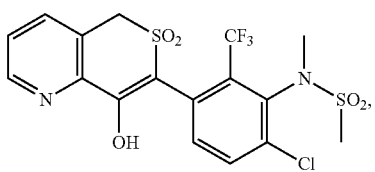

N-[6-chloro-3-(8-hydroxy-5,5-dimethyl-6,6-dioxo-thiopyrano[4,3-b]pyridin-7-yl)-2-(trifluoromethyl)phenyl]-N-methyl-methanesulfonamide of the formula I-32

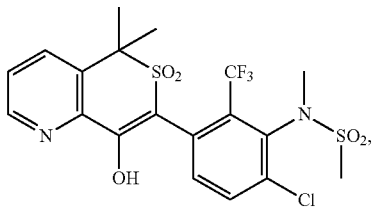

N-[3-(8-hydroxy-6,6-dioxo-5H-thiopyrano[4,3-b]pyridin-7-yl)-2-methylsulfonyl-phenyl]-N-methyl-methanesulfonamide of the formula I-33

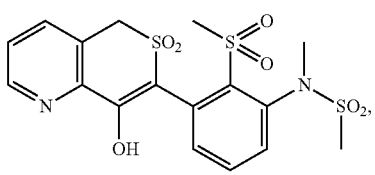

N-[3-(8-hydroxy-5,5-dimethyl-6,6-dioxo-thiopyrano[4,3-b]pyridin-7-yl)-2-methylsulfonyl-phenyl]-N-methyl-methanesulfonamide of the formula I-34

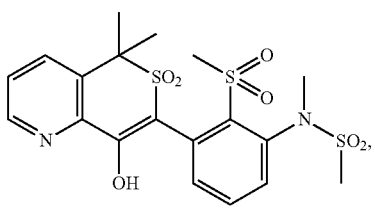

N-[3-(8-hydroxy-6,6-dioxo-5H-thiopyrano[4,3-b]pyridin-7-yl)-2-(trifluoromethyl)phenyl]-N-methyl-methanesulfonamide of the formula I-35

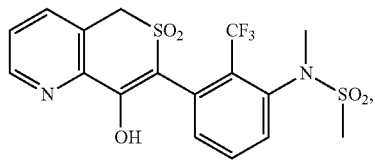

I-35

N-[3-(8-hydroxy-5,5-dimethyl-6,6-dioxo-thiopyrano[4,3-b]pyridin-7-yl)-2-(trifluoromethyl)phenyl]-N-methyl-methanesulfonamide of the formula I-36

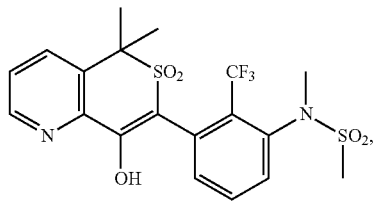

I-36

N-[2,6-dichloro-3-(3-fluoro-8-hydroxy-6,6-dioxo-5H-thiopyrano[4,3-b]pyridin-7-yl)phenyl]-N-methyl-methanesulfonamide of the formula I-37

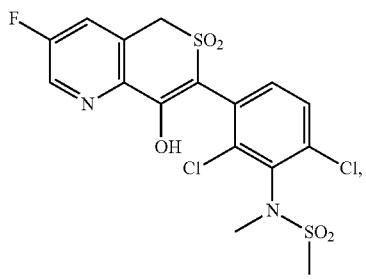

I-37

N-[2,6-dichloro-3-(3-fluoro-8-hydroxy-5,5-dimethyl-6,6-dioxo-thiopyrano[4,3-b]pyridin-7-yl)phenyl]-N-methyl-methanesulfonamide of the formula I-38

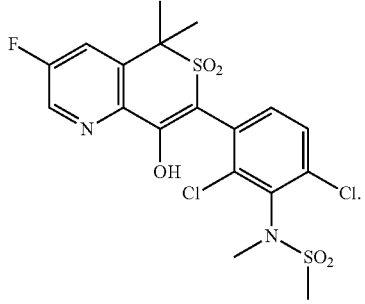

I-38

In a particularly preferred embodiment, the compounds I of this invention are selected from the group consisting of I-2, I-3, I-6, I-7, I-8, I-9, I-11, I-14, I-19, I-25, I-28, I-29, I-30, I-32, I-37 and I-38.

In an especially preferred embodiment, the compound I of this invention is N-[2,6-dichloro-3-(8-hydroxy-6,6-dioxo-5H-thiopyrano[4,3-b]pyridin-7-yl)phenyl]methanesulfonamide of the formula I-1.

In an especially preferred embodiment, the compound I of this invention is N-[2,6-dichloro-3-(8-hydroxy-5,5-dimethyl-6,6-dioxo-thiopyrano[4,3-b]pyridin-7-yl)phenyl]-N-methyl-methanesulfonamide of the formula I-2.

In an especially preferred embodiment, the compound I of this invention is N-[2,6-dichloro-3-(8-hydroxy-6,6-dioxo-5H-thiopyrano[4,3-b]pyridin-7-yl)phenyl]-N-methyl-methanesulfonamide of the formula I-3.

In an especially preferred embodiment, the compound I of this invention is N-[2,4-dichloro-3-(8-hydroxy-6,6-dioxo-5H-thiopyrano[4,3-b]pyridin-7-yl)phenyl]-N-methyl-methanesulfonamide of the formula I-4.

In an especially preferred embodiment, the compound I of this invention is N-[2,4-dichloro-3-(8-hydroxy-6,6-dioxo-5H-thiopyrano[4,3-b]pyridin-7-yl)phenyl]methanesulfonamide of the formula I-5.

In an especially preferred embodiment, the compound I of this invention is N-[2,4-dichloro-3-(8-hydroxy-5,5-dimethyl-6,6-dioxo-thiopyrano[4,3-b]pyridin-7-yl)phenyl]methanesulfonamide of the formula I-6.

In an especially preferred embodiment, the compound I of this invention is N-[2,4-dichloro-3-(8-hydroxy-5,5-dimethyl-6,6-dioxo-thiopyrano[4,3-b]pyridin-7-yl)phenyl]-N-methyl-methanesulfonamide of the formula I-7.

In an especially preferred embodiment, the compound I of this invention is N-[2,6-dichloro-3-(8-hydroxy-6,6-dioxo-5H-thiopyrano[4,3-b]pyridin-7-yl)phenyl]-N-ethyl-methanesulfonamide of the formula I-8.

In an especially preferred embodiment, the compound I of this invention is N-[2,6-dichloro-3-(8-hydroxy-5,5-dimethyl-6,6-dioxo-thiopyrano[4,3-b]pyridin-7-yl)phenyl]-N-ethyl-methanesulfonamide of the formula I-9.

In an especially preferred embodiment, the compound I of this invention is N-[2,6-dichloro-3-(8-hydroxy-6,6-dioxo-5H-thiopyrano[4,3-b]pyridin-7-yl)phenyl]-N-isopropyl-methanesulfonamide of the formula I-10.

In an especially preferred embodiment, the compound I of this invention is N-[2,6-dichloro-3-(8-hydroxy-5,5-dimethyl-6,6-dioxo-thiopyrano[4,3-b]pyridin-7-yl)phenyl]-N-isopropyl-methanesulfonamide of the formula I-11.

In an especially preferred embodiment, the compound I of this invention is N-[3-(8-hydroxy-6,6-dioxo-5H-thiopyrano[4,3-b]pyridin-7-yl)-2-methyl-phenyl]-N-methyl-methanesulfonamide of the formula I-12.

In an especially preferred embodiment, the compound I of this invention is [5,5-dimethyl-7-[2-methyl-3-[methyl(methylsulfonyl)amino]phenyl]-6,6-dioxo-thiopyrano[4,3-b]pyridin-8-yl] 2,2-dimethylpropanoate of the formula I-13.

In an especially preferred embodiment, the compound I of this invention is N-[3-(8-hydroxy-5,5-dimethyl-6,6-dioxo-thiopyrano[4,3-b]pyridin-7-yl)-2-methyl-phenyl]-N-methyl-methanesulfonamide of the formula I-14.

In an especially preferred embodiment, the compound I of this invention is N-[2-chloro-3-(8-hydroxy-6,6-dioxo-5H-thiopyrano[4,3-b]pyridin-7-yl)phenyl]-N-methyl-methanesulfonamide of the formula I-15.

In an especially preferred embodiment, the compound I of this invention is [7-[2-chloro-3-[methyl(methylsulfonyl)amino]phenyl]-5,5-dimethyl-6,6-dioxo-thiopyrano[4,3-b]pyridin-8-yl] 2,2-dimethylpropanoate of the formula I-16.

In an especially preferred embodiment, the compound I of this invention is N-[2-chloro-3-(8-hydroxy-5,5-dimethyl-6,6-dioxo-thiopyrano[4,3-b]pyridin-7-yl)phenyl]-N-methyl-methanesulfonamide of the formula I-17.

In an especially preferred embodiment, the compound I of this invention is N-[2,6-dichloro-3-(8-hydroxy-6,6-dioxo-5H-thiopyrano[4,3-b]pyridin-7-yl)phenyl]-N-methyl-ethanesulfonamide of the formula I-18.

In an especially preferred embodiment, the compound I of this invention is N-[2,6-dichloro-3-(8-hydroxy-5,5-dimethyl-6,6-dioxo-thiopyrano[4,3-b]pyridin-7-yl)phenyl]-N-methyl-ethanesulfonamide of the formula I-19.

In an especially preferred embodiment, the compound I of this invention is 1-cyclopropyl-N-[2,6-dichloro-3-(8-hydroxy-6, 6-dioxo-5H-thiopyrano[4,3-b]pyridin-7-yl)phenyl]-N-methyl-methanesulfonamide of the formula I-20.

In an especially preferred embodiment, the compound I of this invention is 1-cyclopropyl-N-[2,6-dichloro-3-(8-hydroxy-5, 5-dimethyl-6,6-dioxo-thiopyrano[4,3-b]pyridin-7-yl)phenyl]-N-methyl-methanesulfonamide of the formula I-21.

In an especially preferred embodiment, the compound I of this invention is 2,6-dichloro-3-(8-hydroxy-6,6-dioxo-5H-thiopyrano[4,3-b]pyridin-7-yl)phenyl] N,N-dimethylsulfamate of the formula I-22.

In an especially preferred embodiment, the compound I of this invention is 2,6-dichloro-3-(8-hydroxy-5,5-dimethyl-6,6-dioxo-thiopyrano[4,3-b]pyridin-7-yl)phenyl] N,N-dimethylsulfamate of the formula I-23.

In an especially preferred embodiment, the compound I of this invention is N-cyclopropyl-N-[2,6-dichloro-3-(8-hydroxy-6,6-dioxo-5H-thiopyrano[4,3-b]pyridin-7-yl)phenyl]methanesulfonamide of the formula I-24.

In an especially preferred embodiment, the compound I of this invention is N-cyclopropyl-N-[2,6-dichloro-3-(8-hydroxy-5, 5-dimethyl-6,6-dioxo-thiopyrano[4,3-b]pyridin-7-yl)phenyl]methanesulfonamide of the formula I-25.

In an especially preferred embodiment, the compound I of this invention is N-[6-chloro-3-(8-hydroxy-6,6-dioxo-5H-thiopyrano[4,3-b]pyridin-7-yl)-2-methyl-phenyl]-N-methyl-methanesulfonamide of the formula I-26.

In an especially preferred embodiment, the compound I of this invention is N-[2,6-dichloro-3-(8-hydroxy-6,6-dioxo-5H-thiopyrano[4,3-b]pyridin-7-yl)phenyl]-N-methyl-cyclopropanesulfonamide of the formula I-27.

In an especially preferred embodiment, the compound I of this invention is N-[2,6-dichloro-3-(8-hydroxy-5,5-dimethyl-6,6-dioxo-thiopyrano[4,3-b]pyridin-7-yl)phenyl]-N-methyl-cyclopropanesulfonamide of the formula I-28.

In an especially preferred embodiment, the compound I of this invention is N-[6-chloro-3-(8-hydroxy-5,5-dimethyl-6, 6-dioxo-thiopyrano[4,3-b]pyridin-7-yl)-2-methyl-phenyl]-N-methyl-methanesulfonamide of the formula I-29.

In an especially preferred embodiment, the compound I of this invention is 7-[2,4-dichloro-3-[methyl(methylsulfonyl)amino]phenyl]-5,5-dimethyl-6,6-dioxo-thiopyrano[4,3-b]pyridin-8-yl] 2,2-dimethylpropanoate of the formula I-30.

In an especially preferred embodiment, the compound I of this invention is N-[6-chloro-3-(8-hydroxy-6,6-dioxo-5H-thiopyrano[4,3-b]pyridin-7-yl)-2-(trifluoromethyl)phenyl]-N-methyl-methanesulfonamide of the formula I-31.

In an especially preferred embodiment, the compound I of this invention is N-[6-chloro-3-(8-hydroxy-5,5-dimethyl-6, 6-dioxo-thiopyrano[4,3-b]pyridin-7-yl)-2-(trifluoromethyl)phenyl]-N-methyl-methanesulfonamide of the formula I-32.

In an especially preferred embodiment, the compound I of this invention is N-[3-(8-hydroxy-6,6-dioxo-5H-thiopyrano[4,3-b]pyridin-7-yl)-2-methylsulfonyl-phenyl]-N-methyl-methanesulfonamide of the formula I-33.

In an especially preferred embodiment, the compound I of this invention is N-[3-(8-hydroxy-5,5-dimethyl-6,6-dioxo-thiopyrano[4,3-b]pyridin-7-yl)-2-methylsulfonyl-phenyl]-N-methyl-methanesulfonamide of the formula I-34.

In an especially preferred embodiment, the compound I of this invention is N-[3-(8-hydroxy-6,6-dioxo-5H-thiopyrano[4,3-b]pyridin-7-yl)-2-(trifluoromethyl)phenyl]-N-methyl-methanesulfonamide of the formula I-35.

In an especially preferred embodiment, the compound I of this invention is N-[3-(8-hydroxy-5,5-dimethyl-6,6-dioxo-thiopyrano[4,3-b]pyridin-7-yl)-2-(trifluoromethyl)phenyl]-N-methyl-methanesulfonamide of the formula I-36.

In an especially preferred embodiment, the compound I of this invention is N-[2,6-dichloro-3-(3-fluoro-8-hydroxy-6,6-dioxo-5H-thiopyrano[4,3-b]pyridin-7-yl)phenyl]-N-methyl-methanesulfonamide of the formula I-37.

In an especially preferred embodiment, the compound I of this invention is N-[2,6-dichloro-3-(3-fluoro-8-hydroxy-5,5-dimethyl-6,6-dioxo-thiopyrano[4,3-b]pyridin-7-yl)phenyl]-N-methyl-methanesulfonamide of the formula I-38.

The substituted pyridine compounds of formula I according to the invention can be prepared by standard processes of organic chemistry, for example by the following processes.

Picolinic acid derivative of the formula II can be reacted with the thiol compound of the formula III to yield thioether compounds of the formula IV. In the formulae II and III, the variables have the meaning given for the compounds of formula I. The group Hal is a halogen atom, in particular Cl or Br. W is a methyl or ethyl group.

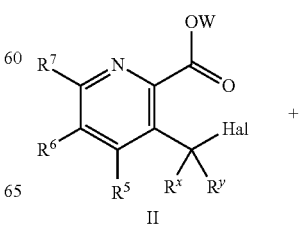

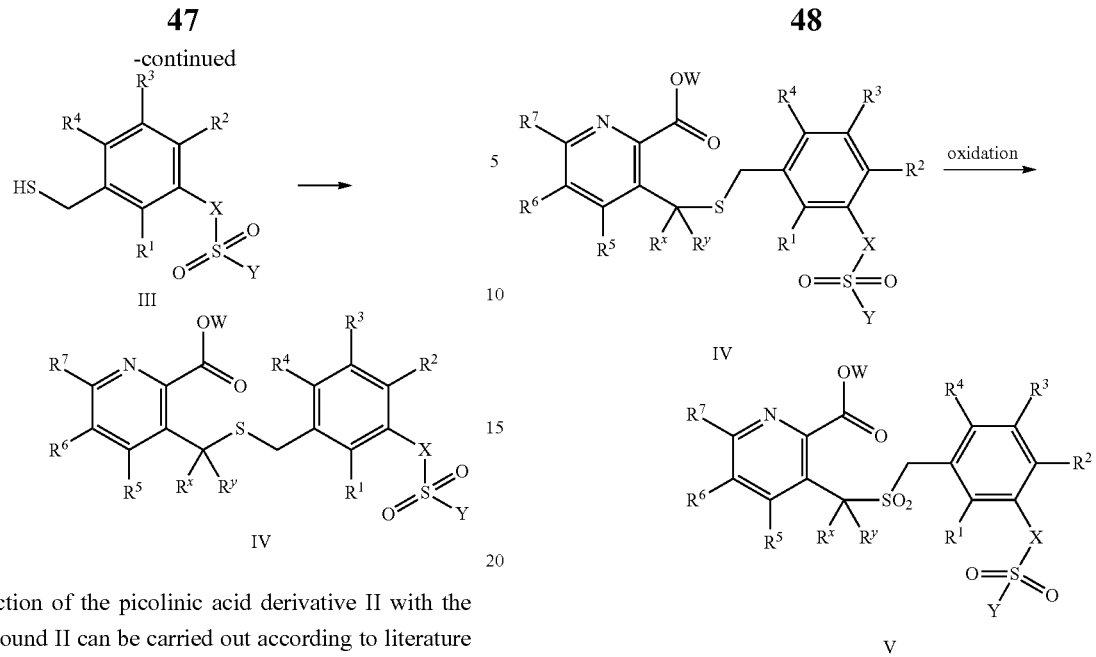

The reaction of the picolinic acid derivative II with the thiol compound II can be carried out according to literature procedures [cf. Journal of the Chemical Society, Perkin Transactions 1: Organic and Bio-Organic Chemistry (1972-1999) (1984), (7), 1501-1505] in an organic solvent, such as, for example acetonitrile or dimethylformamide (DMF), at temperatures between −78° C. and reflux of the solvent, preferably in a temperature range of from 10° C. to 50° C. It is also possible to use mixtures of the solvents mentioned. The starting materials II and II are generally reacted with one another in equimolar amounts.

The picolinic acid derivatives II can be prepared according to literature procedures (cf. Journal of Medicinal Chemistry, 32(4), 827-33; 1989).

The thiol compound Ill can be prepared from e.g. the corresponding thioacetate by cleavage with an alkali metal hydroxide like sodium hydroxide, potassium hydroxide or lithium hydroxide in water at a temperature of from 0° C. to 100° C., preferably at a temperature of from 10° C. to 30° C. Alternatively, they can also be prepared by cleavage of the thioacetate with potassium carbonate in methanol, preferably at a temperature of from 10° C. to 30° C. The thioacetate can be prepared from correspondingly substituted benzoic acids or halobenzenes on the basis of synthesis known in the literature [cf. Journal of Medicinal Chemistry 4912], 3563-3580 (2006); Journal of Medicinal Chemistry 28(10), 1533-6 (1985); US 2004/077901; US 2004/068141; Chemistry-A European Journal 14(26), 7969-7977 (2008); Journal of Enzyme Inhibition and Medicinal Chemistry 17(3), 187-196 (2002)]. The substituted benzoic acids or halobenzenes can be prepared using standard organic chemistry transformations known to the person skilled in the art The thioether compound IV can be reacted with an oxidizing agent to give the sulfone compound V.

Suitable oxidizing agents include, for example, 3-chloroperoxybenzoic acid or hydrogen peroxide. The oxidation of the thioether compound IV to the sulfone compound V is usually carried out in an organic solvent, such as, for example methylene chloride, at a temperature of from 0° C. to reflux of the solvent, preferably at a temperature of from 10° C. to 25° C. The amount of the oxidizing agent is generally at least 2 molar equivalents relative to the thioether compound IV.

The sulfone compound V can be reacted with a base to give compounds of the formula I.1 (which correspond to compounds of the formula I with R=hydroxyl).

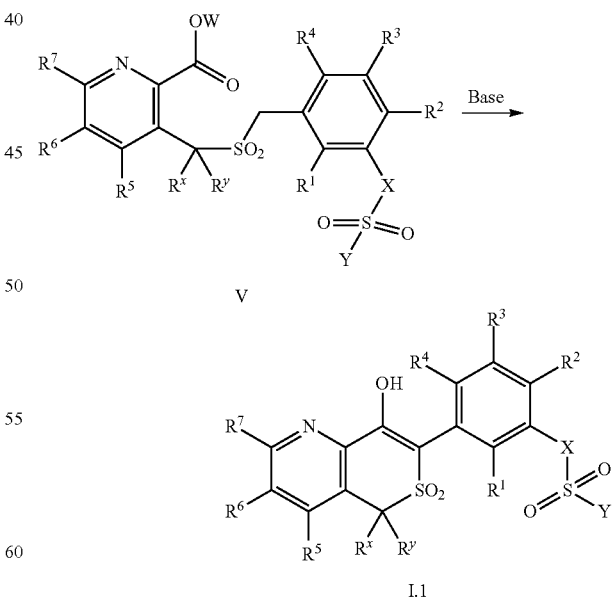

The cyclization reaction is usually carried out at a temperature of from 0° C. to 100° C. in an organic solvent in the presence of a base. Suitable inert organic solvents are tetrahydrofuran (THF), acetonitrile or dimethylformamide.

It is also possible to use mixtures of the solvents mentioned. Suitable bases are sodium tert-butoxide, potassium tert-butoxide, lithium tert-butoxide, cesium carbonate, 1,8-diazabicyclo[5.4.0]undec-7-ene and a phosphazene base such as 1-tert-Butyl-2,2,4,4,4-pentakis(dimethylamino)-$2\lambda^5,4\lambda^5$-catenadi(posphazene) (P2-t-Bu). The bases are generally employed in equimolar amounts; however, they can also be used in excess or, if appropriate, as solvents.

The hydroxyl compound I.1 can be reacted with a base and an electrophile like an alkyl or acyl halide $R^4$-Hal (wherein Hal denotes a halogen atom, in particular Cl or Br) to give compounds of the formula I.2 (which correspond to compounds of the formula I with R=O—$R^4$).

The reaction is usually carried out at a temperature of from 0° C. to 80° C. in an inert organic solvent, such as dichloromethane or tetrahydrofuran in the presence of a base, such as triethylamine, pyridine or potassium tert-butoxide.

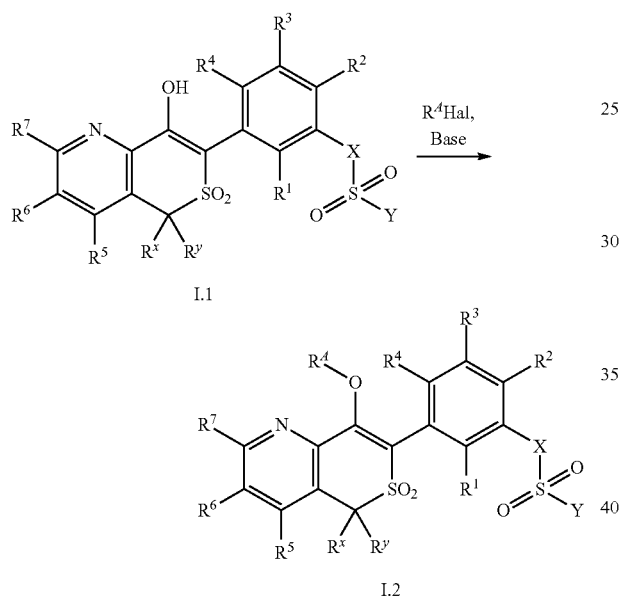

In case the preparation of compounds I with $R^x$ and/or $R^y$=alkyl or cycloalkyl is desired, the compound I.2 which is substituted by hydrogen in the $R^x$ and/or $R^y$ positions can be deprotonated with a base, such as potassium tert-butoxide, cesium carbonate, 1,8-diazabicyclo[5.4.0]undec-7-ene (DBU) or 1-tert-Butyl-2,2,4,4,4-pentakis(dimethylamino)-$2\lambda^5,4\lambda^5$-catenadi(posphazene) (P2-t-Bu) in an inert organic solvent, such as tetrahydrofuran, acetonitrile or dimethylformamide in the presence of an alkylating agent like bromomethane, iodomethane or dibromomethane at a temperature from 0° C. to 80° C.

Compounds of formula I with R=hydroxyl can be obtained by treating compounds of formula I.2 with $R^x$ and/or $R^y$=alkyl or cycloalkyl and $R^4$ is a base or acid labile group with water in the presence of a base, such as lithium hydroxide, in a solvent, such as tetrahydrofuran, or in the presence of an acid, such as concentrated sulfuric acid with or without a solvent.

With respect to the variables, preferred embodiments of the intermediates II, III, IV and V correspond to those described above for the variables of the compound of formula I.

The reaction mixtures are worked up in a customary manner, for example by mixing with water, separating the phases and, if appropriate, chromatographic purification of the crude products.

Some of the intermediates and end products are obtained in the form of colorless or slightly brownish viscous oils which are purified or freed from volatile components under reduced pressure and at moderately elevated temperature. If the intermediates and end products are obtained as solids, the purification can also be carried out by recrystallization or digestion.

If individual compounds I cannot be obtained by the routes described above, they can be prepared by derivatization of other compounds I.

If the synthesis yields mixtures of isomers, a separation is generally however not necessarily required since in some cases the individual isomers can be interconverted during work-up for use or during application (for example under the action of light, acids or bases). Such conversions may also take place after application, for example in the case of the treatment of plants in the treated plant or in the harmful plant to be controlled.

As shown above the thioether compounds of formula IV are novel thioether compounds and suitable intermediates for the preparation of the compounds of formula I according to the present invention.

Therefore the present invention also provides novel thioether compounds of formula IV

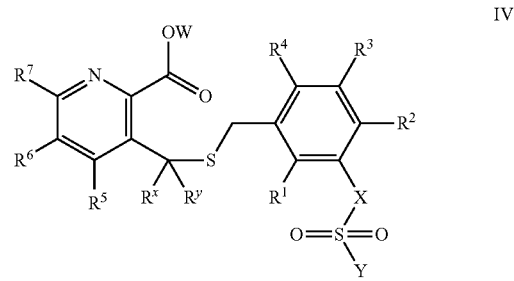

wherein the variables $R^1$, $R^2$, $R^3$, $R^4$, $R^5$, $R^6$, $R^7$, $R^x$, $R^y$, X and Y and have the same meaning given for the compound of formula I and W is methyl or ethyl.

With respect to the variables $R^1$, $R^2$, $R^3$, $R^4$, $R^5$, $R^6$, $R^7$, $R^x$, $R^y$, X and Y, preferred embodiments of the intermediate IV correspond to those described above for the variables of the compound of formula I.

As shown above the sulfone compounds of formula V are novel compounds and suitable intermediates for the preparation of the compounds of formula I according to the present invention.

Therefore the present invention also provides novel sulfone compounds of formula V

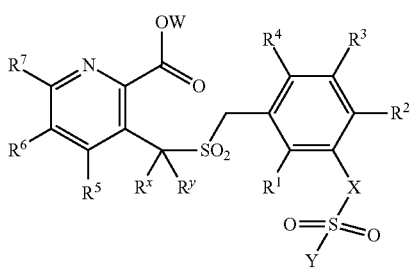

(V)

wherein the variables $R^1$, $R^2$, $R^3$, $R^4$, $R^5$, $R^6$, $R^7$, $R^x$, $R^y$, X and Y have the same meaning given for the compound of formula I and W is methyl or ethyl.

With respect to the variables $R^1$, $R^2$, $R^3$, $R^4$, $R^5$, $R^6$, $R^7$, $R^x$, $R^y$, X and Y, preferred embodiments of the intermediate V correspond to those described above for the variables of the compound of formula I.

To widen the spectrum of action and to achieve synergistic effects, the compounds of formula I may be mixed with a large number of representatives of other herbicidal or growth-regulating active ingredient groups and then applied concomitantly. Suitable components for mixtures are, for example, herbicides from the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ether, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, ureas.

It may furthermore be beneficial to apply the compounds of formula I alone or in combination with other herbicides, or else in the form of a mixture with other crop protection agents, for example together with agents for controlling pests or phytopathogenic fungi or bacteria. Also of interest is the miscibility with mineral salt solutions, which are employed for treating nutritional and trace element deficiencies. Other additives such as non-phytotoxic oils and oil concentrates may also be added.

The further herbicidal compound B (component B or herbicide B) is preferably selected from the herbicides of class b1) to b15):
b1) lipid biosynthesis inhibitors;
b2) acetolactate synthase inhibitors (ALS inhibitors);
b3) photosynthesis inhibitors;
b4) protoporphyrinogen-IX oxidase inhibitors,
b5) bleacher herbicides;
b6) enolpyruvyl shikimate 3-phosphate synthase inhibitors (EPSP inhibitors);
b7) glutamine synthetase inhibitors;
b8) 7,8-dihydropteroate synthase inhibitors (DHP inhibitors);
b9) mitosis inhibitors;
b10) inhibitors of the synthesis of very long chain fatty acids (VLCFA inhibitors);
b11) cellulose biosynthesis inhibitors;
b12) decoupler herbicides;
b13) auxinic herbicides;
b14) auxin transport inhibitors; and
b15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyldymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters;
including their agriculturally acceptable salts or derivatives.

Preference is given to those compositions according to the present invention comprising at least one herbicide B selected from herbicides of class b2, b3, b4, b5, b6, b9 and b10.

Specific preference is given to those compositions according to the present invention which comprise at least one herbicide B selected from the herbicides of class b3, b4, b5, b6, b9 and b10.

Particular preference is given to those compositions according to the present invention which comprise at least one herbicide B selected from the herbicides of class b3, b4, b5, b6 and b10.

Examples of herbicides B which can be used in combination with the compounds of formula I according to the present invention are:
b1) from the group of the lipid biosynthesis inhibitors:
ACC-herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6, 6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); and non ACC herbicides such as benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;

b2) from the group of the ALS inhibitors:
sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron,
imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam,
pyrimidinylbenzoates such as bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5), N-(4-bromophenyl)-2-[(4,6-dimethoxy-2-pyrimidinyl)oxy] benzenemethanamine (CAS 420138-01-8),
sulfonylaminocarbonyl-triazolinone herbicides such as flucarbazone, flucarbazone-sodium, propoxycarbazone, propoxycarbazone-sodium, thiencarbazone and thiencarbazone-methyl; and triafamone;
among these, a preferred embodiment of the invention relates to those compositions comprising at least one imidazolinone herbicide;

b3) from the group of the photosynthesis inhibitors:
amicarbazone, inhibitors of the photosystem II, e.g. triazine herbicides, including of chlorotriazine, triazinones, triazindiones, methylthiotriazines and pyridazinones such as ametryn, atrazine, chloridazon, cyanazine, desmetryn, dimethametryn, hexazinone, metribuzin, prometon, prometryn, propazine, simazine, simetryn, terbumeton, terbuthylazin, terbutryn and trietazin, aryl urea such as chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates such as desmedipham, karbutilat, phenmedipham, phenmedipham-ethyl, nitrile herbicides such as bromofenoxim, bromoxynil and its salts and esters, ioxynil and its salts and esters, uraciles such as bromacil, lenacil and terbacil, and bentazon and bentazon-sodium, pyridate, pyridafol, pentanochlor and propanil and inhibitors of the photosystem I such as diquat, diquat-dibromide, paraquat, paraquat-dichloride and paraquat-dimetilsulfate. Among these, a preferred embodiment of the invention relates to those compositions comprising at least one aryl urea herbicide. Among these, likewise a preferred embodiment of the invention relates to those compositions comprising at least one triazine herbicide. Among these, likewise a preferred embodiment of the invention relates to those compositions comprising at least one nitrile herbicide;

b4) from the group of the protoporphyrinogen-IX oxidase inhibitors:
acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, trifludimoxazin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7), 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0), 1-methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0), methyl (E)-4-[2-chloro-5-[4-chloro-5-(difluoromethoxy)-1H-methyl-pyrazol-3-yl]-4-fluoro-phenoxy]-3-methoxy-but-2-enoate (CAS 948893-00-3), and 3-[7-chloro-5-fluoro-2-(trifluoromethyl)-1H-benzimidazol-4-yl]-1-methyl-6-(trifluoromethyl)-1H-pyrimidine-2,4-dione (CAS 212754-02-4);

b5) from the group of the bleacher herbicides:
PDS inhibitors: beflubutamid, diflufenican, fluridone, flurochloridone, flurtamone, norflurazon, picolinafen, and 4-(3-trifluoromethylphenoxy)-2-(4-trifluoromethylphenyl)pyrimidine (CAS 180608-33-7), HPPD inhibitors: benzobicyclon, benzofenap, bicyclopyrone, clomazone, fenquintrione, isoxaflutole, mesotrione, pyrasulfotole, pyrazolynate, pyrazoxyfen, sulcotrione, tefuryltrione, tembotrione, tolpyralate, topramezone, bleacher, unknown target: aclonifen, amitrole and flumeturon;

b6) from the group of the EPSP synthase inhibitors:
glyphosate, glyphosate-isopropylammonium, glyposate-potassium and glyphosate-trimesium (sulfosate);

b7) from the group of the glutamine synthase inhibitors:
bilanaphos (bialaphos), bilanaphos-sodium, glufosinate, glufosinate-P and glufosinate-ammonium;

b8) from the group of the DHP synthase inhibitors:
asulam;

b9) from the group of the mitosis inhibitors:
compounds of group K1: dinitroanilines such as benfluralin, butralin, dinitramine, ethalfluralin, fluchloralin, oryzalin, pendimethalin, prodiamine and trifluralin, phosphoramidates such as amiprophos, amiprophos-methyl, and butamiphos, benzoic acid herbicides such as chlorthal, chlorthal-dimethyl, pyridines such as dithiopyr and thiazopyr, benzamides such as propyzamide and tebutam; compounds of group K2: carbetamide, chlorpropham, flamprop, flamprop-isopropyl, flamprop-methyl, flamprop-M-isopropyl, flamprop-M-methyl and propham; among these, compounds of group K1, in particular dinitroanilines are preferred;
b10) from the group of the VLCFA inhibitors:
chloroacetamides such as acetochlor, alachlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides such as flufenacet and mefenacet, acetanilides such as diphenamid, napraonilide, napropamide and napropamide-M, tetrazolinones such fentrazamide, and other herbicides such as anilofos, cafenstrole, fenoxasulfone, ipfencarbazone, piperophos, pyroxasulfone and isoxazoline compounds of the formulae II.1, II.2, II.3, II.4, II.5, II.6, II.7, II.8 and II.9

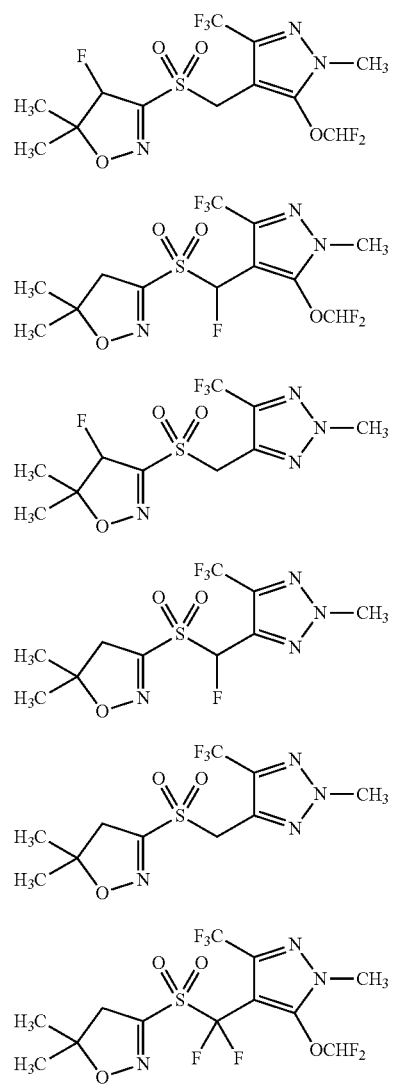

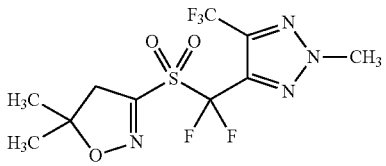

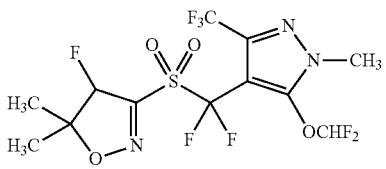

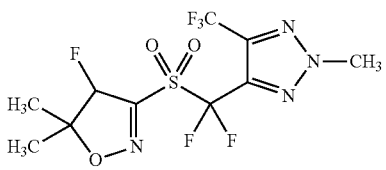

the isoxazoline compounds of the formula (I)I are known in the art, e.g. from WO 2006/024820, WO 2006/037945, WO 2007/071900 and WO 2007/096576;
among the VLCFA inhibitors, preference is given to chloroacetamides and oxyacetamides;
b11) from the group of the cellulose biosynthesis inhibitors:
chlorthiamid, dichlobenil, flupoxam, indaziflam, isoxaben, triaziflam and 1-cyclohexyl-5-pentafluorphenyloxy-1$^4$-[1,2,4,6]thiatriazin-3-ylamine (CAS 175899-01-1);
b12) from the group of the decoupler herbicides:
dinoseb, dinoterb and DNOC and its salts;
b13) from the group of the auxinic herbicides:
2,4-D and its salts and esters such as clacyfos, 2,4-DB and its salts and esters, aminocyclopyrachlor and its salts and esters, aminopyralid and its salts such as aminopyralid-dimethylammonium, aminopyralid-tris(2-hydroxypropyl) ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, fluroxypyr, fluroxypyr-butometyl, fluroxypyr-meptyl, halauxifen and its salts and esters (CAS 943832-60-8); MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters, triclopyr and its salts and esters, 4-amino-3-chloro-6-(4-chloro-2-fluoro-3-methoxyphenyl)-5-fluoropyridine-2-carboxylic acid and benzyl 4-amino-3-chloro-6-(4-chloro-2-fluoro-3-methoxyphenyl)-5-fluoropyridine-2-carboxylate (CAS 1390661-72-9);
b14) from the group of the auxin transport inhibitors:
diflufenzopyr, diflufenzopyr-sodium, naptalam and naptalam-sodium;
b15) from the group of the other herbicides: bromobutide, chlorflurenol, chlorflurenol-methyl, cinmethylin, cumyluron, cyclopyrimorate (CAS 499223-49-3) and its salts and esters, dalapon, dazomet, difenzoquat, difenzoquat-metilsulfate, dimethipin, DSMA, dymron, endothal and its salts, etobenzanid, flurenol, flurenol-butyl, flurprimidol, fosamine, fosamine-ammonium, indanofan, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine and tridiphane.

Preferred herbicides B that can be used in combination with the compounds of the formula I according to the present invention are:

b1) from the group of the lipid biosynthesis inhibitors: clethodim, clodinafop-propargyl, cycloxydim, cyhalofop-butyl, diclofop-methyl, fenoxaprop-P-ethyl, fluazifop-P-butyl, haloxyfop-P-methyl, metamifop, pinoxaden, profoxydim, propaquizafop, quizalofop-P-ethyl, quizalofop-P-tefuryl, sethoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3, 6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1, 1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); benfuresate, dimepiperate, EPTC, esprocarb, ethofumesate, molinate, orbencarb, prosulfocarb, thiobencarb and triallate;

b2) from the group of the ALS inhibitors: amidosulfuron, azimsulfuron, bensulfuron-methyl, bispyribac-sodium, chlorimuron-ethyl, chlorsulfuron, cloransulam-methyl, cyclosulfamuron, diclosulam, ethametsulfuron-methyl, ethoxysulfuron, flazasulfuron, florasulam, flucarbazone-sodium, flucetosulfuron, flumetsulam, flupyrsulfuron-methyl-sodium, foramsulfuron, halosulfuron-methyl, imazamethabenz-methyl, imazamox, imazapic, imazapyr, imazaquin, imazethapyr, imazosulfuron, iodosulfuron, iodosulfuron-methyl-sodium, iofensulfuron, iofensulfuron-sodium, mesosulfuron, metazosulfuron, metosulam, metsulfuron-methyl, nicosulfuron, orthosulfamuron, oxasulfuron, penoxsulam, primisulfuron-methyl, propoxycarbazon-sodium, propyrisulfuron, prosulfuron, pyrazosulfuron-ethyl, pyribenzoxim, pyrimisulfan, pyriftalid, pyriminobac-methyl, pyrithiobac-sodium, pyroxsulam, rimsulfuron, sulfometuron-methyl, sulfosulfuron, thiencarbazone-methyl, thifensulfuron-methyl, triasulfuron, tribenuron-methyl, trifloxysulfuron, triflusulfuron-methyl, tritosulfuron and triafamone;

b3) from the group of the photosynthesis inhibitors: ametryn, amicarbazone, atrazine, bentazon, bentazone-sodium, bromoxynil and its salts and esters, chloridazone, chlorotoluron, cyanazine, desmedipham, diquat-dibromide, diuron, fluometuron, hexazinone, ioxynil and its salts and esters, isoproturon, lenacil, linuron, metamitron, methabenzthiazuron, metribuzin, paraquat, paraquat-dichloride, phenmedipham, propanil, pyridate, simazine, terbutryn, terbuthylazine and thidiazuron;

b4) from the group of the protoporphyrinogen-IX oxidase inhibitors: acifluorfen-sodium, bencarbazone, benzfendizone, butafenacil, carfentrazone-ethyl, cinidon-ethyl, flufenpyr-ethyl, flumiclorac-pentyl, flumioxazin, fluoroglycofen-ethyl, fomesafen, lactofen, oxadiargyl, oxadiazon, oxyfluorfen, pentoxazone, pyraflufen, pyraflufen-ethyl, saflufenacil, sulfentrazone, tiafenacil, trifludimoxazin, ethyl [3-[2-chloro-4-fluoro-5-(1-methyl-6-trifluoromethyl-2,4-dioxo-1, 2,3,4-tetrahydropyrimidin-3-yl)phenoxy]-2-pyridyloxy]acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7), 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0); 1-methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0), and 3-[7-chloro-5-fluoro-2-(trifluoromethyl)-1H-benzimidazol-4-yl]-1-methyl-6-(trifluoromethyl)-1H-pyrimidine-2, 4-dione (CAS 212754-02-4);

b5) from the group of the bleacher herbicides: aclonifen, amitrole, beflubutamid, benzobicyclon, bicyclopyrone, clomazone, diflufenican, fenquintrione, flumeturon, flurochloridone, flurtamone, isoxaflutole, mesotrione, norflurazon, picolinafen, pyrasulfotole, pyrazolynate, sulcotrione, tefuryltrione, tembotrione, tolpyralate, topramezone and 4-(3-trifluoromethylphenoxy)-2-(4-trifluoromethylphenyl)pyrimidine (CAS 180608-33-7);

b6) from the group of the EPSP synthase inhibitors: glyphosate, glyphosate-isopropylammonium, glyphosate-potassium and glyphosate-trimesium (sulfosate);

b7) from the group of the glutamine synthase inhibitors: glufosinate, glufosinate-P, glufosinate-ammonium;

b8) from the group of the DHP synthase inhibitors: asulam;

b9) from the group of the mitosis inhibitors: benfluralin, dithiopyr, ethalfluralin, flamprop, flamprop-isopropyl, flamprop-methyl, flamprop-M-isopropyl, flamprop-M-methyl, oryzalin, pendimethalin, thiazopyr and trifluralin;

b10) from the group of the VLCFA inhibitors: acetochlor, alachlor, anilofos, butachlor, cafenstrole, dimethenamid, dimethenamid-P, fentrazamide, flufenacet, mefenacet, metazachlor, metolachlor, S-metolachlor, napropamide, napropamide-M, pretilachlor, fenoxasulfone, ipfencarbazone, pyroxasulfone thenylchlor and isoxazoline-compounds of the formulae II.1, II.2, II.3, II.4, II.5, II.6, II.7, II.8 and II.9 as mentioned above;

b11) from the group of the cellulose biosynthesis inhibitors: dichlobenil, flupoxam, indaziflam, isoxaben, triaziflam and 1-cyclohexyl-5-pentafluorphenyloxy-1$^4$-[1,2,4,6]thiatriazin-3-ylamine (CAS 175899-01-1);

b13) from the group of the auxinic herbicides:
2,4-D and its salts and esters, aminocyclopyrachlor and its salts and esters, aminopyralid and its salts such as aminopyralid-dimethylammonium, aminopyralid-tris(2-hydroxypropyl)ammonium and its esters, clopyralid and its salts and esters, dicamba and its salts and esters, dichlorprop-P and its salts and esters, fluroxypyr-meptyl, halauxifen and its salts and esters (CAS 943832-60-8), MCPA and its salts and esters, MCPB and its salts and esters, mecoprop-P and its salts and esters, picloram and its salts and esters, quinclorac, quinmerac, triclopyr and its salts and esters, 4-amino-3-chloro-6-(4-chloro-2-fluoro-3-methoxyphenyl)-5-fluoro-pyridine-2-carboxylic acid and benzyl 4-amino-3-chloro-6-(4-chloro-2-fluoro-3-methoxyphenyl)-5-fluoropyridine-2-carboxylate (CAS 1390661-72-9);

b14) from the group of the auxin transport inhibitors: diflufenzopyr and diflufenzopyr-sodium;

b15) from the group of the other herbicides: bromobutide, cinmethylin, cumyluron, cyclopyrimorate (CAS 499223-49-3) and its salts and esters, dalapon, difenzoquat, difenzoquat-metilsulfate, DSMA, dymron (=daimuron), indanofan, metam, methylbromide, MSMA, oxaziclomefone, pyributicarb and tridiphane.

Particularly preferred herbicides B that can be used in combination with the compounds of the formula I according to the present invention are:

b1) from the group of the lipid biosynthesis inhibitors: clodinafop-propargyl, cycloxydim, cyhalofop-butyl, fenoxaprop-P-ethyl, pinoxaden, profoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3 (6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); esprocarb, prosulfocarb, thiobencarb and triallate;

b2) from the group of the ALS inhibitors: bensulfuron-methyl, bispyribac-sodium, cyclosulfamuron, diclosulam, flumetsulam, flupyrsulfuron-methyl-sodium, foramsulfuron, imazamox, imazapic, imazapyr, imazaquin, imazethapyr, imazosulfuron, iodosulfuron, iodosulfuron-methyl-sodium, iofensulfuron, iofensulfuron-sodium, mesosulfuron, metazosulfuron, nicosulfuron, penoxsulam, propoxycarbazon-sodium, propyrisulfuron, pyrazosulfuron-ethyl, pyroxsulam, rimsulfuron, sulfosulfuron, thiencarbazon-methyl, tritosulfuron and triafamone;

b3) from the group of the photosynthesis inhibitors: ametryn, atrazine, diuron, fluometuron, hexazinone, isoproturon, linuron, metribuzin, paraquat, paraquat-dichloride, propanil, terbutryn and terbuthylazine;

b4) from the group of the protoporphyrinogen-IX oxidase inhibitors: flumioxazin, oxyfluorfen, pyraflufen, pyraflufen-ethyl, saflufenacil, sulfentrazone, trifludimoxazin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), 3-[7-fluoro-3-oxo-4-(prop-2-ynyl)-3,4-dihydro-2H-benzo[1,4] oxazin-6-yl]-1,5-dimethyl-6-thioxo-[1,3,5]triazinan-2,4-dione (CAS 451484-50-7), 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0), and 1-methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0);

b5) from the group of the bleacher herbicides: amitrole, bicyclopyrone, clomazone, diflufenican, fenquintrione, flumeturon, flurochloridone, isoxaflutole, mesotrione, picolinafen, sulcotrione, tefuryltrione, tembotrione, tolpyralate and topramezone;

b6) from the group of the EPSP synthase inhibitors: glyphosate, glyphosate-isopropylammonium and glyphosate-trimesium (sulfosate);

b7) from the group of the glutamine synthase inhibitors: glufosinate, glufosinate-P and glufosinate-ammonium;

b9) from the group of the mitosis inhibitors: pendimethalin and trifluralin;

b10) from the group of the VLCFA inhibitors: acetochlor, cafenstrole, dimethenamid-P, fentrazamide, flufenacet, mefenacet, metazachlor, metolachlor, S-metolachlor, fenoxasulfone, ipfencarbazone and pyroxasulfone; likewise, preference is given to isoxazoline compounds of the formulae II.1, II.2, II.3, II.4, II.5, II.6, II.7, II.8 and II.9 as mentioned above;

b11) from the group of the cellulose biosynthesis inhibitors: indaziflam, isoxaben and triaziflam;

b13) from the group of the auxinic herbicides: 2,4-D and its salts and esters such as clacyfos, and aminocyclopyrachlor and its salts and esters, aminopyralid and its salts and its esters, clopyralid and its salts and esters, dicamba and its salts and esters, fluroxypyr-meptyl, halauxifen, halauxifen-methyl, quinclorac, quinmerac, 4-amino-3-chloro-6-(4-chloro-2-fluoro-3-methoxyphenyl)-5-fluoropyridine-2-carboxylic acid and benzyl 4-amino-3-chloro-6-(4-chloro-2-fluoro-3-methoxyphenyl)-5-fluoropyridine-2-carboxylate (CAS 1390661-72-9);

b14) from the group of the auxin transport inhibitors: diflufenzopyr and diflufenzopyr-sodium, b15) from the group of the other herbicides: dymron (=daimuron), indanofan, oxaziclomefone.

Particularly preferred herbicides B are the herbicides B as defined above; in particular the herbicides B.1-B.196 listed below in table B:

TABLE B

| | Herbicide B |
|---|---|
| B.1 | clethodim |
| B.2 | clodinafop-propargyl |
| B.3 | cycloxydim |

TABLE B-continued

Herbicide B

| | |
|---|---|
| B.4 | cyhalofop-butyl |
| B.5 | fenoxaprop-ethyl |
| B.6 | fenoxaprop-P-ethyl |
| B.7 | metamifop |
| B.8 | pinoxaden |
| B.9 | profoxydim |
| B.10 | sethoxydim |
| B.11 | tepraloxydim |
| B.12 | tralkoxydim |
| B.13 | esprocarb |
| B.14 | ethofumesate |
| B.15 | molinate |
| B.16 | prosulfocarb |
| B.17 | thiobencarb |
| B.18 | triallate |
| B.19 | bensulfuron-methyl |
| B.20 | bispyribac-sodium |
| B.21 | cloransulam-methyl |
| B.22 | chlorsulfuron |
| B.23 | clorimuron |
| B.24 | cyclosulfamuron |
| B.25 | diclosulam |
| B.26 | florasulam |
| B.27 | flumetsulam |
| B.28 | flupyrsulfuron-methyl-sodium |
| B.29 | foramsulfuron |
| B.30 | imazamox |
| B.31 | imazamox-ammonium |
| B.32 | imazapic |
| B.33 | imazapic-ammonium |
| B.34 | imazapic-isopropylammonium |
| B.35 | imazapyr |
| B.36 | imazapyr-ammonium |
| B.37 | imazapyr-isopropylammonium |
| B.38 | imazaquin |
| B.39 | imazaquin-ammonium |
| B.40 | imazethapyr |
| B.41 | imazethapyr-ammonium |
| B.42 | imazethapyr-isopropylammonium |
| B.43 | imazosulfuron |
| B.44 | iodosulfuron-methyl-sodium |
| B.45 | iofensulfuron |
| B.46 | iofensulfuron-sodium |
| B.47 | mesosulfuron-methyl |
| B.48 | metazosulfuron |
| B.49 | metsulfuron-methyl |
| B.50 | metosulam |
| B.51 | nicosulfuron |
| B.52 | penoxsulam |
| B.53 | propoxycarbazon-sodium |
| B.54 | pyrazosulfuron-ethyl |
| B.55 | pyribenzoxim |
| B.56 | pyriftalid |
| B.57 | pyroxsulam |
| B.58 | propyrisulfuron |
| B.59 | rimsulfuron |
| B.60 | sulfosulfuron |
| B.61 | thiencarbazone-methyl |
| B.62 | thifensulfuron-methyl |
| B.63 | tribenuron-methyl |
| B.64 | tritosulfuron |
| B.65 | triafamone |
| B.66 | ametryne |
| B.67 | atrazine |
| B.68 | bentazon |
| B.69 | bromoxynil |
| B.70 | bromoxynil-octanoate |
| B.71 | bromoxynil-heptanoate |
| B.72 | bromoxynil-potassium |
| B.73 | diuron |
| B.74 | fluometuron |
| B.75 | hexazinone |
| B.76 | isoproturon |
| B.77 | linuron |
| B.78 | metamitron |
| B.79 | metribuzin |
| B.80 | propanil |
| B.81 | simazin |
| B.82 | terbuthylazine |
| B.83 | terbutryn |
| B.84 | paraquat-dichloride |
| B.85 | acifluorfen |
| B.86 | butafenacil |
| B.87 | carfentrazone-ethyl |
| B.88 | flumioxazin |
| B.89 | fomesafen |
| B.90 | oxadiargyl |
| B.91 | oxyfluorfen |
| B.92 | pyraflufen |
| B.93 | pyraflufen-ethyl |
| B.94 | saflufenacil |
| B.95 | sulfentrazone |
| B.96 | trifludimoxazin |
| B.97 | ethyl [3-[2-chloro-4-fluoro-5-(1-methyl-6-trifluoromethyl-2,4-di-oxo-1,2,3,4-tetrahydropyrimidin-3-yl)phenoxy]-2-pyridyl-oxy]acetate (CAS 353292-31-6) |
| B.98 | benzobicyclon |
| B.99 | bicyclopyrone |
| B.100 | clomazone |
| B.101 | diflufenican |
| B.102 | flurochloridone |
| B.103 | isoxaflutole |
| B.104 | mesotrione |
| B.105 | norflurazone |
| B.106 | picolinafen |
| B.107 | sulcotrione |
| B.108 | tefuryltrione |
| B.109 | tembotrione |
| B.110 | tolpyralate |
| B.111 | topramezone |
| B.112 | topramezone-sodium |
| B.113 | amitrole |
| B.114 | fluometuron |
| B.115 | fenquintrione |
| B.116 | glyphosate |
| B.117 | glyphosate-ammonium |
| B.118 | glyphosate-dimethylammonium |
| B.119 | glyphosate-isopropylammonium |
| B.120 | glyphosate-trimesium (sulfosate) |
| B.121 | glyphosate-potassium |
| B.122 | glufosinate |
| B.123 | glufosinate-ammonium |
| B.124 | glufosinate-P |
| B.125 | glufosinate-P-ammonium |
| B.126 | pendimethalin |
| B.127 | trifluralin |
| B.128 | acetochlor |
| B.129 | butachlor |
| B.130 | cafenstrole |
| B.131 | dimethenamid-P |
| B.132 | fentrazamide |
| B.133 | flufenacet |
| B.134 | mefenacet |
| B.135 | metazachlor |
| B.136 | metolachlor |
| B.137 | S-metolachlor |
| B.138 | pretilachlor |
| B.139 | fenoxasulfone |
| B.140 | indaziflam |
| B.141 | isoxaben |
| B.142 | triaziflam |
| B.143 | ipfencarbazone |
| B.144 | pyroxasulfone |
| B.145 | 2,4-D |
| B.146 | 2,4-D-isobutyl |
| B.147 | 2,4-D-dimethylammonium |
| B.148 | 2,4-D-N,N-trimethylethanolammonium |
| B.149 | aminopyralid |
| B.150 | aminopyralid-methyl |
| B.151 | aminopyralid-dimethyl-ammonium |

TABLE B-continued

| | Herbicide B |
|---|---|
| B.152 | aminopyralid-tris(2-hydroxypropyl)ammonium |
| B.153 | clopyralid |
| B.154 | clopyralid-methyl |
| B.155 | clopyralid-olamine |
| B.156 | dicamba |
| B.157 | dicamba-butotyl |
| B.158 | dicamba-diglycolamine |
| B.159 | dicamba-dimethylammonium |
| B.160 | dicamba-diolamine |
| B.161 | dicamba-isopropylammonium |
| B.162 | dicamba-potassium |
| B.163 | dicamba-sodium |
| B.164 | dicamba-trolamine |
| B.165 | dicamba-N,N-bis-(3-aminopropyl)methylamine |
| B.166 | dicamba-diethylenetriamine |
| B.167 | fluroxypyr |
| B.168 | fluroxypyr-meptyl |
| B.169 | halauxifen |
| B.170 | halauxifen-methyl |
| B.171 | MCPA |
| B.172 | MCPA-2-ethylhexyl |
| B.173 | MCPA-dimethylammonium |
| B.174 | quinclorac |
| B.175 | quinclorac-dimethylammonium |
| B.176 | quinmerac |
| B.177 | quinmerac-dimethylammonium |
| B.178 | 4-amino-3-chloro-6-(4-chloro-2-fluoro-3-methoxyphenyl)-5-fluoropyridine-2-carboxylic acid |
| B.179 | benzyl 4-amino-3-chloro-6-(4-chloro-2-fluoro-3-methoxyphenyl)-5-fluoropyridine-2-carboxylate (CAS 1390661-72-9) |
| B.180 | aminocyclopyrachlor |
| B.181 | aminocyclopyrachlor-potassium |
| B.182 | aminocyclopyrachlor-methyl |
| B.183 | diflufenzopyr |
| B.184 | diflufenzopyr-sodium |
| B.185 | dymron |
| B.186 | indanofan |
| B.187 | oxaziclomefone |
| B.188 | II.1 |
| B.189 | II.2 |
| B.190 | II.3 |
| B.191 | II.4 |
| B.192 | II.5 |
| B.193 | II.6 |
| B.194 | II.7 |
| B.195 | II.8 |
| B.196 | II.9 |

Moreover, it may be useful to apply the compounds of formula I in combination with safeners. Safeners are chemical compounds which prevent or reduce damage on useful plants without having a major impact on the herbicidal action of the compounds of the formula I towards unwanted plants. They can be applied either before sowings (e.g. on seed treatments, shoots or seedlings) or in the pre-emergence application or post-emergence application of the useful plant. The safeners and the compounds of formula I and optionally the herbicides B can be applied simultaneously or in succession.

Suitable safeners are e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diaryl-3-isoxazol carboxylic acids, dichloroacetamides, alpha-oximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenyl-carbamates and their agriculturally acceptable salts and their agriculturally acceptable derivatives such amides, esters, and thioesters, provided they have an acid group.

Examples of preferred safeners C are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro [4.5]decane (MON4660, CAS 71526-07-3), 2,2,5-trimethyl-3-(dichloroacetyl)-1,3-oxazolidine (R-29148, CAS 52836-31-4) and N-(2-Methoxybenzoyl)-4-[(methylaminocarbonyl)amino]benzenesulfonamide (CAS 129531-12-0).

Especially preferred safeners C are benoxacor, cloquintocet, cyprosulfamide, dichlormid, fenchlorazole, fenclorim, flurazole, fluxofenim, furilazole, isoxadifen, mefenpyr, naphthalic anhydride, oxabetrinil, 4-(dichloroacetyl)-1-oxa-4-azaspiro[4.5]decane (MON-4660, CAS 71526-07-3), 2,2,5-trimethyl-3-(dichloroacetyl)-1,3-oxazolidine (R-29148, CAS 52836-31-4) and N-(2-Methoxybenzoyl)-4-[(methylaminocarbonyl)amino]benzenesulfonamide (CAS 129531-12-0).

Particularly preferred safeners C are benoxacor, cloquintocet, cyprosulfamide, dichlormid, fenchlorazole, fenclorim, furilazole, isoxadifen, mefenpyr, naphtalic anhydride, 4-(dichloroacetyl)-1-oxa-4-azaspiro[4.5]decane (MON-4660, CAS 71526-07-3), 2,2,5-trimethyl-3-(dichloroacetyl)-1,3-oxazolidine (R-29148, CAS 52836-31-4) and N-(2-Methoxybenzoyl)-4-[(methylaminocarbonyl)amino]benzenesulfonamide (CAS 129531-12-0).

The active compounds B of groups b1) to b15) and the active compounds C are known herbicides and safeners, see, for example, The Compendium of Pesticide Common Names (http://www.alanwood.net/pesticides/); Farm Chemicals Handbook 2000 volume 86, Meister Publishing Company, 2000; B. Hock, C. Fedtke, R. R. Schmidt, Herbizide [Herbicides], Georg Thieme Verlag, Stuttgart 1995; W. H. Ahrens, Herbicide Handbook, 7th edition, Weed Science Society of America, 1994; and K. K. Hatzios, Herbicide Handbook, Supplement for the 7th edition, Weed Science Society of America, 1998. 2,2,5-Trimethyl-3-(di-chloroacetyl)-1,3-oxazolidine [CAS No. 52836-31-4] is also referred to as R-29148. 4-(Dichloroacetyl)-1-oxa-4-azaspiro [4.5]decane [CAS No. 71526-07-3] is also referred to as AD-67 and MON 4660.

The assignment of the active compounds to the respective mechanisms of action is based on current knowledge. If several mechanisms of action apply to one active compound, this substance was only assigned to one mechanism of action.

Particularly preferred safeners C, which, as component C, are constituent of the composition according to the invention are the safeners C as defined above; in particular the safeners C.1-C.17 listed below in table C:

TABLE C

| | Safener C |
|---|---|
| C.1 | benoxacor |
| C.2 | cloquintocet |
| C.3 | cloquintocet-mexyl |
| C.4 | cyprosulfamide |
| C.5 | dichlormid |
| C.6 | fenchlorazole |
| C.7 | fenchlorazole-ethyl |
| C.8 | fenclorim |

TABLE C-continued

| | Safener C |
|---|---|
| C.9 | furilazole |
| C.10 | isoxadifen |
| C.11 | isoxadifen-ethyl |
| C.12 | mefenpyr |
| C.13 | mefenpyr-diethyl |
| C.14 | naphtalic acid anhydride |
| C.15 | 4-(dichloroacetyl)-1-oxa-4-azaspiro[4.5]decane (MON4660, CAS 71526-07-3) |
| C.16 | 2,2,5-trimethyl-3-(dichloroacetyl)-1,3-oxazolidine (R-29148, CAS 52836-31-4) |
| C.17 | N-(2-Methoxybenzoyl)-4-[(methylaminocarbonyl)amino]benzenesulfonamide (CAS 129531-12-0) |

Active compounds B and C having a carboxyl group can be employed in the form of the acid, in the form of an agriculturally suitable salt as mentioned above or else in the form of an agriculturally acceptable derivative in the compositions according to the invention.

In the case of dicamba, suitable salts include those, where the counterion is an agriculturally acceptable cation. For example, suitable salts of dicamba are dicambasodium, dicamba-potassium, dicamba-methylammonium, dicamba-dimethylammonium, dicamba-isopropylammonium, dicamba-diglycolamine, dicamba-olamine, dicambadiolamine, dicamba-trolamine, dicamba-N,N-bis-(3-aminopropyl)methylamine and dicamba-diethylenetriamine. Examples of a suitable ester are dicamba-methyl and dicamba-butotyl.

Suitable salts of 2,4-D are 2,4-D-ammonium, 2,4-D-dimethylammonium, 2,4-D-diethylammonium, 2,4-D-diethanolammonium (2,4-D-diolamine), 2,4-D-triethanol-ammonium, 2,4-D-isopropylammonium, 2,4-D-triisopropanolammonium, 2,4-D-heptylammonium, 2,4-D-dodecylammonium, 2,4-D-tetradecylammonium, 2,4-D-triethylammonium, 2,4-D-tris(2-hydroxypropyl)ammonium, 2,4-D-tris(isopropyl)-ammonium, 2,4-D-trolamine, 2,4-D-lithium, 2,4-D-sodium. Examples of suitable esters of 2,4-D are 2,4-D-butotyl, 2,4-D-2-butoxy-propyl, 2,4-D-3-butoxypropyl, 2,4-D-butyl, 2,4-D-ethyl, 2,4-D-ethylhexyl, 2,4-D-isobutyl, 2,4-D-isooctyl, 2,4-D-isopropyl, 2,4-D-meptyl, 2,4-D-methyl, 2,4-D-octyl, 2,4-D-pentyl, 2,4-D-propyl, 2,4-D-tefuryl and clacyfos.

Suitable salts of 2,4-DB are for example 2,4-DB-sodium, 2,4-DB-potassium and 2,4-DB-dimethylammonium. Suitable esters of 2,4-DB are for example 2,4-DB-butyl and 2,4-DB-isoctyl.

Suitable salts of dichlorprop are for example dichlorprop-sodium, dichlorproppotassium and dichlorprop-dimethyl-ammonium. Examples of suitable esters of dichlorprop are dichlorprop-butotyl and dichlorprop-isoctyl.

Suitable salts and esters of MCPA include MCPA-butotyl, MCPA-butyl, MCPA-dimethylammonium, MCPA-diolamine, MCPA-ethyl, MCPA-thioethyl, MCPA-2-ethylhexyl, MCPA-isobutyl, MCPA-isoctyl, MCPA-isopropyl, MCPA-isopropylammonium, MCPA-methyl, MCPA-olamine, MCPA-potassium, MCPA-sodium and MCPA-trolamine. A suitable salt of MCPB is MCPB sodium. A suitable ester of MCPB is MCPB-ethyl.

Suitable salts of clopyralid are clopyralid-potassium, clopyralid-olamine and clopyralid-tris-(2-hydroxypropyl)ammonium. Example of suitable esters of clopyralid is clopyralid-methyl.

Examples of a suitable ester of fluroxypyr are fluroxypyr-meptyl and fluroxypyr-2-butoxy-1-methylethyl, wherein fluroxypyr-meptyl is preferred.

Suitable salts of picloram are picloram-dimethylammonium, picloram-potassium, picloram-triisopropanolammonium, picloram-triisopropylammonium and picloram-trolamine.

A suitable ester of picloram is picloram-isoctyl.

A suitable salt of triclopyr is triclopyr-triethylammonium. Suitable esters of triclopyr are for example triclopyr-ethyl and triclopyr-butotyl.

Suitable salts and esters of chloramben include chloramben-ammonium, chlorambendiolamine, chloramben-methyl, chloramben-methylammonium and chloramben-sodium.

Suitable salts and esters of 2,3,6-TBA include 2,3,6-TBA-dimethylammonium, 2,3,6-TBA-lithium, 2,3,6-TBA-potassium and 2,3,6-TBA-sodium.

Suitable salts and esters of aminopyralid include aminopyralid-potassium and amino-pyralid-tris(2-hydroxypropyl)ammonium.

Suitable salts of glyphosate are for example glyphosate-ammonium, glyphosate-diammonium, glyphoste-dimethyl-ammonium, glyphosate-isopropylammonium, glyphosate-potassium, glyphosate-sodium, glyphosate-trimesium as well as the ethanolamine and diethanolamine salts, preferably glyphosate-diammonium, glyphosate-isopropylammonium and glyphosate-trimesium (sulfosate).

A suitable salt of glufosinate is for example glufosinate-ammonium.

A suitable salt of glufosinate-P is for example glufosinate-P-ammonium.

Suitable salts and esters of bromoxynil are for example bromoxynil-butyrate, bromoxynil-heptanoate, bromoxynil-octanoate, bromoxynil-potassium and bromoxynilsodium.

Suitable salts and esters of ioxonil are for example ioxonil-octanoate, ioxonil-potassium and ioxonil-sodium.

Suitable salts and esters of mecoprop include mecoprop-butotyl, mecopropdimethylammonium, mecoprop-diolamine, mecoprop-ethadyl, mecoprop-2-ethylhexyl, mecoprop-isoctyl, mecoprop-methyl, mecoprop-potassium, mecoprop-sodium and mecoprop-trolamine.

Suitable salts of mecoprop-P are for example mecoprop-P-butotyl, mecoprop-P-dimethylammonium, mecoprop-P-2-ethylhexyl, mecoprop-P-isobutyl, mecoprop-P-potassium and mecoprop-P-sodium.

A suitable salt of diflufenzopyr is for example diflufenzopyr-sodium.

A suitable salt of naptalam is for example naptalam-sodium.

Suitable salts and esters of aminocyclopyrachlor are for example aminocyclopyrachlor-dimethylammonium, aminocyclopyrachlor-methyl, aminocyclopyrachlor-triisopropanolammonium, aminocyclopyrachlor-sodium and aminocyclopyrachlor-potassium.

A suitable salt of quinclorac is for example quinclorac-dimethylammonium.

A suitable salt of quinmerac is for example quinclorac-dimethylammonium.

A suitable salt of imazamox is for example imazamox-ammonium.

Suitable salts of imazapic are for example imazapic-ammonium and imazapic-isopropylammonium.

Suitable salts of imazapyr are for example imazapyr-ammonium and imazapyr-isopropylammonium.

A suitable salt of imazaquin is for example imazaquin-ammonium.

Suitable salts of imazethapyr are for example imazethapyr-ammonium and imazethapyr-isopropylammonium.

A suitable salt of topramezone is for example topramezone-sodium.

According to a preferred embodiment of the invention, the composition comprises as herbicidal active compound B or component B at least one, preferably exactly one herbicide B.

According to another preferred embodiment of the invention, the composition comprises as herbicidal active compounds B or component B at least two, preferably exactly two herbicides B different from each other.

According to another preferred embodiment of the invention, the composition comprises as herbicidal active compounds B or component B at least three, preferably exactly three herbicides B different from each other.

According to another preferred embodiment of the invention, the composition comprises as safening component C or component C at least one, preferably exactly one safener C.

According to another preferred embodiment of the invention, the composition comprises as component B at least one, preferably exactly one herbicide B, and as component C at least one, preferably exactly one, safener C.

According to another preferred embodiment of the invention, the composition comprises at least two, preferably exactly two, herbicides B different from each other, and as component C at least one, preferably exactly one, safener C.

According to another preferred embodiment of the invention, the composition comprises at least three, preferably exactly three, herbicides B different from each other, and as component C at least one, preferably exactly one, safener C.

According to another preferred embodiment of the invention, the composition comprises as component A at least one, preferably exactly one compound of formula I, preferably of formula I.a, I.b, I.c or I-1 to I-38, and as component B at least one, preferably exactly one, herbicide B.

According to another preferred embodiment of the invention, the composition comprises as component A at least one, preferably exactly one compound of formula I, preferably of formula I.a, I.b, I.c or I-1 to I-38, and at least two, preferably exactly two, herbicides B different from each other.

According to another preferred embodiment of the invention, the composition comprises as component A at least one, preferably exactly one compound of formula I, preferably of formula I.a, I.b, I.c or I-1 to I-38, and at least three, preferably exactly three, herbicides B different from each other.

According to another preferred embodiment of the invention, the composition comprises as component A at least one, preferably exactly one compound of formula I, preferably of formula I.a, I.b, I.c or I-1 to I-38, and as component C at least one, preferably exactly one, safener C.

According to another preferred embodiment of the invention, the composition comprises as component A at least one, preferably exactly one compound of formula I, preferably of formula I.a, I.b, I.c or I-1 to I-38, as component B at least one, preferably exactly one, herbicide B, and as component C at least one, preferably exactly one safener C.

According to another preferred embodiment of the invention, the composition comprises as component A at least one, preferably exactly one compound of formula I, preferably of formula I.a, I.b, I.c or I-1 to I-38, at least two, preferably exactly two herbicides B different from each other, and as component C at least one, preferably exactly one, safener C.

According to another preferred embodiment of the invention, the composition comprises as component A at least one, preferably exactly one compound of formula I, preferably of formula I.a, I.b, I.c or I-1 to I-38, at least three, preferably exactly three herbicides B different from each other, and as component C at least one, preferably exactly one, safener C.

According to another preferred embodiment of the invention, the composition comprises, in addition to a compounds A of formula I, especially an active compound of formula I.a, I.b, I.c or I-1 to I-38, at least one and especially exactly one herbicidally active compound from group b1), in particular selected from the group consisting of clodinafop-propargyl, cycloxydim, cyhalofop-butyl, fenoxaprop-P-ethyl, pinoxaden, profoxydim, tepraloxydim, tralkoxydim, esprocarb, prosulfocarb, thiobencarb and triallate.

According to another preferred embodiment of the invention, the composition comprises, in addition to a compounds A of formula I, especially an active compound of formula I.a, I.b, I.c or I-1 to I-38, at least one and especially exactly one herbicidally active compound from group b2), in particular selected from the group consisting of bensulfuron-methyl, bispyribac-sodium, cyclosulfamuron, diclosulam, flumetsulam, flupyrsulfuron-methyl-sodium, foramsulfuron, imazamox, imazapic, imazapyr, imazaquin, imazethapyr, imazosulfuron, iodosulfuron, iodosulfuron-methyl-sodium, mesosulfuron, metazosulfuron, nicosulfuron, penoxsulam, propoxycarbazon-sodium, pyrazosulfuron-ethyl, pyroxsulam, rimsulfuron, sulfosulfuron, thiencarbazon-methyl and tritosulfuron.

According to another preferred embodiment of the invention, the composition comprises, in addition to a compounds A of formula I, especially an active compound of formula I.a, I.b, I.c or I-1 to I-38, at least one and especially exactly one herbicidally active compound from group b3), in particular selected from the group consisting of ametryn, atrazine, diuron, fluometuron, hexazinone, isoproturon, linuron, metribuzin, paraquat, paraquat-dichloride, propanil, terbutryn and terbuthylazine.

According to another preferred embodiment of the invention, the composition comprises, in addition to a compounds A of formula I, especially an active compound of formula I.a, I.b, I.c or I-1 to I-38, at least one and especially exactly one herbicidally active compound from group b4), in particular selected from the group consisting of flumioxazin, oxyfluorfen, pyraflufen, pyraflufen-ethyl, saflufenacil, sulfentrazone, trifludimoxazin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7), 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0) and 1-methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0).

According to another preferred embodiment of the invention, the composition comprises, in addition to a compounds A of formula I, especially an active compound of formula I.a, I.b, I.c or I-1 to I-38, at least one and especially exactly one herbicidally active compound from group b5), in particular selected from the group consisting of amitrole, bicyclopyrone, clomazone, diflufenican, flumeturon, flurochloridone, isoxaflutole, mesotrione, picolinafen, sulcotrione, tefuryltrione, tembotrione, tolpyralate and topramezone.

According to another preferred embodiment of the invention, the composition comprises, in addition to a compounds A of formula I, especially an active compound of formula I.a, I.b, I.c or I-1 to I-38, at least one and especially exactly one herbicidally active compound from group b6), in particular selected from the group consisting of glyphosate, glyphosate-isopropylammonium and glyphosate-trimesium (sulfosate).

According to another preferred embodiment of the invention, the composition comprises, in addition to a compounds A of formula I, especially an active compound of formula I.a, I.b, I.c or I-1 to I-38, at least one and especially exactly one herbicidally active compound from group b7), in particular selected from the group consisting of glufosinate, glufosinate-P and glufosinate-ammonium.

According to another preferred embodiment of the invention, the composition comprises, in addition to a compounds A of formula I, especially an active compound of formula I.a, I.b, I.c or I-1 to I-38, at least one and especially exactly one herbicidally active compound from group b9), in particular selected from the group consisting of pendimethalin and trifluralin.

According to another preferred embodiment of the invention, the composition comprises, in addition to a compounds A of formula I, especially an active compound of formula I.a, I.b, I.c or I-1 to I-38, at least one and especially exactly one herbicidally active compound from group b10), in particular selected from the group consisting of acetochlor, cafenstrole, dimethenamid-P, fentrazamide, flufenacet, mefenacet, metazachlor, metolachlor, S-metolachlor, fenoxasulfone and pyroxasulfone. Likewise, preference is given to compositions comprising in addition to a compounds A of formula I, especially an active compound of formula I.a, I.b, I.c or I-1 to I-38, at least one and especially exactly one herbicidally active compound from group b10), in particular selected from the group consisting of isoxazoline compounds of the formulae II.1, II.2, II.3, II.4, II.5, II.6, II.7, II.8 and II.9, as defined above.

According to another preferred embodiment of the invention, the composition comprises, in addition to a compounds A of formula I, especially an active compound of formula I.a, I.b, I.c or I-1 to I-38, at least one and especially exactly one herbicidally active compound from group b11), in particular indaziflam, isoxaben and triaziflam.

According to another preferred embodiment of the invention, the composition comprises, in addition to a compounds A of formula I, especially an active compound of formula I.a, I.b, I.c or I-1 to I-38, at least one and especially exactly one herbicidally active compound from group b13), in particular selected from the group consisting of 2,4-D and its salts and esters, aminocyclopyrachlor and its salts and esters, aminopyralid and its salts such as aminopyralid-dimethylammonium, aminopyralid-tris(2-hydroxypropyl)ammonium and its esters, clopyralid and its salts and esters, dicamba and its salts and esters, fluroxypyr-meptyl, halauxifen, halauxifen-methyl, quinclorac, quinmerac, 4-amino-3-chloro-6-(4-chloro-2-fluoro-3-methoxyphenyl)-5-fluoropyridine-2-carboxylic acid and benzyl 4-amino-3-chloro-6-(4-chloro-2-fluoro-3-methoxyphenyl)-5-fluoropyridine-2-carboxylate (CAS 1390661-72-9).

According to another preferred embodiment of the invention, the composition comprises, in addition to a compounds A of formula I, especially an active compound of formula I.a, I.b, I.c or I-1 to I-38, at least one and especially exactly one herbicidally active compound from group b14), in particular selected from the group consisting of diflufenzopyr and diflufenzopyr-sodium.

According to another preferred embodiment of the invention, the composition comprises, in addition to a compounds A of formula I, especially an active compound of formula I.a, I.b, I.c or I-1 to I-38, at least one and especially exactly one herbicidally active compound from group b15), in particular selected from the group consisting of dymron (=daimuron), indanofan and oxaziclomefone.

According to another preferred embodiment of the invention, the composition comprises, in addition to a compounds A of formula I, especially an active compound of formula I.a, I.b, I.c or I-1 to I-38, at least one and especially exactly one safener C, in particular selected from the group consisting of benoxacor, cloquintocet, cyprosulfamide, dichlormid, fenchlorazole, fenclorim, furilazole, isoxadifen, mefenpyr, 4-(dichloroacetyl)-1-oxa-4-azaspiro[4.5]decane (MON-4660, CAS 71526-07-3) and 2,2,5-trimethyl-3-(dichloroacetyl)-1,3-oxazolidine (R-29148, CAS 52836-31-4).

Further preferred embodiments relate to ternary compositions which correspond to the binary compositions mentioned above and additionally comprise a safener C, in particular selected from the group consisting of benoxacor, cloquintocet, cyprosulfamide, dichlormid, fenchlorazole, fenclorim, furilazole, isoxadifen, mefenpyr, 4-(dichloroacetyl)-1-oxa-4-azaspiro[4.5]decane (MON-4660, CAS 71526-07-3) and 2,2,5-trimethyl-3-(dichloroacetyl)-1,3-oxazolidine (R-29148, CAS 52836-31-4).

Here and below, the term "binary compositions" includes compositions comprising one or more, for example 1, 2 or 3, active compounds of the formula I and either one or more, for example 1, 2 or 3, herbicides B or one or more safeners. Correspondingly, the term "ternary compositions" includes compositions comprising one or more, for example 1, 2 or 3, active compounds of the formula I, one or more, for example 1, 2 or 3, herbicides B and one or more, for example 1, 2 or 3, safeners C.

In binary compositions comprising at least one compound of the formula I as component A and at least one herbicide B, the weight ratio of the active compounds A:B is generally in the range of from 1:1000 to 1000:1, preferably in the range of from 1:500 to 500:1, in particular in the range of from 1:250 to 250:1 and particularly preferably in the range of from 1:75 to 75:1.

In binary compositions comprising at least one compound of the formula I as component A and at least one safener C, the weight ratio of the active compounds A:C is generally in the range of from 1:1000 to 1000:1, preferably in the range of from 1:500 to 500:1, in particular in the range of from 1:250 to 250:1 and particularly preferably in the range of from 1:75 to 75:1.

In ternary compositions comprising both at least one compound of formula I as component A, at least one herbicide B and at least one safener C, the relative proportions by weight of the components A:B are generally in the range of from 1:1000 to 1000:1, preferably in the range of from 1:500 to 500:1, in particular in the range of from 1:250 to 250:1 and particularly preferably in the range of from 1:75 to 75:1, the weight ratio of the components A:C is generally in the range of from 1:1000 to 1000:1, preferably in the range of from 1:500 to 500:1, in particular in the range of from 1:250 to 250:1 and particularly preferably in the range of from 1:75 to 75:1, and the weight ratio of the components B:C is generally in the range of from 1:1000 to 1000:1, preferably in the range of from 1:500 to 500:1, in particular in the range of from 1:250 to 250:1 and particularly preferably in the range of from 1:75 to 75:1. The weight ratio of components A+B to component C is preferably in the range of from 1:500 to 500:1, in particular in the range of from 1:250 to 250:1 and particularly preferably in the range of from 1:75 to 75:1.

The weight ratios of the individual components in the preferred mixtures mentioned below are within the limits given herein, in particular within the preferred limits.

Particularly preferred are the compositions mentioned below comprising the compounds of formula I as defined and the substance(s) as defined in the respective row of table 1;
especially preferred comprising as only herbicidal active compounds the compounds of formula I as defined and the substance(s) as defined in the respective row of table 1; most preferably comprising as only active compounds the compounds of formula I as defined and the substance(s) as defined in the respective row of table 1.

Particularly preferred are compositions 1.1 to 1.3545, comprising the compounds of formula I.a, I.b, I.c or I-1 to I-38 and the substance(s) as defined in the respective row of table 1:

TABLE 1

(compositions 1.1 to 1.3545):

| comp. no. | herbicide B | safener C |
|---|---|---|
| 1.1 | B.1 | — |
| 1.2 | B.2 | — |
| 1.3 | B.3 | — |
| 1.4 | B.4 | — |
| 1.5 | B.5 | — |
| 1.6 | B.6 | — |
| 1.7 | B.7 | — |
| 1.8 | B.8 | — |
| 1.9 | B.9 | — |
| 1.10 | B.10 | — |
| 1.11 | B.11 | — |
| 1.12 | B.12 | — |
| 1.13 | B.13 | — |
| 1.14 | B.14 | — |
| 1.15 | B.15 | — |
| 1.16 | B.16 | — |
| 1.17 | B.17 | — |
| 1.18 | B.18 | — |
| 1.19 | B.19 | — |
| 1.20 | B.20 | — |
| 1.21 | B.21 | — |
| 1.22 | B.22 | — |
| 1.23 | B.23 | — |
| 1.24 | B.24 | — |
| 1.25 | B.25 | — |
| 1.26 | B.26 | — |
| 1.27 | B.27 | — |
| 1.28 | B.28 | — |
| 1.29 | B.29 | — |
| 1.30 | B.30 | — |
| 1.31 | B.31 | — |
| 1.32 | B.32 | — |
| 1.33 | B.33 | — |
| 1.34 | B.34 | — |
| 1.35 | B.35 | — |
| 1.36 | B.36 | — |
| 1.37 | B.37 | — |
| 1.38 | B.38 | — |
| 1.39 | B.39 | — |
| 1.40 | B.40 | — |
| 1.41 | B.41 | — |
| 1.42 | B.42 | — |
| 1.43 | B.43 | — |
| 1.44 | B.44 | — |
| 1.45 | B.45 | — |
| 1.46 | B.46 | — |
| 1.47 | B.47 | — |
| 1.48 | B.48 | — |
| 1.49 | B.49 | — |
| 1.50 | B.50 | — |
| 1.51 | B.51 | — |
| 1.52 | B.52 | — |
| 1.53 | B.53 | — |
| 1.54 | B.54 | — |
| 1.55 | B.55 | — |
| 1.56 | B.56 | — |
| 1.57 | B.57 | — |
| 1.58 | B.58. | — |
| 1.59 | B.59 | — |
| 1.60 | B.60 | — |
| 1.61 | B.61 | — |
| 1.62 | B.62 | — |
| 1.63 | B.63 | — |
| 1.64 | B.64 | — |
| 1.65 | B.65 | — |
| 1.66 | B.66 | — |
| 1.67 | B.67 | — |
| 1.68 | B.68 | — |
| 1.69 | B.69 | — |
| 1.70 | B.70 | — |
| 1.71 | B.71 | — |
| 1.72 | B.72 | — |
| 1.73 | B.73 | — |
| 1.74 | B.74 | — |
| 1.75 | B.75 | — |
| 1.76 | B.76 | — |
| 1.77 | B.77 | — |
| 1.78 | B.78 | — |
| 1.79 | B.79 | — |
| 1.80 | B.80 | — |
| 1.81 | B.81 | — |
| 1.82 | B.82 | — |
| 1.83 | B.83 | — |
| 1.84 | B.84 | — |
| 1.85 | B.85 | — |
| 1.86 | B.86 | — |
| 1.87 | B.87 | — |
| 1.88 | B.88 | — |
| 1.89 | B.89 | — |
| 1.90 | B.90 | — |
| 1.91 | B.91 | — |
| 1.92 | B.92 | — |
| 1.93 | B.93 | — |
| 1.94 | B.94 | — |
| 1.95 | B.95 | — |
| 1.96 | B.96 | — |
| 1.97 | B.97 | — |
| 1.98 | B.98 | — |
| 1.99 | B.99 | — |
| 1.100 | B.100 | — |
| 1.101 | B.101 | — |
| 1.102 | B.102 | — |
| 1.103 | B.103 | — |
| 1.104 | B.104 | — |
| 1.105 | B.105 | — |
| 1.106 | B.106 | — |
| 1.107 | B.107 | — |
| 1.108 | B.108 | — |
| 1.109 | B.109 | — |
| 1.110 | B.110 | — |
| 1.111 | B.111 | — |
| 1.112 | B.112 | — |
| 1.113 | B.113 | — |
| 1.114 | B.114 | — |
| 1.115 | B.115 | — |
| 1.116 | B.116 | — |
| 1.117 | B.117 | — |
| 1.118 | B.118 | — |
| 1.119 | B.119 | — |
| 1.120 | B.120 | — |
| 1.121 | B.121 | — |
| 1.122 | B.122 | — |
| 1.123 | B.123 | — |
| 1.124 | B.124 | — |
| 1.125 | B.125 | — |
| 1.126 | B.126 | — |
| 1.127 | B.127 | — |
| 1.128 | B.128 | — |
| 1.129 | B.129 | — |
| 1.130 | B.130 | — |
| 1.131 | B.131 | — |
| 1.132 | B.132 | — |
| 1.133 | B.133 | — |

TABLE 1-continued (compositions 1.1 to 1.3545):

| comp. no. | herbicide B | safener C |
|---|---|---|
| 1.134 | B.134 | — |
| 1.135 | B.135 | — |
| 1.136 | B.136 | — |
| 1.137 | B.137 | — |
| 1.138 | B.138 | — |
| 1.139 | B.139 | — |
| 1.140 | B.140 | — |
| 1.141 | B.141 | — |
| 1.142 | B.142 | — |
| 1.143 | B.143 | — |
| 1.144 | B.144 | — |
| 1.145 | B.145 | — |
| 1.146 | B.146 | — |
| 1.147 | B.147 | — |
| 1.148 | B.148 | — |
| 1.149 | B.149 | — |
| 1.150 | B.150 | — |
| 1.151 | B.151 | — |
| 1.152 | B.152 | — |
| 1.153 | B.153 | — |
| 1.154 | B.154 | — |
| 1.155 | B.155 | — |
| 1.156 | B.156 | — |
| 1.157 | B.157 | — |
| 1.158 | B.158 | — |
| 1.159 | B.159 | — |
| 1.160 | B.160 | — |
| 1.161 | B.161 | — |
| 1.162 | B.162 | — |
| 1.163 | B.163 | — |
| 1.164 | B.164 | — |
| 1.165 | B.165 | — |
| 1.166 | B.166 | — |
| 1.167 | B.167 | — |
| 1.168 | B.168 | — |
| 1.169 | B.169 | — |
| 1.170 | B.170 | — |
| 1.171 | B.171 | — |
| 1.172 | B.172 | — |
| 1.173 | B.173 | — |
| 1.174 | B.174 | — |
| 1.175 | B.175 | — |
| 1.176 | B.176 | — |
| 1.177 | B.177 | — |
| 1.178 | B.178 | — |
| 1.179 | B.179 | — |
| 1.180 | B.180 | — |
| 1.181 | B.181 | — |
| 1.182 | B.182 | — |
| 1.183 | B.183 | — |
| 1.184 | B.184 | — |
| 1.185 | B.185 | — |
| 1.186 | B.186 | — |
| 1.187 | B.187 | — |
| 1.188 | B.188 | — |
| 1.189 | B.189 | — |
| 1.190 | B.190 | — |
| 1.191 | B.191 | — |
| 1.192 | B.192 | — |
| 1.193 | B.193 | — |
| 1.194 | B.194 | — |
| 1.195 | B.195 | — |
| 1.196 | B.196 | — |
| 1.197 | B.1 | C.1 |
| 1.198 | B.2 | C.1 |
| 1.199 | B.3 | C.1 |
| 1.200 | B.4 | C.1 |
| 1.201 | B.5 | C.1 |
| 1.202 | B.6 | C.1 |
| 1.203 | B.7 | C.1 |
| 1.204 | B.8 | C.1 |
| 1.205 | B.9 | C.1 |
| 1.206 | B.10 | C.1 |
| 1.207 | B.11 | C.1 |
| 1.208 | B.12 | C.1 |
| 1.209 | B.13 | C.1 |
| 1.210 | B.14 | C.1 |
| 1.211 | B.15 | C.1 |
| 1.212 | B.16 | C.1 |
| 1.213 | B.17 | C.1 |
| 1.214 | B.18 | C.1 |
| 1.215 | B.19 | C.1 |
| 1.216 | B.20 | C.1 |
| 1.217 | B.21 | C.1 |
| 1.218 | B.22 | C.1 |
| 1.219 | B.23 | C.1 |
| 1.220 | B.24 | C.1 |
| 1.221 | B.25 | C.1 |
| 1.222 | B.26 | C.1 |
| 1.223 | B.27 | C.1 |
| 1.224 | B.28 | C.1 |
| 1.225 | B.29 | C.1 |
| 1.226 | B.30 | C.1 |
| 1.227 | B.31 | C.1 |
| 1.228 | B.32 | C.1 |
| 1.229 | B.33 | C.1 |
| 1.230 | B.34 | C.1 |
| 1.231 | B.35 | C.1 |
| 1.232 | B.36 | C.1 |
| 1.233 | B.37 | C.1 |
| 1.234 | B.38 | C.1 |
| 1.235 | B.39 | C.1 |
| 1.236 | B.40 | C.1 |
| 1.237 | B.41 | C.1 |
| 1.238 | B.42 | C.1 |
| 1.239 | B.43 | C.1 |
| 1.240 | B.44 | C.1 |
| 1.241 | B.45 | C.1 |
| 1.242 | B.46 | C.1 |
| 1.243 | B.47 | C.1 |
| 1.244 | B.48 | C.1 |
| 1.245 | B.49 | C.1 |
| 1.246 | B.50 | C.1 |
| 1.247 | B.51 | C.1 |
| 1.248 | B.52 | C.1 |
| 1.249 | B.53 | C.1 |
| 1.250 | B.54 | C.1 |
| 1.251 | B.55 | C.1 |
| 1.252 | B.56 | C.1 |
| 1.253 | B.57 | C.1 |
| 1.254 | B.58. | C.1 |
| 1.255 | B.59 | C.1 |
| 1.256 | B.60 | C.1 |
| 1.257 | B.61 | C.1 |
| 1.258 | B.62 | C.1 |
| 1.259 | B.63 | C.1 |
| 1.260 | B.64 | C.1 |
| 1.261 | B.65 | C.1 |
| 1.262 | B.66 | C.1 |
| 1.263 | B.67 | C.1 |
| 1.264 | B.68 | C.1 |
| 1.265 | B.69 | C.1 |
| 1.266 | B.70 | C.1 |
| 1.267 | B.71 | C.1 |
| 1.268 | B.72 | C.1 |
| 1.269 | B.73 | C.1 |
| 1.270 | B.74 | C.1 |
| 1.271 | B.75 | C.1 |
| 1.272 | B.76 | C.1 |
| 1.273 | B.77 | C.1 |
| 1.274 | B.78 | C.1 |
| 1.275 | B.79 | C.1 |
| 1.276 | B.80 | C.1 |
| 1.277 | B.81 | C.1 |
| 1.278 | B.82 | C.1 |
| 1.279 | B.83 | C.1 |
| 1.280 | B.84 | C.1 |
| 1.281 | B.85 | C.1 |
| 1.282 | B.86 | C.1 |
| 1.283 | B.87 | C.1 |
| 1.284 | B.88 | C.1 |
| 1.285 | B.89 | C.1 |

TABLE 1-continued (compositions 1.1 to 1.3545):

| comp. no. | herbicide B | safener C |
|---|---|---|
| 1.286 | B.90 | C.1 |
| 1.287 | B.91 | C.1 |
| 1.288 | B.92 | C.1 |
| 1.289 | B.93 | C.1 |
| 1.290 | B.94 | C.1 |
| 1.291 | B.95 | C.1 |
| 1.292 | B.96 | C.1 |
| 1.293 | B.97 | C.1 |
| 1.294 | B.98 | C.1 |
| 1.295 | B.99 | C.1 |
| 1.296 | B.100 | C.1 |
| 1.297 | B.101 | C.1 |
| 1.298 | B.102 | C.1 |
| 1.299 | B.103 | C.1 |
| 1.300 | B.104 | C.1 |
| 1.301 | B.105 | C.1 |
| 1.302 | B.106 | C.1 |
| 1.303 | B.107 | C.1 |
| 1.304 | B.108 | C.1 |
| 1.305 | B.109 | C.1 |
| 1.306 | B.110 | C.1 |
| 1.307 | B.111 | C.1 |
| 1.308 | B.112 | C.1 |
| 1.309 | B.113 | C.1 |
| 1.310 | B.114 | C.1 |
| 1.311 | B.115 | C.1 |
| 1.312 | B.116 | C.1 |
| 1.313 | B.117 | C.1 |
| 1.314 | B.118 | C.1 |
| 1.315 | B.119 | C.1 |
| 1.316 | B.120 | C.1 |
| 1.317 | B.121 | C.1 |
| 1.318 | B.122 | C.1 |
| 1.319 | B.123 | C.1 |
| 1.320 | B.124 | C.1 |
| 1.321 | B.125 | C.1 |
| 1.322 | B.126 | C.1 |
| 1.323 | B.127 | C.1 |
| 1.324 | B.128 | C.1 |
| 1.325 | B.129 | C.1 |
| 1.326 | B.130 | C.1 |
| 1.327 | B.131 | C.1 |
| 1.328 | B.132 | C.1 |
| 1.329 | B.133 | C.1 |
| 1.330 | B.134 | C.1 |
| 1.331 | B.135 | C.1 |
| 1.332 | B.136 | C.1 |
| 1.333 | B.137 | C.1 |
| 1.334 | B.138 | C.1 |
| 1.335 | B.139 | C.1 |
| 1.336 | B.140 | C.1 |
| 1.337 | B.141 | C.1 |
| 1.338 | B.142 | C.1 |
| 1.339 | B.143 | C.1 |
| 1.340 | B.144 | C.1 |
| 1.341 | B.145 | C.1 |
| 1.342 | B.146 | C.1 |
| 1.343 | B.147 | C.1 |
| 1.344 | B.148 | C.1 |
| 1.345 | B.149 | C.1 |
| 1.346 | B.150 | C.1 |
| 1.347 | B.151 | C.1 |
| 1.348 | B.152 | C.1 |
| 1.349 | B.153 | C.1 |
| 1.350 | B.154 | C.1 |
| 1.351 | B.155 | C.1 |
| 1.352 | B.156 | C.1 |
| 1.353 | B.157 | C.1 |
| 1.354 | B.158 | C.1 |
| 1.355 | B.159 | C.1 |
| 1.356 | B.160 | C.1 |
| 1.357 | B.161 | C.1 |
| 1.358 | B.162 | C.1 |
| 1.359 | B.163 | C.1 |
| 1.360 | B.164 | C.1 |
| 1.361 | B.165 | C.1 |
| 1.362 | B.166 | C.1 |
| 1.363 | B.167 | C.1 |
| 1.364 | B.168 | C.1 |
| 1.365 | B.169 | C.1 |
| 1.366 | B.170 | C.1 |
| 1.367 | B.171 | C.1 |
| 1.368 | B.172 | C.1 |
| 1.369 | B.173 | C.1 |
| 1.370 | B.174 | C.1 |
| 1.371 | B.175 | C.1 |
| 1.372 | B.176 | C.1 |
| 1.373 | B.177 | C.1 |
| 1.374 | B.178 | C.1 |
| 1.375 | B.179 | C.1 |
| 1.376 | B.180 | C.1 |
| 1.377 | B.181 | C.1 |
| 1.378 | B.182 | C.1 |
| 1.379 | B.183 | C.1 |
| 1.380 | B.184 | C.1 |
| 1.381 | B.185 | C.1 |
| 1.382 | B.186 | C.1 |
| 1.383 | B.187 | C.1 |
| 1.384 | B.188 | C.1 |
| 1.385 | B.189 | C.1 |
| 1.386 | B.190 | C.1 |
| 1.387 | B.191 | C.1 |
| 1.388 | B.192 | C.1 |
| 1.389 | B.193 | C.1 |
| 1.390 | B.194 | C.1 |
| 1.391 | B.195 | C.1 |
| 1.392 | B.196 | C.1 |
| 1.393 | B.1 | C.2 |
| 1.394 | B.2 | C.2 |
| 1.395 | B.3 | C.2 |
| 1.396 | B.4 | C.2 |
| 1.397 | B.5 | C.2 |
| 1.398 | B.6 | C.2 |
| 1.399 | B.7 | C.2 |
| 1.400 | B.8 | C.2 |
| 1.401 | B.9 | C.2 |
| 1.402 | B.10 | C.2 |
| 1.403 | B.11 | C.2 |
| 1.404 | B.12 | C.2 |
| 1.405 | B.13 | C.2 |
| 1.406 | B.14 | C.2 |
| 1.407 | B.15 | C.2 |
| 1.408 | B.16 | C.2 |
| 1.409 | B.17 | C.2 |
| 1.410 | B.18 | C.2 |
| 1.411 | B.19 | C.2 |
| 1.412 | B.20 | C.2 |
| 1.413 | B.21 | C.2 |
| 1.414 | B.22 | C.2 |
| 1.415 | B.23 | C.2 |
| 1.416 | B.24 | C.2 |
| 1.417 | B.25 | C.2 |
| 1.418 | B.26 | C.2 |
| 1.419 | B.27 | C.2 |
| 1.420 | B.28 | C.2 |
| 1.421 | B.29 | C.2 |
| 1.422 | B.30 | C.2 |
| 1.423 | B.31 | C.2 |
| 1.424 | B.32 | C.2 |
| 1.425 | B.33 | C.2 |
| 1.426 | B.34 | C.2 |
| 1.427 | B.35 | C.2 |
| 1.428 | B.36 | C.2 |
| 1.429 | B.37 | C.2 |
| 1.430 | B.38 | C.2 |
| 1.431 | B.39 | C.2 |
| 1.432 | B.40 | C.2 |
| 1.433 | B.41 | C.2 |
| 1.434 | B.42 | C.2 |
| 1.435 | B.43 | C.2 |
| 1.436 | B.44 | C.2 |
| 1.437 | B.45 | C.2 |

TABLE 1-continued (compositions 1.1 to 1.3545):

| comp. no. | herbicide B | safener C |
|---|---|---|
| 1.438 | B.46 | C.2 |
| 1.439 | B.47 | C.2 |
| 1.440 | B.48 | C.2 |
| 1.441 | B.49 | C.2 |
| 1.442 | B.50 | C.2 |
| 1.443 | B.51 | C.2 |
| 1.444 | B.52 | C.2 |
| 1.445 | B.53 | C.2 |
| 1.446 | B.54 | C.2 |
| 1.447 | B.55 | C.2 |
| 1.448 | B.56 | C.2 |
| 1.449 | B.57 | C.2 |
| 1.450 | B.58. | C.2 |
| 1.451 | B.59 | C.2 |
| 1.452 | B.60 | C.2 |
| 1.453 | B.61 | C.2 |
| 1.454 | B.62 | C.2 |
| 1.455 | B.63 | C.2 |
| 1.456 | B.64 | C.2 |
| 1.457 | B.65 | C.2 |
| 1.458 | B.66 | C.2 |
| 1.459 | B.67 | C.2 |
| 1.460 | B.68 | C.2 |
| 1.461 | B.69 | C.2 |
| 1.462 | B.70 | C.2 |
| 1.463 | B.71 | C.2 |
| 1.464 | B.72 | C.2 |
| 1.465 | B.73 | C.2 |
| 1.466 | B.74 | C.2 |
| 1.467 | B.75 | C.2 |
| 1.468 | B.76 | C.2 |
| 1.469 | B.77 | C.2 |
| 1.470 | B.78 | C.2 |
| 1.471 | B.79 | C.2 |
| 1.472 | B.80 | C.2 |
| 1.473 | B.81 | C.2 |
| 1.474 | B.82 | C.2 |
| 1.475 | B.83 | C.2 |
| 1.476 | B.84 | C.2 |
| 1.477 | B.85 | C.2 |
| 1.478 | B.86 | C.2 |
| 1.479 | B.87 | C.2 |
| 1.480 | B.88 | C.2 |
| 1.481 | B.89 | C.2 |
| 1.482 | B.90 | C.2 |
| 1.483 | B.91 | C.2 |
| 1.484 | B.92 | C.2 |
| 1.485 | B.93 | C.2 |
| 1.486 | B.94 | C.2 |
| 1.487 | B.95 | C.2 |
| 1.488 | B.96 | C.2 |
| 1.489 | B.97 | C.2 |
| 1.490 | B.98 | C.2 |
| 1.491 | B.99 | C.2 |
| 1.492 | B.100 | C.2 |
| 1.493 | B.101 | C.2 |
| 1.494 | B.102 | C.2 |
| 1.495 | B.103 | C.2 |
| 1.496 | B.104 | C.2 |
| 1.497 | B.105 | C.2 |
| 1.498 | B.106 | C.2 |
| 1.499 | B.107 | C.2 |
| 1.500 | B.108 | C.2 |
| 1.501 | B.109 | C.2 |
| 1.502 | B.110 | C.2 |
| 1.503 | B.111 | C.2 |
| 1.504 | B.112 | C.2 |
| 1.505 | B.113 | C.2 |
| 1.506 | B.114 | C.2 |
| 1.507 | B.115 | C.2 |
| 1.508 | B.116 | C.2 |
| 1.509 | B.117 | C.2 |
| 1.510 | B.118 | C.2 |
| 1.511 | B.119 | C.2 |
| 1.512 | B.120 | C.2 |
| 1.513 | B.121 | C.2 |
| 1.514 | B.122 | C.2 |
| 1.515 | B.123 | C.2 |
| 1.516 | B.124 | C.2 |
| 1.517 | B.125 | C.2 |
| 1.518 | B.126 | C.2 |
| 1.519 | B.127 | C.2 |
| 1.520 | B.128 | C.2 |
| 1.521 | B.129 | C.2 |
| 1.522 | B.130 | C.2 |
| 1.523 | B.131 | C.2 |
| 1.524 | B.132 | C.2 |
| 1.525 | B.133 | C.2 |
| 1.526 | B.134 | C.2 |
| 1.527 | B.135 | C.2 |
| 1.528 | B.136 | C.2 |
| 1.529 | B.137 | C.2 |
| 1.530 | B.138 | C.2 |
| 1.531 | B.139 | C.2 |
| 1.532 | B.140 | C.2 |
| 1.533 | B.141 | C.2 |
| 1.534 | B.142 | C.2 |
| 1.535 | B.143 | C.2 |
| 1.536 | B.144 | C.2 |
| 1.537 | B.145 | C.2 |
| 1.538 | B.146 | C.2 |
| 1.539 | B.147 | C.2 |
| 1.540 | B.148 | C.2 |
| 1.541 | B.149 | C.2 |
| 1.542 | B.150 | C.2 |
| 1.543 | B.151 | C.2 |
| 1.544 | B.152 | C.2 |
| 1.545 | B.153 | C.2 |
| 1.546 | B.154 | C.2 |
| 1.547 | B.155 | C.2 |
| 1.548 | B.156 | C.2 |
| 1.549 | B.157 | C.2 |
| 1.550 | B.158 | C.2 |
| 1.551 | B.159 | C.2 |
| 1.552 | B.160 | C.2 |
| 1.553 | B.161 | C.2 |
| 1.554 | B.162 | C.2 |
| 1.555 | B.163 | C.2 |
| 1.556 | B.164 | C.2 |
| 1.557 | B.165 | C.2 |
| 1.558 | B.166 | C.2 |
| 1.559 | B.167 | C.2 |
| 1.560 | B.168 | C.2 |
| 1.561 | B.169 | C.2 |
| 1.562 | B.170 | C.2 |
| 1.563 | B.171 | C.2 |
| 1.564 | B.172 | C.2 |
| 1.565 | B.173 | C.2 |
| 1.566 | B.174 | C.2 |
| 1.567 | B.175 | C.2 |
| 1.568 | B.176 | C.2 |
| 1.569 | B.177 | C.2 |
| 1.570 | B.178 | C.2 |
| 1.571 | B.179 | C.2 |
| 1.572 | B.180 | C.2 |
| 1.573 | B.181 | C.2 |
| 1.574 | B.182 | C.2 |
| 1.575 | B.183 | C.2 |
| 1.576 | B.184 | C.2 |
| 1.577 | B.185 | C.2 |
| 1.578 | B.186 | C.2 |
| 1.579 | B.187 | C.2 |
| 1.580 | B.188 | C.2 |
| 1.581 | B.189 | C.2 |
| 1.582 | B.190 | C.2 |
| 1.583 | B.191 | C.2 |
| 1.584 | B.192 | C.2 |
| 1.585 | B.193 | C.2 |
| 1.586 | B.194 | C.2 |
| 1.587 | B.195 | C.2 |
| 1.588 | B.196 | C.2 |
| 1.589 | B.1 | C.3 |

TABLE 1-continued (compositions 1.1 to 1.3545):

| comp. no. | herbicide B | safener C |
|---|---|---|
| 1.590 | B.2 | C.3 |
| 1.591 | B.3 | C.3 |
| 1.592 | B.4 | C.3 |
| 1.593 | B.5 | C.3 |
| 1.594 | B.6 | C.3 |
| 1.595 | B.7 | C.3 |
| 1.596 | B.8 | C.3 |
| 1.597 | B.9 | C.3 |
| 1.598 | B.10 | C.3 |
| 1.599 | B.11 | C.3 |
| 1.600 | B.12 | C.3 |
| 1.601 | B.13 | C.3 |
| 1.602 | B.14 | C.3 |
| 1.603 | B.15 | C.3 |
| 1.604 | B.16 | C.3 |
| 1.605 | B.17 | C.3 |
| 1.606 | B.18 | C.3 |
| 1.607 | B.19 | C.3 |
| 1.608 | B.20 | C.3 |
| 1.609 | B.21 | C.3 |
| 1.610 | B.22 | C.3 |
| 1.611 | B.23 | C.3 |
| 1.612 | B.24 | C.3 |
| 1.613 | B.25 | C.3 |
| 1.614 | B.26 | C.3 |
| 1.615 | B.27 | C.3 |
| 1.616 | B.28 | C.3 |
| 1.617 | B.29 | C.3 |
| 1.618 | B.30 | C.3 |
| 1.619 | B.31 | C.3 |
| 1.620 | B.32 | C.3 |
| 1.621 | B.33 | C.3 |
| 1.622 | B.34 | C.3 |
| 1.623 | B.35 | C.3 |
| 1.624 | B.36 | C.3 |
| 1.625 | B.37 | C.3 |
| 1.626 | B.38 | C.3 |
| 1.627 | B.39 | C.3 |
| 1.628 | B.40 | C.3 |
| 1.629 | B.41 | C.3 |
| 1.630 | B.42 | C.3 |
| 1.631 | B.43 | C.3 |
| 1.632 | B.44 | C.3 |
| 1.633 | B.45 | C.3 |
| 1.634 | B.46 | C.3 |
| 1.635 | B.47 | C.3 |
| 1.636 | B.48 | C.3 |
| 1.637 | B.49 | C.3 |
| 1.638 | B.50 | C.3 |
| 1.639 | B.51 | C.3 |
| 1.640 | B.52 | C.3 |
| 1.641 | B.53 | C.3 |
| 1.642 | B.54 | C.3 |
| 1.643 | B.55 | C.3 |
| 1.644 | B.56 | C.3 |
| 1.645 | B.57 | C.3 |
| 1.646 | B.58. | C.3 |
| 1.647 | B.59 | C.3 |
| 1.648 | B.60 | C.3 |
| 1.649 | B.61 | C.3 |
| 1.650 | B.62 | C.3 |
| 1.651 | B.63 | C.3 |
| 1.652 | B.64 | C.3 |
| 1.653 | B.65 | C.3 |
| 1.654 | B.66 | C.3 |
| 1.655 | B.67 | C.3 |
| 1.656 | B.68 | C.3 |
| 1.657 | B.69 | C.3 |
| 1.658 | B.70 | C.3 |
| 1.659 | B.71 | C.3 |
| 1.660 | B.72 | C.3 |
| 1.661 | B.73 | C.3 |
| 1.662 | B.74 | C.3 |
| 1.663 | B.75 | C.3 |
| 1.664 | B.76 | C.3 |
| 1.665 | B.77 | C.3 |
| 1.666 | B.78 | C.3 |
| 1.667 | B.79 | C.3 |
| 1.668 | B.80 | C.3 |
| 1.669 | B.81 | C.3 |
| 1.670 | B.82 | C.3 |
| 1.671 | B.83 | C.3 |
| 1.672 | B.84 | C.3 |
| 1.673 | B.85 | C.3 |
| 1.674 | B.86 | C.3 |
| 1.675 | B.87 | C.3 |
| 1.676 | B.88 | C.3 |
| 1.677 | B.89 | C.3 |
| 1.678 | B.90 | C.3 |
| 1.679 | B.91 | C.3 |
| 1.680 | B.92 | C.3 |
| 1.681 | B.93 | C.3 |
| 1.682 | B.94 | C.3 |
| 1.683 | B.95 | C.3 |
| 1.684 | B.96 | C.3 |
| 1.685 | B.97 | C.3 |
| 1.686 | B.98 | C.3 |
| 1.687 | B.99 | C.3 |
| 1.688 | B.100 | C.3 |
| 1.689 | B.101 | C.3 |
| 1.690 | B.102 | C.3 |
| 1.691 | B.103 | C.3 |
| 1.692 | B.104 | C.3 |
| 1.693 | B.105 | C.3 |
| 1.694 | B.106 | C.3 |
| 1.695 | B.107 | C.3 |
| 1.696 | B.108 | C.3 |
| 1.697 | B.109 | C.3 |
| 1.698 | B.110 | C.3 |
| 1.699 | B.111 | C.3 |
| 1.700 | B.112 | C.3 |
| 1.701 | B.113 | C.3 |
| 1.702 | B.114 | C.3 |
| 1.703 | B.115 | C.3 |
| 1.704 | B.116 | C.3 |
| 1.705 | B.117 | C.3 |
| 1.706 | B.118 | C.3 |
| 1.707 | B.119 | C.3 |
| 1.708 | B.120 | C.3 |
| 1.709 | B.121 | C.3 |
| 1.710 | B.122 | C.3 |
| 1.711 | B.123 | C.3 |
| 1.712 | B.124 | C.3 |
| 1.713 | B.125 | C.3 |
| 1.714 | B.126 | C.3 |
| 1.715 | B.127 | C.3 |
| 1.716 | B.128 | C.3 |
| 1.717 | B.129 | C.3 |
| 1.718 | B.130 | C.3 |
| 1.719 | B.131 | C.3 |
| 1.720 | B.132 | C.3 |
| 1.721 | B.133 | C.3 |
| 1.722 | B.134 | C.3 |
| 1.723 | B.135 | C.3 |
| 1.724 | B.136 | C.3 |
| 1.725 | B.137 | C.3 |
| 1.726 | B.138 | C.3 |
| 1.727 | B.139 | C.3 |
| 1.728 | B.140 | C.3 |
| 1.729 | B.141 | C.3 |
| 1.730 | B.142 | C.3 |
| 1.731 | B.143 | C.3 |
| 1.732 | B.144 | C.3 |
| 1.733 | B.145 | C.3 |
| 1.734 | B.146 | C.3 |
| 1.735 | B.147 | C.3 |
| 1.736 | B.148 | C.3 |
| 1.737 | B.149 | C.3 |
| 1.738 | B.150 | C.3 |
| 1.739 | B.151 | C.3 |
| 1.740 | B.152 | C.3 |
| 1.741 | B.153 | C.3 |

TABLE 1-continued (compositions 1.1 to 1.3545):

| comp. no. | herbicide B | safener C |
|---|---|---|
| 1.742 | B.154 | C.3 |
| 1.743 | B.155 | C.3 |
| 1.744 | B.156 | C.3 |
| 1.745 | B.157 | C.3 |
| 1.746 | B.158 | C.3 |
| 1.747 | B.159 | C.3 |
| 1.748 | B.160 | C.3 |
| 1.749 | B.161 | C.3 |
| 1.750 | B.162 | C.3 |
| 1.751 | B.163 | C.3 |
| 1.752 | B.164 | C.3 |
| 1.753 | B.165 | C.3 |
| 1.754 | B.166 | C.3 |
| 1.755 | B.167 | C.3 |
| 1.756 | B.168 | C.3 |
| 1.757 | B.169 | C.3 |
| 1.758 | B.170 | C.3 |
| 1.759 | B.171 | C.3 |
| 1.760 | B.172 | C.3 |
| 1.761 | B.173 | C.3 |
| 1.762 | B.174 | C.3 |
| 1.763 | B.175 | C.3 |
| 1.764 | B.176 | C.3 |
| 1.765 | B.177 | C.3 |
| 1.766 | B.178 | C.3 |
| 1.767 | B.179 | C.3 |
| 1.768 | B.180 | C.3 |
| 1.769 | B.181 | C.3 |
| 1.770 | B.182 | C.3 |
| 1.771 | B.183 | C.3 |
| 1.772 | B.184 | C.3 |
| 1.773 | B.185 | C.3 |
| 1.774 | B.186 | C.3 |
| 1.775 | B.187 | C.3 |
| 1.776 | B.188 | C.3 |
| 1.777 | B.189 | C.3 |
| 1.778 | B.190 | C.3 |
| 1.779 | B.191 | C.3 |
| 1.780 | B.192 | C.3 |
| 1.781 | B.193 | C.3 |
| 1.782 | B.194 | C.3 |
| 1.783 | B.195 | C.3 |
| 1.784 | B.196 | C.3 |
| 1.785 | B.1 | C.4 |
| 1.786 | B.2 | C.4 |
| 1.787 | B.3 | C.4 |
| 1.788 | B.4 | C.4 |
| 1.789 | B.5 | C.4 |
| 1.790 | B.6 | C.4 |
| 1.791 | B.7 | C.4 |
| 1.792 | B.8 | C.4 |
| 1.793 | B.9 | C.4 |
| 1.794 | B.10 | C.4 |
| 1.795 | B.11 | C.4 |
| 1.796 | B.12 | C.4 |
| 1.797 | B.13 | C.4 |
| 1.798 | B.14 | C.4 |
| 1.799 | B.15 | C.4 |
| 1.800 | B.16 | C.4 |
| 1.801 | B.17 | C.4 |
| 1.802 | B.18 | C.4 |
| 1.803 | B.19 | C.4 |
| 1.804 | B.20 | C.4 |
| 1.805 | B.21 | C.4 |
| 1.806 | B.22 | C.4 |
| 1.807 | B.23 | C.4 |
| 1.808 | B.24 | C.4 |
| 1.809 | B.25 | C.4 |
| 1.810 | B.26 | C.4 |
| 1.811 | B.27 | C.4 |
| 1.812 | B.28 | C.4 |
| 1.813 | B.29 | C.4 |
| 1.814 | B.30 | C.4 |
| 1.815 | B.31 | C.4 |
| 1.816 | B.32 | C.4 |
| 1.817 | B.33 | C.4 |
| 1.818 | B.34 | C.4 |
| 1.819 | B.35 | C.4 |
| 1.820 | B.36 | C.4 |
| 1.821 | B.37 | C.4 |
| 1.822 | B.38 | C.4 |
| 1.823 | B.39 | C.4 |
| 1.824 | B.40 | C.4 |
| 1.825 | B.41 | C.4 |
| 1.826 | B.42 | C.4 |
| 1.827 | B.43 | C.4 |
| 1.828 | B.44 | C.4 |
| 1.829 | B.45 | C.4 |
| 1.830 | B.46 | C.4 |
| 1.831 | B.47 | C.4 |
| 1.832 | B.48 | C.4 |
| 1.833 | B.49 | C.4 |
| 1.834 | B.50 | C.4 |
| 1.835 | B.51 | C.4 |
| 1.836 | B.52 | C.4 |
| 1.837 | B.53 | C.4 |
| 1.838 | B.54 | C.4 |
| 1.839 | B.55 | C.4 |
| 1.840 | B.56 | C.4 |
| 1.841 | B.57 | C.4 |
| 1.842 | B.58. | C.4 |
| 1.843 | B.59 | C.4 |
| 1.844 | B.60 | C.4 |
| 1.845 | B.61 | C.4 |
| 1.846 | B.62 | C.4 |
| 1.847 | B.63 | C.4 |
| 1.848 | B.64 | C.4 |
| 1.849 | B.65 | C.4 |
| 1.850 | B.66 | C.4 |
| 1.851 | B.67 | C.4 |
| 1.852 | B.68 | C.4 |
| 1.853 | B.69 | C.4 |
| 1.854 | B.70 | C.4 |
| 1.855 | B.71 | C.4 |
| 1.856 | B.72 | C.4 |
| 1.857 | B.73 | C.4 |
| 1.858 | B.74 | C.4 |
| 1.859 | B.75 | C.4 |
| 1.860 | B.76 | C.4 |
| 1.861 | B.77 | C.4 |
| 1.862 | B.78 | C.4 |
| 1.863 | B.79 | C.4 |
| 1.864 | B.80 | C.4 |
| 1.865 | B.81 | C.4 |
| 1.866 | B.82 | C.4 |
| 1.867 | B.83 | C.4 |
| 1.868 | B.84 | C.4 |
| 1.869 | B.85 | C.4 |
| 1.870 | B.86 | C.4 |
| 1.871 | B.87 | C.4 |
| 1.872 | B.88 | C.4 |
| 1.873 | B.89 | C.4 |
| 1.874 | B.90 | C.4 |
| 1.875 | B.91 | C.4 |
| 1.876 | B.92 | C.4 |
| 1.877 | B.93 | C.4 |
| 1.878 | B.94 | C.4 |
| 1.879 | B.95 | C.4 |
| 1.880 | B.96 | C.4 |
| 1.881 | B.97 | C.4 |
| 1.882 | B.98 | C.4 |
| 1.883 | B.99 | C.4 |
| 1.884 | B.100 | C.4 |
| 1.885 | B.101 | C.4 |
| 1.886 | B.102 | C.4 |
| 1.887 | B.103 | C.4 |
| 1.888 | B.104 | C.4 |
| 1.889 | B.105 | C.4 |
| 1.890 | B.106 | C.4 |
| 1.891 | B.107 | C.4 |
| 1.892 | B.108 | C.4 |
| 1.893 | B.109 | C.4 |

TABLE 1-continued (compositions 1.1 to 1.3545):

| comp. no. | herbicide B | safener C |
|---|---|---|
| 1.894 | B.110 | C.4 |
| 1.895 | B.111 | C.4 |
| 1.896 | B.112 | C.4 |
| 1.897 | B.113 | C.4 |
| 1.898 | B.114 | C.4 |
| 1.899 | B.115 | C.4 |
| 1.900 | B.116 | C.4 |
| 1.901 | B.117 | C.4 |
| 1.902 | B.118 | C.4 |
| 1.903 | B.119 | C.4 |
| 1.904 | B.120 | C.4 |
| 1.905 | B.121 | C.4 |
| 1.906 | B.122 | C.4 |
| 1.907 | B.123 | C.4 |
| 1.908 | B.124 | C.4 |
| 1.909 | B.125 | C.4 |
| 1.910 | B.126 | C.4 |
| 1.911 | B.127 | C.4 |
| 1.912 | B.128 | C.4 |
| 1.913 | B.129 | C.4 |
| 1.914 | B.130 | C.4 |
| 1.915 | B.131 | C.4 |
| 1.916 | B.132 | C.4 |
| 1.917 | B.133 | C.4 |
| 1.918 | B.134 | C.4 |
| 1.919 | B.135 | C.4 |
| 1.920 | B.136 | C.4 |
| 1.921 | B.137 | C.4 |
| 1.922 | B.138 | C.4 |
| 1.923 | B.139 | C.4 |
| 1.924 | B.140 | C.4 |
| 1.925 | B.141 | C.4 |
| 1.926 | B.142 | C.4 |
| 1.927 | B.143 | C.4 |
| 1.928 | B.144 | C.4 |
| 1.929 | B.145 | C.4 |
| 1.930 | B.146 | C.4 |
| 1.931 | B.147 | C.4 |
| 1.932 | B.148 | C.4 |
| 1.933 | B.149 | C.4 |
| 1.934 | B.150 | C.4 |
| 1.935 | B.151 | C.4 |
| 1.936 | B.152 | C.4 |
| 1.937 | B.153 | C.4 |
| 1.938 | B.154 | C.4 |
| 1.939 | B.155 | C.4 |
| 1.940 | B.156 | C.4 |
| 1.941 | B.157 | C.4 |
| 1.942 | B.158 | C.4 |
| 1.943 | B.159 | C.4 |
| 1.944 | B.160 | C.4 |
| 1.945 | B.161 | C.4 |
| 1.946 | B.162 | C.4 |
| 1.947 | B.163 | C.4 |
| 1.948 | B.164 | C.4 |
| 1.949 | B.165 | C.4 |
| 1.950 | B.166 | C.4 |
| 1.951 | B.167 | C.4 |
| 1.952 | B.168 | C.4 |
| 1.953 | B.169 | C.4 |
| 1.954 | B.170 | C.4 |
| 1.955 | B.171 | C.4 |
| 1.956 | B.172 | C.4 |
| 1.957 | B.173 | C.4 |
| 1.958 | B.174 | C.4 |
| 1.959 | B.175 | C.4 |
| 1.960 | B.176 | C.4 |
| 1.961 | B.177 | C.4 |
| 1.962 | B.178 | C.4 |
| 1.963 | B.179 | C.4 |
| 1.964 | B.180 | C.4 |
| 1.965 | B.181 | C.4 |
| 1.966 | B.182 | C.4 |
| 1.967 | B.183 | C.4 |
| 1.968 | B.184 | C.4 |
| 1.969 | B.185 | C.4 |
| 1.970 | B.186 | C.4 |
| 1.971 | B.187 | C.4 |
| 1.972 | B.188 | C.4 |
| 1.973 | B.189 | C.4 |
| 1.974 | B.190 | C.4 |
| 1.975 | B.191 | C.4 |
| 1.976 | B.192 | C.4 |
| 1.977 | B.193 | C.4 |
| 1.978 | B.194 | C.4 |
| 1.979 | B.195 | C.4 |
| 1.980 | B.196 | C.4 |
| 1.981 | B.1 | C.5 |
| 1.982 | B.2 | C.5 |
| 1.983 | B.3 | C.5 |
| 1.984 | B.4 | C.5 |
| 1.985 | B.5 | C.5 |
| 1.986 | B.6 | C.5 |
| 1.987 | B.7 | C.5 |
| 1.988 | B.8 | C.5 |
| 1.989 | B.9 | C.5 |
| 1.990 | B.10 | C.5 |
| 1.991 | B.11 | C.5 |
| 1.992 | B.12 | C.5 |
| 1.993 | B.13 | C.5 |
| 1.994 | B.14 | C.5 |
| 1.995 | B.15 | C.5 |
| 1.996 | B.16 | C.5 |
| 1.997 | B.17 | C.5 |
| 1.998 | B.18 | C.5 |
| 1.999 | B.19 | C.5 |
| 1.1000 | B.20 | C.5 |
| 1.1001 | B.21 | C.5 |
| 1.1002 | B.22 | C.5 |
| 1.1003 | B.23 | C.5 |
| 1.1004 | B.24 | C.5 |
| 1.1005 | B.25 | C.5 |
| 1.1006 | B.26 | C.5 |
| 1.1007 | B.27 | C.5 |
| 1.1008 | B.28 | C.5 |
| 1.1009 | B.29 | C.5 |
| 1.1010 | B.30 | C.5 |
| 1.1011 | B.31 | C.5 |
| 1.1012 | B.32 | C.5 |
| 1.1013 | B.33 | C.5 |
| 1.1014 | B.34 | C.5 |
| 1.1015 | B.35 | C.5 |
| 1.1016 | B.36 | C.5 |
| 1.1017 | B.37 | C.5 |
| 1.1018 | B.38 | C.5 |
| 1.1019 | B.39 | C.5 |
| 1.1020 | B.40 | C.5 |
| 1.1021 | B.41 | C.5 |
| 1.1022 | B.42 | C.5 |
| 1.1023 | B.43 | C.5 |
| 1.1024 | B.44 | C.5 |
| 1.1025 | B.45 | C.5 |
| 1.1026 | B.46 | C.5 |
| 1.1027 | B.47 | C.5 |
| 1.1028 | B.48 | C.5 |
| 1.1029 | B.49 | C.5 |
| 1.1030 | B.50 | C.5 |
| 1.1031 | B.51 | C.5 |
| 1.1032 | B.52 | C.5 |
| 1.1033 | B.53 | C.5 |
| 1.1034 | B.54 | C.5 |
| 1.1035 | B.55 | C.5 |
| 1.1036 | B.56 | C.5 |
| 1.1037 | B.57 | C.5 |
| 1.1038 | B.58. | C.5 |
| 1.1039 | B.59 | C.5 |
| 1.1040 | B.60 | C.5 |
| 1.1041 | B.61 | C.5 |
| 1.1042 | B.62 | C.5 |
| 1.1043 | B.63 | C.5 |
| 1.1044 | B.64 | C.5 |
| 1.1045 | B.65 | C.5 |

TABLE 1-continued (compositions 1.1 to 1.3545):

| comp. no. | herbicide B | safener C |
|---|---|---|
| 1.1046 | B.66 | C.5 |
| 1.1047 | B.67 | C.5 |
| 1.1048 | B.68 | C.5 |
| 1.1049 | B.69 | C.5 |
| 1.1050 | B.70 | C.5 |
| 1.1051 | B.71 | C.5 |
| 1.1052 | B.72 | C.5 |
| 1.1053 | B.73 | C.5 |
| 1.1054 | B.74 | C.5 |
| 1.1055 | B.75 | C.5 |
| 1.1056 | B.76 | C.5 |
| 1.1057 | B.77 | C.5 |
| 1.1058 | B.78 | C.5 |
| 1.1059 | B.79 | C.5 |
| 1.1060 | B.80 | C.5 |
| 1.1061 | B.81 | C.5 |
| 1.1062 | B.82 | C.5 |
| 1.1063 | B.83 | C.5 |
| 1.1064 | B.84 | C.5 |
| 1.1065 | B.85 | C.5 |
| 1.1066 | B.86 | C.5 |
| 1.1067 | B.87 | C.5 |
| 1.1068 | B.88 | C.5 |
| 1.1069 | B.89 | C.5 |
| 1.1070 | B.90 | C.5 |
| 1.1071 | B.91 | C.5 |
| 1.1072 | B.92 | C.5 |
| 1.1073 | B.93 | C.5 |
| 1.1074 | B.94 | C.5 |
| 1.1075 | B.95 | C.5 |
| 1.1076 | B.96 | C.5 |
| 1.1077 | B.97 | C.5 |
| 1.1078 | B.98 | C.5 |
| 1.1079 | B.99 | C.5 |
| 1.1080 | B.100 | C.5 |
| 1.1081 | B.101 | C.5 |
| 1.1082 | B.102 | C.5 |
| 1.1083 | B.103 | C.5 |
| 1.1084 | B.104 | C.5 |
| 1.1085 | B.105 | C.5 |
| 1.1086 | B.106 | C.5 |
| 1.1087 | B.107 | C.5 |
| 1.1088 | B.108 | C.5 |
| 1.1089 | B.109 | C.5 |
| 1.1090 | B.110 | C.5 |
| 1.1091 | B.111 | C.5 |
| 1.1092 | B.112 | C.5 |
| 1.1093 | B.113 | C.5 |
| 1.1094 | B.114 | C.5 |
| 1.1095 | B.115 | C.5 |
| 1.1096 | B.116 | C.5 |
| 1.1097 | B.117 | C.5 |
| 1.1098 | B.118 | C.5 |
| 1.1099 | B.119 | C.5 |
| 1.1100 | B.120 | C.5 |
| 1.1101 | B.121 | C.5 |
| 1.1102 | B.122 | C.5 |
| 1.1103 | B.123 | C.5 |
| 1.1104 | B.124 | C.5 |
| 1.1105 | B.125 | C.5 |
| 1.1106 | B.126 | C.5 |
| 1.1107 | B.127 | C.5 |
| 1.1108 | B.128 | C.5 |
| 1.1109 | B.129 | C.5 |
| 1.1110 | B.130 | C.5 |
| 1.1111 | B.131 | C.5 |
| 1.1112 | B.132 | C.5 |
| 1.1113 | B.133 | C.5 |
| 1.1114 | B.134 | C.5 |
| 1.1115 | B.135 | C.5 |
| 1.1116 | B.136 | C.5 |
| 1.1117 | B.137 | C.5 |
| 1.1118 | B.138 | C.5 |
| 1.1119 | B.139 | C.5 |
| 1.1120 | B.140 | C.5 |
| 1.1121 | B.141 | C.5 |
| 1.1122 | B.142 | C.5 |
| 1.1123 | B.143 | C.5 |
| 1.1124 | B.144 | C.5 |
| 1.1125 | B.145 | C.5 |
| 1.1126 | B.146 | C.5 |
| 1.1127 | B.147 | C.5 |
| 1.1128 | B.148 | C.5 |
| 1.1129 | B.149 | C.5 |
| 1.1130 | B.150 | C.5 |
| 1.1131 | B.151 | C.5 |
| 1.1132 | B.152 | C.5 |
| 1.1133 | B.153 | C.5 |
| 1.1134 | B.154 | C.5 |
| 1.1135 | B.155 | C.5 |
| 1.1136 | B.156 | C.5 |
| 1.1137 | B.157 | C.5 |
| 1.1138 | B.158 | C.5 |
| 1.1139 | B.159 | C.5 |
| 1.1140 | B.160 | C.5 |
| 1.1141 | B.161 | C.5 |
| 1.1142 | B.162 | C.5 |
| 1.1143 | B.163 | C.5 |
| 1.1144 | B.164 | C.5 |
| 1.1145 | B.165 | C.5 |
| 1.1146 | B.166 | C.5 |
| 1.1147 | B.167 | C.5 |
| 1.1148 | B.168 | C.5 |
| 1.1149 | B.169 | C.5 |
| 1.1150 | B.170 | C.5 |
| 1.1151 | B.171 | C.5 |
| 1.1152 | B.172 | C.5 |
| 1.1153 | B.173 | C.5 |
| 1.1154 | B.174 | C.5 |
| 1.1155 | B.175 | C.5 |
| 1.1156 | B.176 | C.5 |
| 1.1157 | B.177 | C.5 |
| 1.1158 | B.178 | C.5 |
| 1.1159 | B.179 | C.5 |
| 1.1160 | B.180 | C.5 |
| 1.1161 | B.181 | C.5 |
| 1.1162 | B.182 | C.5 |
| 1.1163 | B.183 | C.5 |
| 1.1164 | B.184 | C.5 |
| 1.1165 | B.185 | C.5 |
| 1.1166 | B.186 | C.5 |
| 1.1167 | B.187 | C.5 |
| 1.1168 | B.188 | C.5 |
| 1.1169 | B.189 | C.5 |
| 1.1170 | B.190 | C.5 |
| 1.1171 | B.191 | C.5 |
| 1.1172 | B.192 | C.5 |
| 1.1173 | B.193 | C.5 |
| 1.1174 | B.194 | C.5 |
| 1.1175 | B.195 | C.5 |
| 1.1176 | B.196 | C.5 |
| 1.1177 | B.1 | C.6 |
| 1.1178 | B.2 | C.6 |
| 1.1179 | B.3 | C.6 |
| 1.1180 | B.4 | C.6 |
| 1.1181 | B.5 | C.6 |
| 1.1182 | B.6 | C.6 |
| 1.1183 | B.7 | C.6 |
| 1.1184 | B.8 | C.6 |
| 1.1185 | B.9 | C.6 |
| 1.1186 | B.10 | C.6 |
| 1.1187 | B.11 | C.6 |
| 1.1188 | B.12 | C.6 |
| 1.1189 | B.13 | C.6 |
| 1.1190 | B.14 | C.6 |
| 1.1191 | B.15 | C.6 |
| 1.1192 | B.16 | C.6 |
| 1.1193 | B.17 | C.6 |
| 1.1194 | B.18 | C.6 |
| 1.1195 | B.19 | C.6 |
| 1.1196 | B.20 | C.6 |
| 1.1197 | B.21 | C.6 |

TABLE 1-continued (compositions 1.1 to 1.3545):

| comp. no. | herbicide B | safener C |
|---|---|---|
| 1.1198 | B.22 | C.6 |
| 1.1199 | B.23 | C.6 |
| 1.1200 | B.24 | C.6 |
| 1.1201 | B.25 | C.6 |
| 1.1202 | B.26 | C.6 |
| 1.1203 | B.27 | C.6 |
| 1.1204 | B.28 | C.6 |
| 1.1205 | B.29 | C.6 |
| 1.1206 | B.30 | C.6 |
| 1.1207 | B.31 | C.6 |
| 1.1208 | B.32 | C.6 |
| 1.1209 | B.33 | C.6 |
| 1.1210 | B.34 | C.6 |
| 1.1211 | B.35 | C.6 |
| 1.1212 | B.36 | C.6 |
| 1.1213 | B.37 | C.6 |
| 1.1214 | B.38 | C.6 |
| 1.1215 | B.39 | C.6 |
| 1.1216 | B.40 | C.6 |
| 1.1217 | B.41 | C.6 |
| 1.1218 | B.42 | C.6 |
| 1.1219 | B.43 | C.6 |
| 1.1220 | B.44 | C.6 |
| 1.1221 | B.45 | C.6 |
| 1.1222 | B.46 | C.6 |
| 1.1223 | B.47 | C.6 |
| 1.1224 | B.48 | C.6 |
| 1.1225 | B.49 | C.6 |
| 1.1226 | B.50 | C.6 |
| 1.1227 | B.51 | C.6 |
| 1.1228 | B.52 | C.6 |
| 1.1229 | B.53 | C.6 |
| 1.1230 | B.54 | C.6 |
| 1.1231 | B.55 | C.6 |
| 1.1232 | B.56 | C.6 |
| 1.1233 | B.57 | C.6 |
| 1.1234 | B.58. | C.6 |
| 1.1235 | B.59 | C.6 |
| 1.1236 | B.60 | C.6 |
| 1.1237 | B.61 | C.6 |
| 1.1238 | B.62 | C.6 |
| 1.1239 | B.63 | C.6 |
| 1.1240 | B.64 | C.6 |
| 1.1241 | B.65 | C.6 |
| 1.1242 | B.66 | C.6 |
| 1.1243 | B.67 | C.6 |
| 1.1244 | B.68 | C.6 |
| 1.1245 | B.69 | C.6 |
| 1.1246 | B.70 | C.6 |
| 1.1247 | B.71 | C.6 |
| 1.1248 | B.72 | C.6 |
| 1.1249 | B.73 | C.6 |
| 1.1250 | B.74 | C.6 |
| 1.1251 | B.75 | C.6 |
| 1.1252 | B.76 | C.6 |
| 1.1253 | B.77 | C.6 |
| 1.1254 | B.78 | C.6 |
| 1.1255 | B.79 | C.6 |
| 1.1256 | B.80 | C.6 |
| 1.1257 | B.81 | C.6 |
| 1.1258 | B.82 | C.6 |
| 1.1259 | B.83 | C.6 |
| 1.1260 | B.84 | C.6 |
| 1.1261 | B.85 | C.6 |
| 1.1262 | B.86 | C.6 |
| 1.1263 | B.87 | C.6 |
| 1.1264 | B.88 | C.6 |
| 1.1265 | B.89 | C.6 |
| 1.1266 | B.90 | C.6 |
| 1.1267 | B.91 | C.6 |
| 1.1268 | B.92 | C.6 |
| 1.1269 | B.93 | C.6 |
| 1.1270 | B.94 | C.6 |
| 1.1271 | B.95 | C.6 |
| 1.1272 | B.96 | C.6 |
| 1.1273 | B.97 | C.6 |
| 1.1274 | B.98 | C.6 |
| 1.1275 | B.99 | C.6 |
| 1.1276 | B.100 | C.6 |
| 1.1277 | B.101 | C.6 |
| 1.1278 | B.102 | C.6 |
| 1.1279 | B.103 | C.6 |
| 1.1280 | B.104 | C.6 |
| 1.1281 | B.105 | C.6 |
| 1.1282 | B.106 | C.6 |
| 1.1283 | B.107 | C.6 |
| 1.1284 | B.108 | C.6 |
| 1.1285 | B.109 | C.6 |
| 1.1286 | B.110 | C.6 |
| 1.1287 | B.111 | C.6 |
| 1.1288 | B.112 | C.6 |
| 1.1289 | B.113 | C.6 |
| 1.1290 | B.114 | C.6 |
| 1.1291 | B.115 | C.6 |
| 1.1292 | B.116 | C.6 |
| 1.1293 | B.117 | C.6 |
| 1.1294 | B.118 | C.6 |
| 1.1295 | B.119 | C.6 |
| 1.1296 | B.120 | C.6 |
| 1.1297 | B.121 | C.6 |
| 1.1298 | B.122 | C.6 |
| 1.1299 | B.123 | C.6 |
| 1.1300 | B.124 | C.6 |
| 1.1301 | B.125 | C.6 |
| 1.1302 | B.126 | C.6 |
| 1.1303 | B.127 | C.6 |
| 1.1304 | B.128 | C.6 |
| 1.1305 | B.129 | C.6 |
| 1.1306 | B.130 | C.6 |
| 1.1307 | B.131 | C.6 |
| 1.1308 | B.132 | C.6 |
| 1.1309 | B.133 | C.6 |
| 1.1310 | B.134 | C.6 |
| 1.1311 | B.135 | C.6 |
| 1.1312 | B.136 | C.6 |
| 1.1313 | B.137 | C.6 |
| 1.1314 | B.138 | C.6 |
| 1.1315 | B.139 | C.6 |
| 1.1316 | B.140 | C.6 |
| 1.1317 | B.141 | C.6 |
| 1.1318 | B.142 | C.6 |
| 1.1319 | B.143 | C.6 |
| 1.1320 | B.144 | C.6 |
| 1.1321 | B.145 | C.6 |
| 1.1322 | B.146 | C.6 |
| 1.1323 | B.147 | C.6 |
| 1.1324 | B.148 | C.6 |
| 1.1325 | B.149 | C.6 |
| 1.1326 | B.150 | C.6 |
| 1.1327 | B.151 | C.6 |
| 1.1328 | B.152 | C.6 |
| 1.1329 | B.153 | C.6 |
| 1.1330 | B.154 | C.6 |
| 1.1331 | B.155 | C.6 |
| 1.1332 | B.156 | C.6 |
| 1.1333 | B.157 | C.6 |
| 1.1334 | B.158 | C.6 |
| 1.1335 | B.159 | C.6 |
| 1.1336 | B.160 | C.6 |
| 1.1337 | B.161 | C.6 |
| 1.1338 | B.162 | C.6 |
| 1.1339 | B.163 | C.6 |
| 1.1340 | B.164 | C.6 |
| 1.1341 | B.165 | C.6 |
| 1.1342 | B.166 | C.6 |
| 1.1343 | B.167 | C.6 |
| 1.1344 | B.168 | C.6 |
| 1.1345 | B.169 | C.6 |
| 1.1346 | B.170 | C.6 |
| 1.1347 | B.171 | C.6 |
| 1.1348 | B.172 | C.6 |
| 1.1349 | B.173 | C.6 |

TABLE 1-continued (compositions 1.1 to 1.3545):

| comp. no. | herbicide B | safener C |
|---|---|---|
| 1.1350 | B.174 | C.6 |
| 1.1351 | B.175 | C.6 |
| 1.1352 | B.176 | C.6 |
| 1.1353 | B.177 | C.6 |
| 1.1354 | B.178 | C.6 |
| 1.1355 | B.179 | C.6 |
| 1.1356 | B.180 | C.6 |
| 1.1357 | B.181 | C.6 |
| 1.1358 | B.182 | C.6 |
| 1.1359 | B.183 | C.6 |
| 1.1360 | B.184 | C.6 |
| 1.1361 | B.185 | C.6 |
| 1.1362 | B.186 | C.6 |
| 1.1363 | B.187 | C.6 |
| 1.1364 | B.188 | C.6 |
| 1.1365 | B.189 | C.6 |
| 1.1366 | B.190 | C.6 |
| 1.1367 | B.191 | C.6 |
| 1.1368 | B.192 | C.6 |
| 1.1369 | B.193 | C.6 |
| 1.1370 | B.194 | C.6 |
| 1.1371 | B.195 | C.6 |
| 1.1372 | B.196 | C.6 |
| 1.1373 | B.1 | C.7 |
| 1.1374 | B.2 | C.7 |
| 1.1375 | B.3 | C.7 |
| 1.1376 | B.4 | C.7 |
| 1.1377 | B.5 | C.7 |
| 1.1378 | B.6 | C.7 |
| 1.1379 | B.7 | C.7 |
| 1.1380 | B.8 | C.7 |
| 1.1381 | B.9 | C.7 |
| 1.1382 | B.10 | C.7 |
| 1.1383 | B.11 | C.7 |
| 1.1384 | B.12 | C.7 |
| 1.1385 | B.13 | C.7 |
| 1.1386 | B.14 | C.7 |
| 1.1387 | B.15 | C.7 |
| 1.1388 | B.16 | C.7 |
| 1.1389 | B.17 | C.7 |
| 1.1390 | B.18 | C.7 |
| 1.1391 | B.19 | C.7 |
| 1.1392 | B.20 | C.7 |
| 1.1393 | B.21 | C.7 |
| 1.1394 | B.22 | C.7 |
| 1.1395 | B.23 | C.7 |
| 1.1396 | B.24 | C.7 |
| 1.1397 | B.25 | C.7 |
| 1.1398 | B.26 | C.7 |
| 1.1399 | B.27 | C.7 |
| 1.1400 | B.28 | C.7 |
| 1.1401 | B.29 | C.7 |
| 1.1402 | B.30 | C.7 |
| 1.1403 | B.31 | C.7 |
| 1.1404 | B.32 | C.7 |
| 1.1405 | B.33 | C.7 |
| 1.1406 | B.34 | C.7 |
| 1.1407 | B.35 | C.7 |
| 1.1408 | B.36 | C.7 |
| 1.1409 | B.37 | C.7 |
| 1.1410 | B.38 | C.7 |
| 1.1411 | B.39 | C.7 |
| 1.1412 | B.40 | C.7 |
| 1.1413 | B.41 | C.7 |
| 1.1414 | B.42 | C.7 |
| 1.1415 | B.43 | C.7 |
| 1.1416 | B.44 | C.7 |
| 1.1417 | B.45 | C.7 |
| 1.1418 | B.46 | C.7 |
| 1.1419 | B.47 | C.7 |
| 1.1420 | B.48 | C.7 |
| 1.1421 | B.49 | C.7 |
| 1.1422 | B.50 | C.7 |
| 1.1423 | B.51 | C.7 |
| 1.1424 | B.52 | C.7 |
| 1.1425 | B.53 | C.7 |
| 1.1426 | B.54 | C.7 |
| 1.1427 | B.55 | C.7 |
| 1.1428 | B.56 | C.7 |
| 1.1429 | B.57 | C.7 |
| 1.1430 | B.58. | C.7 |
| 1.1431 | B.59 | C.7 |
| 1.1432 | B.60 | C.7 |
| 1.1433 | B.61 | C.7 |
| 1.1434 | B.62 | C.7 |
| 1.1435 | B.63 | C.7 |
| 1.1436 | B.64 | C.7 |
| 1.1437 | B.65 | C.7 |
| 1.1438 | B.66 | C.7 |
| 1.1439 | B.67 | C.7 |
| 1.1440 | B.68 | C.7 |
| 1.1441 | B.69 | C.7 |
| 1.1442 | B.70 | C.7 |
| 1.1443 | B.71 | C.7 |
| 1.1444 | B.72 | C.7 |
| 1.1445 | B.73 | C.7 |
| 1.1446 | B.74 | C.7 |
| 1.1447 | B.75 | C.7 |
| 1.1448 | B.76 | C.7 |
| 1.1449 | B.77 | C.7 |
| 1.1450 | B.78 | C.7 |
| 1.1451 | B.79 | C.7 |
| 1.1452 | B.80 | C.7 |
| 1.1453 | B.81 | C.7 |
| 1.1454 | B.82 | C.7 |
| 1.1455 | B.83 | C.7 |
| 1.1456 | B.84 | C.7 |
| 1.1457 | B.85 | C.7 |
| 1.1458 | B.86 | C.7 |
| 1.1459 | B.87 | C.7 |
| 1.1460 | B.88 | C.7 |
| 1.1461 | B.89 | C.7 |
| 1.1462 | B.90 | C.7 |
| 1.1463 | B.91 | C.7 |
| 1.1464 | B.92 | C.7 |
| 1.1465 | B.93 | C.7 |
| 1.1466 | B.94 | C.7 |
| 1.1467 | B.95 | C.7 |
| 1.1468 | B.96 | C.7 |
| 1.1469 | B.97 | C.7 |
| 1.1470 | B.98 | C.7 |
| 1.1471 | B.99 | C.7 |
| 1.1472 | B.100 | C.7 |
| 1.1473 | B.101 | C.7 |
| 1.1474 | B.102 | C.7 |
| 1.1475 | B.103 | C.7 |
| 1.1476 | B.104 | C.7 |
| 1.1477 | B.105 | C.7 |
| 1.1478 | B.106 | C.7 |
| 1.1479 | B.107 | C.7 |
| 1.1480 | B.108 | C.7 |
| 1.1481 | B.109 | C.7 |
| 1.1482 | B.110 | C.7 |
| 1.1483 | B.111 | C.7 |
| 1.1484 | B.112 | C.7 |
| 1.1485 | B.113 | C.7 |
| 1.1486 | B.114 | C.7 |
| 1.1487 | B.115 | C.7 |
| 1.1488 | B.116 | C.7 |
| 1.1489 | B.117 | C.7 |
| 1.1490 | B.118 | C.7 |
| 1.1491 | B.119 | C.7 |
| 1.1492 | B.120 | C.7 |
| 1.1493 | B.121 | C.7 |
| 1.1494 | B.122 | C.7 |
| 1.1495 | B.123 | C.7 |
| 1.1496 | B.124 | C.7 |
| 1.1497 | B.125 | C.7 |
| 1.1498 | B.126 | C.7 |
| 1.1499 | B.127 | C.7 |
| 1.1500 | B.128 | C.7 |
| 1.1501 | B.129 | C.7 |

TABLE 1-continued (compositions 1.1 to 1.3545):

| comp. no. | herbicide B | safener C |
|---|---|---|
| 1.1502 | B.130 | C.7 |
| 1.1503 | B.131 | C.7 |
| 1.1504 | B.132 | C.7 |
| 1.1505 | B.133 | C.7 |
| 1.1506 | B.134 | C.7 |
| 1.1507 | B.135 | C.7 |
| 1.1508 | B.136 | C.7 |
| 1.1509 | B.137 | C.7 |
| 1.1510 | B.138 | C.7 |
| 1.1511 | B.139 | C.7 |
| 1.1512 | B.140 | C.7 |
| 1.1513 | B.141 | C.7 |
| 1.1514 | B.142 | C.7 |
| 1.1515 | B.143 | C.7 |
| 1.1516 | B.144 | C.7 |
| 1.1517 | B.145 | C.7 |
| 1.1518 | B.146 | C.7 |
| 1.1519 | B.147 | C.7 |
| 1.1520 | B.148 | C.7 |
| 1.1521 | B.149 | C.7 |
| 1.1522 | B.150 | C.7 |
| 1.1523 | B.151 | C.7 |
| 1.1524 | B.152 | C.7 |
| 1.1525 | B.153 | C.7 |
| 1.1526 | B.154 | C.7 |
| 1.1527 | B.155 | C.7 |
| 1.1528 | B.156 | C.7 |
| 1.1529 | B.157 | C.7 |
| 1.1530 | B.158 | C.7 |
| 1.1531 | B.159 | C.7 |
| 1.1532 | B.160 | C.7 |
| 1.1533 | B.161 | C.7 |
| 1.1534 | B.162 | C.7 |
| 1.1535 | B.163 | C.7 |
| 1.1536 | B.164 | C.7 |
| 1.1537 | B.165 | C.7 |
| 1.1538 | B.166 | C.7 |
| 1.1539 | B.167 | C.7 |
| 1.1540 | B.168 | C.7 |
| 1.1541 | B.169 | C.7 |
| 1.1542 | B.170 | C.7 |
| 1.1543 | B.171 | C.7 |
| 1.1544 | B.172 | C.7 |
| 1.1545 | B.173 | C.7 |
| 1.1546 | B.174 | C.7 |
| 1.1547 | B.175 | C.7 |
| 1.1548 | B.176 | C.7 |
| 1.1549 | B.177 | C.7 |
| 1.1550 | B.178 | C.7 |
| 1.1551 | B.179 | C.7 |
| 1.1552 | B.180 | C.7 |
| 1.1553 | B.181 | C.7 |
| 1.1554 | B.182 | C.7 |
| 1.1555 | B.183 | C.7 |
| 1.1556 | B.184 | C.7 |
| 1.1557 | B.185 | C.7 |
| 1.1558 | B.186 | C.7 |
| 1.1559 | B.187 | C.7 |
| 1.1560 | B.188 | C.7 |
| 1.1561 | B.189 | C.7 |
| 1.1562 | B.190 | C.7 |
| 1.1563 | B.191 | C.7 |
| 1.1564 | B.192 | C.7 |
| 1.1565 | B.193 | C.7 |
| 1.1566 | B.194 | C.7 |
| 1.1567 | B.195 | C.7 |
| 1.1568 | B.196 | C.7 |
| 1.1569 | B.1 | C.8 |
| 1.1570 | B.2 | C.8 |
| 1.1571 | B.3 | C.8 |
| 1.1572 | B.4 | C.8 |
| 1.1573 | B.5 | C.8 |
| 1.1574 | B.6 | C.8 |
| 1.1575 | B.7 | C.8 |
| 1.1576 | B.8 | C.8 |
| 1.1577 | B.9 | C.8 |
| 1.1578 | B.10 | C.8 |
| 1.1579 | B.11 | C.8 |
| 1.1580 | B.12 | C.8 |
| 1.1581 | B.13 | C.8 |
| 1.1582 | B.14 | C.8 |
| 1.1583 | B.15 | C.8 |
| 1.1584 | B.16 | C.8 |
| 1.1585 | B.17 | C.8 |
| 1.1586 | B.18 | C.8 |
| 1.1587 | B.19 | C.8 |
| 1.1588 | B.20 | C.8 |
| 1.1589 | B.21 | C.8 |
| 1.1590 | B.22 | C.8 |
| 1.1591 | B.23 | C.8 |
| 1.1592 | B.24 | C.8 |
| 1.1593 | B.25 | C.8 |
| 1.1594 | B.26 | C.8 |
| 1.1595 | B.27 | C.8 |
| 1.1596 | B.28 | C.8 |
| 1.1597 | B.29 | C.8 |
| 1.1598 | B.30 | C.8 |
| 1.1599 | B.31 | C.8 |
| 1.1600 | B.32 | C.8 |
| 1.1601 | B.33 | C.8 |
| 1.1602 | B.34 | C.8 |
| 1.1603 | B.35 | C.8 |
| 1.1604 | B.36 | C.8 |
| 1.1605 | B.37 | C.8 |
| 1.1606 | B.38 | C.8 |
| 1.1607 | B.39 | C.8 |
| 1.1608 | B.40 | C.8 |
| 1.1609 | B.41 | C.8 |
| 1.1610 | B.42 | C.8 |
| 1.1611 | B.43 | C.8 |
| 1.1612 | B.44 | C.8 |
| 1.1613 | B.45 | C.8 |
| 1.1614 | B.46 | C.8 |
| 1.1615 | B.47 | C.8 |
| 1.1616 | B.48 | C.8 |
| 1.1617 | B.49 | C.8 |
| 1.1618 | B.50 | C.8 |
| 1.1619 | B.51 | C.8 |
| 1.1620 | B.52 | C.8 |
| 1.1621 | B.53 | C.8 |
| 1.1622 | B.54 | C.8 |
| 1.1623 | B.55 | C.8 |
| 1.1624 | B.56 | C.8 |
| 1.1625 | B.57 | C.8 |
| 1.1626 | B.58. | C.8 |
| 1.1627 | B.59 | C.8 |
| 1.1628 | B.60 | C.8 |
| 1.1629 | B.61 | C.8 |
| 1.1630 | B.62 | C.8 |
| 1.1631 | B.63 | C.8 |
| 1.1632 | B.64 | C.8 |
| 1.1633 | B.65 | C.8 |
| 1.1634 | B.66 | C.8 |
| 1.1635 | B.67 | C.8 |
| 1.1636 | B.68 | C.8 |
| 1.1637 | B.69 | C.8 |
| 1.1638 | B.70 | C.8 |
| 1.1639 | B.71 | C.8 |
| 1.1640 | B.72 | C.8 |
| 1.1641 | B.73 | C.8 |
| 1.1642 | B.74 | C.8 |
| 1.1643 | B.75 | C.8 |
| 1.1644 | B.76 | C.8 |
| 1.1645 | B.77 | C.8 |
| 1.1646 | B.78 | C.8 |
| 1.1647 | B.79 | C.8 |
| 1.1648 | B.80 | C.8 |
| 1.1649 | B.81 | C.8 |
| 1.1650 | B.82 | C.8 |
| 1.1651 | B.83 | C.8 |
| 1.1652 | B.84 | C.8 |
| 1.1653 | B.85 | C.8 |

TABLE 1-continued (compositions 1.1 to 1.3545):

| comp. no. | herbicide B | safener C |
|---|---|---|
| 1.1654 | B.86 | C.8 |
| 1.1655 | B.87 | C.8 |
| 1.1656 | B.88 | C.8 |
| 1.1657 | B.89 | C.8 |
| 1.1658 | B.90 | C.8 |
| 1.1659 | B.91 | C.8 |
| 1.1660 | B.92 | C.8 |
| 1.1661 | B.93 | C.8 |
| 1.1662 | B.94 | C.8 |
| 1.1663 | B.95 | C.8 |
| 1.1664 | B.96 | C.8 |
| 1.1665 | B.97 | C.8 |
| 1.1666 | B.98 | C.8 |
| 1.1667 | B.99 | C.8 |
| 1.1668 | B.100 | C.8 |
| 1.1669 | B.101 | C.8 |
| 1.1670 | B.102 | C.8 |
| 1.1671 | B.103 | C.8 |
| 1.1672 | B.104 | C.8 |
| 1.1673 | B.105 | C.8 |
| 1.1674 | B.106 | C.8 |
| 1.1675 | B.107 | C.8 |
| 1.1676 | B.108 | C.8 |
| 1.1677 | B.109 | C.8 |
| 1.1678 | B.110 | C.8 |
| 1.1679 | B.111 | C.8 |
| 1.1680 | B.112 | C.8 |
| 1.1681 | B.113 | C.8 |
| 1.1682 | B.114 | C.8 |
| 1.1683 | B.115 | C.8 |
| 1.1684 | B.116 | C.8 |
| 1.1685 | B.117 | C.8 |
| 1.1686 | B.118 | C.8 |
| 1.1687 | B.119 | C.8 |
| 1.1688 | B.120 | C.8 |
| 1.1689 | B.121 | C.8 |
| 1.1690 | B.122 | C.8 |
| 1.1691 | B.123 | C.8 |
| 1.1692 | B.124 | C.8 |
| 1.1693 | B.125 | C.8 |
| 1.1694 | B.126 | C.8 |
| 1.1695 | B.127 | C.8 |
| 1.1696 | B.128 | C.8 |
| 1.1697 | B.129 | C.8 |
| 1.1698 | B.130 | C.8 |
| 1.1699 | B.131 | C.8 |
| 1.1700 | B.132 | C.8 |
| 1.1701 | B.133 | C.8 |
| 1.1702 | B.134 | C.8 |
| 1.1703 | B.135 | C.8 |
| 1.1704 | B.136 | C.8 |
| 1.1705 | B.137 | C.8 |
| 1.1706 | B.138 | C.8 |
| 1.1707 | B.139 | C.8 |
| 1.1708 | B.140 | C.8 |
| 1.1709 | B.141 | C.8 |
| 1.1710 | B.142 | C.8 |
| 1.1711 | B.143 | C.8 |
| 1.1712 | B.144 | C.8 |
| 1.1713 | B.145 | C.8 |
| 1.1714 | B.146 | C.8 |
| 1.1715 | B.147 | C.8 |
| 1.1716 | B.148 | C.8 |
| 1.1717 | B.149 | C.8 |
| 1.1718 | B.150 | C.8 |
| 1.1719 | B.151 | C.8 |
| 1.1720 | B.152 | C.8 |
| 1.1721 | B.153 | C.8 |
| 1.1722 | B.154 | C.8 |
| 1.1723 | B.155 | C.8 |
| 1.1724 | B.156 | C.8 |
| 1.1725 | B.157 | C.8 |
| 1.1726 | B.158 | C.8 |
| 1.1727 | B.159 | C.8 |
| 1.1728 | B.160 | C.8 |
| 1.1729 | B.161 | C.8 |
| 1.1730 | B.162 | C.8 |
| 1.1731 | B.163 | C.8 |
| 1.1732 | B.164 | C.8 |
| 1.1733 | B.165 | C.8 |
| 1.1734 | B.166 | C.8 |
| 1.1735 | B.167 | C.8 |
| 1.1736 | B.168 | C.8 |
| 1.1737 | B.169 | C.8 |
| 1.1738 | B.170 | C.8 |
| 1.1739 | B.171 | C.8 |
| 1.1740 | B.172 | C.8 |
| 1.1741 | B.173 | C.8 |
| 1.1742 | B.174 | C.8 |
| 1.1743 | B.175 | C.8 |
| 1.1744 | B.176 | C.8 |
| 1.1745 | B.177 | C.8 |
| 1.1746 | B.178 | C.8 |
| 1.1747 | B.179 | C.8 |
| 1.1748 | B.180 | C.8 |
| 1.1749 | B.181 | C.8 |
| 1.1750 | B.182 | C.8 |
| 1.1751 | B.183 | C.8 |
| 1.1752 | B.184 | C.8 |
| 1.1753 | B.185 | C.8 |
| 1.1754 | B.186 | C.8 |
| 1.1755 | B.187 | C.8 |
| 1.1756 | B.188 | C.8 |
| 1.1757 | B.189 | C.8 |
| 1.1758 | B.190 | C.8 |
| 1.1759 | B.191 | C.8 |
| 1.1760 | B.192 | C.8 |
| 1.1761 | B.193 | C.8 |
| 1.1762 | B.194 | C.8 |
| 1.1763 | B.195 | C.8 |
| 1.1764 | B.196 | C.8 |
| 1.1765 | B.1 | C.9 |
| 1.1766 | B.2 | C.9 |
| 1.1767 | B.3 | C.9 |
| 1.1768 | B.4 | C.9 |
| 1.1769 | B.5 | C.9 |
| 1.1770 | B.6 | C.9 |
| 1.1771 | B.7 | C.9 |
| 1.1772 | B.8 | C.9 |
| 1.1773 | B.9 | C.9 |
| 1.1774 | B.10 | C.9 |
| 1.1775 | B.11 | C.9 |
| 1.1776 | B.12 | C.9 |
| 1.1777 | B.13 | C.9 |
| 1.1778 | B.14 | C.9 |
| 1.1779 | B.15 | C.9 |
| 1.1780 | B.16 | C.9 |
| 1.1781 | B.17 | C.9 |
| 1.1782 | B.18 | C.9 |
| 1.1783 | B.19 | C.9 |
| 1.1784 | B.20 | C.9 |
| 1.1785 | B.21 | C.9 |
| 1.1786 | B.22 | C.9 |
| 1.1787 | B.23 | C.9 |
| 1.1788 | B.24 | C.9 |
| 1.1789 | B.25 | C.9 |
| 1.1790 | B.26 | C.9 |
| 1.1791 | B.27 | C.9 |
| 1.1792 | B.28 | C.9 |
| 1.1793 | B.29 | C.9 |
| 1.1794 | B.30 | C.9 |
| 1.1795 | B.31 | C.9 |
| 1.1796 | B.32 | C.9 |
| 1.1797 | B.33 | C.9 |
| 1.1798 | B.34 | C.9 |
| 1.1799 | B.35 | C.9 |
| 1.1800 | B.36 | C.9 |
| 1.1801 | B.37 | C.9 |
| 1.1802 | B.38 | C.9 |
| 1.1803 | B.39 | C.9 |
| 1.1804 | B.40 | C.9 |
| 1.1805 | B.41 | C.9 |

TABLE 1-continued (compositions 1.1 to 1.3545):

| comp. no. | herbicide B | safener C |
|---|---|---|
| 1.1806 | B.42 | C.9 |
| 1.1807 | B.43 | C.9 |
| 1.1808 | B.44 | C.9 |
| 1.1809 | B.45 | C.9 |
| 1.1810 | B.46 | C.9 |
| 1.1811 | B.47 | C.9 |
| 1.1812 | B.48 | C.9 |
| 1.1813 | B.49 | C.9 |
| 1.1814 | B.50 | C.9 |
| 1.1815 | B.51 | C.9 |
| 1.1816 | B.52 | C.9 |
| 1.1817 | B.53 | C.9 |
| 1.1818 | B.54 | C.9 |
| 1.1819 | B.55 | C.9 |
| 1.1820 | B.56 | C.9 |
| 1.1821 | B.57 | C.9 |
| 1.1822 | B.58. | C.9 |
| 1.1823 | B.59 | C.9 |
| 1.1824 | B.60 | C.9 |
| 1.1825 | B.61 | C.9 |
| 1.1826 | B.62 | C.9 |
| 1.1827 | B.63 | C.9 |
| 1.1828 | B.64 | C.9 |
| 1.1829 | B.65 | C.9 |
| 1.1830 | B.66 | C.9 |
| 1.1831 | B.67 | C.9 |
| 1.1832 | B.68 | C.9 |
| 1.1833 | B.69 | C.9 |
| 1.1834 | B.70 | C.9 |
| 1.1835 | B.71 | C.9 |
| 1.1836 | B.72 | C.9 |
| 1.1837 | B.73 | C.9 |
| 1.1838 | B.74 | C.9 |
| 1.1839 | B.75 | C.9 |
| 1.1840 | B.76 | C.9 |
| 1.1841 | B.77 | C.9 |
| 1.1842 | B.78 | C.9 |
| 1.1843 | B.79 | C.9 |
| 1.1844 | B.80 | C.9 |
| 1.1845 | B.81 | C.9 |
| 1.1846 | B.82 | C.9 |
| 1.1847 | B.83 | C.9 |
| 1.1848 | B.84 | C.9 |
| 1.1849 | B.85 | C.9 |
| 1.1850 | B.86 | C.9 |
| 1.1851 | B.87 | C.9 |
| 1.1852 | B.88 | C.9 |
| 1.1853 | B.89 | C.9 |
| 1.1854 | B.90 | C.9 |
| 1.1855 | B.91 | C.9 |
| 1.1856 | B.92 | C.9 |
| 1.1857 | B.93 | C.9 |
| 1.1858 | B.94 | C.9 |
| 1.1859 | B.95 | C.9 |
| 1.1860 | B.96 | C.9 |
| 1.1861 | B.97 | C.9 |
| 1.1862 | B.98 | C.9 |
| 1.1863 | B.99 | C.9 |
| 1.1864 | B.100 | C.9 |
| 1.1865 | B.101 | C.9 |
| 1.1866 | B.102 | C.9 |
| 1.1867 | B.103 | C.9 |
| 1.1868 | B.104 | C.9 |
| 1.1869 | B.105 | C.9 |
| 1.1870 | B.106 | C.9 |
| 1.1871 | B.107 | C.9 |
| 1.1872 | B.108 | C.9 |
| 1.1873 | B.109 | C.9 |
| 1.1874 | B.110 | C.9 |
| 1.1875 | B.111 | C.9 |
| 1.1876 | B.112 | C.9 |
| 1.1877 | B.113 | C.9 |
| 1.1878 | B.114 | C.9 |
| 1.1879 | B.115 | C.9 |
| 1.1880 | B.116 | C.9 |
| 1.1881 | B.117 | C.9 |
| 1.1882 | B.118 | C.9 |
| 1.1883 | B.119 | C.9 |
| 1.1884 | B.120 | C.9 |
| 1.1885 | B.121 | C.9 |
| 1.1886 | B.122 | C.9 |
| 1.1887 | B.123 | C.9 |
| 1.1888 | B.124 | C.9 |
| 1.1889 | B.125 | C.9 |
| 1.1890 | B.126 | C.9 |
| 1.1891 | B.127 | C.9 |
| 1.1892 | B.128 | C.9 |
| 1.1893 | B.129 | C.9 |
| 1.1894 | B.130 | C.9 |
| 1.1895 | B.131 | C.9 |
| 1.1896 | B.132 | C.9 |
| 1.1897 | B.133 | C.9 |
| 1.1898 | B.134 | C.9 |
| 1.1899 | B.135 | C.9 |
| 1.1900 | B.136 | C.9 |
| 1.1901 | B.137 | C.9 |
| 1.1902 | B.138 | C.9 |
| 1.1903 | B.139 | C.9 |
| 1.1904 | B.140 | C.9 |
| 1.1905 | B.141 | C.9 |
| 1.1906 | B.142 | C.9 |
| 1.1907 | B.143 | C.9 |
| 1.1908 | B.144 | C.9 |
| 1.1909 | B.145 | C.9 |
| 1.1910 | B.146 | C.9 |
| 1.1911 | B.147 | C.9 |
| 1.1912 | B.148 | C.9 |
| 1.1913 | B.149 | C.9 |
| 1.1914 | B.150 | C.9 |
| 1.1915 | B.151 | C.9 |
| 1.1916 | B.152 | C.9 |
| 1.1917 | B.153 | C.9 |
| 1.1918 | B.154 | C.9 |
| 1.1919 | B.155 | C.9 |
| 1.1920 | B.156 | C.9 |
| 1.1921 | B.157 | C.9 |
| 1.1922 | B.158 | C.9 |
| 1.1923 | B.159 | C.9 |
| 1.1924 | B.160 | C.9 |
| 1.1925 | B.161 | C.9 |
| 1.1926 | B.162 | C.9 |
| 1.1927 | B.163 | C.9 |
| 1.1928 | B.164 | C.9 |
| 1.1929 | B.165 | C.9 |
| 1.1930 | B.166 | C.9 |
| 1.1931 | B.167 | C.9 |
| 1.1932 | B.168 | C.9 |
| 1.1933 | B.169 | C.9 |
| 1.1934 | B.170 | C.9 |
| 1.1935 | B.171 | C.9 |
| 1.1936 | B.172 | C.9 |
| 1.1937 | B.173 | C.9 |
| 1.1938 | B.174 | C.9 |
| 1.1939 | B.175 | C.9 |
| 1.1940 | B.176 | C.9 |
| 1.1941 | B.177 | C.9 |
| 1.1942 | B.178 | C.9 |
| 1.1943 | B.179 | C.9 |
| 1.1944 | B.180 | C.9 |
| 1.1945 | B.181 | C.9 |
| 1.1946 | B.182 | C.9 |
| 1.1947 | B.183 | C.9 |
| 1.1948 | B.184 | C.9 |
| 1.1949 | B.185 | C.9 |
| 1.1950 | B.186 | C.9 |
| 1.1951 | B.187 | C.9 |
| 1.1952 | B.188 | C.9 |
| 1.1953 | B.189 | C.9 |
| 1.1954 | B.190 | C.9 |
| 1.1955 | B.191 | C.9 |
| 1.1956 | B.192 | C.9 |
| 1.1957 | B.193 | C.9 |

TABLE 1-continued (compositions 1.1 to 1.3545):

| comp. no. | herbicide B | safener C |
|---|---|---|
| 1.1958 | B.194 | C.9 |
| 1.1959 | B.195 | C.9 |
| 1.1960 | B.196 | C.9 |
| 1.1961 | B.1 | C.10 |
| 1.1962 | B.2 | C.10 |
| 1.1963 | B.3 | C.10 |
| 1.1964 | B.4 | C.10 |
| 1.1965 | B.5 | C.10 |
| 1.1966 | B.6 | C.10 |
| 1.1967 | B.7 | C.10 |
| 1.1968 | B.8 | C.10 |
| 1.1969 | B.9 | C.10 |
| 1.1970 | B.10 | C.10 |
| 1.1971 | B.11 | C.10 |
| 1.1972 | B.12 | C.10 |
| 1.1973 | B.13 | C.10 |
| 1.1974 | B.14 | C.10 |
| 1.1975 | B.15 | C.10 |
| 1.1976 | B.16 | C.10 |
| 1.1977 | B.17 | C.10 |
| 1.1978 | B.18 | C.10 |
| 1.1979 | B.19 | C.10 |
| 1.1980 | B.20 | C.10 |
| 1.1981 | B.21 | C.10 |
| 1.1982 | B.22 | C.10 |
| 1.1983 | B.23 | C.10 |
| 1.1984 | B.24 | C.10 |
| 1.1985 | B.25 | C.10 |
| 1.1986 | B.26 | C.10 |
| 1.1987 | B.27 | C.10 |
| 1.1988 | B.28 | C.10 |
| 1.1989 | B.29 | C.10 |
| 1.1990 | B.30 | C.10 |
| 1.1991 | B.31 | C.10 |
| 1.1992 | B.32 | C.10 |
| 1.1993 | B.33 | C.10 |
| 1.1994 | B.34 | C.10 |
| 1.1995 | B.35 | C.10 |
| 1.1996 | B.36 | C.10 |
| 1.1997 | B.37 | C.10 |
| 1.1998 | B.38 | C.10 |
| 1.1999 | B.39 | C.10 |
| 1.2000 | B.40 | C.10 |
| 1.2001 | B.41 | C.10 |
| 1.2002 | B.42 | C.10 |
| 1.2003 | B.43 | C.10 |
| 1.2004 | B.44 | C.10 |
| 1.2005 | B.45 | C.10 |
| 1.2006 | B.46 | C.10 |
| 1.2007 | B.47 | C.10 |
| 1.2008 | B.48 | C.10 |
| 1.2009 | B.49 | C.10 |
| 1.2010 | B.50 | C.10 |
| 1.2011 | B.51 | C.10 |
| 1.2012 | B.52 | C.10 |
| 1.2013 | B.53 | C.10 |
| 1.2014 | B.54 | C.10 |
| 1.2015 | B.55 | C.10 |
| 1.2016 | B.56 | C.10 |
| 1.2017 | B.57 | C.10 |
| 1.2018 | B.58. | C.10 |
| 1.2019 | B.59 | C.10 |
| 1.2020 | B.60 | C.10 |
| 1.2021 | B.61 | C.10 |
| 1.2022 | B.62 | C.10 |
| 1.2023 | B.63 | C.10 |
| 1.2024 | B.64 | C.10 |
| 1.2025 | B.65 | C.10 |
| 1.2026 | B.66 | C.10 |
| 1.2027 | B.67 | C.10 |
| 1.2028 | B.68 | C.10 |
| 1.2029 | B.69 | C.10 |
| 1.2030 | B.70 | C.10 |
| 1.2031 | B.71 | C.10 |
| 1.2032 | B.72 | C.10 |
| 1.2033 | B.73 | C.10 |
| 1.2034 | B.74 | C.10 |
| 1.2035 | B.75 | C.10 |
| 1.2036 | B.76 | C.10 |
| 1.2037 | B.77 | C.10 |
| 1.2038 | B.78 | C.10 |
| 1.2039 | B.79 | C.10 |
| 1.2040 | B.80 | C.10 |
| 1.2041 | B.81 | C.10 |
| 1.2042 | B.82 | C.10 |
| 1.2043 | B.83 | C.10 |
| 1.2044 | B.84 | C.10 |
| 1.2045 | B.85 | C.10 |
| 1.2046 | B.86 | C.10 |
| 1.2047 | B.87 | C.10 |
| 1.2048 | B.88 | C.10 |
| 1.2049 | B.89 | C.10 |
| 1.2050 | B.90 | C.10 |
| 1.2051 | B.91 | C.10 |
| 1.2052 | B.92 | C.10 |
| 1.2053 | B.93 | C.10 |
| 1.2054 | B.94 | C.10 |
| 1.2055 | B.95 | C.10 |
| 1.2056 | B.96 | C.10 |
| 1.2057 | B.97 | C.10 |
| 1.2058 | B.98 | C.10 |
| 1.2059 | B.99 | C.10 |
| 1.2060 | B.100 | C.10 |
| 1.2061 | B.101 | C.10 |
| 1.2062 | B.102 | C.10 |
| 1.2063 | B.103 | C.10 |
| 1.2064 | B.104 | C.10 |
| 1.2065 | B.105 | C.10 |
| 1.2066 | B.106 | C.10 |
| 1.2067 | B.107 | C.10 |
| 1.2068 | B.108 | C.10 |
| 1.2069 | B.109 | C.10 |
| 1.2070 | B.110 | C.10 |
| 1.2071 | B.111 | C.10 |
| 1.2072 | B.112 | C.10 |
| 1.2073 | B.113 | C.10 |
| 1.2074 | B.114 | C.10 |
| 1.2075 | B.115 | C.10 |
| 1.2076 | B.116 | C.10 |
| 1.2077 | B.117 | C.10 |
| 1.2078 | B.118 | C.10 |
| 1.2079 | B.119 | C.10 |
| 1.2080 | B.120 | C.10 |
| 1.2081 | B.121 | C.10 |
| 1.2082 | B.122 | C.10 |
| 1.2083 | B.123 | C.10 |
| 1.2084 | B.124 | C.10 |
| 1.2085 | B.125 | C.10 |
| 1.2086 | B.126 | C.10 |
| 1.2087 | B.127 | C.10 |
| 1.2088 | B.128 | C.10 |
| 1.2089 | B.129 | C.10 |
| 1.2090 | B.130 | C.10 |
| 1.2091 | B.131 | C.10 |
| 1.2092 | B.132 | C.10 |
| 1.2093 | B.133 | C.10 |
| 1.2094 | B.134 | C.10 |
| 1.2095 | B.135 | C.10 |
| 1.2096 | B.136 | C.10 |
| 1.2097 | B.137 | C.10 |
| 1.2098 | B.138 | C.10 |
| 1.2099 | B.139 | C.10 |
| 1.2100 | B.140 | C.10 |
| 1.2101 | B.141 | C.10 |
| 1.2102 | B.142 | C.10 |
| 1.2103 | B.143 | C.10 |
| 1.2104 | B.144 | C.10 |
| 1.2105 | B.145 | C.10 |
| 1.2106 | B.146 | C.10 |
| 1.2107 | B.147 | C.10 |
| 1.2108 | B.148 | C.10 |
| 1.2109 | B.149 | C.10 |

TABLE 1-continued (compositions 1.1 to 1.3545):

| comp. no. | herbicide B | safener C |
|---|---|---|
| 1.2110 | B.150 | C.10 |
| 1.2111 | B.151 | C.10 |
| 1.2112 | B.152 | C.10 |
| 1.2113 | B.153 | C.10 |
| 1.2114 | B.154 | C.10 |
| 1.2115 | B.155 | C.10 |
| 1.2116 | B.156 | C.10 |
| 1.2117 | B.157 | C.10 |
| 1.2118 | B.158 | C.10 |
| 1.2119 | B.159 | C.10 |
| 1.2120 | B.160 | C.10 |
| 1.2121 | B.161 | C.10 |
| 1.2122 | B.162 | C.10 |
| 1.2123 | B.163 | C.10 |
| 1.2124 | B.164 | C.10 |
| 1.2125 | B.165 | C.10 |
| 1.2126 | B.166 | C.10 |
| 1.2127 | B.167 | C.10 |
| 1.2128 | B.168 | C.10 |
| 1.2129 | B.169 | C.10 |
| 1.2130 | B.170 | C.10 |
| 1.2131 | B.171 | C.10 |
| 1.2132 | B.172 | C.10 |
| 1.2133 | B.173 | C.10 |
| 1.2134 | B.174 | C.10 |
| 1.2135 | B.175 | C.10 |
| 1.2136 | B.176 | C.10 |
| 1.2137 | B.177 | C.10 |
| 1.2138 | B.178 | C.10 |
| 1.2139 | B.179 | C.10 |
| 1.2140 | B.180 | C.10 |
| 1.2141 | B.181 | C.10 |
| 1.2142 | B.182 | C.10 |
| 1.2143 | B.183 | C.10 |
| 1.2144 | B.184 | C.10 |
| 1.2145 | B.185 | C.10 |
| 1.2146 | B.186 | C.10 |
| 1.2147 | B.187 | C.10 |
| 1.2148 | B.188 | C.10 |
| 1.2149 | B.189 | C.10 |
| 1.2150 | B.190 | C.10 |
| 1.2151 | B.191 | C.10 |
| 1.2152 | B.192 | C.10 |
| 1.2153 | B.193 | C.10 |
| 1.2154 | B.194 | C.10 |
| 1.2155 | B.195 | C.10 |
| 1.2156 | B.196 | C.10 |
| 1.2157 | B.1 | C.11 |
| 1.2158 | B.2 | C.11 |
| 1.2159 | B.3 | C.11 |
| 1.2160 | B.4 | C.11 |
| 1.2161 | B.5 | C.11 |
| 1.2162 | B.6 | C.11 |
| 1.2163 | B.7 | C.11 |
| 1.2164 | B.8 | C.11 |
| 1.2165 | B.9 | C.11 |
| 1.2166 | B.10 | C.11 |
| 1.2167 | B.11 | C.11 |
| 1.2168 | B.12 | C.11 |
| 1.2169 | B.13 | C.11 |
| 1.2170 | B.14 | C.11 |
| 1.2171 | B.15 | C.11 |
| 1.2172 | B.16 | C.11 |
| 1.2173 | B.17 | C.11 |
| 1.2174 | B.18 | C.11 |
| 1.2175 | B.19 | C.11 |
| 1.2176 | B.20 | C.11 |
| 1.2177 | B.21 | C.11 |
| 1.2178 | B.22 | C.11 |
| 1.2179 | B.23 | C.11 |
| 1.2180 | B.24 | C.11 |
| 1.2181 | B.25 | C.11 |
| 1.2182 | B.26 | C.11 |
| 1.2183 | B.27 | C.11 |
| 1.2184 | B.28 | C.11 |
| 1.2185 | B.29 | C.11 |
| 1.2186 | B.30 | C.11 |
| 1.2187 | B.31 | C.11 |
| 1.2188 | B.32 | C.11 |
| 1.2189 | B.33 | C.11 |
| 1.2190 | B.34 | C.11 |
| 1.2191 | B.35 | C.11 |
| 1.2192 | B.36 | C.11 |
| 1.2193 | B.37 | C.11 |
| 1.2194 | B.38 | C.11 |
| 1.2195 | B.39 | C.11 |
| 1.2196 | B.40 | C.11 |
| 1.2197 | B.41 | C.11 |
| 1.2198 | B.42 | C.11 |
| 1.2199 | B.43 | C.11 |
| 1.2200 | B.44 | C.11 |
| 1.2201 | B.45 | C.11 |
| 1.2202 | B.46 | C.11 |
| 1.2203 | B.47 | C.11 |
| 1.2204 | B.48 | C.11 |
| 1.2205 | B.49 | C.11 |
| 1.2206 | B.50 | C.11 |
| 1.2207 | B.51 | C.11 |
| 1.2208 | B.52 | C.11 |
| 1.2209 | B.53 | C.11 |
| 1.2210 | B.54 | C.11 |
| 1.2211 | B.55 | C.11 |
| 1.2212 | B.56 | C.11 |
| 1.2213 | B.57 | C.11 |
| 1.2214 | B.58. | C.11 |
| 1.2215 | B.59 | C.11 |
| 1.2216 | B.60 | C.11 |
| 1.2217 | B.61 | C.11 |
| 1.2218 | B.62 | C.11 |
| 1.2219 | B.63 | C.11 |
| 1.2220 | B.64 | C.11 |
| 1.2221 | B.65 | C.11 |
| 1.2222 | B.66 | C.11 |
| 1.2223 | B.67 | C.11 |
| 1.2224 | B.68 | C.11 |
| 1.2225 | B.69 | C.11 |
| 1.2226 | B.70 | C.11 |
| 1.2227 | B.71 | C.11 |
| 1.2228 | B.72 | C.11 |
| 1.2229 | B.73 | C.11 |
| 1.2230 | B.74 | C.11 |
| 1.2231 | B.75 | C.11 |
| 1.2232 | B.76 | C.11 |
| 1.2233 | B.77 | C.11 |
| 1.2234 | B.78 | C.11 |
| 1.2235 | B.79 | C.11 |
| 1.2236 | B.80 | C.11 |
| 1.2237 | B.81 | C.11 |
| 1.2238 | B.82 | C.11 |
| 1.2239 | B.83 | C.11 |
| 1.2240 | B.84 | C.11 |
| 1.2241 | B.85 | C.11 |
| 1.2242 | B.86 | C.11 |
| 1.2243 | B.87 | C.11 |
| 1.2244 | B.88 | C.11 |
| 1.2245 | B.89 | C.11 |
| 1.2246 | B.90 | C.11 |
| 1.2247 | B.91 | C.11 |
| 1.2248 | B.92 | C.11 |
| 1.2249 | B.93 | C.11 |
| 1.2250 | B.94 | C.11 |
| 1.2251 | B.95 | C.11 |
| 1.2252 | B.96 | C.11 |
| 1.2253 | B.97 | C.11 |
| 1.2254 | B.98 | C.11 |
| 1.2255 | B.99 | C.11 |
| 1.2256 | B.100 | C.11 |
| 1.2257 | B.101 | C.11 |
| 1.2258 | B.102 | C.11 |
| 1.2259 | B.103 | C.11 |
| 1.2260 | B.104 | C.11 |
| 1.2261 | B.105 | C.11 |

TABLE 1-continued (compositions 1.1 to 1.3545):

| comp. no. | herbicide B | safener C |
|---|---|---|
| 1.2262 | B.106 | C.11 |
| 1.2263 | B.107 | C.11 |
| 1.2264 | B.108 | C.11 |
| 1.2265 | B.109 | C.11 |
| 1.2266 | B.110 | C.11 |
| 1.2267 | B.111 | C.11 |
| 1.2268 | B.112 | C.11 |
| 1.2269 | B.113 | C.11 |
| 1.2270 | B.114 | C.11 |
| 1.2271 | B.115 | C.11 |
| 1.2272 | B.116 | C.11 |
| 1.2273 | B.117 | C.11 |
| 1.2274 | B.118 | C.11 |
| 1.2275 | B.119 | C.11 |
| 1.2276 | B.120 | C.11 |
| 1.2277 | B.121 | C.11 |
| 1.2278 | B.122 | C.11 |
| 1.2279 | B.123 | C.11 |
| 1.2280 | B.124 | C.11 |
| 1.2281 | B.125 | C.11 |
| 1.2282 | B.126 | C.11 |
| 1.2283 | B.127 | C.11 |
| 1.2284 | B.128 | C.11 |
| 1.2285 | B.129 | C.11 |
| 1.2286 | B.130 | C.11 |
| 1.2287 | B.131 | C.11 |
| 1.2288 | B.132 | C.11 |
| 1.2289 | B.133 | C.11 |
| 1.2290 | B.134 | C.11 |
| 1.2291 | B.135 | C.11 |
| 1.2292 | B.136 | C.11 |
| 1.2293 | B.137 | C.11 |
| 1.2294 | B.138 | C.11 |
| 1.2295 | B.139 | C.11 |
| 1.2296 | B.140 | C.11 |
| 1.2297 | B.141 | C.11 |
| 1.2298 | B.142 | C.11 |
| 1.2299 | B.143 | C.11 |
| 1.2300 | B.144 | C.11 |
| 1.2301 | B.145 | C.11 |
| 1.2302 | B.146 | C.11 |
| 1.2303 | B.147 | C.11 |
| 1.2304 | B.148 | C.11 |
| 1.2305 | B.149 | C.11 |
| 1.2306 | B.150 | C.11 |
| 1.2307 | B.151 | C.11 |
| 1.2308 | B.152 | C.11 |
| 1.2309 | B.153 | C.11 |
| 1.2310 | B.154 | C.11 |
| 1.2311 | B.155 | C.11 |
| 1.2312 | B.156 | C.11 |
| 1.2313 | B.157 | C.11 |
| 1.2314 | B.158 | C.11 |
| 1.2315 | B.159 | C.11 |
| 1.2316 | B.160 | C.11 |
| 1.2317 | B.161 | C.11 |
| 1.2318 | B.162 | C.11 |
| 1.2319 | B.163 | C.11 |
| 1.2320 | B.164 | C.11 |
| 1.2321 | B.165 | C.11 |
| 1.2322 | B.166 | C.11 |
| 1.2323 | B.167 | C.11 |
| 1.2324 | B.168 | C.11 |
| 1.2325 | B.169 | C.11 |
| 1.2326 | B.170 | C.11 |
| 1.2327 | B.171 | C.11 |
| 1.2328 | B.172 | C.11 |
| 1.2329 | B.173 | C.11 |
| 1.2330 | B.174 | C.11 |
| 1.2331 | B.175 | C.11 |
| 1.2332 | B.176 | C.11 |
| 1.2333 | B.177 | C.11 |
| 1.2334 | B.178 | C.11 |
| 1.2335 | B.179 | C.11 |
| 1.2336 | B.180 | C.11 |
| 1.2337 | B.181 | C.11 |
| 1.2338 | B.182 | C.11 |
| 1.2339 | B.183 | C.11 |
| 1.2340 | B.184 | C.11 |
| 1.2341 | B.185 | C.11 |
| 1.2342 | B.186 | C.11 |
| 1.2343 | B.187 | C.11 |
| 1.2344 | B.188 | C.11 |
| 1.2345 | B.189 | C.11 |
| 1.2346 | B.190 | C.11 |
| 1.2347 | B.191 | C.11 |
| 1.2348 | B.192 | C.11 |
| 1.2349 | B.193 | C.11 |
| 1.2350 | B.194 | C.11 |
| 1.2351 | B.195 | C.11 |
| 1.2352 | B.196 | C.11 |
| 1.2353 | B.1 | C.12 |
| 1.2354 | B.2 | C.12 |
| 1.2355 | B.3 | C.12 |
| 1.2356 | B.4 | C.12 |
| 1.2357 | B.5 | C.12 |
| 1.2358 | B.6 | C.12 |
| 1.2359 | B.7 | C.12 |
| 1.2360 | B.8 | C.12 |
| 1.2361 | B.9 | C.12 |
| 1.2362 | B.10 | C.12 |
| 1.2363 | B.11 | C.12 |
| 1.2364 | B.12 | C.12 |
| 1.2365 | B.13 | C.12 |
| 1.2366 | B.14 | C.12 |
| 1.2367 | B.15 | C.12 |
| 1.2368 | B.16 | C.12 |
| 1.2369 | B.17 | C.12 |
| 1.2370 | B.18 | C.12 |
| 1.2371 | B.19 | C.12 |
| 1.2372 | B.20 | C.12 |
| 1.2373 | B.21 | C.12 |
| 1.2374 | B.22 | C.12 |
| 1.2375 | B.23 | C.12 |
| 1.2376 | B.24 | C.12 |
| 1.2377 | B.25 | C.12 |
| 1.2378 | B.26 | C.12 |
| 1.2379 | B.27 | C.12 |
| 1.2380 | B.28 | C.12 |
| 1.2381 | B.29 | C.12 |
| 1.2382 | B.30 | C.12 |
| 1.2383 | B.31 | C.12 |
| 1.2384 | B.32 | C.12 |
| 1.2385 | B.33 | C.12 |
| 1.2386 | B.34 | C.12 |
| 1.2387 | B.35 | C.12 |
| 1.2388 | B.36 | C.12 |
| 1.2389 | B.37 | C.12 |
| 1.2390 | B.38 | C.12 |
| 1.2391 | B.39 | C.12 |
| 1.2392 | B.40 | C.12 |
| 1.2393 | B.41 | C.12 |
| 1.2394 | B.42 | C.12 |
| 1.2395 | B.43 | C.12 |
| 1.2396 | B.44 | C.12 |
| 1.2397 | B.45 | C.12 |
| 1.2398 | B.46 | C.12 |
| 1.2399 | B.47 | C.12 |
| 1.2400 | B.48 | C.12 |
| 1.2401 | B.49 | C.12 |
| 1.2402 | B.50 | C.12 |
| 1.2403 | B.51 | C.12 |
| 1.2404 | B.52 | C.12 |
| 1.2405 | B.53 | C.12 |
| 1.2406 | B.54 | C.12 |
| 1.2407 | B.55 | C.12 |
| 1.2408 | B.56 | C.12 |
| 1.2409 | B.57 | C.12 |
| 1.2410 | B.58. | C.12 |
| 1.2411 | B.59 | C.12 |
| 1.2412 | B.60 | C.12 |
| 1.2413 | B.61 | C.12 |

TABLE 1-continued (compositions 1.1 to 1.3545):

| comp. no. | herbicide B | safener C |
|---|---|---|
| 1.2414 | B.62 | C.12 |
| 1.2415 | B.63 | C.12 |
| 1.2416 | B.64 | C.12 |
| 1.2417 | B.65 | C.12 |
| 1.2418 | B.66 | C.12 |
| 1.2419 | B.67 | C.12 |
| 1.2420 | B.68 | C.12 |
| 1.2421 | B.69 | C.12 |
| 1.2422 | B.70 | C.12 |
| 1.2423 | B.71 | C.12 |
| 1.2424 | B.72 | C.12 |
| 1.2425 | B.73 | C.12 |
| 1.2426 | B.74 | C.12 |
| 1.2427 | B.75 | C.12 |
| 1.2428 | B.76 | C.12 |
| 1.2429 | B.77 | C.12 |
| 1.2430 | B.78 | C.12 |
| 1.2431 | B.79 | C.12 |
| 1.2432 | B.80 | C.12 |
| 1.2433 | B.81 | C.12 |
| 1.2434 | B.82 | C.12 |
| 1.2435 | B.83 | C.12 |
| 1.2436 | B.84 | C.12 |
| 1.2437 | B.85 | C.12 |
| 1.2438 | B.86 | C.12 |
| 1.2439 | B.87 | C.12 |
| 1.2440 | B.88 | C.12 |
| 1.2441 | B.89 | C.12 |
| 1.2442 | B.90 | C.12 |
| 1.2443 | B.91 | C.12 |
| 1.2444 | B.92 | C.12 |
| 1.2445 | B.93 | C.12 |
| 1.2446 | B.94 | C.12 |
| 1.2447 | B.95 | C.12 |
| 1.2448 | B.96 | C.12 |
| 1.2449 | B.97 | C.12 |
| 1.2450 | B.98 | C.12 |
| 1.2451 | B.99 | C.12 |
| 1.2452 | B.100 | C.12 |
| 1.2453 | B.101 | C.12 |
| 1.2454 | B.102 | C.12 |
| 1.2455 | B.103 | C.12 |
| 1.2456 | B.104 | C.12 |
| 1.2457 | B.105 | C.12 |
| 1.2458 | B.106 | C.12 |
| 1.2459 | B.107 | C.12 |
| 1.2460 | B.108 | C.12 |
| 1.2461 | B.109 | C.12 |
| 1.2462 | B.110 | C.12 |
| 1.2463 | B.111 | C.12 |
| 1.2464 | B.112 | C.12 |
| 1.2465 | B.113 | C.12 |
| 1.2466 | B.114 | C.12 |
| 1.2467 | B.115 | C.12 |
| 1.2468 | B.116 | C.12 |
| 1.2469 | B.117 | C.12 |
| 1.2470 | B.118 | C.12 |
| 1.2471 | B.119 | C.12 |
| 1.2472 | B.120 | C.12 |
| 1.2473 | B.121 | C.12 |
| 1.2474 | B.122 | C.12 |
| 1.2475 | B.123 | C.12 |
| 1.2476 | B.124 | C.12 |
| 1.2477 | B.125 | C.12 |
| 1.2478 | B.126 | C.12 |
| 1.2479 | B.127 | C.12 |
| 1.2480 | B.128 | C.12 |
| 1.2481 | B.129 | C.12 |
| 1.2482 | B.130 | C.12 |
| 1.2483 | B.131 | C.12 |
| 1.2484 | B.132 | C.12 |
| 1.2485 | B.133 | C.12 |
| 1.2486 | B.134 | C.12 |
| 1.2487 | B.135 | C.12 |
| 1.2488 | B.136 | C.12 |
| 1.2489 | B.137 | C.12 |
| 1.2490 | B.138 | C.12 |
| 1.2491 | B.139 | C.12 |
| 1.2492 | B.140 | C.12 |
| 1.2493 | B.141 | C.12 |
| 1.2494 | B.142 | C.12 |
| 1.2495 | B.143 | C.12 |
| 1.2496 | B.144 | C.12 |
| 1.2497 | B.145 | C.12 |
| 1.2498 | B.146 | C.12 |
| 1.2499 | B.147 | C.12 |
| 1.2500 | B.148 | C.12 |
| 1.2501 | B.149 | C.12 |
| 1.2502 | B.150 | C.12 |
| 1.2503 | B.151 | C.12 |
| 1.2504 | B.152 | C.12 |
| 1.2505 | B.153 | C.12 |
| 1.2506 | B.154 | C.12 |
| 1.2507 | B.155 | C.12 |
| 1.2508 | B.156 | C.12 |
| 1.2509 | B.157 | C.12 |
| 1.2510 | B.158 | C.12 |
| 1.2511 | B.159 | C.12 |
| 1.2512 | B.160 | C.12 |
| 1.2513 | B.161 | C.12 |
| 1.2514 | B.162 | C.12 |
| 1.2515 | B.163 | C.12 |
| 1.2516 | B.164 | C.12 |
| 1.2517 | B.165 | C.12 |
| 1.2518 | B.166 | C.12 |
| 1.2519 | B.167 | C.12 |
| 1.2520 | B.168 | C.12 |
| 1.2521 | B.169 | C.12 |
| 1.2522 | B.170 | C.12 |
| 1.2523 | B.171 | C.12 |
| 1.2524 | B.172 | C.12 |
| 1.2525 | B.173 | C.12 |
| 1.2526 | B.174 | C.12 |
| 1.2527 | B.175 | C.12 |
| 1.2528 | B.176 | C.12 |
| 1.2529 | B.177 | C.12 |
| 1.2530 | B.178 | C.12 |
| 1.2531 | B.179 | C.12 |
| 1.2532 | B.180 | C.12 |
| 1.2533 | B.181 | C.12 |
| 1.2534 | B.182 | C.12 |
| 1.2535 | B.183 | C.12 |
| 1.2536 | B.184 | C.12 |
| 1.2537 | B.185 | C.12 |
| 1.2538 | B.186 | C.12 |
| 1.2539 | B.187 | C.12 |
| 1.2540 | B.188 | C.12 |
| 1.2541 | B.189 | C.12 |
| 1.2542 | B.190 | C.12 |
| 1.2543 | B.191 | C.12 |
| 1.2544 | B.192 | C.12 |
| 1.2545 | B.193 | C.12 |
| 1.2546 | B.194 | C.12 |
| 1.2547 | B.195 | C.12 |
| 1.2548 | B.196 | C.12 |
| 1.2549 | B.1 | C.13 |
| 1.2550 | B.2 | C.13 |
| 1.2551 | B.3 | C.13 |
| 1.2552 | B.4 | C.13 |
| 1.2553 | B.5 | C.13 |
| 1.2554 | B.6 | C.13 |
| 1.2555 | B.7 | C.13 |
| 1.2556 | B.8 | C.13 |
| 1.2557 | B.9 | C.13 |
| 1.2558 | B.10 | C.13 |
| 1.2559 | B.11 | C.13 |
| 1.2560 | B.12 | C.13 |
| 1.2561 | B.13 | C.13 |
| 1.2562 | B.14 | C.13 |
| 1.2563 | B.15 | C.13 |
| 1.2564 | B.16 | C.13 |
| 1.2565 | B.17 | C.13 |

TABLE 1-continued (compositions 1.1 to 1.3545):

| comp. no. | herbicide B | safener C |
|---|---|---|
| 1.2566 | B.18 | C.13 |
| 1.2567 | B.19 | C.13 |
| 1.2568 | B.20 | C.13 |
| 1.2569 | B.21 | C.13 |
| 1.2570 | B.22 | C.13 |
| 1.2571 | B.23 | C.13 |
| 1.2572 | B.24 | C.13 |
| 1.2573 | B.25 | C.13 |
| 1.2574 | B.26 | C.13 |
| 1.2575 | B.27 | C.13 |
| 1.2576 | B.28 | C.13 |
| 1.2577 | B.29 | C.13 |
| 1.2578 | B.30 | C.13 |
| 1.2579 | B.31 | C.13 |
| 1.2580 | B.32 | C.13 |
| 1.2581 | B.33 | C.13 |
| 1.2582 | B.34 | C.13 |
| 1.2583 | B.35 | C.13 |
| 1.2584 | B.36 | C.13 |
| 1.2585 | B.37 | C.13 |
| 1.2586 | B.38 | C.13 |
| 1.2587 | B.39 | C.13 |
| 1.2588 | B.40 | C.13 |
| 1.2589 | B.41 | C.13 |
| 1.2590 | B.42 | C.13 |
| 1.2591 | B.43 | C.13 |
| 1.2592 | B.44 | C.13 |
| 1.2593 | B.45 | C.13 |
| 1.2594 | B.46 | C.13 |
| 1.2595 | B.47 | C.13 |
| 1.2596 | B.48 | C.13 |
| 1.2597 | B.49 | C.13 |
| 1.2598 | B.50 | C.13 |
| 1.2599 | B.51 | C.13 |
| 1.2600 | B.52 | C.13 |
| 1.2601 | B.53 | C.13 |
| 1.2602 | B.54 | C.13 |
| 1.2603 | B.55 | C.13 |
| 1.2604 | B.56 | C.13 |
| 1.2605 | B.57 | C.13 |
| 1.2606 | B.58. | C.13 |
| 1.2607 | B.59 | C.13 |
| 1.2608 | B.60 | C.13 |
| 1.2609 | B.61 | C.13 |
| 1.2610 | B.62 | C.13 |
| 1.2611 | B.63 | C.13 |
| 1.2612 | B.64 | C.13 |
| 1.2613 | B.65 | C.13 |
| 1.2614 | B.66 | C.13 |
| 1.2615 | B.67 | C.13 |
| 1.2616 | B.68 | C.13 |
| 1.2617 | B.69 | C.13 |
| 1.2618 | B.70 | C.13 |
| 1.2619 | B.71 | C.13 |
| 1.2620 | B.72 | C.13 |
| 1.2621 | B.73 | C.13 |
| 1.2622 | B.74 | C.13 |
| 1.2623 | B.75 | C.13 |
| 1.2624 | B.76 | C.13 |
| 1.2625 | B.77 | C.13 |
| 1.2626 | B.78 | C.13 |
| 1.2627 | B.79 | C.13 |
| 1.2628 | B.80 | C.13 |
| 1.2629 | B.81 | C.13 |
| 1.2630 | B.82 | C.13 |
| 1.2631 | B.83 | C.13 |
| 1.2632 | B.84 | C.13 |
| 1.2633 | B.85 | C.13 |
| 1.2634 | B.86 | C.13 |
| 1.2635 | B.87 | C.13 |
| 1.2636 | B.88 | C.13 |
| 1.2637 | B.89 | C.13 |
| 1.2638 | B.90 | C.13 |
| 1.2639 | B.91 | C.13 |
| 1.2640 | B.92 | C.13 |
| 1.2641 | B.93 | C.13 |
| 1.2642 | B.94 | C.13 |
| 1.2643 | B.95 | C.13 |
| 1.2644 | B.96 | C.13 |
| 1.2645 | B.97 | C.13 |
| 1.2646 | B.98 | C.13 |
| 1.2647 | B.99 | C.13 |
| 1.2648 | B.100 | C.13 |
| 1.2649 | B.101 | C.13 |
| 1.2650 | B.102 | C.13 |
| 1.2651 | B.103 | C.13 |
| 1.2652 | B.104 | C.13 |
| 1.2653 | B.105 | C.13 |
| 1.2654 | B.106 | C.13 |
| 1.2655 | B.107 | C.13 |
| 1.2656 | B.108 | C.13 |
| 1.2657 | B.109 | C.13 |
| 1.2658 | B.110 | C.13 |
| 1.2659 | B.111 | C.13 |
| 1.2660 | B.112 | C.13 |
| 1.2661 | B.113 | C.13 |
| 1.2662 | B.114 | C.13 |
| 1.2663 | B.115 | C.13 |
| 1.2664 | B.116 | C.13 |
| 1.2665 | B.117 | C.13 |
| 1.2666 | B.118 | C.13 |
| 1.2667 | B.119 | C.13 |
| 1.2668 | B.120 | C.13 |
| 1.2669 | B.121 | C.13 |
| 1.2670 | B.122 | C.13 |
| 1.2671 | B.123 | C.13 |
| 1.2672 | B.124 | C.13 |
| 1.2673 | B.125 | C.13 |
| 1.2674 | B.126 | C.13 |
| 1.2675 | B.127 | C.13 |
| 1.2676 | B.128 | C.13 |
| 1.2677 | B.129 | C.13 |
| 1.2678 | B.130 | C.13 |
| 1.2679 | B.131 | C.13 |
| 1.2680 | B.132 | C.13 |
| 1.2681 | B.133 | C.13 |
| 1.2682 | B.134 | C.13 |
| 1.2683 | B.135 | C.13 |
| 1.2684 | B.136 | C.13 |
| 1.2685 | B.137 | C.13 |
| 1.2686 | B.138 | C.13 |
| 1.2687 | B.139 | C.13 |
| 1.2688 | B.140 | C.13 |
| 1.2689 | B.141 | C.13 |
| 1.2690 | B.142 | C.13 |
| 1.2691 | B.143 | C.13 |
| 1.2692 | B.144 | C.13 |
| 1.2693 | B.145 | C.13 |
| 1.2694 | B.146 | C.13 |
| 1.2695 | B.147 | C.13 |
| 1.2696 | B.148 | C.13 |
| 1.2697 | B.149 | C.13 |
| 1.2698 | B.150 | C.13 |
| 1.2699 | B.151 | C.13 |
| 1.2700 | B.152 | C.13 |
| 1.2701 | B.153 | C.13 |
| 1.2702 | B.154 | C.13 |
| 1.2703 | B.155 | C.13 |
| 1.2704 | B.156 | C.13 |
| 1.2705 | B.157 | C.13 |
| 1.2706 | B.158 | C.13 |
| 1.2707 | B.159 | C.13 |
| 1.2708 | B.160 | C.13 |
| 1.2709 | B.161 | C.13 |
| 1.2710 | B.162 | C.13 |
| 1.2711 | B.163 | C.13 |
| 1.2712 | B.164 | C.13 |
| 1.2713 | B.165 | C.13 |
| 1.2714 | B.166 | C.13 |
| 1.2715 | B.167 | C.13 |
| 1.2716 | B.168 | C.13 |
| 1.2717 | B.169 | C.13 |

TABLE 1-continued (compositions 1.1 to 1.3545):

| comp. no. | herbicide B | safener C |
|---|---|---|
| 1.2718 | B.170 | C.13 |
| 1.2719 | B.171 | C.13 |
| 1.2720 | B.172 | C.13 |
| 1.2721 | B.173 | C.13 |
| 1.2722 | B.174 | C.13 |
| 1.2723 | B.175 | C.13 |
| 1.2724 | B.176 | C.13 |
| 1.2725 | B.177 | C.13 |
| 1.2726 | B.178 | C.13 |
| 1.2727 | B.179 | C.13 |
| 1.2728 | B.180 | C.13 |
| 1.2729 | B.181 | C.13 |
| 1.2730 | B.182 | C.13 |
| 1.2731 | B.183 | C.13 |
| 1.2732 | B.184 | C.13 |
| 1.2733 | B.185 | C.13 |
| 1.2734 | B.186 | C.13 |
| 1.2735 | B.187 | C.13 |
| 1.2736 | B.188 | C.13 |
| 1.2737 | B.189 | C.13 |
| 1.2738 | B.190 | C.13 |
| 1.2739 | B.191 | C.13 |
| 1.2740 | B.192 | C.13 |
| 1.2741 | B.193 | C.13 |
| 1.2742 | B.194 | C.13 |
| 1.2743 | B.195 | C.13 |
| 1.2744 | B.196 | C.13 |
| 1.2745 | B.1 | C.14 |
| 1.2746 | B.2 | C.14 |
| 1.2747 | B.3 | C.14 |
| 1.2748 | B.4 | C.14 |
| 1.2749 | B.5 | C.14 |
| 1.2750 | B.6 | C.14 |
| 1.2751 | B.7 | C.14 |
| 1.2752 | B.8 | C.14 |
| 1.2753 | B.9 | C.14 |
| 1.2754 | B.10 | C.14 |
| 1.2755 | B.11 | C.14 |
| 1.2756 | B.12 | C.14 |
| 1.2757 | B.13 | C.14 |
| 1.2758 | B.14 | C.14 |
| 1.2759 | B.15 | C.14 |
| 1.2760 | B.16 | C.14 |
| 1.2761 | B.17 | C.14 |
| 1.2762 | B.18 | C.14 |
| 1.2763 | B.19 | C.14 |
| 1.2764 | B.20 | C.14 |
| 1.2765 | B.21 | C.14 |
| 1.2766 | B.22 | C.14 |
| 1.2767 | B.23 | C.14 |
| 1.2768 | B.24 | C.14 |
| 1.2769 | B.25 | C.14 |
| 1.2770 | B.26 | C.14 |
| 1.2771 | B.27 | C.14 |
| 1.2772 | B.28 | C.14 |
| 1.2773 | B.29 | C.14 |
| 1.2774 | B.30 | C.14 |
| 1.2775 | B.31 | C.14 |
| 1.2776 | B.32 | C.14 |
| 1.2777 | B.33 | C.14 |
| 1.2778 | B.34 | C.14 |
| 1.2779 | B.35 | C.14 |
| 1.2780 | B.36 | C.14 |
| 1.2781 | B.37 | C.14 |
| 1.2782 | B.38 | C.14 |
| 1.2783 | B.39 | C.14 |
| 1.2784 | B.40 | C.14 |
| 1.2785 | B.41 | C.14 |
| 1.2786 | B.42 | C.14 |
| 1.2787 | B.43 | C.14 |
| 1.2788 | B.44 | C.14 |
| 1.2789 | B.45 | C.14 |
| 1.2790 | B.46 | C.14 |
| 1.2791 | B.47 | C.14 |
| 1.2792 | B.48 | C.14 |
| 1.2793 | B.49 | C.14 |
| 1.2794 | B.50 | C.14 |
| 1.2795 | B.51 | C.14 |
| 1.2796 | B.52 | C.14 |
| 1.2797 | B.53 | C.14 |
| 1.2798 | B.54 | C.14 |
| 1.2799 | B.55 | C.14 |
| 1.2800 | B.56 | C.14 |
| 1.2801 | B.57 | C.14 |
| 1.2802 | B.58. | C.14 |
| 1.2803 | B.59 | C.14 |
| 1.2804 | B.60 | C.14 |
| 1.2805 | B.61 | C.14 |
| 1.2806 | B.62 | C.14 |
| 1.2807 | B.63 | C.14 |
| 1.2808 | B.64 | C.14 |
| 1.2809 | B.65 | C.14 |
| 1.2810 | B.66 | C.14 |
| 1.2811 | B.67 | C.14 |
| 1.2812 | B.68 | C.14 |
| 1.2813 | B.69 | C.14 |
| 1.2814 | B.70 | C.14 |
| 1.2815 | B.71 | C.14 |
| 1.2816 | B.72 | C.14 |
| 1.2817 | B.73 | C.14 |
| 1.2818 | B.74 | C.14 |
| 1.2819 | B.75 | C.14 |
| 1.2820 | B.76 | C.14 |
| 1.2821 | B.77 | C.14 |
| 1.2822 | B.78 | C.14 |
| 1.2823 | B.79 | C.14 |
| 1.2824 | B.80 | C.14 |
| 1.2825 | B.81 | C.14 |
| 1.2826 | B.82 | C.14 |
| 1.2827 | B.83 | C.14 |
| 1.2828 | B.84 | C.14 |
| 1.2829 | B.85 | C.14 |
| 1.2830 | B.86 | C.14 |
| 1.2831 | B.87 | C.14 |
| 1.2832 | B.88 | C.14 |
| 1.2833 | B.89 | C.14 |
| 1.2834 | B.90 | C.14 |
| 1.2835 | B.91 | C.14 |
| 1.2836 | B.92 | C.14 |
| 1.2837 | B.93 | C.14 |
| 1.2838 | B.94 | C.14 |
| 1.2839 | B.95 | C.14 |
| 1.2840 | B.96 | C.14 |
| 1.2841 | B.97 | C.14 |
| 1.2842 | B.98 | C.14 |
| 1.2843 | B.99 | C.14 |
| 1.2844 | B.100 | C.14 |
| 1.2845 | B.101 | C.14 |
| 1.2846 | B.102 | C.14 |
| 1.2847 | B.103 | C.14 |
| 1.2848 | B.104 | C.14 |
| 1.2849 | B.105 | C.14 |
| 1.2850 | B.106 | C.14 |
| 1.2851 | B.107 | C.14 |
| 1.2852 | B.108 | C.14 |
| 1.2853 | B.109 | C.14 |
| 1.2854 | B.110 | C.14 |
| 1.2855 | B.111 | C.14 |
| 1.2856 | B.112 | C.14 |
| 1.2857 | B.113 | C.14 |
| 1.2858 | B.114 | C.14 |
| 1.2859 | B.115 | C.14 |
| 1.2860 | B.116 | C.14 |
| 1.2861 | B.117 | C.14 |
| 1.2862 | B.118 | C.14 |
| 1.2863 | B.119 | C.14 |
| 1.2864 | B.120 | C.14 |
| 1.2865 | B.121 | C.14 |
| 1.2866 | B.122 | C.14 |
| 1.2867 | B.123 | C.14 |
| 1.2868 | B.124 | C.14 |
| 1.2869 | B.125 | C.14 |

TABLE 1-continued (compositions 1.1 to 1.3545):

| comp. no. | herbicide B | safener C |
|---|---|---|
| 1.2870 | B.126 | C.14 |
| 1.2871 | B.127 | C.14 |
| 1.2872 | B.128 | C.14 |
| 1.2873 | B.129 | C.14 |
| 1.2874 | B.130 | C.14 |
| 1.2875 | B.131 | C.14 |
| 1.2876 | B.132 | C.14 |
| 1.2877 | B.133 | C.14 |
| 1.2878 | B.134 | C.14 |
| 1.2879 | B.135 | C.14 |
| 1.2880 | B.136 | C.14 |
| 1.2881 | B.137 | C.14 |
| 1.2882 | B.138 | C.14 |
| 1.2883 | B.139 | C.14 |
| 1.2884 | B.140 | C.14 |
| 1.2885 | B.141 | C.14 |
| 1.2886 | B.142 | C.14 |
| 1.2887 | B.143 | C.14 |
| 1.2888 | B.144 | C.14 |
| 1.2889 | B.145 | C.14 |
| 1.2890 | B.146 | C.14 |
| 1.2891 | B.147 | C.14 |
| 1.2892 | B.148 | C.14 |
| 1.2893 | B.149 | C.14 |
| 1.2894 | B.150 | C.14 |
| 1.2895 | B.151 | C.14 |
| 1.2896 | B.152 | C.14 |
| 1.2897 | B.153 | C.14 |
| 1.2898 | B.154 | C.14 |
| 1.2899 | B.155 | C.14 |
| 1.2900 | B.156 | C.14 |
| 1.2901 | B.157 | C.14 |
| 1.2902 | B.158 | C.14 |
| 1.2903 | B.159 | C.14 |
| 1.2904 | B.160 | C.14 |
| 1.2905 | B.161 | C.14 |
| 1.2906 | B.162 | C.14 |
| 1.2907 | B.163 | C.14 |
| 1.2908 | B.164 | C.14 |
| 1.2909 | B.165 | C.14 |
| 1.2910 | B.166 | C.14 |
| 1.2911 | B.167 | C.14 |
| 1.2912 | B.168 | C.14 |
| 1.2913 | B.169 | C.14 |
| 1.2914 | B.170 | C.14 |
| 1.2915 | B.171 | C.14 |
| 1.2916 | B.172 | C.14 |
| 1.2917 | B.173 | C.14 |
| 1.2918 | B.174 | C.14 |
| 1.2919 | B.175 | C.14 |
| 1.2920 | B.176 | C.14 |
| 1.2921 | B.177 | C.14 |
| 1.2922 | B.178 | C.14 |
| 1.2923 | B.179 | C.14 |
| 1.2924 | B.180 | C.14 |
| 1.2925 | B.181 | C.14 |
| 1.2926 | B.182 | C.14 |
| 1.2927 | B.183 | C.14 |
| 1.2928 | B.184 | C.14 |
| 1.2929 | B.185 | C.14 |
| 1.2930 | B.186 | C.14 |
| 1.2931 | B.187 | C.14 |
| 1.2932 | B.188 | C.14 |
| 1.2933 | B.189 | C.14 |
| 1.2934 | B.190 | C.14 |
| 1.2935 | B.191 | C.14 |
| 1.2936 | B.192 | C.14 |
| 1.2937 | B.193 | C.14 |
| 1.2938 | B.194 | C.14 |
| 1.2939 | B.195 | C.14 |
| 1.2940 | B.196 | C.14 |
| 1.2941 | B.1 | C.15 |
| 1.2942 | B.2 | C.15 |
| 1.2943 | B.3 | C.15 |
| 1.2944 | B.4 | C.15 |
| 1.2945 | B.5 | C.15 |
| 1.2946 | B.6 | C.15 |
| 1.2947 | B.7 | C.15 |
| 1.2948 | B.8 | C.15 |
| 1.2949 | B.9 | C.15 |
| 1.2950 | B.10 | C.15 |
| 1.2951 | B.11 | C.15 |
| 1.2952 | B.12 | C.15 |
| 1.2953 | B.13 | C.15 |
| 1.2954 | B.14 | C.15 |
| 1.2955 | B.15 | C.15 |
| 1.2956 | B.16 | C.15 |
| 1.2957 | B.17 | C.15 |
| 1.2958 | B.18 | C.15 |
| 1.2959 | B.19 | C.15 |
| 1.2960 | B.20 | C.15 |
| 1.2961 | B.21 | C.15 |
| 1.2962 | B.22 | C.15 |
| 1.2963 | B.23 | C.15 |
| 1.2964 | B.24 | C.15 |
| 1.2965 | B.25 | C.15 |
| 1.2966 | B.26 | C.15 |
| 1.2967 | B.27 | C.15 |
| 1.2968 | B.28 | C.15 |
| 1.2969 | B.29 | C.15 |
| 1.2970 | B.30 | C.15 |
| 1.2971 | B.31 | C.15 |
| 1.2972 | B.32 | C.15 |
| 1.2973 | B.33 | C.15 |
| 1.2974 | B.34 | C.15 |
| 1.2975 | B.35 | C.15 |
| 1.2976 | B.36 | C.15 |
| 1.2977 | B.37 | C.15 |
| 1.2978 | B.38 | C.15 |
| 1.2979 | B.39 | C.15 |
| 1.2980 | B.40 | C.15 |
| 1.2981 | B.41 | C.15 |
| 1.2982 | B.42 | C.15 |
| 1.2983 | B.43 | C.15 |
| 1.2984 | B.44 | C.15 |
| 1.2985 | B.45 | C.15 |
| 1.2986 | B.46 | C.15 |
| 1.2987 | B.47 | C.15 |
| 1.2988 | B.48 | C.15 |
| 1.2989 | B.49 | C.15 |
| 1.2990 | B.50 | C.15 |
| 1.2991 | B.51 | C.15 |
| 1.2992 | B.52 | C.15 |
| 1.2993 | B.53 | C.15 |
| 1.2994 | B.54 | C.15 |
| 1.2995 | B.55 | C.15 |
| 1.2996 | B.56 | C.15 |
| 1.2997 | B.57 | C.15 |
| 1.2998 | B.58. | C.15 |
| 1.2999 | B.59 | C.15 |
| 1.3000 | B.60 | C.15 |
| 1.3001 | B.61 | C.15 |
| 1.3002 | B.62 | C.15 |
| 1.3003 | B.63 | C.15 |
| 1.3004 | B.64 | C.15 |
| 1.3005 | B.65 | C.15 |
| 1.3006 | B.66 | C.15 |
| 1.3007 | B.67 | C.15 |
| 1.3008 | B.68 | C.15 |
| 1.3009 | B.69 | C.15 |
| 1.3010 | B.70 | C.15 |
| 1.3011 | B.71 | C.15 |
| 1.3012 | B.72 | C.15 |
| 1.3013 | B.73 | C.15 |
| 1.3014 | B.74 | C.15 |
| 1.3015 | B.75 | C.15 |
| 1.3016 | B.76 | C.15 |
| 1.3017 | B.77 | C.15 |
| 1.3018 | B.78 | C.15 |
| 1.3019 | B.79 | C.15 |
| 1.3020 | B.80 | C.15 |
| 1.3021 | B.81 | C.15 |

TABLE 1-continued (compositions 1.1 to 1.3545):

| comp. no. | herbicide B | safener C |
|---|---|---|
| 1.3022 | B.82 | C.15 |
| 1.3023 | B.83 | C.15 |
| 1.3024 | B.84 | C.15 |
| 1.3025 | B.85 | C.15 |
| 1.3026 | B.86 | C.15 |
| 1.3027 | B.87 | C.15 |
| 1.3028 | B.88 | C.15 |
| 1.3029 | B.89 | C.15 |
| 1.3030 | B.90 | C.15 |
| 1.3031 | B.91 | C.15 |
| 1.3032 | B.92 | C.15 |
| 1.3033 | B.93 | C.15 |
| 1.3034 | B.94 | C.15 |
| 1.3035 | B.95 | C.15 |
| 1.3036 | B.96 | C.15 |
| 1.3037 | B.97 | C.15 |
| 1.3038 | B.98 | C.15 |
| 1.3039 | B.99 | C.15 |
| 1.3040 | B.100 | C.15 |
| 1.3041 | B.101 | C.15 |
| 1.3042 | B.102 | C.15 |
| 1.3043 | B.103 | C.15 |
| 1.3044 | B.104 | C.15 |
| 1.3045 | B.105 | C.15 |
| 1.3046 | B.106 | C.15 |
| 1.3047 | B.107 | C.15 |
| 1.3048 | B.108 | C.15 |
| 1.3049 | B.109 | C.15 |
| 1.3050 | B.110 | C.15 |
| 1.3051 | B.111 | C.15 |
| 1.3052 | B.112 | C.15 |
| 1.3053 | B.113 | C.15 |
| 1.3054 | B.114 | C.15 |
| 1.3055 | B.115 | C.15 |
| 1.3056 | B.116 | C.15 |
| 1.3057 | B.117 | C.15 |
| 1.3058 | B.118 | C.15 |
| 1.3059 | B.119 | C.15 |
| 1.3060 | B.120 | C.15 |
| 1.3061 | B.121 | C.15 |
| 1.3062 | B.122 | C.15 |
| 1.3063 | B.123 | C.15 |
| 1.3064 | B.124 | C.15 |
| 1.3065 | B.125 | C.15 |
| 1.3066 | B.126 | C.15 |
| 1.3067 | B.127 | C.15 |
| 1.3068 | B.128 | C.15 |
| 1.3069 | B.129 | C.15 |
| 1.3070 | B.130 | C.15 |
| 1.3071 | B.131 | C.15 |
| 1.3072 | B.132 | C.15 |
| 1.3073 | B.133 | C.15 |
| 1.3074 | B.134 | C.15 |
| 1.3075 | B.135 | C.15 |
| 1.3076 | B.136 | C.15 |
| 1.3077 | B.137 | C.15 |
| 1.3078 | B.138 | C.15 |
| 1.3079 | B.139 | C.15 |
| 1.3080 | B.140 | C.15 |
| 1.3081 | B.141 | C.15 |
| 1.3082 | B.142 | C.15 |
| 1.3083 | B.143 | C.15 |
| 1.3084 | B.144 | C.15 |
| 1.3085 | B.145 | C.15 |
| 1.3086 | B.146 | C.15 |
| 1.3087 | B.147 | C.15 |
| 1.3088 | B.148 | C.15 |
| 1.3089 | B.149 | C.15 |
| 1.3090 | B.150 | C.15 |
| 1.3091 | B.151 | C.15 |
| 1.3092 | B.152 | C.15 |
| 1.3093 | B.153 | C.15 |
| 1.3094 | B.154 | C.15 |
| 1.3095 | B.155 | C.15 |
| 1.3096 | B.156 | C.15 |
| 1.3097 | B.157 | C.15 |
| 1.3098 | B.158 | C.15 |
| 1.3099 | B.159 | C.15 |
| 1.3100 | B.160 | C.15 |
| 1.3101 | B.161 | C.15 |
| 1.3102 | B.162 | C.15 |
| 1.3103 | B.163 | C.15 |
| 1.3104 | B.164 | C.15 |
| 1.3105 | B.165 | C.15 |
| 1.3106 | B.166 | C.15 |
| 1.3107 | B.167 | C.15 |
| 1.3108 | B.168 | C.15 |
| 1.3109 | B.169 | C.15 |
| 1.3110 | B.170 | C.15 |
| 1.3111 | B.171 | C.15 |
| 1.3112 | B.172 | C.15 |
| 1.3113 | B.173 | C.15 |
| 1.3114 | B.174 | C.15 |
| 1.3115 | B.175 | C.15 |
| 1.3116 | B.176 | C.15 |
| 1.3117 | B.177 | C.15 |
| 1.3118 | B.178 | C.15 |
| 1.3119 | B.179 | C.15 |
| 1.3120 | B.180 | C.15 |
| 1.3121 | B.181 | C.15 |
| 1.3122 | B.182 | C.15 |
| 1.3123 | B.183 | C.15 |
| 1.3124 | B.184 | C.15 |
| 1.3125 | B.185 | C.15 |
| 1.3126 | B.186 | C.15 |
| 1.3127 | B.187 | C.15 |
| 1.3128 | B.188 | C.15 |
| 1.3129 | B.189 | C.15 |
| 1.3130 | B.190 | C.15 |
| 1.3131 | B.191 | C.15 |
| 1.3132 | B.192 | C.15 |
| 1.3133 | B.193 | C.15 |
| 1.3134 | B.194 | C.15 |
| 1.3135 | B.195 | C.15 |
| 1.3136 | B.196 | C.15 |
| 1.3137 | B.1 | C.16 |
| 1.3138 | B.2 | C.16 |
| 1.3139 | B.3 | C.16 |
| 1.3140 | B.4 | C.16 |
| 1.3141 | B.5 | C.16 |
| 1.3142 | B.6 | C.16 |
| 1.3143 | B.7 | C.16 |
| 1.3144 | B.8 | C.16 |
| 1.3145 | B.9 | C.16 |
| 1.3146 | B.10 | C.16 |
| 1.3147 | B.11 | C.16 |
| 1.3148 | B.12 | C.16 |
| 1.3149 | B.13 | C.16 |
| 1.3150 | B.14 | C.16 |
| 1.3151 | B.15 | C.16 |
| 1.3152 | B.16 | C.16 |
| 1.3153 | B.17 | C.16 |
| 1.3154 | B.18 | C.16 |
| 1.3155 | B.19 | C.16 |
| 1.3156 | B.20 | C.16 |
| 1.3157 | B.21 | C.16 |
| 1.3158 | B.22 | C.16 |
| 1.3159 | B.23 | C.16 |
| 1.3160 | B.24 | C.16 |
| 1.3161 | B.25 | C.16 |
| 1.3162 | B.26 | C.16 |
| 1.3163 | B.27 | C.16 |
| 1.3164 | B.28 | C.16 |
| 1.3165 | B.29 | C.16 |
| 1.3166 | B.30 | C.16 |
| 1.3167 | B.31 | C.16 |
| 1.3168 | B.32 | C.16 |
| 1.3169 | B.33 | C.16 |
| 1.3170 | B.34 | C.16 |
| 1.3171 | B.35 | C.16 |
| 1.3172 | B.36 | C.16 |
| 1.3173 | B.37 | C.16 |

TABLE 1-continued (compositions 1.1 to 1.3545):

| comp. no. | herbicide B | safener C |
|---|---|---|
| 1.3174 | B.38 | C.16 |
| 1.3175 | B.39 | C.16 |
| 1.3176 | B.40 | C.16 |
| 1.3177 | B.41 | C.16 |
| 1.3178 | B.42 | C.16 |
| 1.3179 | B.43 | C.16 |
| 1.3180 | B.44 | C.16 |
| 1.3181 | B.45 | C.16 |
| 1.3182 | B.46 | C.16 |
| 1.3183 | B.47 | C.16 |
| 1.3184 | B.48 | C.16 |
| 1.3185 | B.49 | C.16 |
| 1.3186 | B.50 | C.16 |
| 1.3187 | B.51 | C.16 |
| 1.3188 | B.52 | C.16 |
| 1.3189 | B.53 | C.16 |
| 1.3190 | B.54 | C.16 |
| 1.3191 | B.55 | C.16 |
| 1.3192 | B.56 | C.16 |
| 1.3193 | B.57 | C.16 |
| 1.3194 | B.58. | C.16 |
| 1.3195 | B.59 | C.16 |
| 1.3196 | B.60 | C.16 |
| 1.3197 | B.61 | C.16 |
| 1.3198 | B.62 | C.16 |
| 1.3199 | B.63 | C.16 |
| 1.3200 | B.64 | C.16 |
| 1.3201 | B.65 | C.16 |
| 1.3202 | B.66 | C.16 |
| 1.3203 | B.67 | C.16 |
| 1.3204 | B.68 | C.16 |
| 1.3205 | B.69 | C.16 |
| 1.3206 | B.70 | C.16 |
| 1.3207 | B.71 | C.16 |
| 1.3208 | B.72 | C.16 |
| 1.3209 | B.73 | C.16 |
| 1.3210 | B.74 | C.16 |
| 1.3211 | B.75 | C.16 |
| 1.3212 | B.76 | C.16 |
| 1.3213 | B.77 | C.16 |
| 1.3214 | B.78 | C.16 |
| 1.3215 | B.79 | C.16 |
| 1.3216 | B.80 | C.16 |
| 1.3217 | B.81 | C.16 |
| 1.3218 | B.82 | C.16 |
| 1.3219 | B.83 | C.16 |
| 1.3220 | B.84 | C.16 |
| 1.3221 | B.85 | C.16 |
| 1.3222 | B.86 | C.16 |
| 1.3223 | B.87 | C.16 |
| 1.3224 | B.88 | C.16 |
| 1.3225 | B.89 | C.16 |
| 1.3226 | B.90 | C.16 |
| 1.3227 | B.91 | C.16 |
| 1.3228 | B.92 | C.16 |
| 1.3229 | B.93 | C.16 |
| 1.3230 | B.94 | C.16 |
| 1.3231 | B.95 | C.16 |
| 1.3232 | B.96 | C.16 |
| 1.3233 | B.97 | C.16 |
| 1.3234 | B.98 | C.16 |
| 1.3235 | B.99 | C.16 |
| 1.3236 | B.100 | C.16 |
| 1.3237 | B.101 | C.16 |
| 1.3238 | B.102 | C.16 |
| 1.3239 | B.103 | C.16 |
| 1.3240 | B.104 | C.16 |
| 1.3241 | B.105 | C.16 |
| 1.3242 | B.106 | C.16 |
| 1.3243 | B.107 | C.16 |
| 1.3244 | B.108 | C.16 |
| 1.3245 | B.109 | C.16 |
| 1.3246 | B.110 | C.16 |
| 1.3247 | B.111 | C.16 |
| 1.3248 | B.112 | C.16 |
| 1.3249 | B.113 | C.16 |
| 1.3250 | B.114 | C.16 |
| 1.3251 | B.115 | C.16 |
| 1.3252 | B.116 | C.16 |
| 1.3253 | B.117 | C.16 |
| 1.3254 | B.118 | C.16 |
| 1.3255 | B.119 | C.16 |
| 1.3256 | B.120 | C.16 |
| 1.3257 | B.121 | C.16 |
| 1.3258 | B.122 | C.16 |
| 1.3259 | B.123 | C.16 |
| 1.3260 | B.124 | C.16 |
| 1.3261 | B.125 | C.16 |
| 1.3262 | B.126 | C.16 |
| 1.3263 | B.127 | C.16 |
| 1.3264 | B.128 | C.16 |
| 1.3265 | B.129 | C.16 |
| 1.3266 | B.130 | C.16 |
| 1.3267 | B.131 | C.16 |
| 1.3268 | B.132 | C.16 |
| 1.3269 | B.133 | C.16 |
| 1.3270 | B.134 | C.16 |
| 1.3271 | B.135 | C.16 |
| 1.3272 | B.136 | C.16 |
| 1.3273 | B.137 | C.16 |
| 1.3274 | B.138 | C.16 |
| 1.3275 | B.139 | C.16 |
| 1.3276 | B.140 | C.16 |
| 1.3277 | B.141 | C.16 |
| 1.3278 | B.142 | C.16 |
| 1.3279 | B.143 | C.16 |
| 1.3280 | B.144 | C.16 |
| 1.3281 | B.145 | C.16 |
| 1.3282 | B.146 | C.16 |
| 1.3283 | B.147 | C.16 |
| 1.3284 | B.148 | C.16 |
| 1.3285 | B.149 | C.16 |
| 1.3286 | B.150 | C.16 |
| 1.3287 | B.151 | C.16 |
| 1.3288 | B.152 | C.16 |
| 1.3289 | B.153 | C.16 |
| 1.3290 | B.154 | C.16 |
| 1.3291 | B.155 | C.16 |
| 1.3292 | B.156 | C.16 |
| 1.3293 | B.157 | C.16 |
| 1.3294 | B.158 | C.16 |
| 1.3295 | B.159 | C.16 |
| 1.3296 | B.160 | C.16 |
| 1.3297 | B.161 | C.16 |
| 1.3298 | B.162 | C.16 |
| 1.3299 | B.163 | C.16 |
| 1.3300 | B.164 | C.16 |
| 1.3301 | B.165 | C.16 |
| 1.3302 | B.166 | C.16 |
| 1.3303 | B.167 | C.16 |
| 1.3304 | B.168 | C.16 |
| 1.3305 | B.169 | C.16 |
| 1.3306 | B.170 | C.16 |
| 1.3307 | B.171 | C.16 |
| 1.3308 | B.172 | C.16 |
| 1.3309 | B.173 | C.16 |
| 1.3310 | B.174 | C.16 |
| 1.3311 | B.175 | C.16 |
| 1.3312 | B.176 | C.16 |
| 1.3313 | B.177 | C.16 |
| 1.3314 | B.178 | C.16 |
| 1.3315 | B.179 | C.16 |
| 1.3316 | B.180 | C.16 |
| 1.3317 | B.181 | C.16 |
| 1.3318 | B.182 | C.16 |
| 1.3319 | B.183 | C.16 |
| 1.3320 | B.184 | C.16 |
| 1.3321 | B.185 | C.16 |
| 1.3322 | B.186 | C.16 |
| 1.3323 | B.187 | C.16 |
| 1.3324 | B.188 | C.16 |
| 1.3325 | B.189 | C.16 |

TABLE 1-continued (compositions 1.1 to 1.3545):

| comp. no. | herbicide B | safener C |
|---|---|---|
| 1.3326 | B.190 | C.16 |
| 1.3327 | B.191 | C.16 |
| 1.3328 | B.192 | C.16 |
| 1.3329 | B.193 | C.16 |
| 1.3330 | B.194 | C.16 |
| 1.3331 | B.195 | C.16 |
| 1.3332 | B.196 | C.16 |
| 1.3333 | B.1 | C.17 |
| 1.3334 | B.2 | C.17 |
| 1.3335 | B.3 | C.17 |
| 1.3336 | B.4 | C.17 |
| 1.3337 | B.5 | C.17 |
| 1.3338 | B.6 | C.17 |
| 1.3339 | B.7 | C.17 |
| 1.3340 | B.8 | C.17 |
| 1.3341 | B.9 | C.17 |
| 1.3342 | B.10 | C.17 |
| 1.3343 | B.11 | C.17 |
| 1.3344 | B.12 | C.17 |
| 1.3345 | B.13 | C.17 |
| 1.3346 | B.14 | C.17 |
| 1.3347 | B.15 | C.17 |
| 1.3348 | B.16 | C.17 |
| 1.3349 | B.17 | C.17 |
| 1.3350 | B.18 | C.17 |
| 1.3351 | B.19 | C.17 |
| 1.3352 | B.20 | C.17 |
| 1.3353 | B.21 | C.17 |
| 1.3354 | B.22 | C.17 |
| 1.3355 | B.23 | C.17 |
| 1.3356 | B.24 | C.17 |
| 1.3357 | B.25 | C.17 |
| 1.3358 | B.26 | C.17 |
| 1.3359 | B.27 | C.17 |
| 1.3360 | B.28 | C.17 |
| 1.3361 | B.29 | C.17 |
| 1.3362 | B.30 | C.17 |
| 1.3363 | B.31 | C.17 |
| 1.3364 | B.32 | C.17 |
| 1.3365 | B.33 | C.17 |
| 1.3366 | B.34 | C.17 |
| 1.3367 | B.35 | C.17 |
| 1.3368 | B.36 | C.17 |
| 1.3369 | B.37 | C.17 |
| 1.3370 | B.38 | C.17 |
| 1.3371 | B.39 | C.17 |
| 1.3372 | B.40 | C.17 |
| 1.3373 | B.41 | C.17 |
| 1.3374 | B.42 | C.17 |
| 1.3375 | B.43 | C.17 |
| 1.3376 | B.44 | C.17 |
| 1.3377 | B.45 | C.17 |
| 1.3378 | B.46 | C.17 |
| 1.3379 | B.47 | C.17 |
| 1.3380 | B.48 | C.17 |
| 1.3381 | B.49 | C.17 |
| 1.3382 | B.50 | C.17 |
| 1.3383 | B.51 | C.17 |
| 1.3384 | B.52 | C.17 |
| 1.3385 | B.53 | C.17 |
| 1.3386 | B.54 | C.17 |
| 1.3387 | B.55 | C.17 |
| 1.3388 | B.56 | C.17 |
| 1.3389 | B.57 | C.17 |
| 1.3390 | B.58. | C.17 |
| 1.3391 | B.59 | C.17 |
| 1.3392 | B.60 | C.17 |
| 1.3393 | B.61 | C.17 |
| 1.3394 | B.62 | C.17 |
| 1.3395 | B.63 | C.17 |
| 1.3396 | B.64 | C.17 |
| 1.3397 | B.65 | C.17 |
| 1.3398 | B.66 | C.17 |
| 1.3399 | B.67 | C.17 |
| 1.3400 | B.68 | C.17 |
| 1.3401 | B.69 | C.17 |
| 1.3402 | B.70 | C.17 |
| 1.3403 | B.71 | C.17 |
| 1.3404 | B.72 | C.17 |
| 1.3405 | B.73 | C.17 |
| 1.3406 | B.74 | C.17 |
| 1.3407 | B.75 | C.17 |
| 1.3408 | B.76 | C.17 |
| 1.3409 | B.77 | C.17 |
| 1.3410 | B.78 | C.17 |
| 1.3411 | B.79 | C.17 |
| 1.3412 | B.80 | C.17 |
| 1.3413 | B.81 | C.17 |
| 1.3414 | B.82 | C.17 |
| 1.3415 | B.83 | C.17 |
| 1.3416 | B.84 | C.17 |
| 1.3417 | B.85 | C.17 |
| 1.3418 | B.86 | C.17 |
| 1.3419 | B.87 | C.17 |
| 1.3420 | B.88 | C.17 |
| 1.3421 | B.89 | C.17 |
| 1.3422 | B.90 | C.17 |
| 1.3423 | B.91 | C.17 |
| 1.3424 | B.92 | C.17 |
| 1.3425 | B.93 | C.17 |
| 1.3426 | B.94 | C.17 |
| 1.3427 | B.95 | C.17 |
| 1.3428 | B.96 | C.17 |
| 1.3429 | B.97 | C.17 |
| 1.3430 | B.98 | C.17 |
| 1.3431 | B.99 | C.17 |
| 1.3432 | B.100 | C.17 |
| 1.3433 | B.101 | C.17 |
| 1.3434 | B.102 | C.17 |
| 1.3435 | B.103 | C.17 |
| 1.3436 | B.104 | C.17 |
| 1.3437 | B.105 | C.17 |
| 1.3438 | B.106 | C.17 |
| 1.3439 | B.107 | C.17 |
| 1.3440 | B.108 | C.17 |
| 1.3441 | B.109 | C.17 |
| 1.3442 | B.110 | C.17 |
| 1.3443 | B.111 | C.17 |
| 1.3444 | B.112 | C.17 |
| 1.3445 | B.113 | C.17 |
| 1.3446 | B.114 | C.17 |
| 1.3447 | B.115 | C.17 |
| 1.3448 | B.116 | C.17 |
| 1.3449 | B.117 | C.17 |
| 1.3450 | B.118 | C.17 |
| 1.3451 | B.119 | C.17 |
| 1.3452 | B.120 | C.17 |
| 1.3453 | B.121 | C.17 |
| 1.3454 | B.122 | C.17 |
| 1.3455 | B.123 | C.17 |
| 1.3456 | B.124 | C.17 |
| 1.3457 | B.125 | C.17 |
| 1.3458 | B.126 | C.17 |
| 1.3459 | B.127 | C.17 |
| 1.3460 | B.128 | C.17 |
| 1.3461 | B.129 | C.17 |
| 1.3462 | B.130 | C.17 |
| 1.3463 | B.131 | C.17 |
| 1.3464 | B.132 | C.17 |
| 1.3465 | B.133 | C.17 |
| 1.3466 | B.134 | C.17 |
| 1.3467 | B.135 | C.17 |
| 1.3468 | B.136 | C.17 |
| 1.3469 | B.137 | C.17 |
| 1.3470 | B.138 | C.17 |
| 1.3471 | B.139 | C.17 |
| 1.3472 | B.140 | C.17 |
| 1.3473 | B.141 | C.17 |
| 1.3474 | B.142 | C.17 |
| 1.3475 | B.143 | C.17 |
| 1.3476 | B.144 | C.17 |
| 1.3477 | B.145 | C.17 |

TABLE 1-continued (compositions 1.1 to 1.3545):

| comp. no. | herbicide B | safener C |
|---|---|---|
| 1.3478 | B.146 | C.17 |
| 1.3479 | B.147 | C.17 |
| 1.3480 | B.148 | C.17 |
| 1.3481 | B.149 | C.17 |
| 1.3482 | B.150 | C.17 |
| 1.3483 | B.151 | C.17 |
| 1.3484 | B.152 | C.17 |
| 1.3485 | B.153 | C.17 |
| 1.3486 | B.154 | C.17 |
| 1.3487 | B.155 | C.17 |
| 1.3488 | B.156 | C.17 |
| 1.3489 | B.157 | C.17 |
| 1.3490 | B.158 | C.17 |
| 1.3491 | B.159 | C.17 |
| 1.3492 | B.160 | C.17 |
| 1.3493 | B.161 | C.17 |
| 1.3494 | B.162 | C.17 |
| 1.3495 | B.163 | C.17 |
| 1.3496 | B.164 | C.17 |
| 1.3497 | B.165 | C.17 |
| 1.3498 | B.166 | C.17 |
| 1.3499 | B.167 | C.17 |
| 1.3500 | B.168 | C.17 |
| 1.3501 | B.169 | C.17 |
| 1.3502 | B.170 | C.17 |
| 1.3503 | B.171 | C.17 |
| 1.3504 | B.172 | C.17 |
| 1.3505 | B.173 | C.17 |
| 1.3506 | B.174 | C.17 |
| 1.3507 | B.175 | C.17 |
| 1.3508 | B.176 | C.17 |
| 1.3509 | B.177 | C.17 |
| 1.3510 | B.178 | C.17 |
| 1.3511 | B.179 | C.17 |
| 1.3512 | B.180 | C.17 |
| 1.3513 | B.181 | C.17 |
| 1.3514 | B.182 | C.17 |
| 1.3515 | B.183 | C.17 |
| 1.3516 | B.184 | C.17 |
| 1.3517 | B.185 | C.17 |
| 1.3518 | B.186 | C.17 |
| 1.3519 | B.187 | C.17 |
| 1.3520 | B.188 | C.17 |
| 1.3521 | B.189 | C.17 |
| 1.3522 | B.190 | C.17 |
| 1.3523 | B.191 | C.17 |
| 1.3524 | B.192 | C.17 |
| 1.3525 | B.193 | C.17 |
| 1.3526 | B.194 | C.17 |
| 1.3527 | B.195 | C.17 |
| 1.3528 | B.196 | C.17 |
| 1.3529 | — | C.1 |
| 1.3530 | — | C.2 |
| 1.3531 | — | C.3 |
| 1.3532 | — | C.4 |
| 1.3533 | — | C.5 |
| 1.3534 | — | C.6 |
| 1.3535 | — | C.7 |
| 1.3536 | — | C.8 |
| 1.3537 | — | C.9 |
| 1.3538 | — | C.10 |
| 1.3539 | — | C.11 |
| 1.3540 | — | C.12 |
| 1.3541 | — | C.13 |
| 1.3542 | — | C.14 |
| 1.3543 | — | C.15 |
| 1.3544 | — | C.16 |
| 1.3545 | — | C.17 |

The specific number for each single composition is deductible as follows: Composition 1.200 for example comprises the compound I.a, I.b, I.c or I-1 to I-38, cyhalofop-butyl (B.4) and benoxacor (C.1) (see table 1, entry 1.200; as well as table B, entry B.4 and table C, entry C.1).

The invention also relates to agrochemical compositions comprising at least one auxiliary and at least one compound of formula I according to the invention.

An agrochemical composition comprises a pesticidally effective amount of a compound of formula I. The term "effective amount" denotes an amount of the composition or of the compounds I, which is sufficient for controlling unwanted plants, especially for controlling unwanted plants in cultivated plants and which does not result in a substantial damage to the treated plants. Such an amount can vary in a broad range and is dependent on various factors, such as the plants to be controlled, the treated cultivated plant or material, the climatic conditions and the specific compound of formula I used.

The compound of formula I, their N-oxides, salts or derivatives can be converted into customary types of agrochemical compositions, e. g. solutions, emulsions, suspensions, dusts, powders, pastes, granules, pressings, capsules, and mixtures thereof. Examples for agrochemical composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further agrochemical compositions types are defined in the "Catalogue of pesticide formulation types and international coding system", Technical Monograph No. 2, $6^{th}$ Ed. May 2008, CropLife International.

The agrochemical compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyland tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides.

Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B—C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compounds of formula (I) on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), inorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for agrochemical composition types and their preparation are:

i) Water-Soluble Concentrates (SL, LS)

10-60 wt % of a compound of formula I or a herbicidal composition comprising at least one compound of formula I (component A) and at least one further compound selected from the herbicidal compounds B (component B) and safeners C (component C) according to the invention and 5-15 wt % wetting agent (e.g. alcohol alkoxylates) are dissolved in water and/or in a water-soluble solvent (e.g. alcohols) ad 100 wt %. The active substance dissolves upon dilution with water.

ii) Dispersible Concentrates (DC)

5-25 wt % of a compound of formula I or a herbicidal composition comprising at least one compound of formula I (component A) and at least one further compound selected from the herbicidal compounds B (component B) and safeners C (component C) according to the invention and 1-10 wt % dispersant (e. g. polyvinylpyrrolidone) are dissolved in organic solvent (e.g. cyclohexanone) ad 100 wt %. Dilution with water gives a dispersion.

iii) Emulsifiable Concentrates (EC)

15-70 wt % of compound of formula I or a herbicidal composition comprising at least one compound of formula I (component A) and at least one further compound selected from the herbicidal compounds B (component B) and safeners C (component C) according to the invention and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.

iv) Emulsions (EW, EO, ES)

5-40 wt % of compound of formula I or a herbicidal composition comprising at least one compound of formula I (component A) and at least one further compound selected from the herbicidal compounds B (component B) and safeners C (component C) according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of a compound of formula I or a herbicidal composition comprising at least one compound of formula I (component A) and at least one further compound selected from the herbicidal compounds B (component B) and safeners C (component C) according to the invention are comminuted with addition of 2-10 wt % dispersants and wetting agents (e.g. sodium lignosulfonate and alcohol ethoxylate), 0.1-2 wt % thickener (e.g. xanthan gum) and water ad 100 wt % to give a fine active substance suspension. Dilution with water gives a stable suspension of the active substance. For FS type composition up to 40 wt % binder (e.g. polyvinylalcohol) is added.

vi) Water-Dispersible Granules and Water-Soluble Granules (WG, SG)

50-80 wt % of a compound of formula I or a herbicidal composition comprising at least one compound of formula I (component A) and at least one further compound selected from the herbicidal compounds B (component B) and safeners C (component C) according to the invention are ground finely with addition of dispersants and wetting agents (e.g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance.

vii) Water-Dispersible Powders and Water-Soluble Powders (WP, SP, WS)

50-80 wt % of a compound of formula I or a herbicidal composition comprising at least one compound of formula I (component A) and at least one further compound selected from the herbicidal compounds B (component B) and safeners C (component C) according to the invention are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % of a compound of formula I or a herbicidal composition comprising at least one compound of formula I (component A) and at least one further compound selected from the herbicidal compounds B (component B) and safeners C (component C) according to the invention are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.

iv) Microemulsion (ME)

5-20 wt % of a compound of formula I or a herbicidal composition comprising at least one compound of formula I (component A) and at least one further compound selected from the herbicidal compounds B (component B) and safeners C (component C) according to the invention are added to 5-30 wt % organic solvent blend (e.g. fatty acid dimethylamide and cyclohexanone), 10-25 wt % surfactant blend (e.g. alcohol ethoxylate and arylphenol ethoxylate), and water ad 100%. This mixture is stirred for 1 h to produce spontaneously a thermodynamically stable microemulsion.

iv) Microcapsules (CS)

An oil phase comprising 5-50 wt % of a compound of formula I or a herbicidal composition comprising at least one compound of formula I (component A) and at least one further compound selected from the herbicidal compounds B (component B) and safeners C (component C) according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound of formula I according to the invention, 0-40 wt % water insoluble organic solvent (e.g. aromatic hydrocarbon), and an isocyanate monomer (e.g. diphenylmethene-4,4'-diisocyanate) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS composition.

ix) Dustable Powders (DP, DS)

1-10 wt % of a compound of formula I or a herbicidal composition comprising at least one compound of formula I (component A) and at least one further compound selected from the herbicidal compounds B (component B) and safeners C (component C) according to the invention are ground finely and mixed intimately with solid carrier (e.g. finely divided kaolin) ad 100 wt %.

x) Granules (GR, FG)

0.5-30 wt % of a compound of formula (I) or a herbicidal composition comprising at least one compound of formula I (component A) and at least one further compound selected from the herbicidal compounds B (component B) and safeners C (component C) according to the invention is ground finely and associated with solid carrier (e.g. silicate) ad 100 wt %. Granulation is achieved by extrusion, spray-drying or the fluidized bed.

xi) Ultra-Low Volume Liquids (UL)

1-50 wt % of a compound of formula I or a herbicidal composition comprising at least one compound of formula I (component A) and at least one further compound selected from the herbicidal compounds B (component B) and safeners C (component C) according to the invention are dissolved in organic solvent (e.g. aromatic hydrocarbon) ad 100 wt %.

The agrochemical compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions and/or herbicidal compositions generally comprise between 0.01 and 95%, preferably between 0.1 and 90%, and in particular between 0.5 and 75%, by weight of the compound of formula I. The compound of formula I are employed in a purity of from 90% to 100%, preferably from 95% to 100% (according to NMR spectrum).

Solutions for seed treatment (LS), suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The agrochemical compositions in question give, after two-to-tenfold dilution, active substance concentrations of from 0.01 to 60% by weight, preferably from 0.1 to 40% by weight, in the ready-to-use preparations. Application can be carried out before or during sowing.

Methods for applying compounds of formula I, agrochemical compositions and/or herbicidal compositions thereof, on to plant propagation material, especially seeds, include dressing, coating, pelleting, dusting, soaking and in-furrow application methods of the propagation material. Preferably, compounds of formula I, agrochemical compositions and/or herbicidal compositions thereof, respectively, are applied on to the plant propagation material by a method such that germination is not induced, e. g. by seed dressing, pelleting, coating and dusting.

Various types of oils, wetters, adjuvants, fertilizer, or micronutrients, and further pesticides (e.g. herbicides, insecticides, fungicides, growth regulators, safeners) may be added to the compounds of formula I, the agrochemical compositions and/or the herbicidal compositions comprising them as premix or, if appropriate not until immediately prior to use (tank mix). These agents can be admixed with the agrochemical compositions according to the invention in a weight ratio of 1:100 to 100:1, preferably 1:10 to 10:1.

The user applies the compounds of formula I according to the invention, the agrochemical compositions and/or the herbicidal compositions comprising them usually from a pre-dosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained.

Usually, 20 to 2000 liters, preferably 50 to 400 liters, of the ready-to-use spray liquor are applied per hectare of agricultural useful area.

According to one embodiment, either individual components of the agrochemical composition according to the invention or partially premixed components, e. g. components comprising compounds of formula I and optionally active substances from the groups B and/or C), may be mixed by the user in a spray tank and further auxiliaries and additives may be added, if appropriate.

In a further embodiment, individual components of the agrochemical composition according to the invention such as parts of a kit or parts of a binary or ternary mixture may be mixed by the user himself in a spray tank and further auxiliaries may be added, if appropriate.

In a further embodiment, either individual components of the agrochemical composition according to the invention or partially premixed components, e. g components comprising compounds of formula I and optionally active substances from the groups B and/or C), can be applied jointly (e.g. after tank mix) or consecutively.

The compounds of formula I are suitable as herbicides. They are suitable as such, as an appropriately formulated composition (agrochemical composition) or as an herbicidal composition in combination with at least one further compound selected from the herbicidal active compounds B (component B) and safeners C (component C).

The compounds of formula I, or the agrochemical compositions and/or herbicidal compositions comprising the compounds of formula I, control vegetation on non-crop areas very efficiently, especially at high rates of application. They act against broadleaved weeds and grass weeds in crops such as wheat, rice, maize, soya and cotton without causing any significant damage to the crop plants. This effect is mainly observed at low rates of application.

The compounds of formula I, or the agrochemical compositions and/or the herbicidal compositions comprising them, are applied to the plants mainly by spraying the leaves. Here, the application can be carried out using, for example, water as carrier by customary spraying techniques using spray liquor amounts of from about 100 to 1000 l/ha (for example from 300 to 400 l/ha). The compounds of formula I, or the agrochemical compositions and/or the herbicidal compositions comprising them, may also be applied by the low-volume or the ultra-low-volume method, or in the form of microgranules. Application of the compounds of formula I, or the agrochemical compositions and/or the herbicidal compositions comprising them, can be done before, during and/or after, preferably during and/or after, the emergence of the undesirable plants.

The compounds of formula I, or the agrochemical compositions and/or the herbicidal compositions comprising them, can be applied pre-, post-emergence or pre-plant, or together with the seed of a crop plant. It is also possible to apply the compounds of formula I, or the agrochemical compositions and/or the herbicidal compositions comprising them, by applying seed, pretreated with the compounds of formula I, or the agrochemical compositions and/or the herbicidal compositions comprising them, of a crop plant. If the active ingredients are less well tolerated by certain crop plants, application techniques may be used in which the herbicidal compositions are sprayed, with the aid of the spraying equipment, in such a way that as far as possible they do not come into contact with the leaves of the sensitive crop plants, while the active ingredients reach the leaves of undesirable plants growing underneath, or the bare soil surface (postdirected, lay-by).

In a further embodiment, the compounds of formula I, or the agrochemical compositions and/or the herbicidal compositions comprising them, can be applied by treating seed. The treatment of seeds comprises essentially all procedures familiar to the person skilled in the art (seed dressing, seed coating, seed dusting, seed soaking, seed film coating, seed multilayer coating, seed encrusting, seed dripping and seed pelleting) based on the compounds of formula I, or the agrochemical compositions and/or the herbicidal compositions prepared therefrom. Here, the herbicidal compositions can be applied diluted or undiluted.

The term "seed" comprises seed of all types, such as, for example, corns, seeds, fruits, tubers, seedlings and similar forms. Here, preferably, the term seed describes corns and seeds. The seed used can be seed of the useful plants mentioned above, but also the seed of transgenic plants or plants obtained by customary breeding methods.

When employed in plant protection, the amounts of active substances applied, i.e. the compounds of formula I, component B and, if appropriate, component C without formulation auxiliaries, are, depending on the kind of effect desired, from 0.001 to 2 kg per ha, preferably from 0.005 to 2 kg per ha, more preferably from 0.05 to 0.9 kg per ha and in particular from 0.1 to 0.75 kg per ha.

In another embodiment of the invention, the application rate of the compounds of formula I, component B and, if appropriate, component C, is from 0.001 to 3 kg/ha, preferably from 0.005 to 2.5 kg/ha and in particular from 0.01 to 2 kg/ha of active substance (a.s.).

In another preferred embodiment of the invention, the rates of application of the compounds of formula I according to the present invention (total amount of compounds of formula I) are from 0.1 g/ha to 3000 g/ha, preferably 10 g/ha to 1000 g/ha, depending on the control target, the season, the target plants and the growth stage.

In another preferred embodiment of the invention, the application rates of the compounds of formula I are in the range from 0.1 g/ha to 5000 g/ha and preferably in the range from 1 g/ha to 2500 g/ha or from 5 g/ha to 2000 g/ha.

In another preferred embodiment of the invention, the application rate of the compounds of formula I is 0.1 to 1000 g/ha, preferably 1 to 750 g/ha, more preferably 5 to 500 g/ha.

The required application rates of herbicidal compounds B are generally in the range of from 0.0005 kg/ha to 2.5 kg/ha and preferably in the range of from 0.005 kg/ha to 2 kg/ha or 0.01 kg/ha to 1.5 kg/h of a.s.

The required application rates of safeners C are generally in the range of from 0.0005 kg/ha to 2.5 kg/ha and preferably in the range of from 0.005 kg/ha to 2 kg/ha or 0.01 kg/ha to 1.5 kg/h of a.s.

In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

In another embodiment of the invention, to treat the seed, the amounts of active substances applied, i.e. the compounds of formula I, component B and, if appropriate, component C are generally employed in amounts of from 0.001 to 10 kg per 100 kg of seed.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

In case of herbicidal compositions according to the present invention it is immaterial whether the compounds of formula I, and the further component B and/or the component C are formulated and applied jointly or separately.

In the case of separate application it is of minor importance, in which order the application takes place. It is only necessary, that the compounds of formula I, and the further component B and/or the component C are applied in a time frame that allows simultaneous action of the active ingredients on the plants, preferably within a time-frame of at most 14 days, in particular at most 7 days.

Depending on the application method in question, the compounds of formula I, or the agrochemical compositions and/or herbicidal compositions comprising them, can additionally be employed in a further number of crop plants for eliminating undesirable plants. Examples of suitable crops are the following:

*Allium cepa, Ananas comosus, Arachis hypogaea, Asparagus officinalis, Avena sativa, Beta vulgaris* spec. *altissima, Beta vulgaris* spec. *rapa, Brassica napus* var. *napus, Brassica napus* var. *napobrassica, Brassica rapa* var. *silvestris, Brassica oleracea, Brassica nigra, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N. rustica*), *Olea europaea, Oryza sativa, Phaseolus lunatus, Phaseolus vulgaris, Picea abies, Pinus* spec., *Pistacia vera, Pisum sativum, Prunus avium, Prunus persica, Pyrus communis, Prunus armeniaca, Prunus cerasus, Prunus dulcis* and *Prunus domestica, Ribes sylvestre, Ricinus communis, Saccharum officinarum, Secale cereale, Sinapis alba, Solanum tuberosum, Sorghum bicolor* (*S. vulgare*), *Theobroma cacao, Trifolium pratense, Triticum aestivum, Triticale, Triticum durum, Vicia faba, Vitis vinifera* and *Zea mays*.

Preferred crops are *Arachis hypogaea, Beta vulgaris* spec. *altissima, Brassica napus* var. *napus, Brassica oleracea, Citrus limon, Citrus sinensis, Coffea arabica* (*Coffea canephora, Coffea liberica*), *Cynodon dactylon, Glycine max, Gossypium hirsutum,* (*Gossypium arboreum, Gossypium herbaceum, Gossypium vitifolium*), *Helianthus annuus, Hordeum vulgare, Juglans regia, Lens culinaris, Linum usitatissimum, Lycopersicon lycopersicum, Malus* spec., *Medicago sativa, Nicotiana tabacum* (*N. rustica*), *Olea europaea, Oryza sativa, Phaseolus lunatus, Phaseolus vulgaris, Pistacia vera, Pisum sativum, Prunus dulcis, Saccharum officinarum, Secale cereale, Solanum tuberosum, Sorghum bicolor* (*S. vulgare*), *Triticale, Triticum aestivum, Triticum durum, Vicia faba, Vitis vinifera* and *Zea mays*.

Especially preferred crops are crops of cereals, corn, soybeans, rice, oilseed rape, cotton, potatoes, peanuts or permanent crops.

Surprisingly, it has been found that the compounds of formula I can be used as selective herbicides on monocot crops. The compounds of formula I do not cause an undesirable amount of phytotoxicity to the monocot crops while at the same time possessing excellent herbicidal action against the harmful plants.

Preferably, the monocot crop is selected from the group consisting of *Avena* (oats), *Hordeum* (barleys), *Oryza* (rice), *Sorghum* (sorghum), *Triticum* (wheats), *Dactylis* (cocksfoot, orchard grass), *Saccharum* (sugar cane), and *Zea mays* (corn or maize).

More preferably, the monocot crop is selected from the group of genera consisting of *Hordeum* (barleys), *Oryza* (rice), and *Zea mays* (corn or maize) and is in particular of the genus *Oryza* (rice) or *Zea mays* (corn or maize).

In another embodiment, the monocot crop is selected from a species of the family Poaceae (also known as Gramineae or true grasses), in particular corn, rice, sugar cane, switch grass, turf grass species, *sorghum*, barley, wheat, and oats, and durum The compounds of formula I according to the invention, or the agrochemical compositions and/or herbicidal compositions comprising them, can also be used in genetically modified plants. The term "genetically modified plants" is to be understood as plants whose genetic material has been modified by the use of recombinant DNA techniques to include an inserted sequence of DNA that is not native to that plant species' genome or to exhibit a deletion of DNA that was native to that species' genome, wherein the modification(s) cannot readily be obtained by cross breeding, mutagenesis or natural recombination alone. Often, a particular genetically modified plant will be one that has obtained its genetic modification(s) by inheritance through a natural breeding or propagation process from an ancestral plant whose genome was the one directly treated by use of a recombinant DNA technique. Typically, one or more genes have been integrated into the genetic material of a genetically modified plant in order to improve certain properties of the plant. Such genetic modifications also include but are not limited to targeted post-translational modification of protein(s), oligo- or polypeptides. e. g., by inclusion therein of amino acid mutation(s) that permit, decrease, or promote glycosylation or polymer additions such as prenylation, acetylation farnesylation, or PEG moiety attachment.

Plants that have been modified by breeding, mutagenesis or genetic engineering, e.g. have been rendered tolerant to applications of specific classes of herbicides, such as auxin herbicides such as dicamba or 2,4-D; bleacher herbicides such as hydroxyphenylpyruvate dioxygenase (HPPD) inhibitors or phytoene desaturase (PDS) inhibitors; acetolactate synthase (ALS) inhibitors such as sulfonyl ureas or imidazolinones; enolpyruvyl shikimate 3-phosphate synthase (EPSP) inhibitors such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering; furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are, for example, described in Pest Management Science 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. Several cultivated plants have been rendered tolerant to herbicides by mutagenesis and conventional methods of breeding, e. g., Clearfield® summer rape (Canola, BASF SE, Germany) being tolerant to imidazolinones, e. g., imazamox, or ExpressSun® sunflowers (DuPont, USA) being tolerant to sulfonyl ureas, e. g., tribenuron. Genetic engineering methods have been used to render cultivated plants such as soybean, cotton, corn, beets and rape, tolerant to herbicides such as glyphosate, imidazolinones and glufosinate, some of which are under development or commercially available under the brands or trade names RoundupReady® (glyphosate tolerant, Monsanto, USA), Cultivance® (imidazolinone tolerant, BASF SE, Germany) and LibertyLink® (glufosinate tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as deltaendotoxins, e. g., CryIA(b), CryIA(c), CryIF, CryIF(a2), CryIIA(b), CryIIIA, CryIIIB(b1) or Cry9c; vegetative insecticidal proteins (VIP), e. g., VIP1, VIP2, VIP3 or VIP3A; insecticidal proteins of bacteria colonizing nematodes, e. g., *Photorhabdus* spp. or *Xenorhabdus* spp.; toxins produced by animals, such as scorpion toxins, arachnid toxins, wasp toxins, or other insect-specific neurotoxins; toxins produced by fungi, such as Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as including pre-toxins, hybrid proteins, truncated or otherwise modified proteins. Hybrid proteins are characterized by a new combination of protein domains, (see, e. g., WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 und WO 03/52073. The methods for producing such genetically modified plants are generally known to the person skilled in the art and are described, e. g., in the publications mentioned above. These insecticidal proteins contained in the genetically modified plants impart to the plants producing these proteins tolerance to harmful pests from all taxonomic groups of arthropods, especially to beetles (*Coeloptera*), two-winged insects (*Diptera*), and moths (*Lepidoptera*) and to nematodes (*Nematoda*). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton culti-vars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g., Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g., EP-A 392 225), plant disease resistance genes (e. g., potato culti-vars, which express resistance genes acting against *Phytophthora infestans* derived from the Mexican wild potato, *Solanum bulbocastanum*) or T4-lyso-zym (e.g., potato cultivars capable of synthesizing these proteins with increased resistance against bacteria such as *Erwinia amylovora*). The methods for producing such genetically modified plants are generally known to the person skilled in the art and are described, e.g., in the publications mentioned above.

Furthermore, plants are also covered that are by the use of recombinant DNA techniques capable to synthesize one or more proteins to increase the productivity (e.g., bio-mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of ingredients or new ingredients, specifically to improve human or animal nutrition, e. g., oil crops that produce health-promoting long-chain omega-3 fatty acids or unsaturated omega-9 fatty acids (e. g., Nexera® rape, Dow Agro-Sciences, Canada).

Furthermore, plants are also covered that contain by the use of recombinant DNA techniques a modified amount of ingredients or new ingredients, specifically to improve raw material production, e.g., potatoes that produce increased amounts of amylopectin (e.g. Amflora® potato, BASF SE, Germany).

Furthermore, it has been found that the compounds of formula I according to the invention, or the agrochemical compositions and/or herbicidal compositions comprising them, are also suitable for the defoliation and/or desiccation of plant parts, for which crop plants such as cotton, potato, oilseed rape, sunflower, soybean or field beans, in particular cotton, are suitable. In this regard, agrochemical compositions and/or herbicidal compositions for the desiccation and/or defoliation of plants, processes for preparing these agrochemical compositions and/or herbicidal compositions and methods for desiccating and/or defoliating plants using the compounds of formula I have been found.

As desiccants, the compounds of formula I are particularly suitable for desiccating the above-ground parts of crop plants such as potato, oilseed rape, sunflower and soybean, but also cereals. This makes possible the fully mechanical harvesting of these important crop plants.

Also of economic interest is to facilitate harvesting, which is made possible by concentrating within a certain period of time the dehiscence, or reduction of adhesion to the tree, in *citrus* fruit, olives and other species and varieties of pernicious fruit, stone fruit and nuts. The same mechanism, i.e. the promotion of the development of abscission tissue between fruit part or leaf part and shoot part of the plants is also essential for the controlled defoliation of useful plants, in particular cotton.

Moreover, a shortening of the time interval in which the individual cotton plants mature leads to an increased fiber quality after harvesting.

The preparation of the compounds of formula I is illustrated by examples; however, the subject matter of the present invention is not limited to the examples given.

I. SYNTHESIS EXAMPLES

With appropriate modification of the starting materials, the procedures given in the synthesis examples below were used to obtain further compounds I. The compounds obtained in this manner are listed in the table that follows, together with physical data. The products shown below were characterized by determination of the melting point, NMR spectroscopy or the masses ([m/z]) determined by HPLC-MS spectrometry.

HPLC-MS=high performance liquid chromatography coupled with mass spectrometry;

HPLC column:

RP-18 column (Chromolith Speed ROD from Merck KgaA, Germany), 50*4.6 mm; mobile phase: acetonitrile+ 0.1% trifluoroacetic acid (TFA)/water+0.1% TFA, using a gradient from 5:95 to 100:0 over 5 minutes at 40° C., flow rate 1.8 ml/min.

MS: quadrupole electrospray ionization, 80 V (positive mode).

AcSK: potassium thioacetate
p-HPLC=preparative HPLC

Example 1: Preparation of N-[3-(8-hydroxy-6,6-dioxo-5H-thiopyrano[4,3-b]pyridin-7-yl)-2-(trifluoromethyl)phenyl]-N-methyl-methanesulfonamide of the formula I-35 (see Table I below)

Step 1: N-[3-bromo-2-(trifluoromethyl)phenyl]-N-methyl-methanesulfonamide

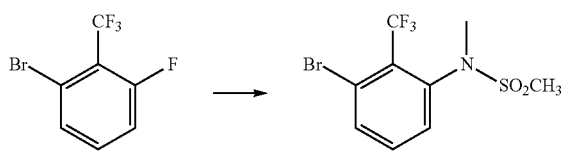 [SMILES: Fc1cccc(Br)c1C(F)(F)F ; CN(c1cccc(Br)c1C(F)(F)F)S(C)(=O)=O]

A mixture of 1-bromo-3-fluoro-2-(trifluoromethyl)benzene (10 g, 41 mmol), N-methyl-methanesulfonamide (4.5 g, 41 mmol) and $Cs_2CO_3$ (26.7 g, 82 mmol) in acetonitrile (200 ml) was stirred at 80° C. overnight. Water was added and the mixture extracted with ethyl acetate. The combined organic layers was washed with brine, dried over anhydrous $Na_2SO_4$, filtered and concentrated to give the crude product which was purified by column chromatography on silica gel (petrol ether:ethyl acetate=10:1) to afford the title compound as a white solid (12 g, 83%).

$^1$H NMR (400 MHz, $CDCl_3$) δ 7.78 (d, 1H J=7.20 Hz), 7.47-7.40 (m, 2H), 3.24 (s, 3H), 3.03 (s, 3H)

Step 2: Ethyl 3-[methyl(methylsulfonyl)amino]-2-(trifluoromethyl)benzoate

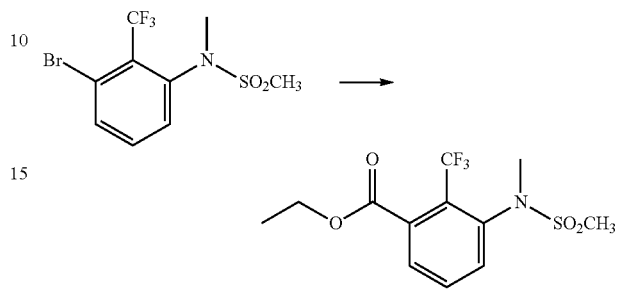

A mixture of N-[3-bromo-2-(trifluoromethyl)phenyl]-N-methyl-methanesulfonamide (12 g, 36.2 mmol), palladium (II)acetate (0.8 g, 3.62 mmol), 1,4-Bis(diphenylphosphino) butane (1.5 g, 3.62 mmol) in ethanol (1000 ml) was stirred at 150° C. under CO at 5 MPa overnight. The mixture was filtered and concentrated. The residue was partitioned between ethyl acetate and water. The organic layers were combined, washed with brine, dried over anhydrous $Na_2SO_4$, filtered and concentrated to afford the crude product, which was purified by column chromatography on silica gel (petrol ether: ethyl acetate=10:1) to afford the title compound as a white solid (6 g, 55%).

$^1$H NMR (400 MHz, $CDCl_3$) δ 1.35-1.39 (m, 3H), 3.07 (s, 3H), 3.23 (s, 3H), 4.38-4.39 (m, 3H), 7.55-7.64 (m, 3H)

Step 3: N-[3-(hydroxymethyl)-2-(trifluoromethyl) phenyl]-N-methyl-methanesulfonamide

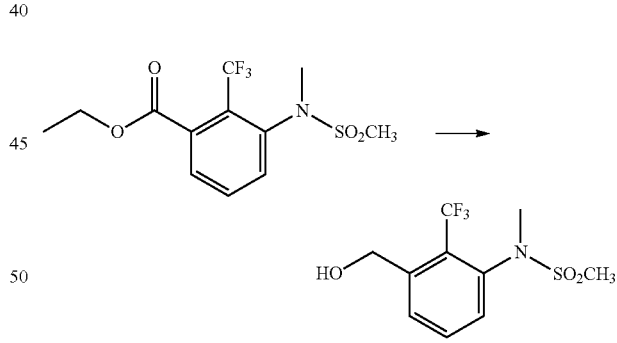

To a solution of ethyl 3-[methyl(methylsulfonyl)amino]-2-(trifluoromethyl)benzoate (6 g, 19.3 mmol) in tetrahydrofuran (100 ml) was added lithium aluminium hydride (1.5 g, 38.6 mmol) at 0° C. under nitrogen. The resulting mixture was stirred at room temperature overnight. The reaction was quenched with water and the mixture extracted with ethyl acetate. The organic layers were combined, washed with saturated brine, dried over anhydrous $Na_2SO_4$, filtered and concentrated to afford the title compound as a colourless oil (2.4 g, 44%).

$^1$H NMR (400 MHz, $CDCl_3$) δ 3.03 (s, 3H), 3.23 (s, 3H), 4.90 (s, 2H), 7.43 (d, J=8.00 Hz), 7.60-7.64 (m, 1H), 7.81 (d, J=7.60 Hz, 1H)

Step 4: [3-[methyl(methylsulfonyl)amino]-2-(trifluoromethyl)phenyl]methyl methanesulfonate

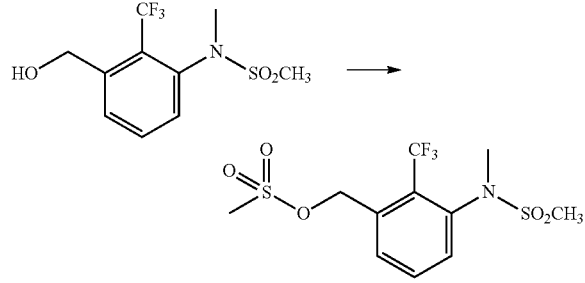

To a mixture of N-[3-(hydroxymethyl)-2-(trifluoromethyl)phenyl]-N-methyl-methanesulfonamide (2.4 g, 8.5 mmol) in dichloromethane (24 ml) was added tiethylamine (1.7 g, 17.0 mmol) and methanesulfonyl chloride (4.6 g, 6.7 mmol). The reaction mixture was stirred at room temperature for 2 h. Water was added and the mixture extracted with dichloromethane. The organic layers were combined, washed with saturated brine, dried over anhydrous $Na_2SO_4$, filtered and concentrated to afford the title compound as a yellow oil (2.46 g, crude).

Step 5: S-[[3-[methyl(methylsulfonyl)amino]-2-(trifluoromethyl)phenyl]methyl] ethanethioate

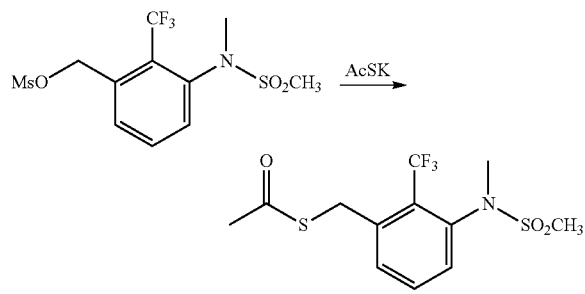

To a solution of the crude product of step 4 (2.5 g, 6.8 mmol) in acetone (60 ml) was added potassium thioacetate (1.2 g, 10.2 mmol). The reaction mixture was stirred at room temperature overnight. The mixture was filtered through a plug of silica gel. Acetone was used to wash the gel. The combined filtrate was concentrated under reduced pressure to give the title compound as an oil (1.8 g, 89%).

$^1$H NMR (400 MHz, $CDCl_3$) δ 2.36 (s, 3H), 3.03 (s, 3H), 3.22 (s, 3H), 4.24-4.41 (m, 2H), 7.38-7.44 (m, 1H), 7.52 (t, J=7.78 Hz, 1H), 7.57-7.62 (m, 1H)

Step 6: Ethyl 3-[[3-[methyl(methylsulfonyl)amino]-2-(trifluoromethyl)phenyl]methylsulfanylmethyl]pyridine-2-carboxylate

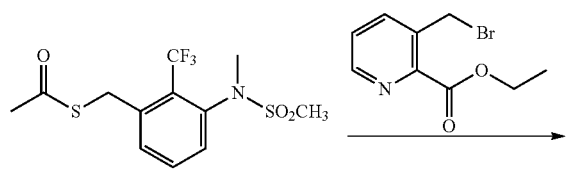

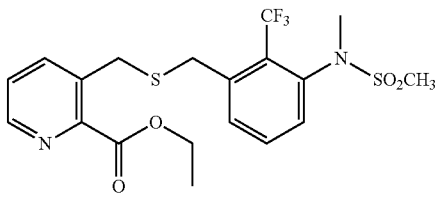

To a solution of S-[[3-[methyl(methylsulfonyl)amino]-2-(trifluoromethyl)phenyl]methyl]ethanethioate (1.8 g, 5.3 mmol) in anhydrous methanol (18 ml) was added $K_2CO_3$ (1.5 g, 5.3 mmol) at room temperature. The resulting mixture was stirred at room temperature for 0.5 h and then ethyl 3-(bromomethyl)pyridine-2-carboxylate (1.3 g, 5.3 mmol) was added. The resulting mixture was stirred at room temperature for additional 3 h. The mixture was concentrated and the residue partitioned between ethyl acetate and water. The organic layer was separated, washed with saturated brine, dried over anhydrous $Na_2SO_4$ and filtered. The filtrate was concentrated under reduced pressure to afford the title compound as a brown solid (2.6 g, crude).

Step 7: Ethyl 3-[[3-[methyl(methylsulfonyl)amino]-2-(trifluoromethyl)phenyl]methylsulfonylmethyl]pyridine-2-carboxylate

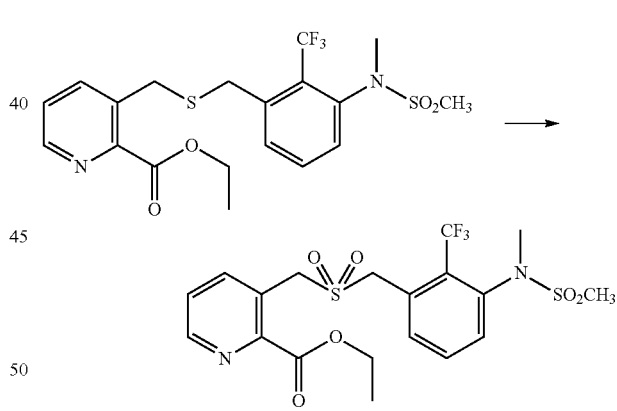

To a solution of ethyl 3-[[3-[methyl(methylsulfonyl)amino]-2-(trifluoromethyl)phenyl]methylsulfanylmethyl]pyridine-2-carboxylate (2.6 g, 5.6 mmol) in dry THF (45 ml) and water (15 ml) was added potassium peroxymonosulfate (13.8 g, 22.5 mmol) at 0° C. The resulting mixture was stirred at room temperature for 4 h and extracted with ethyl acetate. The organic layers were combined, washed with saturated $Na_2S_2O_3$ twice, and brine once, dried over anhydrous $Na_2SO_4$, filtered and concentrates to afford the title compound as a white solid (2.6 g, crude).

Step 8: N-[3-(8-hydroxy-6,6-dioxo-5H-thiopyrano[4,3-b]pyridin-7-yl)-2-(trifluoromethyl)phenyl]-N-methyl-methanesulfonamide of the formula I-35
(see Table I below)

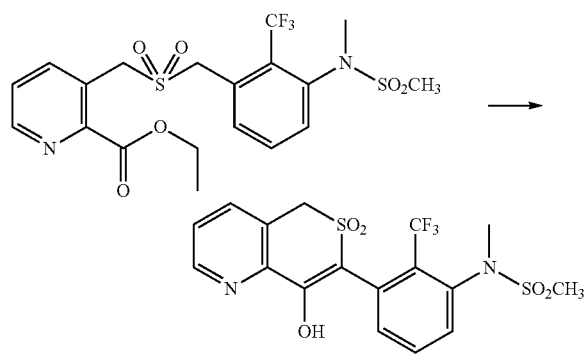

To a solution of the crude product of step 7 (2.6 g) in anhydrous acetonitrile was added 1,8-Diazabicyclo[5.4.0]undec-7-ene (15.8 g, 16 mmol) at room temperature. The resulting mixture was heated to reflux overnight. Water was added and the mixture extracted with ethyl acetate. The aqueous phase was acidified to pH 5 and extracted with ethyl acetate. The organic layers were combined, washed with saturated brine, dried over anhydrous $Na_2SO_4$, filtered and concentrated to give the crude product which was purified by p-HPLC to afford the title compound as a yellow solid (800 mg, 34%).

$^1$H NMR (400 MHz, $CDCl_3$) δ 3.02 (s, 3H), 3.26 (s, 3H), 4.53 (d, J=16.06 Hz, 1H), 4.71 (d, J=15.81 Hz, 1H), 7.51 (dd, J=7.65, 4.89 Hz, 1H), 7.61 (d, J=6.78 Hz, 1H), 7.64-7.75 (m, 2H), 7.77 (d, J=7.78 Hz, 1H), 8.66 (d, J=4.77 Hz, 1H)

Step 9: [7-[3-[methyl(methylsulfonyl)amino]-2-(trifluoromethyl)phenyl]-6,6-dioxo-5H-thiopyrano[4,3-b]pyridin-8-yl] 2,2-dimethylpropanoate

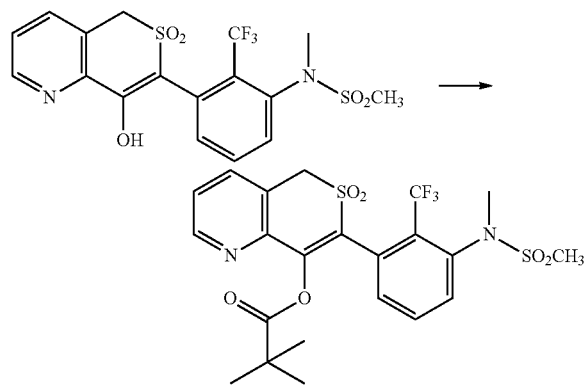

To a solution of N-[3-(8-hydroxy-6,6-dioxo-5H-thiopyrano[4,3-b]pyridin-7-yl)-2-(trifluoromethyl)phenyl]-N-methyl-methanesulfonamide (800 mg, 1.8 mmol) in anhydrous dichloromethane (8 ml) was added triethylamine (190 mg, 1.9 mmol) at room temperature. Pivaloyl chloride (500 mg, 1.9 mmol) was the added dropwise and the resulting mixture stirred at room temperature overnight. Water was added and the mixture extracted with dichloromethane. The organics were combined, washed with saturated brine, dried over anhydrous sodium sulfate and concentrated under reduced pressure to give a crude product, which was purified by column chromatography on silica gel to afford the title compound as a tan solid (780 mg, 82%).

$^1$H NMR (400 MHz, $CDCl_3$) δ 1.23-1.28 (m, 9H), 2.94-3.12 (m, 3H), 3.18-3.33 (m, 3H), 4.52 (m, 1H), 4.75 (m, 1H), 7.30 (m, 1H), 7.36 (m, 1H), 7.53 (m, 1H), 7.65-7.73 (m, 2H), 8.61-8.66 (m, 1H)

Step 10: [5,5-dimethyl-7-[3-[methyl(methylsulfonyl)amino]-2-(trifluoromethyl)phenyl]-6,6-dioxo-thiopyrano[4,3-b]pyridin-8-yl] 2,2-dimethylpropanoate

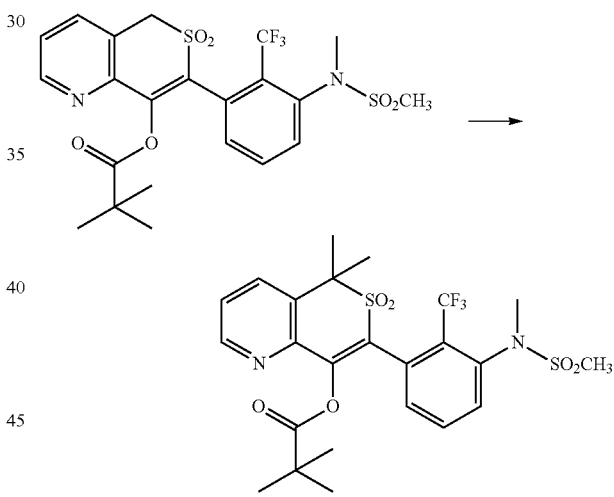

To a solution of [7-[3-[methyl(methylsulfonyl)amino]-2-(trifluoromethyl)phenyl]-6,6-dioxo-5H-thiopyrano[4,3-b]pyridin-8-yl] 2,2-dimethylpropanoate (780 mg, 1.5 mmol) in anhydrous N,N-dimethylformamide (20 ml) was added $Cs_2CO_3$ (1.9 mmol, 5.9 mmol) at room temperature. The mixture was stirred at room temperature for 0.5 h and then methyl iodide (620 g, 4.5 mmol was added dropwise. The resulting mixture was stirred at room temperature overnight. Water was added and the mixture extracted with ethyl acetate. The organic layers were combined, washed with saturated brine, dried over anhydrous sodium sulfate and concentrated in vacuum to give the title compound as a brown oil (800 mg, crude).

Step 11: N-[3-(8-hydroxy-5,5-dimethyl-6,6-dioxo-thiopyrano[4,3-b]pyridin-7-yl)-2-(trifluoromethyl)phenyl]-N-methyl-methanesulfonamide of the formula I-36 (see Table I below)

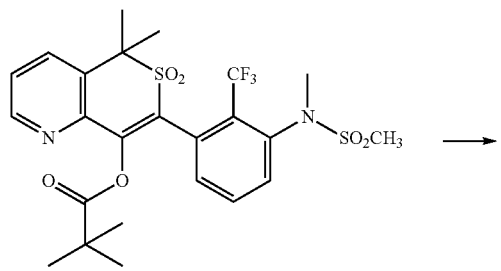

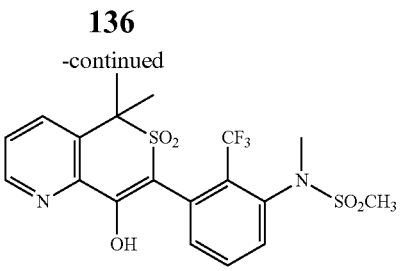

To a solution of the crude product of step 10 (800 mg) in tetrahydrofurane (5 ml) and water (1.5 ml) was added LiOH (200 mg, 4.2 mmol). The reaction mixture was stirred at room temperature overnight, diluted with water, acidified to pH 3 and extracted with ethyl acetate. The organic layers were combined, washed with saturated brine, dried over anhydrous sodium sulfate and concentrated under reduced pressure to give the crude product which was purified by p-HPLC to afford the title compound as a brown solid (300 mg)

$^1$H NMR (400 MHz, MeOD) δ 8.69 (d, J=4.02 Hz, 1H), 8.15 (d, J=4.02 Hz, 1H), 7.73-7.82 (m, 2H), 7.57-7.66 (m, 2H), 3.26 (s, 3H), 3.15 (s, 3H), 1.86 (s, 3H), 1.75 (s, 3H)

TABLE I

Compounds of the formula I.a as shown above wherein the variables R, $R^1$, X, Y, $R^2$, $R^x$, $R^y$, $R^4$ and $R^6$ have the following meanings:

| No. | R | $R^1$ | X | Y | $R^2$ | $R^x$ | $R^y$ | $R^4$ | $R^6$ | LC-MS (M + H) |
|---|---|---|---|---|---|---|---|---|---|---|
| I-1 | OH | Cl | NH | Me | Cl | H | H | H | H | 434.9 |
| I-2 | OH | Cl | NMe | Me | Cl | Me | Me | H | H | 476.8 |
| I-3 | OH | Cl | NMe | Me | Cl | H | H | H | H | 448.8 |
| I-4 | OH | Cl | NMe | Me | H | H | H | Cl | H | 448.9 |
| I-5 | OH | Cl | NH | Me | H | H | H | Cl | H | 434.9 |
| I-6 | OH | Cl | NH | Me | H | Me | Me | Cl | H | 462.9 |
| I-7 | OH | Cl | NMe | Me | H | Me | Me | Cl | H | 476.9 |
| I-8 | OH | Cl | NEt | Me | Cl | H | H | H | H | 462.9 |
| I-9 | OH | Cl | NEt | Me | Cl | Me | Me | H | H | 490.9 |
| I-10 | OH | Cl | N—iPr | Me | Cl | H | H | H | H | 477.0 |
| I-11 | OH | Cl | N—iPr | Me | Cl | Me | Me | H | H | 505.0 |
| I-12 | OH | Me | NMe | Me | H | H | H | H | H | 395.2 |
| I-13 | OPiv | Me | NMe | Me | H | Me | Me | H | H | 507.4 |
| I-14 | OH | Me | NMe | Me | H | Me | Me | H | H | 423.3 |
| I-15 | OH | Cl | NMe | Me | H | H | H | H | H | 414.9 |
| I-16 | OPiv | Cl | NMe | Me | H | Me | Me | H | H | 549.2 |
| I-17 | OH | Cl | NMe | Me | H | Me | Me | H | H | 443.2 |
| I-18 | OH | Cl | NMe | Et | Cl | H | H | H | H | 464.9 |
| I-19 | OH | Cl | NMe | Et | Cl | Me | Me | H | H | 491.2 |
| I-20 | OH | Cl | NMe | CH$_2$—cPr | Cl | H | H | H | H | 489.2 |
| I-21 | OH | Cl | NMe | CH$_2$—cPr | Cl | Me | Me | H | H | 517.3 |
| I-22 | OH | Cl | O | N(Me)$_2$ | Cl | H | H | H | H | 465.2 |
| I-23 | OH | Cl | O | N(Me)$_2$ | Cl | Me | Me | H | H | 493.1 |
| I-24 | OH | Cl | N—cPr | Me | Cl | H | H | H | H | 474.9 |
| I-25 | OH | Cl | N—cPr | Me | Cl | Me | Me | H | H | 503.0 |
| I-26 | OH | Me | NMe | Me | Cl | H | H | H | H | 429.0 |
| I-27 | OH | Cl | NMe | cPr | Cl | H | H | H | H | 475.1 |
| I-28 | OH | Cl | NMe | cPr | Cl | Me | Me | H | H | 503.0 |
| I-29 | OH | Me | NMe | Me | Cl | Me | Me | H | H | 457.0 |
| I-30 | OPiv | Cl | NMe | Me | Cl | Me | Me | H | H | 562.6 |
| I-31 | OH | CF$_3$ | NMe | Me | Cl | H | H | H | H | 483.0 |
| I-32 | OH | CF$_3$ | NMe | Me | Cl | Me | Me | H | H | 511.1 |
| I-33 | OH | SO$_2$Me | NMe | Me | H | H | H | H | H | 459.1 |
| I-34 | OH | SO$_2$Me | NMe | Me | H | Me | Me | H | H | 487.1 |
| I-35 | OH | CF$_3$ | NMe | Me | H | H | H | H | H | 449.0 |
| I-36 | OH | CF$_3$ | NMe | Me | H | Me | Me | H | H | 477.1 |
| I-37 | OH | Cl | NMe | Me | Cl | H | H | H | F | 467.1 |
| I-38 | OH | Cl | NMe | Me | Cl | Me | Me | H | F | 495.1 | wherein OPiv denotes OCO—tBu (wherein tBu denotes tert-butyl, —C(CH$_3$)$_3$), Me denotes methyl (CH$_3$), Et denotes ethyl (CH$_2$CH$_3$), iPr denotes iso-propyl (—CH(CH$_3$)$_2$) and cPr denotes cyclopropyl

II. USE EXAMPLES

The herbicidal activity of the compounds of formula (I) was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active ingredients, which had been suspended or emulsified in water, were applied directly after sowing by means of finely distributing nozzles. The containers were irrigated gently to promote germination and growth and subsequently covered with transparent plastic hoods until the plants had rooted. This cover caused uniform germination of the test plants, unless this had been impaired by the active ingredients.

For the post-emergence treatment, the test plants were first grown to a height of 3 to 15 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment.

Depending on the species, the plants were kept at 10-25° C. or 20-35° C., respectively.

The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial moieties, and 0 means no damage, or normal course of growth. A good herbicidal activity is given at values of at least 70 and a very good herbicidal activity is given at values of at least 85.

The plants used in the greenhouse experiments were of the following species:

| Bayer code | Scientific name |
|---|---|
| ABUTH | *Abutilon theophrasti* |
| AMARE | *Amaranthus retroflexus* |
| AMBEL | *Ambrosia artemisiifolia* |
| BRADC | *Brachiaria decumbens* |
| BRADE | *Brachiaria deflexa* |
| BRAPL | *Brachiaria plantaginea* |
| CAPBP | *Capsella bursa-pastoris* |
| CHEAL | *Chenopodium album* |
| CIRAR | *Cirsium arvense* |
| COMBE | *Commelina benghalensis* |
| DIGSA | *Digitaria sanguinalis* |
| ECHCG | *Echinocloa crus-galli* |
| ERICA | *Erigeron canadensis* |
| ERBVI | *Eriochloa villosa* |
| IPOHE | *Ipomoea hederacea* |
| KCHSC | *Kochia scoparia* |
| ORYSA | *Oryza sativa*[1] |
| PANMI | *Panicum miliaceum* |
| POLAV | *Polygonum aviculare* |
| POLPE | *Polygonum persicaria* |
| SEBEX | *Sesbania herbacea* |
| SETFA | *Setaria faberi* |
| SETVI | *Setaria viridis* |
| STEME | *Stellaria media* |
| VERAR | *Veronica arvensis* |
| ZEAMX | *Zea mays*[2] |

[1] rice,
[2] corn (maize)

The results of the herbicidal activity of compounds I against various weed species and certain monocot crop plants at different application rates are summarized in Tables II.1 to II.36 below.

TABLE II.1

Herbicidal activity of the compound I-1 (N-[2,6-dichloro-3-(8-hydroxy-6,6-dioxo-5H-thiopyrano[4,3-b]pyridin-7-yl)phenyl]methanesulfonamide) applied by the post-emergence method

| Application rate (kg/ha) | Plant species | Herbicidal activity |
|---|---|---|
| 0.25 | AMARE | 80 |
| 0.25 | CHEAL | 95 |
| 0.25 | ECHCG | 80 |
| 0.25 | ORYSA | 0 |
| 0.125 | AMARE | 75 |
| 0.125 | CHEAL | 80 |
| 0.125 | ECHCG | 70 |
| 0.125 | ORYSA | 0 |
| 0.125 | ZEAMX | 0 |

TABLE II.2

Herbicidal activity of the compound I-2 (N-[2,6-dichloro-3-(8-hydroxy-5,5-dimethyl-6,6-dioxo-thiopyrano[4,3-b]pyridin-7-yl)phenyl]-N-methyl-methanesulfonamide) applied by the post-emergence method

| Application rate (kg/ha) | Plant species | Herbicidal activity |
|---|---|---|
| 2 | ABUTH | 100 |
| 2 | AMARE | 100 |
| 2 | ECHCG | 100 |
| 0.125 | BRADC | 100 |
| 0.125 | CAPBP | 100 |
| 0.125 | KCHSC | 100 |
| 0.063 | STEME | 100 |
| 0.063 | CIRAR | 98 |
| 0.063 | KCHSC | 98 |
| 0.063 | ZEAMX | 5 |
| 0.031 | STEME | 100 |
| 0.031 | POLPE | 98 |
| 0.031 | KCHSC | 95 |

TABLE II.3

Herbicidal activity of the compound I-4 (N-[2,4-dichloro-3-(8-hydroxy-6,6-dioxo-5H-thiopyrano[4,3-b]pyridin-7-yl)phenyl]-N-methyl-methanesulfonamide) applied by the post-emergence method

| Application rate (kg/ha) | Plant species | Herbicidal activity |
|---|---|---|
| 0.25 | AMARE | 98 |
| 0.25 | ECHCG | 100 |
| 0.25 | CHEAL | 100 |
| 0.125 | AMARE | 98 |
| 0.125 | CHEAL | 100 |
| 0.125 | ECHCG | 98 |
| 0.125 | ORYSA | 50 |
| 0.125 | ZEAMX | 55 |
| 0.063 | AMARE | 90 |
| 0.063 | CHEAL | 95 |
| 0.063 | ECHCG | 90 |
| 0.063 | ORYSA | 35 |
| 0.063 | ZEAMX | 20 |
| 0.031 | AMARE | 90 |
| 0.031 | CHEAL | 85 |
| 0.031 | ECHCG | 98 |
| 0.031 | ORYSA | 25 |
| 0.031 | ZEAMX | 0 |

TABLE II.4

Herbicidal activity of the compound I-5 (N-[2,4-dichloro-3-(8-hydroxy-6,6-dioxo-5H-thiopyrano[4,3-b]pyridin-7-yl)phenyl]methanesulfonamide) applied by the post-emergence method

| Application rate (kg/ha) | Plant species | Herbicidal activity |
|---|---|---|
| 2 | AMARE | 98 |
| 2 | SETFA | 100 |
| 0.125 | AMARE | 95 |
| 0.125 | CIRAR | 90 |
| 0.125 | DIGSA | 95 |
| 0.125 | ZEAMX | 0 |
| 0.063 | AMARE | 95 |
| 0.063 | DIGSA | 90 |
| 0.063 | KCHSC | 95 |
| 0.063 | ORYSA | 35 |
| 0.063 | ZEAMX | 0 |
| 0.031 | AMARE | 75 |
| 0.031 | CIRAR | 75 |
| 0.031 | KCHSC | 90 |
| 0.031 | ORYSA | 25 |
| 0.031 | ZEAMX | 0 |

TABLE II.5

Herbicidal activity of the compound I-6 (N-[2,4-dichloro-3-(8-hydroxy-5,5-dimethyl-6,6-dioxo-thiopyrano[4,3-b]pyridin-7-yl)phenyl]methanesulfonamide) applied by the post-emergence method

| Application rate (kg/ha) | Plant species | Herbicidal activity |
|---|---|---|
| 2 | AMARE | 100 |
| 2 | ECHCG | 100 |
| 2 | ABUTH | 100 |
| 0.125 | AMARE | 98 |
| 0.125 | CIRAR | 100 |
| 0.125 | CHEAL | 98 |
| 0.063 | AMARE | 95 |
| 0.063 | CHEAL | 98 |
| 0.063 | KCHSC | 98 |
| 0.063 | ORYSA | 40 |
| 0.031 | AMARE | 85 |
| 0.031 | CHEAL | 95 |
| 0.031 | KCHSC | 90 |
| 0.031 | ORYSA | 0 |

TABLE II.6

Herbicidal activity of the compound I-7 (N-[2,4-dichloro-3-(8-hydroxy-5,5-dimethyl-6,6-dioxo-thiopyrano[4,3-b]pyridin-7-yl)phenyl]-N-methyl-methanesulfonamide) applied by the post-emergence method

| Application rate (kg/ha) | Plant species | Herbicidal activity |
|---|---|---|
| 0.25 | STEME | 100 |
| 0.25 | CHEAL | 100 |
| 0.25 | ABUTH | 100 |
| 0.25 | ORYSA | 15 |
| 0.125 | AMARE | 90 |
| 0.125 | STEME | 100 |
| 0.125 | CHEAL | 98 |
| 0.125 | ORYSA | 10 |
| 0.125 | ZEAMX | 20 |
| 0.063 | STEME | 100 |
| 0.063 | CHEAL | 85 |
| 0.063 | POLPE | 80 |
| 0.063 | ORYSA | 0 |
| 0.063 | ZEAMX | 0 |
| 0.031 | CHEAL | 95 |
| 0.031 | ORYSA | 0 |
| 0.031 | ZEAMX | 0 |

TABLE II.7

Herbicidal activity of the compound I-8 (N-[2,6-dichloro-3-(8-hydroxy-6,6-dioxo-5H-thiopyrano[4,3-b]pyridin-7-yl)phenyl]-N-ethyl-methanesulfonamide) applied by the post-emergence method

| Application rate (kg/ha) | Plant species | Herbicidal activity |
|---|---|---|
| 2 | AMARE | 100 |
| 2 | ECHCG | 100 |
| 2 | ABUTH | 100 |
| 0.125 | ECHCG | 95 |
| 0.125 | CHEAL | 100 |
| 0.063 | AMARE | 90 |
| 0.063 | CHEAL | 100 |
| 0.063 | ECHCG | 95 |
| 0.063 | ORYSA | 25 |
| 0.063 | ZEAMX | 0 |
| 0.031 | AMARE | 100 |
| 0.031 | CHEAL | 100 |
| 0.031 | ECHCG | 90 |
| 0.031 | ORYSA | 0 |
| 0.031 | ZEAMX | 0 |

TABLE II.8

Herbicidal activity of the compound I-9 (N-[2,6-dichloro-3-(8-hydroxy-5,5-dimethyl-6,6-dioxo-thiopyrano[4,3-b]pyridin-7-yl)phenyl]-N-ethyl-methanesulfonamide) applied by the post-emergence method

| Application rate (kg/ha) | Plant species | Herbicidal activity |
|---|---|---|
| 2 | ECHCG | 100 |
| 2 | SETVI | 100 |
| 2 | ABUTH | 98 |
| 0.125 | AMARE | 98 |
| 0.125 | ECHCG | 98 |
| 0.125 | CIRAR | 100 |
| 0.125 | ZEAMX | 50 |
| 0.063 | AMARE | 98 |
| 0.063 | ERBVI | 98 |
| 0.063 | KCHSC | 100 |
| 0.063 | ZEAMX | 10 |
| 0.031 | AMARE | 98 |
| 0.031 | CHEAL | 98 |
| 0.031 | BRADE | 100 |
| 0.031 | ZEAMX | 5 |

TABLE II.9

Herbicidal activity of the compound I-10 (N-[2,6-dichloro-3-(8-hydroxy-6,6-dioxo-5H-thiopyrano[4,3-b]pyridin-7-yl)phenyl]-N-isopropyl-methanesulfonamide) applied by the post-emergence method

| Application rate (kg/ha) | Plant species | Herbicidal activity |
|---|---|---|
| 2 | AMARE | 100 |
| 2 | SETVI | 98 |
| 2 | ABUTH | 98 |
| 0.125 | AMARE | 70 |
| 0.125 | CHEAL | 90 |
| 0.125 | ORYSA | 15 |
| 0.125 | ZEAMX | 10 |
| 0.063 | CHEAL | 85 |
| 0.063 | ORYSA | 10 |
| 0.031 | CHEAL | 85 |
| 0.031 | ORYSA | 10 |

TABLE II.10

Herbicidal activity of the compound I-11 (N-[2,6-dichloro-3-(8-hydroxy-5,5-dimethyl-6,6-dioxo-thiopyrano[4,3-b]pyridin-7-yl)phenyl]-N-isopropyl-methanesulfonamide) applied by the post-emergence method

| Application rate (kg/ha) | Plant species | Herbicidal activity |
|---|---|---|
| 2 | AMARE | 100 |
| 2 | ECHCG | 100 |
| 2 | SETVI | 100 |
| 0.125 | CAPBP | 100 |
| 0.125 | CHEAL | 100 |
| 0.125 | COMBE | 100 |
| 0.125 | ORYSA | 20 |
| 0.063 | CAPBP | 100 |
| 0.063 | CHEAL | 98 |
| 0.063 | CIRAR | 95 |
| 0.031 | CAPBP | 98 |
| 0.031 | CHEAL | 98 |
| 0.031 | CIRAR | 90 |
| 0.031 | ZEAMX | 0 |

TABLE II.11

Herbicidal activity of the compound I-13 ([5,5-dimethyl-7-[2-methyl-3-[methyl(methylsulfonyl)amino]phenyl]-6,6-dioxo-thiopyrano[4,3-b]pyridin-8-yl] 2,2-dimethylpropanoate) applied by the post-emergence method

| Application rate (kg/ha) | Plant species | Herbicidal activity |
|---|---|---|
| 2 | ECHCG | 75 |
| 2 | AMARE | 100 |
| 0.125 | KCHSC | 90 |
| 0.125 | ORYSA | 0 |
| 0.125 | ZEAMX | 0 |

TABLE II.12

Herbicidal activity of the compound I-14 (N-[3-(8-hydroxy-5,5-dimethyl-6,6-dioxo-thiopyrano[4,3-b]pyridin-7-yl)-2-methyl-phenyl]-N-methyl-methanesulfonamide) applied by the post-emergence method

| Application rate (kg/ha) | Plant species | Herbicidal activity |
|---|---|---|
| 2 | ECHCG | 98 |
| 2 | AMARE | 100 |
| 2 | SETVI | 100 |
| 0.125 | AMBEL | 100 |
| 0.125 | CHEAL | 100 |
| 0.125 | STEME | 100 |
| 0.125 | ORYSA | 10 |
| 0.125 | ZEAMX | 35 |
| 0.063 | AMBEL | 100 |
| 0.063 | KCHSC | 100 |
| 0.063 | VERAR | 100 |
| 0.063 | ORYSA | 0 |
| 0.063 | ZEAMX | 20 |
| 0.031 | KCHSC | 95 |
| 0.031 | CHEAL | 98 |
| 0.031 | VERAR | 100 |
| 0.031 | ORYSA | 0 |
| 0.031 | ZEAMX | 15 |

TABLE II.13

Herbicidal activity of the compound I-15 (N-[2-chloro-3-(8-hydroxy-6,6-dioxo-5H-thiopyrano[4,3-b]pyridin-7-yl)phenyl]-N-methyl-methanesulfonamide) applied by the post-emergence method

| Application rate (kg/ha) | Plant species | Herbicidal activity |
|---|---|---|
| 0.125 | ECHCG | 98 |
| 0.125 | CHEAL | 98 |
| 0.125 | AMARE | 90 |
| 0.125 | ORYSA | 20 |
| 0.125 | ZEAMX | 35 |
| 0.063 | ECHCG | 90 |
| 0.063 | CHEAL | 98 |
| 0.063 | AMARE | 85 |
| 0.063 | ORYSA | 0 |
| 0.031 | ECHCG | 85 |
| 0.031 | CHEAL | 90 |
| 0.031 | AMARE | 75 |
| 0.031 | ORYSA | 0 |

TABLE II.14

Herbicidal activity of the compound I-16 ([7-[2-chloro-3-[methyl(methylsulfonyl)amino]phenyl]-5,5-dimethyl-6,6-dioxo-thiopyrano[4,3-b]pyridin-8-yl] 2,2-dimethylpropanoate) applied by the post-emergence method

| Application rate (kg/ha) | Plant species | Herbicidal activity |
|---|---|---|
| 0.25 | AMBEL | 100 |
| 0.25 | VERAR | 100 |
| 0.25 | CHEAL | 100 |
| 0.25 | ORYSA | 0 |
| 0.125 | AMARE | 90 |
| 0.125 | CHEAL | 98 |
| 0.125 | AMBEL | 100 |
| 0.125 | ORYSA | 0 |
| 0.125 | ZEAMX | 0 |
| 0.063 | CIRAR | 85 |
| 0.063 | CHEAL | 98 |
| 0.063 | AMBEL | 100 |
| 0.063 | ORYSA | 0 |
| 0.063 | ZEAMX | 0 |
| 0.031 | IPOHE | 70 |
| 0.031 | CHEAL | 95 |
| 0.031 | AMARE | 75 |
| 0.031 | ORYSA | 0 |
| 0.031 | ZEAMX | 0 |

TABLE II.15

Herbicidal activity of the compound I-17 (N-[2-chloro-3-(8-hydroxy-5,5-dimethyl-6,6-dioxo-thiopyrano[4,3-b]pyridin-7-yl)phenyl]-N-methyl-methanesulfonamide) applied by the post-emergence method

| Application rate (kg/ha) | Plant species | Herbicidal activity |
|---|---|---|
| 2 | AMARE | 100 |
| 2 | ABUTH | 100 |
| 2 | ECHCG | 100 |
| 0.125 | AMARE | 100 |
| 0.125 | CHEAL | 100 |
| 0.125 | AMBEL | 100 |
| 0.063 | AMARE | 100 |
| 0.063 | CHEAL | 100 |
| 0.063 | AMBEL | 100 |
| 0.063 | ORYSA | 10 |
| 0.031 | ECHCG | 95 |
| 0.031 | CHEAL | 100 |
| 0.031 | AMARE | 98 |

TABLE II.16

Herbicidal activity of the compound I-18 (N-[2,6-dichloro-3-(8-hydroxy-6,6-dioxo-5H-thiopyrano[4,3-b]pyridin-7-yl)phenyl]-N-methyl-ethanesulfonamide) applied by the post-emergence method

| Application rate (kg/ha) | Plant species | Herbicidal activity |
| --- | --- | --- |
| 0.25 | CHEAL | 100 |
| 0.25 | AMARE | 100 |
| 0.25 | ECHCG | 100 |
| 0.25 | ZEAMX | 35 |
| 0.125 | AMARE | 100 |
| 0.125 | CHEAL | 100 |
| 0.125 | ECHCG | 100 |
| 0.125 | ZEAMX | 25 |
| 0.063 | AMARE | 100 |
| 0.063 | CHEAL | 100 |
| 0.063 | ECHCG | 100 |
| 0.063 | ZEAMX | 25 |
| 0.031 | AMARE | 100 |
| 0.031 | CHEAL | 100 |
| 0.031 | ECHCG | 98 |
| 0.031 | ORYSA | 30 |
| 0.031 | ZEAMX | 0 |

TABLE II.17

Herbicidal activity of the compound I-19 (N-[2,6-dichloro-3-(8-hydroxy-5,5-dimethyl-6,6-dioxo-thiopyrano[4,3-b]pyridin-7-yl)phenyl]-N-methyl-ethanesulfonamide) applied by the post-emergence method

| Application rate (kg/ha) | Plant species | Herbicidal activity |
| --- | --- | --- |
| 2 | ABUTH | 98 |
| 2 | AMARE | 100 |
| 2 | SETVI | 100 |
| 0.125 | AMARE | 100 |
| 0.125 | CHEAL | 100 |
| 0.125 | ECHCG | 100 |
| 0.063 | AMARE | 100 |
| 0.063 | CAPBP | 100 |
| 0.063 | CIRAR | 100 |
| 0.063 | ZEAMX | 0 |
| 0.031 | AMARE | 98 |
| 0.031 | CHEAL | 98 |
| 0.031 | ECHCG | 98 |

TABLE II.18

Herbicidal activity of the compound I-20 (1-cyclopropyl-N-[2,6-dichloro-3-(8-hydroxy-6,6-dioxo-5H-thiopyrano[4,3-b]pyridin-7-yl)phenyl]-N-methyl-methanesulfonamide) applied by the post-emergence method

| Application rate (kg/ha) | Plant species | Herbicidal activity |
| --- | --- | --- |
| 0.125 | AMARE | 100 |
| 0.125 | CHEAL | 100 |
| 0.125 | ECHCG | 100 |
| 0.125 | ZEAMX | 0 |
| 0.063 | AMARE | 90 |
| 0.063 | CHEAL | 100 |
| 0.063 | ECHCG | 100 |
| 0.063 | ZEAMX | 0 |
| 0.031 | AMARE | 90 |
| 0.031 | CHEAL | 100 |
| 0.031 | ECHCG | 100 |
| 0.031 | ZEAMX | 0 |

TABLE II.19

Herbicidal activity of the compound I-21 (1-cyclopropyl-N-[2,6-dichloro-3-(8-hydroxy-5,5-dimethyl-6,6-dioxo-thiopyrano[4,3-b]pyridin-7-yl)phenyl]-N-methyl-methanesulfonamide) applied by the post-emergence method

| Application rate (kg/ha) | Plant species | Herbicidal activity |
| --- | --- | --- |
| 2 | AMARE | 100 |
| 2 | ABUTH | 100 |
| 2 | ECHCG | 100 |
| 0.125 | AMARE | 100 |
| 0.125 | CIRAR | 100 |
| 0.125 | ERICA | 100 |
| 0.125 | ORYSA | 45 |
| 0.063 | AMARE | 98 |
| 0.063 | CHEAL | 98 |
| 0.063 | ERICA | 100 |
| 0.063 | ORYSA | 30 |
| 0.031 | AMARE | 98 |
| 0.031 | CHEAL | 95 |
| 0.031 | ECHCG | 98 |
| 0.031 | ORYSA | 0 |

TABLE II.20

Herbicidal activity of the compound I-22 (2,6-dichloro-3-(8-hydroxy-6,6-dioxo-5H-thiopyrano[4,3-b]pyridin-7-yl)phenyl] N,N-dimethylsulfamate) applied by the post-emergence method

| Application rate (kg/ha) | Plant species | Herbicidal activity |
| --- | --- | --- |
| 2 | AMARE | 100 |
| 2 | ECHCG | 100 |
| 2 | SETVI | 98 |
| 0.125 | AMARE | 75 |
| 0.125 | CHEAL | 100 |
| 0.125 | ECHCG | 95 |
| 0.125 | ORYSA | 40 |
| 0.125 | ZEAMX | 15 |
| 0.063 | AMARE | 70 |
| 0.063 | CHEAL | 95 |
| 0.063 | ECHCG | 90 |
| 0.063 | ORYSA | 35 |
| 0.063 | ZEAMX | 0 |
| 0.031 | ECHCG | 80 |
| 0.031 | ORYSA | 30 |
| 0.031 | ZEAMX | 0 |

TABLE II.21

Herbicidal activity of the compound I-23 (2,6-dichloro-3-(8-hydroxy-5,5-dimethyl-6,6-dioxo-thiopyrano[4,3-b]pyridin-7-yl)phenyl] N,N-dimethylsulfamate) applied by the post-emergence method

| Application rate (kg/ha) | Plant species | Herbicidal activity |
| --- | --- | --- |
| 1 | AMARE | 100 |
| 1 | ECHCG | 95 |
| 1 | ABUTH | 80 |
| 0.125 | IPOHE | 95 |
| 0.125 | SEBEX | 98 |
| 0.125 | CHEAL | 98 |
| 0.125 | ORYSA | 0 |
| 0.125 | ZEAMX | 15 |
| 0.063 | CIRAR | 80 |
| 0.063 | CHEAL | 95 |
| 0.063 | AMARE | 70 |
| 0.063 | ORYSA | 0 |
| 0.063 | ZEAMX | 0 |
| 0.031 | CIRAR | 75 |
| 0.031 | CHEAL | 85 |
| 0.031 | ORYSA | 0 |
| 0.031 | ZEAMX | 0 |

TABLE II.22

Herbicidal activity of the compound I-24 (N-cyclopropyl-N-[2,6-dichloro-3-(8-hydroxy-6,6-dioxo-5H-thiopyrano[4,3-b]pyridin-7-yl)phenyl]methanesulfonamide) applied by the post-emergence method

| Application rate (kg/ha) | Plant species | Herbicidal activity |
|---|---|---|
| 0.25 | AMARE | 90 |
| 0.25 | ECHCG | 95 |
| 0.25 | CHEAL | 98 |
| 0.25 | ZEAMX | 15 |
| 0.125 | AMARE | 85 |
| 0.125 | ECHCG | 90 |
| 0.125 | CHEAL | 90 |
| 0.125 | ORYSA | 20 |
| 0.125 | ZEAMX | 15 |
| 0.063 | AMARE | 75 |
| 0.063 | ECHCG | 85 |
| 0.063 | CHEAL | 85 |
| 0.063 | ORYSA | 15 |
| 0.063 | ZEAMX | 0 |
| 0.031 | AMARE | 70 |
| 0.031 | ECHCG | 80 |
| 0.031 | CHEAL | 80 |
| 0.031 | ORYSA | 0 |
| 0.031 | ZEAMX | 0 |

TABLE II.23

Herbicidal activity of the compound I-25 (N-cyclopropyl-N-[2,6-dichloro-3-(8-hydroxy-5,5-dimethyl-6,6-dioxo-thiopyrano[4,3-b]pyridin-7-yl)phenyl]methanesulfonamide) applied by the post-emergence method

| Application rate (kg/ha) | Plant species | Herbicidal activity |
|---|---|---|
| 0.25 | AMARE | 98 |
| 0.25 | AMBEL | 100 |
| 0.25 | POLAV | 100 |
| 0.25 | ORYSA | 35 |
| 0.125 | AMARE | 98 |
| 0.125 | SETFA | 95 |
| 0.125 | CAPBP | 95 |
| 0.125 | ZEAMX | 20 |
| 0.063 | AMARE | 98 |
| 0.063 | SETFA | 95 |
| 0.063 | CHEAL | 95 |
| 0.063 | ORYSA | 35 |
| 0.031 | AMARE | 95 |
| 0.031 | SETFA | 95 |
| 0.031 | CIRAR | 95 |
| 0.031 | ZEAMX | 5 |

TABLE II.24

Herbicidal activity of the compound I-26 (N-[6-chloro-3-(8-hydroxy-6,6-dioxo-5H-thiopyrano[4,3-b]pyridin-7-yl)-2-methyl-phenyl]-N-methyl-methanesulfonamide) applied by the post-emergence method

| Application rate (kg/ha) | Plant species | Herbicidal activity |
|---|---|---|
| 2 | AMARE | 100 |
| 2 | ABUTH | 100 |
| 2 | ECHCG | 100 |
| 0.125 | ERBVI | 95 |
| 0.125 | AMARE | 90 |
| 0.125 | CHEAL | 98 |
| 0.125 | ORYSA | 45 |
| 0.125 | ZEAMX | 15 |
| 0.063 | ERBVI | 95 |
| 0.063 | AMARE | 85 |
| 0.063 | BRAPL | 90 |
| 0.063 | ZEAMX | 15 |
| 0.031 | ERBVI | 90 |

TABLE II.24-continued

Herbicidal activity of the compound I-26 (N-[6-chloro-3-(8-hydroxy-6,6-dioxo-5H-thiopyrano[4,3-b]pyridin-7-yl)-2-methyl-phenyl]-N-methyl-methanesulfonamide) applied by the post-emergence method

| Application rate (kg/ha) | Plant species | Herbicidal activity |
|---|---|---|
| 0.031 | VERAR | 90 |
| 0.031 | BRAPL | 90 |

TABLE II.25

Herbicidal activity of the compound I-28 (N-[2,6-dichloro-3-(8-hydroxy-5,5-dimethyl-6,6-dioxo-thiopyrano[4,3-b]pyridin-7-yl)phenyl]-N-methyl-cyclopropanesulfonamide) applied by the post-emergence method

| Application rate (kg/ha) | Plant species | Herbicidal activity |
|---|---|---|
| 0.25 | AMARE | 98 |
| 0.25 | ECHCG | 100 |
| 0.25 | SETFA | 100 |
| 0.125 | ECHCG | 100 |
| 0.125 | AMARE | 98 |
| 0.125 | CHEAL | 98 |
| 0.063 | ECHCG | 98 |
| 0.063 | AMARE | 98 |
| 0.063 | CHEAL | 98 |
| 0.063 | ZEAMX | 30 |
| 0.031 | ERBVI | 95 |
| 0.031 | AMARE | 98 |
| 0.031 | CHEAL | 98 |
| 0.031 | ZEAMX | 20 |

TABLE II.26

Herbicidal activity of the compound I-27 (N-[2,6-dichloro-3-(8-hydroxy-6,6-dioxo-5H-thiopyrano[4,3-b]pyridin-7-yl)phenyl]-N-methyl-cyclopropanesulfonamide) applied by the post-emergence method

| Application rate (kg/ha) | Plant species | Herbicidal activity |
|---|---|---|
| 1 | AMARE | 100 |
| 1 | ABUTH | 95 |
| 1 | ECHCG | 98 |
| 0.125 | ECHCG | 98 |
| 0.125 | ABUTH | 80 |
| 0.125 | CHEAL | 100 |
| 0.063 | ECHCG | 98 |
| 0.063 | AMBEL | 75 |
| 0.063 | CHEAL | 100 |
| 0.063 | ZEAMX | 20 |
| 0.031 | PANMI | 75 |
| 0.031 | AMBEL | 70 |
| 0.031 | CHEAL | 100 |
| 0.031 | ORYSA | 40 |
| 0.031 | ZEAMX | 15 |

TABLE II.27

Herbicidal activity of the compound I-29 (N-[6-chloro-3-(8-hydroxy-5,5-dimethyl-6,6-dioxo-thiopyrano[4,3-b]pyridin-7-yl)-2-methyl-phenyl]-N-methyl-methanesulfonamide) applied by the post-emergence method

| Application rate (kg/ha) | Plant species | Herbicidal activity |
|---|---|---|
| 0.25 | AMARE | 98 |
| 0.25 | CHEAL | 98 |
| 0.25 | STEME | 98 |
| 0.125 | AMARE | 98 |
| 0.125 | CHEAL | 98 |
| 0.125 | ECHCG | 95 |
| 0.125 | ORYSA | 35 |
| 0.125 | ZEAMX | 15 |
| 0.063 | AMARE | 95 |

TABLE II.27-continued

Herbicidal activity of the compound I-29 (N-[6-chloro-3-(8-hydroxy-5,5-dimethyl-6,6-dioxo-thiopyrano[4,3-b]pyridin-7-yl)-2-methyl-phenyl]-N-methyl-methanesulfonamide) applied by the post-emergence method

| Application rate (kg/ha) | Plant species | Herbicidal activity |
| --- | --- | --- |
| 0.063 | CHEAL | 98 |
| 0.063 | ECHCG | 90 |
| 0.063 | ORYSA | 25 |
| 0.063 | ZEAMX | 5 |
| 0.031 | AMARE | 95 |
| 0.031 | CHEAL | 98 |
| 0.031 | ECHCG | 85 |
| 0.031 | ORYSA | 0 |
| 0.031 | ZEAMX | 0 |

TABLE II.28

Herbicidal activity of the compound I-30 (7-[2,4-dichloro-3-[methyl(methylsulfonyl)amino]phenyl]-5,5-dimethyl-6,6-dioxo-thiopyrano[4,3-b]pyridin-8-yl] 2,2-dimethylpropanoate) applied by the post-emergence method

| Application rate (kg/ha) | Plant species | Herbicidal activity |
| --- | --- | --- |
| 2 | ABUTH | 100 |
| 2 | AMARE | 100 |
| 2 | ECHCG | 100 |

TABLE II.29

Herbicidal activity of the compound I-31 (N-[6-chloro-3-(8-hydroxy-6,6-dioxo-5H-thiopyrano[4,3-b]pyridin-7-yl)-2-(trifluoromethyl)phenyl]-N-methyl-methanesulfonamide) applied by the post-emergence method

| Application rate (kg/ha) | Plant species | Herbicidal activity |
| --- | --- | --- |
| 0.25 | AMARE | 98 |
| 0.25 | CHEAL | 98 |
| 0.25 | ECHCG | 98 |
| 0.125 | AMARE | 98 |
| 0.125 | CHEAL | 98 |
| 0.125 | ECHCG | 98 |
| 0.063 | ABUTH | 90 |
| 0.063 | CHEAL | 98 |
| 0.063 | STEME | 100 |
| 0.031 | ABUTH | 70 |
| 0.031 | STEME | 80 |
| 0.031 | ZEAMX | 5 |

TABLE II.30

Herbicidal activity of the compound I-32 (N-[6-chloro-3-(8-hydroxy-5,5-dimethyl-6,6-dioxo-thiopyrano[4,3-b]pyridin-7-yl)-2-(trifluoromethyl)phenyl]-N-methyl-methanesulfonamide) applied by the post-emergence method

| Application rate (kg/ha) | Plant species | Herbicidal activity |
| --- | --- | --- |
| 0.25 | ABUTH | 98 |
| 0.25 | AMARE | 98 |
| 0.25 | ERICA | 100 |
| 0.25 | ORYSA | 30 |
| 0.125 | AMARE | 98 |
| 0.125 | ABUTH | 95 |
| 0.125 | ECHCG | 95 |
| 0.125 | ZEAMX | 15 |
| 0.063 | AMARE | 98 |
| 0.063 | ABUTH | 90 |
| 0.063 | ECHCG | 98 |
| 0.063 | ZEAMX | 5 |

TABLE II.30-continued

Herbicidal activity of the compound I-32 (N-[6-chloro-3-(8-hydroxy-5,5-dimethyl-6,6-dioxo-thiopyrano[4,3-b]pyridin-7-yl)-2-(trifluoromethyl)phenyl]-N-methyl-methanesulfonamide) applied by the post-emergence method

| Application rate (kg/ha) | Plant species | Herbicidal activity |
| --- | --- | --- |
| 0.031 | AMARE | 98 |
| 0.031 | ABUTH | 95 |
| 0.031 | ECHCG | 90 |
| 0.031 | ZEAMX | 5 |

TABLE II.31

Herbicidal activity of the compound I-33 (N-[3-(8-hydroxy-6,6-dioxo-5H-thiopyrano[4,3-b]pyridin-7-yl)-2-methylsulfonyl-phenyl]-N-methyl-methanesulfonamide) applied by the post-emergence method

| Application rate (kg/ha) | Plant species | Herbicidal activity |
| --- | --- | --- |
| 0.125 | CHEAL | 90 |
| 0.125 | AMARE | 90 |
| 0.125 | ORYSA | 10 |
| 0.125 | ZEAMX | 0 |
| 0.063 | CHEAL | 98 |
| 0.063 | AMARE | 85 |
| 0.063 | ORYSA | 20 |
| 0.063 | ZEAMX | 0 |
| 0.031 | CHEAL | 85 |
| 0.031 | ORYSA | 0 |
| 0.031 | ZEAMX | 0 |

TABLE II.32

Herbicidal activity of the compound I-34 (N-[3-(8-hydroxy-5,5-dimethyl-6,6-dioxo-thiopyrano[4,3-b]pyridin-7-yl)-2-methylsulfonyl-phenyl]-N-methyl-methanesulfonamide) applied by the post-emergence method

| Application rate (kg/ha) | Plant species | Herbicidal activity |
| --- | --- | --- |
| 0.125 | CHEAL | 100 |
| 0.125 | AMARE | 98 |
| 0.125 | ECHCG | 70 |
| 0.125 | ORYSA | 0 |
| 0.125 | ZEAMX | 15 |
| 0.063 | CHEAL | 98 |
| 0.063 | AMARE | 95 |
| 0.063 | ORYSA | 0 |
| 0.063 | ZEAMX | 0 |
| 0.031 | CHEAL | 95 |
| 0.031 | AMARE | 90 |
| 0.031 | ORYSA | 0 |
| 0.031 | ZEAMX | 0 |

TABLE II.33

Herbicidal activity of the compound I-35 (N-[3-(8-hydroxy-6,6-dioxo-5H-thiopyrano[4,3-b]pyridin-7-yl)-2-(trifluoromethyl)phenyl]-N-methyl-methanesulfonamide) applied by the post-emergence method

| Application rate (kg/ha) | Plant species | Herbicidal activity |
| --- | --- | --- |
| 0.125 | CHEAL | 100 |
| 0.125 | AMARE | 100 |
| 0.125 | ECHCG | 90 |
| 0.125 | ORYSA | 25 |
| 0.125 | ZEAMX | 0 |
| 0.063 | CHEAL | 100 |
| 0.063 | AMARE | 75 |
| 0.063 | ECHCG | 90 |
| 0.063 | ORYSA | 15 |
| 0.063 | ZEAMX | 0 |

TABLE II.33-continued

Herbicidal activity of the compound I-35 (N-[3-(8-hydroxy-6,6-dioxo-5H-thiopyrano[4,3-b]pyridin-7-yl)-2-(trifluoromethyl)phenyl]-N-methyl-methanesulfonamide) applied by the post-emergence method

| Application rate (kg/ha) | Plant species | Herbicidal activity |
| --- | --- | --- |
| 0.031 | CHEAL | 95 |
| 0.031 | ECHCG | 80 |
| 0.031 | ORYSA | 0 |
| 0.031 | ZEAMX | 0 |

TABLE II.34

Herbicidal activity of the compound I-36 (N-[3-(8-hydroxy-5,5-dimethyl-6,6-dioxo-thiopyrano[4,3-b]pyridin-7-yl)-2-(trifluoromethyl)phenyl]-N-methyl-methanesulfonamide) applied by the post-emergence method

| Application rate (kg/ha) | Plant species | Herbicidal activity |
| --- | --- | --- |
| 0.125 | ECHCG | 95 |
| 0.125 | AMARE | 98 |
| 0.125 | CHEAL | 100 |
| 0.125 | ORYSA | 45 |
| 0.125 | ZEAMX | 0 |
| 0.063 | CHEAL | 100 |
| 0.063 | AMARE | 95 |
| 0.063 | ECHCG | 90 |
| 0.063 | ORYSA | 40 |
| 0.063 | ZEAMX | 0 |
| 0.031 | CHEAL | 100 |
| 0.031 | AMARE | 90 |
| 0.031 | ECHCG | 70 |
| 0.031 | ORYSA | 30 |
| 0.031 | ZEAMX | 0 |

TABLE II.35

Herbicidal activity of the compound I-37 (N-[2,6-dichloro-3-(3-fluoro-8-hydroxy-6,6-dioxo-5H-thiopyrano[4,3-b]pyridin-7-yl)phenyl]-N-methyl-methanesulfonamide) applied by the post-emergence method

| Application rate (kg/ha) | Plant species | Herbicidal activity |
| --- | --- | --- |
| 0.125 | ECHCG | 95 |
| 0.125 | CHEAL | 90 |
| 0.125 | ORYSA | 0 |
| 0.063 | ECHCG | 90 |
| 0.063 | CHEAL | 90 |
| 0.063 | ORYSA | 0 |
| 0.063 | ZEAMX | 0 |
| 0.031 | ECHCG | 90 |
| 0.031 | CHEAL | 90 |
| 0.031 | ORYSA | 0 |
| 0.031 | ZEAMX | 0 |

TABLE II.36

Herbicidal activity of the compound I-38 (N-[2,6-dichloro-3-(3-fluoro-8-hydroxy-5,5-dimethyl-6,6-dioxo-thiopyrano[4,3-b]pyridin-7-yl)phenyl]-N-methyl-methanesulfonamide) applied by the post-emergence method

| Application rate (kg/ha) | Plant species | Herbicidal activity |
| --- | --- | --- |
| 0.125 | SETVI | 100 |
| 0.125 | ECHCG | 100 |
| 0.125 | AMARE | 98 |
| 0.125 | CHEAL | 98 |
| 0.125 | ZEAMX | 15 |
| 0.063 | CHEAL | 95 |
| 0.063 | AMARE | 98 |

TABLE II.36-continued

Herbicidal activity of the compound I-38 (N-[2,6-dichloro-3-(3-fluoro-8-hydroxy-5,5-dimethyl-6,6-dioxo-thiopyrano[4,3-b]pyridin-7-yl)phenyl]-N-methyl-methanesulfonamide) applied by the post-emergence method

| Application rate (kg/ha) | Plant species | Herbicidal activity |
| --- | --- | --- |
| 0.063 | ECHCG | 95 |
| 0.063 | ZEAMX | 0 |
| 0.031 | CHEAL | 98 |
| 0.031 | AMARE | 98 |
| 0.031 | ECHCG | 95 |
| 0.031 | ORYSA | 35 |
| 0.031 | ZEAMX | 0 |

As can be seen from Tables II.1 to II.36, the compounds of formula I possess excellent herbicidal activity against harmful plants without exhibiting unacceptable phytotoxicity to monocot crops such as corn (maize) or rice.

The invention claimed is:
1. A compound of the formula I

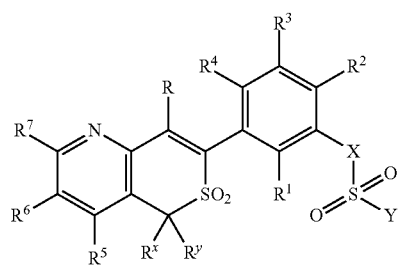

wherein
R is hydroxyl or O—$R^A$ wherein $R^A$ is selected from the group consisting of $C_1$-$C_8$-alkyl, $C_2$-$C_8$-alkenyl, $C_2$-$C_8$-alkynyl, $C_1$-$C_8$-alkylcarbonyl-, $C_3$-$C_6$-cycloalkylcarbonyl-, $C_1$-$C_8$-alkoxycarbonyl-, $C_1$-$C_8$-alkylthiocarbonyl-, $C_1$-$C_8$-alkoxycarbonyloxy-$C_1$-$C_3$-alkyl-, $C_1$-$C_8$-alkylcarbonyloxy-$C_1$-$C_3$-alkyl-, $C_1$-$C_8$-alkyl-S(O)$_n$—, aryl-S(O)$_n$—, aryl-$C_1$-$C_4$-alkyl- and arylcarbonyl-, wherein the aryl moiety is unsubstituted or substituted by one to five IV and each leis independently selected from the group consisting of halogen, nitro, cyano, $C_1$-$C_8$-alkyl, $C_1$-$C_6$-haloalkyl, $C_1$-$C_8$-alkoxy, $C_1$-$C_8$-haloalkoxy, and $C_1$-$C_4$-alkyl-S(O)$_n$—;
$R^1$ and $R^2$ independently of one another are selected from the group consisting of hydrogen, halogen, cyano, nitro, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy, $C_1$-$C_6$-alkoxy-$C_1$-$C_4$-alkyl-, $C_1$-$C_6$-haloalkoxy-$C_1$-$C_4$-alkyl-, $C_3$-$C_6$-cycloalkyl-$C_1$-$C_3$-alkyl-, $C_3$-$C_6$-cycloakyl-$C_1$-$C_3$-alkoxy-, $C_1$-$C_6$-alkoxy-$C_2$-$C_6$-alkoxy-, $C_1$-$C_6$-alkoxy-$C_2$-$C_6$-alkoxy-$C_1$-$C_3$-alkyl-, $C_1$-$C_6$-alkylthio-, $C_1$-$C_6$-haloalkylthio-, $C_1$-$C_6$-alkylsulfonyl-, $C_1$-$C_6$-haloalkylsulfonyl-, $C_1$-$C_3$-alkylaminosulfonyl-, $C_1$-$C_3$-dialkylaminosulfonyl-, $C_1$-$C_3$-alkylamino-sulfonyl-$C_1$-$C_3$-alkyl-, $C_1$-$C_3$-dialkylamino-sulfonyl-$C_1$-$C_3$-alkyl-, $C_1$-$C_3$-alkylcarbonylamino-, N—$C_1$-$C_3$-alkyl-N—$C_1$-$C_3$-alkylcarbonylamino-, $C_1$-$C_3$-alkylsulfonylamino-, N—$C_1$-$C_3$-alkyl-N—$C_1$-$C_3$-alkylsulfonylamino-, $C_1$-$C_3$-alkylsulfonylamino-$C_1$-$C_3$-alkyl-, $C_1$-$C_3$-alkylaminocarbonyl-$C_1$-$C_3$-alkyl-, $C_1$-$C_3$-dialkylaminocarbonyl-$C_1$-$C_3$-alkyl-, N—$C_1$-$C_3$-alkylcarbonyl-N—$C_1$-$C_3$-alkylamino-$C_1$-$C_3$-alkyl-, N—$C_1$-$C_3$-alkylsulfonyl- N—$C_1$-$C_3$-alkylamino-$C_1$-$C_3$-alkyl-, $C_1$-$C_3$-alkylcarbonylamino-$C_1$-$C_3$-alkyl-, Z-heterocyclyl and Z-heterocyclyloxy wherein said heterocyclyls are 5- or 6-membered heterocyclyls containing 1, 2 or 3 heteroatoms selected from the group consisting of O, N and S, and are unsubstituted or partially or fully substituted by substituents selected from the group consisting of halogen, $C_1$-$C_3$-alkyl, $C_3$-$C_6$-cycloalkyl, $C_1$-$C_3$-haloalkyl, $C_1$-$C_3$-alkoxy, $C_1$-$C_3$-haloalkoxy, $C_1$-$C_6$-alkyl-S$(O)_n$—, cyano, nitro and phenyl;

$R^3$ is hydrogen;
$R^4$ is hydrogen or halogen;
$R^5$, $R^6$, and $R^7$ independently of one another are selected from the group consisting of hydrogen, halogen and $C_1$-$C_4$-alkyl;
$R^x$, $R^y$ independently of one another are selected from the group consisting of hydrogen, $C_1$-$C_5$-alkyl, $C_2$-$C_5$-alkenyl, $C_2$-$C_5$-alkynyl, $C_1$-$C_5$-haloalkyl, $C_1$-$C_2$-alkoxy-$C_1$-$C_2$-alkyl- and halogen; or $R^x$ and $R^y$ are together a $C_2$-$C_5$-alkylene or $C_2$-$C_5$-alkenylene chain and form a 3-, 4-, 5- or 6-membered saturated, partially unsaturated or fully unsaturated monocyclic ring together with the carbon atom they are bonded to, wherein 1 or 2 of any of the $CH_2$ or CH groups in the $C_2$-$C_5$-alkylene or $C_2$-$C_5$-alkenylene chain may be replaced by 1 or 2 heteroatoms independently selected from 0 or S;
X is selected from the group consisting of O, NH, N—$C_1$-$C_4$-alkyl, N—$C_1$-$C_4$-alkoxy-$C_1$-$C_4$-alkyl, N—$C_3$-$C_6$-cycloalkyl, and N-allyl;
Y is selected from the group consisting of $C_1$-$C_4$-alkyl, $C_1$-$C_4$-haloalkyl, $C_3$-$C_6$-cycloalkyl, $C_3$-$C_6$-cycloalkyl-$C_1$-$C_3$-alkyl-, and $C_1$-$C_3$-dialkylamino-;
Z is independently a covalent bond or $C_1$-$C_4$-alkylene;
n is independently 0, 1 or 2;
or an agriculturally suitable salt or N-oxide thereof.

2. The compound of claim 1, wherein R is selected from the group consisting of hydroxyl, benzyloxy-, allyloxy-, propargyloxy-, methoxy-, cyclopropylcarbonyloxy-, propyl-2-ylcarbonyloxy-, 2-methyl-prop-2-ylcarbonyloxy-, methylsulfonyloxy-, ethoxycarbonyloxy-, isopropoxycarbonyloxy-, ethylthiocarbonyloxy-, 2-methyl-prop-2-ylcarbonyloxymethoxy-, ethoxycarbonyloxyethoxy-, isopropoxycarbonlyoxymethoxy-, methoxycarbonyloxyethoxy-, and ethoxycarbonyloxymethoxy-.

3. The compound of claim 1, wherein $R^1$ is selected from the group consisting of fluoro, chloro, bromo, methyl, ethyl, cyclopropyl, trifluoromethyl, trifluoromethoxy, methoxy, ethoxy, methoxyethoxymethyl, methylsulfonyl, ethylsulfonyl, isoxazolin-3-yl, isoxazolin-5-yl, dimethylaminosulfonyl, and trifluoromethoxymethyl.

4. The compound of claim 3, wherein $R^1$ is selected from the group consisting of chloro, methyl, trifluoromethyl and methylsulfonyl.

5. The compound of claim 1, wherein $R^2$ is selected from the group consisting of hydrogen, halogen, cyano, $C_1$-$C_4$-alkyl, $C_3$-$C_6$-cycloalkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-alkylsulfonyl.

6. The compound of claim 5, wherein $R^2$ is selected from the group consisting of hydrogen, fluoro, chloro, bromo, methyl, cyclopropyl, trifluoromethyl, difluoromethyl, methoxy, trifluoromethoxy, difluoromethoxy, thiomethyl, thioethyl methylsulfonyl and ethylsulfonyl.

7. The compound of claim 1, wherein $R^4$ is selected from the group consisting of hydrogen, fluorine and chlorine.

8. The compound of claim 1, wherein $R^5$ is hydrogen, $R^6$ is hydrogen or fluorine and $R^7$ is hydrogen.

9. The compound of claim 1, wherein $R^x$ and $R^y$, independently of one another, are H or $C_1$-$C_5$-alkyl.

10. The compound of claim 1, wherein X is selected from the group consisting of O, N-methyl, N-ethyl, N-isopropyl, N-methoxymethyl and N-cyclopropyl.

11. The compound of claim 1, wherein Y is selected from the group consisting of methyl, ethyl, isopropyl, cyclopropyl, difluoromethyl, trifluoromethyl, cyclopropylmethyl and dimethylamino.

12. The compound of claim 1, being selected from the group consisting of the compounds I-1 to I-38 as listed below:

N-[2,6-dichloro-3-(8-hydroxy-6,6-dioxo-5H-thiopyrano[4,3-b]pyridin-7-yl)phenyl]methanesulfonamide of the formula I-1

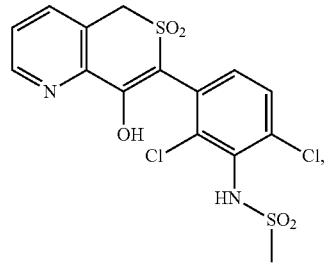

I-1

N-[2,6-dichloro-3-(8-hydroxy-5,5-dimethyl-6,6-dioxo-thiopyrano[4,3-b]pyridin-7-yl)phenyl]-N-methyl-methanesulfonamide of the formula I-2

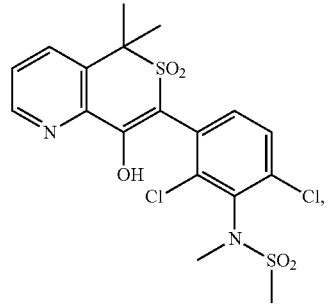

I-2

N-[2,6-dichloro-3-(8-hydroxy-6,6-dioxo-5H-thiopyrano[4,3-b]pyridin-7-yl)phenyl]-N-methyl-methanesulfonamide of the formula I-3

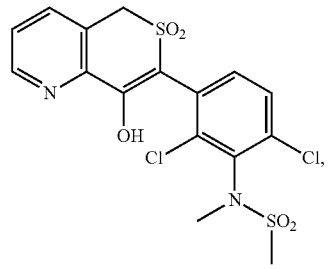

I-3

N-[2,4-dichloro-3-(8-hydroxy-6,6-dioxo-5H-thiopyrano[4,3-b]pyridin-7-yl)phenyl]-N-methyl-methanesulfonamide of the formula I-4

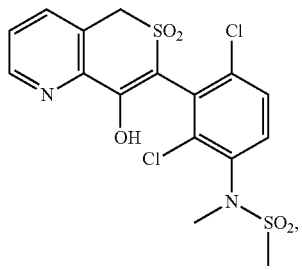

I-4

N-[2,4-dichloro-3-(8-hydroxy-6,6-dioxo-5H-thiopyrano[4,3-b]pyridin-7-yl)phenyl]methanesulfonamide of the formula I-5

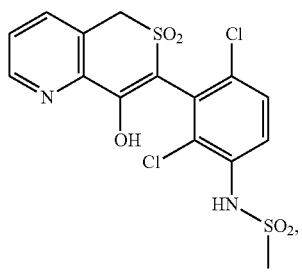

I-5

N-[2,4-dichloro-3-(8-hydroxy-5,5-dimethyl-6,6-dioxo-thiopyrano[4,3-b]pyridin-7-yl)phenyl]methanesulfonamide of the formula I-6

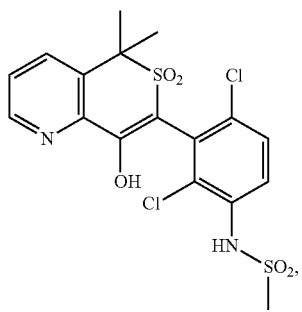

I-6

N-[2,4-dichloro-3-(8-hydroxy-5,5-dimethyl-6,6-dioxo-thiopyrano[4,3-b]pyridin-7-yl)phenyl]-N-methyl-methanesulfonamide of the formula I-7

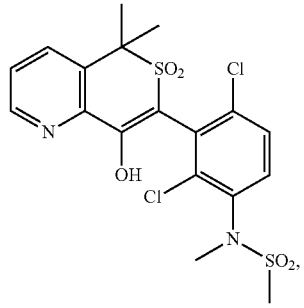

I-7

N-[2,6-dichloro-3-(8-hydroxy-6,6-dioxo-5H-thiopyrano[4,3-b]pyridin-7-yl)phenyl]-N-ethyl-methanesulfonamide of the formula I-8

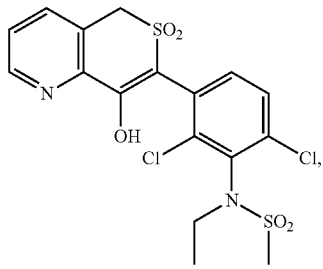

I-8

N-[2,6-dichloro-3-(8-hydroxy-5,5-dimethyl-6,6-dioxo-thiopyrano[4,3-b]pyridin-7-yl)phenyl]-N-ethyl-methanesulfonamide of the formula I-9

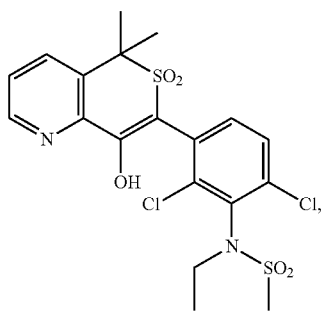

I-9

N-[2,6-dichloro-3-(8-hydroxy-6,6-dioxo-5H-thiopyrano[4,3-b]pyridin-7-yl)phenyl]-N-isopropyl-methanesulfonamide of the formula I-10

I-10
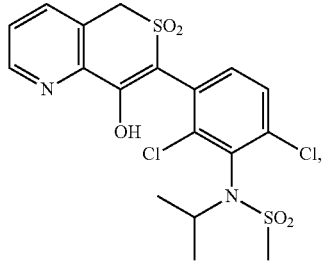

N-[2,6-dichloro-3-(8-hydroxy-5,5-dimethyl-6,6-dioxo-thiopyrano[4,3-b]pyridin-7-yl)phenyl]-N-isopropyl-methanesulfonamide of the formula I-11

I-11
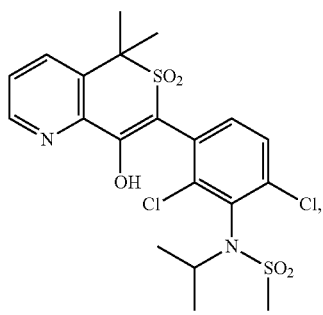

N-[3-(8-hydroxy-6,6-dioxo-5H-thiopyrano[4,3-b]pyridin-7-yl)-2-methyl-phenyl]-N-methyl-methanesulfonamide of the formula I-12

I-12
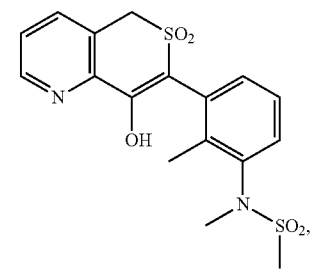

[5,5-dimethyl-7-[2-methyl-3-[methyl(methylsulfonyl)amino]phenyl]-6,6-dioxo-thiopyrano[4,3-b]pyridin-8-yl] 2,2-dimethylpropanoate of the formula I-13

I-13
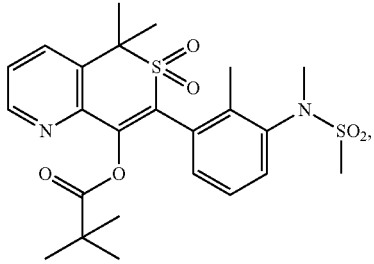

N-[3-(8-hydroxy-5,5-dimethyl-6,6-dioxo-thiopyrano[4,3-b]pyridin-7-yl)-2-methyl-phenyl]-N-methyl-methanesulfonamide of the formula I-14

I-14
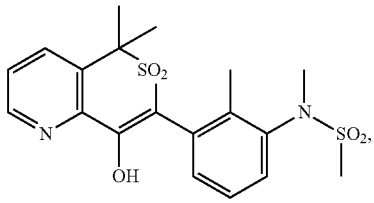

N-[2-chloro-3-(8-hydroxy-6,6-dioxo-5H-thiopyrano[4,3-b]pyridin-7-yl)phenyl]-N-methyl-methanesulfonamide of the formula I-15

I-15
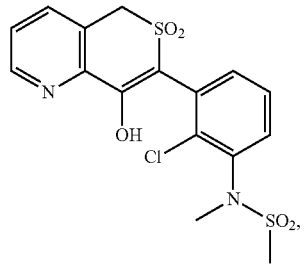

[7-[2-chloro-3-[methyl(methylsulfonyl)amino]phenyl]-5,5-dimethyl-6,6-dioxo-thiopyrano[4,3-b]pyridin-8-yl] 2,2-dimethylpropanoate of the formula I-16

I-16
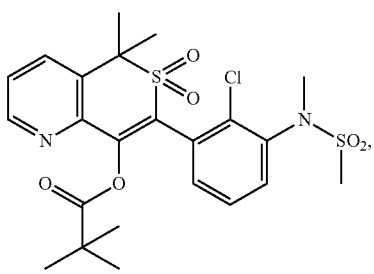

N-[2-chloro-3-(8-hydroxy-5,5-dimethyl-6,6-dioxo-thio-
pyrano[4,3-b]pyridin-7-yl)phenyl]-N-methyl-methane-
sulfonamide of the formula I-17

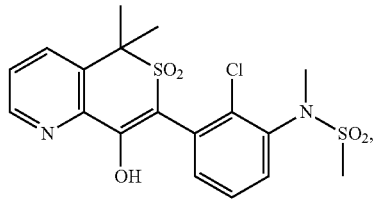

N-[2,6-dichloro-3-(8-hydroxy-6,6-dioxo-5H-thiopyrano
[4,3-b]pyridin-7-yl)phenyl]-N-methyl-ethanesulfona-
mide of the formula I-18

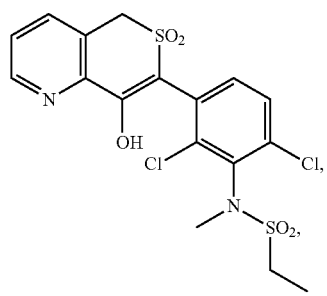

N-[2,6-dichloro-3-(8-hydroxy-5,5-dimethyl-6,6-dioxo-
thiopyrano[4,3-b]pyridin-7-yl)phenyl]-N-methyl-eth-
anesulfonamide of the formula I-19

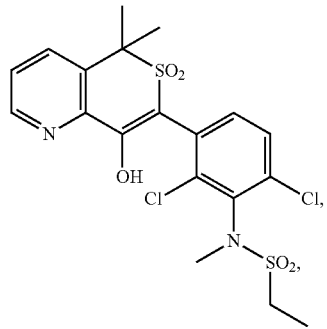

1-cyclopropyl-N-[2,6-dichloro-3-(8-hydroxy-6,6-dioxo-
5H-thiopyrano[4,3-b]pyridin-7-yl)phenyl]-N-methyl-
methanesulfonamide of the formula I-20

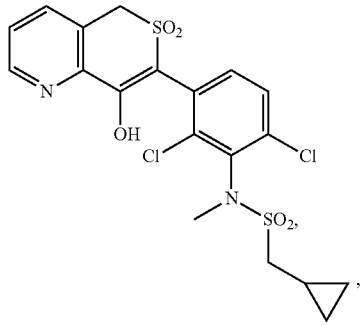

1-cyclopropyl-N-[2,6-dichloro-3-(8-hydroxy-5,5-dim-
ethyl-6,6-dioxo-thiopyrano[4,3-b]pyridin-7-yl)phe-
nyl]-N-methyl-methanesulfonamide of the formula
I-21

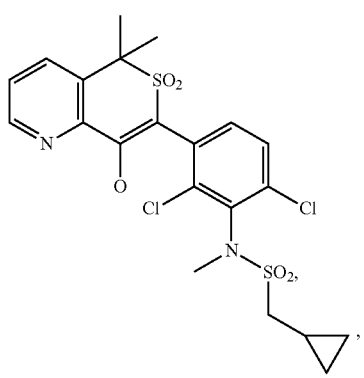

2,6-dichloro-3-(8-hydroxy-6,6-dioxo-5H-thiopyrano[4,3-
b] pyridin-7-yl)phenyl]N,N-dimethylsulfamate of the
formula I-22

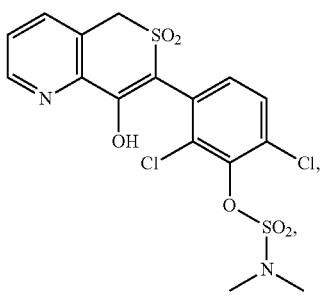

2,6-dichloro-3-(8-hydroxy-5,5-dimethyl-6,6-dioxo-thio-pyrano[4,3-b]pyridin-7-yl)phenyl]N,N-dimethylsulfa-mate of the formula I-23

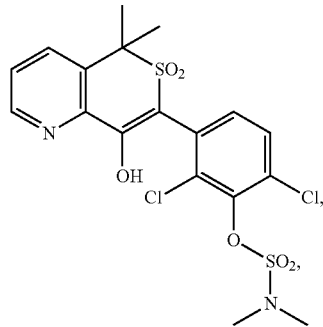

N-cyclopropyl-N-[2,6-dichloro-3-(8-hydroxy-6,6-dioxo-5H-thiopyrano[4,3-b]pyridin-7-yl)phenyl]methanesul-fonamide of the formula I-24

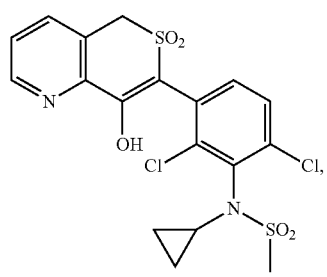

N-cyclopropyl-N-[2,6-dichloro-3-(8-hydroxy-5,5-dim-ethyl-6,6-dioxo-thiopyrano[4,3-b]pyridin-7-yl)phenyl]methanesulfonamide of the formula I-25

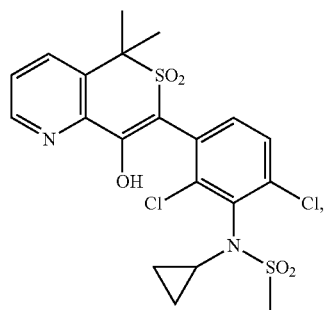

N-[6-chloro-3-(8-hydroxy-6,6-dioxo-5H-thiopyrano[4,3-b]pyridin-7-yl)-2-methyl-phenyl]-N-methyl-methane-sulfonamide of the formula I-26

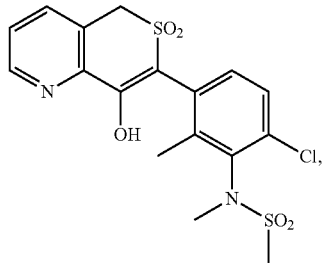

N-[2,6-dichloro-3-(8-hydroxy-6,6-dioxo-5H-thiopyrano[4,3-b]pyridin-7-yl)phenyl]-N-methyl-cyclopropane-sulfonamide of the formula I-27

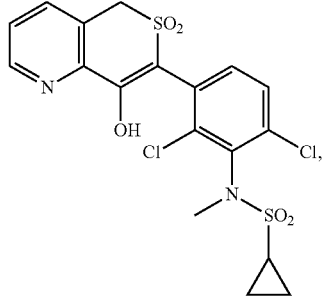

N-[2,6-dichloro-3-(8-hydroxy-5,5-dimethyl-6,6-dioxo-thiopyrano[4,3-b]pyridin-7-yl)phenyl]-N-methyl-cy-clopropanesulfonamide of the formula I-28

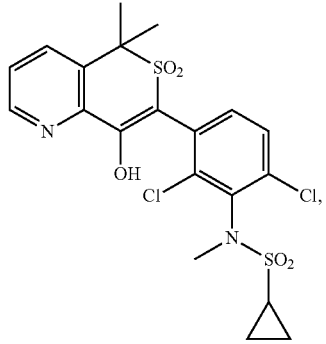

N-[6-chloro-3-(8-hydroxy-5,5-dimethyl-6,6-dioxo-thiopyrano[4,3-b]pyridin-7-yl)-2-methyl-phenyl]-N-methyl-methanesulfonamide of the formula I-29

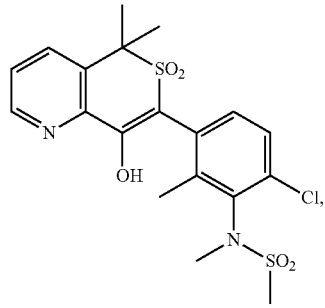

7-[2,4-dichloro-3-[methyl(methylsulfonyl)amino]phenyl]-5,5-dimethyl-6,6-dioxo-thiopyrano[4,3-b]pyridin-8-yl] 2,2-dimethylpropanoate of the formula I-30

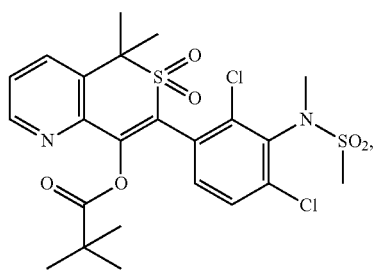

N-[6-chloro-3-(8-hydroxy-6,6-dioxo-5H-thiopyrano[4,3-b]pyridin-7-yl)-2-(trifluoromethyl)phenyl]-N-methyl-methanesulfonamide of the formula I-31

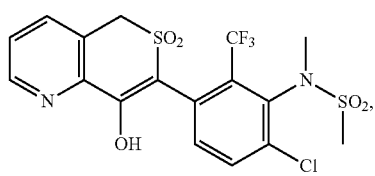

N-[6-chloro-3-(8-hydroxy-5,5-dimethyl-6,6-dioxo-thiopyrano[4,3-b]pyridin-7-yl)-2-(trifluoromethyl)phenyl]-N-methyl-methanesulfonamide of the formula I-32

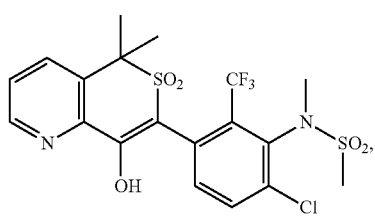

N-[3-(8-hydroxy-6,6-dioxo-5H-thiopyrano[4,3-b]pyridin-7-yl)-2-methylsulfonyl-phenyl]-N-methyl-methanesulfonamide of the formula I-33

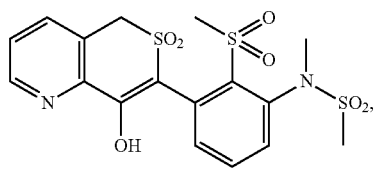

N-[3-(8-hydroxy-5,5-dimethyl-6,6-dioxo-thiopyrano[4,3-b]pyridin-7-yl)-2-methylsulfonyl-phenyl]-N-methyl-methanesulfonamide of the formula I-34

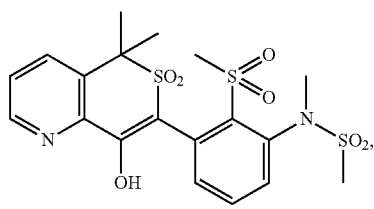

N-[3-(8-hydroxy-6,6-dioxo-5H-thiopyrano[4,3-b]pyridin-7-yl)-2-(trifluoromethyl)phenyl]-N-methyl-methanesulfonamide of the formula I-35

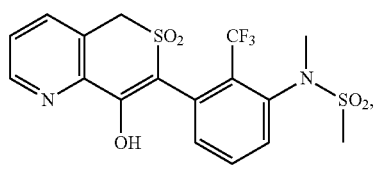

N-[3-(8-hydroxy-5,5-dimethyl-6,6-dioxo-thiopyrano[4,3-b]pyridin-7-yl)-2-(trifluoromethyl)phenyl]-N-methyl-methanesulfonamide of the formula I-36

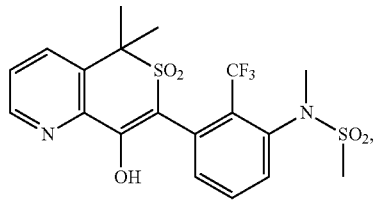

N-[2,6-dichloro-3-(3-fluoro-8-hydroxy-6,6-dioxo-5H-thiopyrano[4,3-b]pyridin-7-yl)phenyl]-N-methyl-methanesulfonamide of the formula I-37 and

N-[2,6-dichloro-3-(3-fluoro-8-hydroxy-5,5-dimethyl-6,6-dioxo-thiopyrano[4,3-b]pyridin-7-yl)phenyl]-N-methyl-methanesulfonamide of the formula I-38

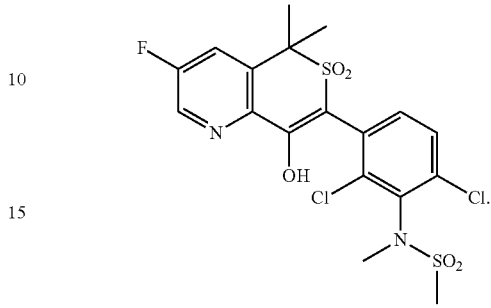

I-38

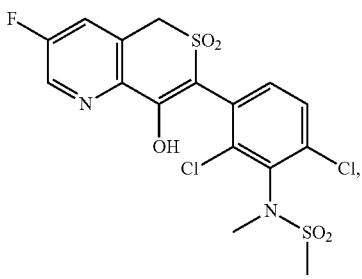

I-37

13. A composition comprising a herbicidally effective amount of at least one compound of the formula I or an agriculturally suitable salt or N-oxide thereof as defined in claim 1 and auxiliaries customary for formulating crop protection agents.

14. A method for controlling unwanted vegetation which comprises allowing a herbicidally effective amount of at least one compound of the formula I or of an agriculturally suitable salt or N-oxide thereof as defined in claim 1 to act on plants, their seed and/or their habitat.

15. The method of claim 14, wherein the plants are monocotyledonous crops.

* * * * *